United States Patent
Brunette et al.

(10) Patent No.: US 11,485,740 B2
(45) Date of Patent: Nov. 1, 2022

(54) INHIBITORS OF TRPC6

(71) Applicants: Boehringer Ingelheim International GmbH, Ingelheim am Rhein (DE); Hydra Biosciences, LLC, Belmont, MA (US)

(72) Inventors: Steven Brunette, Ridgefield, CT (US); Jianwen Cui, Ridgefield, CT (US); Michael D. Lowe, Pleasantville, NY (US); Christopher Ronald Sarko, San Ramon, CA (US); Simon Surprenant, Boisbriand (CA); Michael Robert Turner, Danbury, CT (US); Xinyuan Wu, Newton, MA (US); Lana Louise Smith Keenan, Poughquag, NY (US); Thierry Bouyssou, Ingelheim am Rhein (DE); Paul Nicklin, Ingelheim am Rhein (DE)

(73) Assignees: Boehringer Ingelheim International GmbH, Ingelheim am Rhein (DE); Hydra Biosciences, LLC, Belmont, MA (US)

(*) Notice: Subject to any disclaimer, the term of this patent is extended or adjusted under 35 U.S.C. 154(b) by 243 days.

(21) Appl. No.: 16/970,129

(22) PCT Filed: Feb. 13, 2019

(86) PCT No.: PCT/EP2019/053525
§ 371 (c)(1),
(2) Date: Aug. 14, 2020

(87) PCT Pub. No.: WO2019/158572
PCT Pub. Date: Aug. 22, 2019

(65) Prior Publication Data
US 2020/0399282 A1 Dec. 24, 2020

Related U.S. Application Data

(60) Provisional application No. 62/630,907, filed on Feb. 15, 2018.

(51) Int. Cl.
*C07D 487/08* (2006.01)
*C07D 401/04* (2006.01)
*C07D 401/14* (2006.01)
*C07D 405/14* (2006.01)

(52) U.S. Cl.
CPC ........ *C07D 487/08* (2013.01); *C07D 401/04* (2013.01); *C07D 401/14* (2013.01); *C07D 405/14* (2013.01)

(58) Field of Classification Search
CPC .. C07D 487/08; C07D 401/04; C07D 401/14; C07D 405/14
See application file for complete search history.

(56) References Cited

U.S. PATENT DOCUMENTS

| | | | | |
|---|---|---|---|---|
| 10,800,757 B2* | 10/2020 | Bouyssou | ............ | A61K 31/501 |
| 10,889,568 B2* | 1/2021 | Bouyssou | ............ | C07D 213/04 |
| 2008/0280916 A1* | 11/2008 | Bilich | ............ | A61K 31/501 |
| | | | | 514/252.02 |
| 2019/0169167 A1* | 6/2019 | Bouyssou | ............ | A61K 31/45 |
| 2021/0053935 A1* | 2/2021 | Berry | ............ | C07D 401/04 |
| 2021/0163449 A1* | 6/2021 | Bouyssou | ............ | C07D 498/08 |

FOREIGN PATENT DOCUMENTS

| | | | | |
|---|---|---|---|---|
| CN | 107253952 | * | 10/2017 | .......... C07D 213/04 |
| EP | 2 556 820 A2 | | 2/2013 | |
| EP | 2 556 829 A1 | | 2/2013 | |
| WO | WO 2012/037349 A2 | | 3/2012 | |
| WO | WO-2019081637 A1 * | | 5/2019 | .......... C07D 213/04 |
| WO | WO-2019161010 A1 * | | 8/2019 | .......... C07D 405/14 |
| WO | WO-2020208002 A1 * | | 10/2020 | ............ A61P 13/12 |
| WO | WO 2021209510 | * | 10/2021 | |

OTHER PUBLICATIONS

Dietrich (2014) TRPC6: Physiological Function and Pathophysiological Relevance. In: Nilius B., Flockerzi V. (eds) Mammalian Transient Receptor Potential (TRP) Cation Channels. Handbook of Experimental Pharmacology, vol. 222. Springer, Berlin, Heidelberg, https://doi.org/10.1007/978-3-642 (Year: 2014).*
Urban; Molecular Pharmacology 2016, 89, 197-213. DOI: https://doi.org/10.1124/mol.115.100792 (Year: 2016).*
Zhou; J. Nat. Prod. 2018, 81, 4, 913-917. DOI: https://doi.org/10.1021/acs.jnatprod.7b01037 (Year: 2018).*
International Search Report and Written Opinion dated Oct. 4, 2019 in connection with PCT/EP2019/053525.

* cited by examiner

*Primary Examiner* — Daniel R Carcanague
(74) *Attorney, Agent, or Firm* — Wolf, Greenfield & Sacks, P.C.

(57) ABSTRACT

The present invention relates to compounds of formula (I) and pharmaceutically acceptable salts therefore, wherein $R^1$ to $R^6$, A, U, V, W, X, Y, and Z are as defined herein. The invention also relates to pharmaceutical compositions comprising these compounds, methods of using these compounds in the treatment of various diseases and disorders, processes for preparing these compounds and intermediates useful in these processes.

(I)

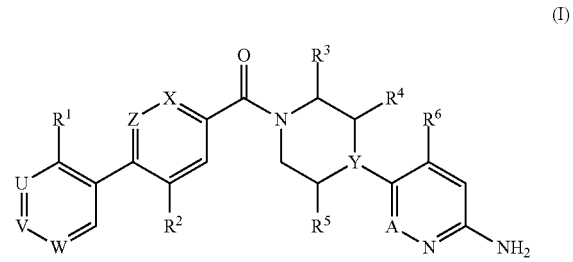

20 Claims, No Drawings

INHIBITORS OF TRPC6

CROSS REFERENCE TO RELATED APPLICATION(S)

This Application is a National Stage filing under 35 U.S.C. § 371 of International Patent Application No. PCT/EP2019/053525, filed Feb. 13, 2019, which claims priority under 35 U.S.C. § 119(e) to U.S. Provisional patent application No. 62/630,907, filed Feb. 15, 2018, the entire contents of which are incorporated herein by reference.

FIELD OF THE INVENTION

The present invention relates to pharmaceutical compounds, compositions, and methods for the treatment of cardiac and respiratory conditions, renal disease, liver disease, muscular dystrophy, fibrotic disorders, pain, ischemia or ischemic reperfusion injury, and cancer, as well as inhibiting the Transient Receptor Potential C6 ion channel (TRPC6).

BACKGROUND

A variety of ion channel proteins exist to mediate ion flux across cellular membranes. The proper expression and function of ion channel proteins is essential for the maintenance of cellular function, intracellular communication, and the like. An important aspect of achieving cellular homeostasis is the maintenance of appropriate ion concentrations in various cell types during development and in response to numerous stimuli. Large numbers of diverse types of ion channels act to maintain cellular homeostasis by moving ions into and out of cells across the plasma membrane, and within cells by moving ions across membranes of intracellular organelles including, for example, the endoplasmic reticulum, sarcoplasmic reticulum, mitochondria and endocytic organelles including endosomes and lysosomes. Numerous diseases are the result of dysregulation of membrane potential or aberrant calcium handling. Given the central importance of ion channels in modulating membrane potential and ion flux in cells, identification of agents that can promote or inhibit particular ion channels is of great interest as research tools and as possible therapeutic agents.

One such channel is the Transient Receptor Potential C6 (TRPC6) channel. TRPC6 belongs to the larger family of TRP ion channels (see, Desai et al., 2005 Eur J Physiol 451:11-18; Clapham et al., 2001 Nat Neurosci 2:387-396; Clapham, 2003 Nature 426: 517-524; Clapham et al., Pharmacol Rev 55: 591-596, 2003). TRPC6 is a calcium permeable channel, specifically a non-selective calcium permeable cation channel. In addition to calcium ions, TRPC6 channels are permeable to other cations, for example sodium. Thus, TRPC6 channels modulate not only intracellular calcium concentration, but also membrane potential by modulating the flux of cations including calcium and sodium ions. Although non-selective cation channels such as TRPC6 modulate, among other things, calcium ion flux, they are mechanistically distinct from voltage-gated calcium channels. Generally, voltage-gated calcium channels respond to depolarization of the potential difference across the membrane and can open to permit an influx of calcium from the extracellular medium and a rapid increase in intracellular calcium levels or concentrations. In contrast, non-selective cation channels such as TRPC6 are generally signal transduction gated, long-lasting, and produce less rapid changes in ion concentration. They show increased activity in response to the production of the second messenger, diacylglycerol (Hofmann et al., 1999). In addition, TRPC6 can respond to changes in pressure. These mechanistic differences are accompanied by structural differences among voltage-gated and cation permeable channels. Thus, although many diverse channels act to regulate ion flux and membrane potential in various cell types and in response to numerous stimuli, it is important to recognize the significant structural, functional, and mechanistic differences among different classes of ion channels.

TRPC6 function has been implicated in, among other things, the modulation of myogenic tone. TRPC6 is highly expressed in smooth muscle cells, vascular smooth muscle cells, endothelial cells, cardiomyocytes, pulmonary arteries, the aorta, heart, liver, brain, and kidney. The expression of TRPC6, along with experiments conducted in knock-out mice and cells in culture, suggest that TRPC6 may provide a useful target for the treatment of hypertension and other cardiac and vascular conditions, preeclampsia.

Mutation in the human TRPC6 channel can cause focal segmental glomerulsclerosis (FSGS) (Winn et al., 2005, Reiser et al., 2005). These mutations that are reported to be gain-of-function (Reiser et al., 2005), are sufficient to induce disease. In addition, elevated TRPC6 expression has been associated with nephrotic syndrome, minimal change disease, and diabetic nephropathy (Moller et al., 2006, Ilatovskaya et al., 2013, Thilo et al., 2011), or other kidney conditions.

Based on its expression and work implicating it in TGF-B signaling, TRPC6 is also thought to be important in respiratory conditions, restenosis, liver disease, muscular dystrophy, fibrotic disorders, pain, ischemia and ischemic reperfusion injury, and certain forms of cancer.

Yue et al. studied TRPC6 channels for a role in mediating the pulmonary artery smooth muscle cell proliferation that can lead to idiopathic pulmonary arterial hypertension (IPAH). Pulmonary vascular medial hypertrophy caused by excessive pulmonary artery smooth muscle cell (PASMC) proliferation is a major cause for the elevated pulmonary vascular resistance in patients with IPAH. The authors found that TRPC6 was highly expressed and TRPC3 was minimally expressed in PASMC from healthy lung tissue. However, in lung tissue from IPAH patients, mRNA and protein expression of TRPC3 and TRPC6 were significantly elevated in comparison to that in normotensive patients. Furthermore, proliferation of PASMC cells derived from IPAH patients was markedly reduced following incubation with TRPC6 siRNA. Based on these results, the authors concluded that TRPC6 may be important in mediating proper PASMC proliferation, and that dysregulation of TRPC6 may lead to increased PASMC proliferation and pulmonary vascular medial hypertrophy observed in IPAH patients (Yu et al., 2004 Proc Natl Acad Sci 101(38):13861-6). Further support is provided by the observation that in IPAH patients the frequency of a single-nucleotide polymorphism in the promoter of TRPC6 which increases expression was significantly higher when compared to normal subjects (Yue, et al., 2009 Circulation 119: 2313-22).

Additional evidence implicating TRPC6 dysregulation in IPAH comes from studies of bosentan, a dual endothelin receptor blocker, that has been used clinically to treat IPAH. This inhibitor decreases proliferation of PASMCs, but the mechanism by which this occurs is unclear. Interestingly, bosentan both decreases proliferation of PASMC and also decreases expression of TRPC6 in lung tissue of IPAH patients (Kunichika et al., 2004 Am J Respir Crit Care Med 170(10):1101-7).

Chronic exposure of cigarette smoke (CS) to rats resulted in an increase in TRPC6 mRNA and protein expression in distal pulmonary arteries and similar effects were observed using PASMCs in vitro. Nicotine treatment of cultured rat PASMCs upregulated TRPC6 expression and increased intracellular calcium levels, both of which were reduced by TRPC6 siRNA silencing (Wang et al., 2014 Am J Physiol Cell Physiol 306:C364-73). These results suggest a role for TRPC6 in CS-induced lung injury.

Evidence supports a role of TRPC6 in additional pulmonary disorders. In alveolar macrophages from patients with chronic obstructive pulmonary disease (COPD), TRPC6 expression was found to be elevated when compared with controls (Finney-Hayward et al., 2010 Am J Respir Cell Mol Biol 43:296-304). In human cystic fibrosis epithelial cells, the TRPC6-mediated calcium influx is abnormally increased and may contribute to the hypersecretion of mucus. siRNA-TRPC6 was able to reduce this abnormal calcium influx (Antigny et al. 2011 Am J Resp Cell Mol Biol, 44:83-90). In mouse lung fibroblasts, the pro-fibrotic activity of PDGF is dependent on the activation of TRPC6, suggesting that TRPC6 inhibition would reduce lung fibrosis (Lei et al., 2014 Biomaterials 35:2868-77). A role of TRPC6 in pulmonary endothelial cell function was demonstrated in mouse lung models of ischemia-reperfusion induced-edema and lipopolysaccharide-induced inflammation in which TRPC6 deficiency was able to reduce acute lung injury by preserving endothelial barrier function (Weissmann et al., Nature Communications Volume 3, Article number: 649 (2012), DOI: 10.1038/ncomms1660 and Tauseef et al., 2012 J Exp Med 209:1953-68).

Recent studies also implicate the role of TRPC6 in other cardiac conditions, including cardiac hypertrophy. The hearts of patients with dilated cardiomyopathy have elevated TRPC6 mRNA expression when compared with normal hearts (Kuwahara et al., 2006 J Clin Invest 116:3114-26). In mouse models of cardiac hypertrophy, TRPC6 cardiac mRNA levels are elevated by pressure overload (Kuwahara et al., 2006 J Clin Invest 116:3114-26), chronic isoproterenol treatment (Xie et al., 2012 Nat Commun 3:1238), and uremic cardiomyopathy induced by partial nephrectomy (Xie et al., 2015 J Am Soc Nephrol 26:1150-60). Furthermore, cardiac-specific overexpression of TRPC6 in the cardiomyoctes of transgenic mice induced cardiac hypertrophy and premature death (Kuwahara et al., 2006 J Clin Invest 116:3114-26).

Wu and colleagues found that transgenic mice expressing dominant-negative TRPC6 in a cardiac-specific fashion had an attenuated cardiac hypertrophic response following either neuroendocrine agonist infusion or pressure-overload simulation, indicating that TRPC6 is a component of channel complexes that are essential mediators of hypertrophy (Wu et al., 2010 Proc Natl Acad Sci. 107:7000-05). Small molecule drugs targeting TRPC6 have also recently begun to show promise in treating cardiac conditions. For example, Seo and coworkers demonstrated that TRPC6 and TRPC3 antagonists (GSK2332255B and GSK833503A) exhibited dose-dependent inhibition of cell hypertrophy signaling in neonatal and adult cardiac myocytes (Seo et al., 2014 Proc Natl Acad Sci 111:1551-1556). Similarly, mice deficient for TRPC6 were protected from isoproterenol-induced cardiac hypertrophy (Xie et al., 2012 Nat Commun 3:1238).

Reducing TRPC6 activity may be beneficial for the treatment of cardiovascular disease. In vitro, atheroprone shear stress-induces increased TRPC6 mRNA levels in human vascular endothelial cells (EC) when compared to atheroprotective flow conditions (Thilo, et al., 2012 Hypertension 59:1232-40). EC migration is important for healing after arterial injury, and lysophosphatidylcholine-mediated inhibition of EC migration was prevented in vitro in cells from TRPC6 deficient mice. Furthermore, high cholesterol diet combined with carotid injury did not impair healing in TRPC6 deficient mice when compared with wild-type controls (Rosembaum et al., 2015 J Vasc Surg 62:1040-47 and Chaudhuri et al., 2008 Mol Biol Cell 19: 3203-11). Similarly, balloon dilatation-induced injury of human internal mammary arteries ex vivo resulted in increased TRPC6 mRNA levels when compared with undilated arteries (Bergdahl et al., 2005 Am J Physiol Cell Physiol 288:C872-80). Apoptosis of endothelial cells is involved in the initiation and progression of atherosclerotic lesions, and oxidized low-density lipoprotein-induced apoptosis of human aortic ECs was demonstrated to be dependent on TRPC6 (Zhang et al., 2015 Sci Rep 5:9401-10). In a rat model of forebrain ischaemia, TRPC6 mRNA levels were increased in vascular SMCs and correlated with reduced cerebral blood flow (Johannson et al., 2015 Acta Physiol 214:376-89).

Studies by Reiser, Winn, and Schlondorff identified mutations in TRPC6 in patients as being causative in FSGS (Reiser et al., 2005 Nature Genet 37:739-744; Winn et al., 2005 Science 308:1801-1804; Schlondorff et al., 2009 Am J Physiol Cell Physiol 296:C558-69). Subsequent studies identified additional TRPC6 mutations associated with steroid-resistant nephrotic syndrome (C. Sadowski et al., 2014 J Am Soc Nephrol 26:1279-89). Further studies demonstrated that TRPC6 is important in normal podocyte function by controlling calcium influx and nuclear factor of activated T cell activation in which elevated current through the channel is associated with renal injury and the induction of proteinuria (Moller et al., 2007 J Am Soc Nephrol 18:29-36 and Schlondorff et al., 2009 Am J Physiol Cell Physiol 296:C558-69). In addition to Gain of Function mutations, it has been shown that expression of TRPC6 is elevated in human chronic kidney diseases including FSGS, minimal change disease, membraneous glomerulonephritis, and diabetic nephropathy (Moller et al., 2007 J Am Soc Nephrol 18:29-36 and Thilo et al., 2011 Nephrol. Dial. Transplant 27:921-9) as well as in mouse models of podocyte injury (Moller et al., 2007 J Am Soc Nephrol 18:29-36). TRPC6 deficient mice have been demonstrated to have reduced angiotensin II (Ang II)-induced albuminuria (Eckel et al., 2011 J Am Soc Nephrol 22:526-35) whereas transgenic podocyte-specific expression of human GoF mutations in mice induces albuminuria and glomerular lesions (Krall et al., 2010 PLoS ONE e12859 and Canales et al., 2015 Brit J Medicine Med Res 5:1198-1212). Consequently, inhibition of TRPC6 may be useful in the treatment of chronic kidney diseases. These findings not only suggest that TRPC6 normally functions to maintain proper kidney function, but also implicates TRPC6 as a specific cause of at least certain cases of FSGS. Based on the likely role of TRPC6 in kidney function, TRPC6 inhibitor compounds can be used in treating or ameliorating chronic kidney diseases or conditions caused (in whole or in part) by TRPC6 dysfunction. Additionally, TRPC6 inhibitor compounds can be used in treating or ameliorating symptoms of kidney diseases (e.g., hypertension, proteinuria, etc.), regardless of the cause of the disease.

TRPC6 is expressed in the myometrium and placenta during pregnancy (Ku et al., 2006 J Soc Gynecol Investig 13:217-225; Clarson et al., 2003 J Physiol 550:515-528). As such TRPC6 may contribute to maintaining proper myogenic tone in the placenta and/or in maintaining proper fetal and maternal blood pressure during pregnancy.

Recent evidence has emerged implicating TRPC6 in certain forms of cancer. Several groups have established that TRPC6 expression is elevated in cells taken from patients with gliobastoma multiforme, the most frequent and incurable type of brain cancer (Chigurupati, et al., 2010 Cancer Res, 70:418-427; Ding et al., 2010 J Natl Cancer Inst. 102:1052-1068). Similarly, Ding et al. found elevated levels of TRPC6 in human glioma cells, and inhibition of TRPC6 pharmacologically or with a dominant-negative mutant suppressed cell growth in vitro. In two xenograft models of human gliomas, lentiviral-mediated expression of dominant-negative TRPC6 in the tumor cells prior subcutaneous or intracranial implantation reduced tumor volume when compared to controls (Ding et al., J. Natl. Cancer Inst. 2010, 102, 1052-1068). Increased levels of TRPC6 was also found to be associated with cervical cancer (Wan et al, 2012 Onco Targets Ther 5:171-176), breast cancer (Dhennin-Duthille et al., 2011 Cell Physiol Biochem 28:813-822), renal cell carcinoma (Song et al, 2013 Mol Biol Rep 40:5115-5122), head and neck squamous cell carcinoma (de Quiros, et al. 2013 BMC Cancer 13:116-127), and esophageal squamous cell carcinoma (Zhang et al., 2013 Med Oncol 30:607), among others. In hepatocellular carcinoma cells, it was demonstrated that doxorubicin, hypoxia, and ionizing radiation increased TRPC6 mRNA expression, and that TRPC6 is found at higher levels in tumor tissues than in the non-involved tissues. Elevated TRPC6 was associated with drug resistance which was diminished by TRPC6 RNA silencing in vitro. Lentiviral delivery of TRPC6 specific short hairpin RNA into Huh7 tumor cells prior to implantation in a mouse subcutaneous xenograft model reduced tumor growth and sensitized the tumors to doxorubicin (Wen et al., 2016 Sci Rep 6:23269). These findings suggest that TRPC6 may be a promising therapeutic target for cancer treatment.

Liver diseases including non-alcoholic steatohepatitis may be treated by reducing TRPC6 activity. Hypoxia increased TRPC6 expression in an human hepatic stellate cell line when compared to normoxic conditions. Using these cells, TRPC6 RNA silencing down-regulated transcripts for alpha smooth muscle actin and collagen 1A1, both of which are associated with fibrosis, in response to hypoxia Oyer et al, 2015 Exp Cell Res 336:66-75).

Inhibition of TRPC6 may provide benefit to patients with Duchenne muscular dystrophy (DMD). In the mdx/utrn$^{+/-}$ model of DMD using isolated cardiomyoctes, TRPC6 deficiency restored the stress-stimulated contractility force and calcium transient response to normal when compared with mice possessing the wild-type TRPC6 gene, suggesting that TRPC6 inhibition will preserve cardiac function in DMD patients (Seo et al., 2014 Circ Res 114:823-32).

Fibrotic disorders may be treated with TRPC6 inhibitors. Overexpression of TRPC6 induced myofibroblast activation while deletion of TRPC6 reduced transforming growth factor beta-induced myofibroblast transformation. Furthermore, TRPC6 deficient mice demonstrated reduced dermal and cardiac wound healing (Davis et al., 2012 Dev Cell 23:705-15). TRPC6 inhibitors may be useful for the treatment of pain. Spinal delivery of TRPC6 antisense oligonucleotides reduced hyperalgesia induced by mechanical, hypotonic, and thermal stimuli in preclinical pain models (Alessandri-Haber et al., 2009 J Neurosci 29:6217-28).

Modulating a function of TRPC6 provides a means for modulating calcium homeostasis, sodium homeostasis, intracellular calcium levels, membrane polarization (resting membrane potential), and/or cation levels in a cell. Compounds that can modulate one or more TRPC6 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or dysregulation of TRPC6 expression or function.

There is a need for highly selective TRPC6 antagonists for treating diseases or disorders that can be alleviated by modulating TRPC6.

BRIEF SUMMARY OF THE INVENTION

The present invention provides novel compounds that modulate TRPC6 and thus are useful for treating a variety of diseases and disorders that can be alleviated by modulating TRPC6 including hypertension, preeclampsia, restenosis, a cardiac or respiratory condition, renal disease, liver disease, muscular dystrophy, fibrotic disorders, pain, ischemia or ischemic reperfusion injury, and cancer. This invention also relates to pharmaceutical compositions comprising these compounds, methods of using these compounds in the treatment of various diseases and disorders, processes for preparing these compounds and intermediates useful in these processes.

In a first embodiment (embodiment one), the inventions relates to a compound of formula (I)

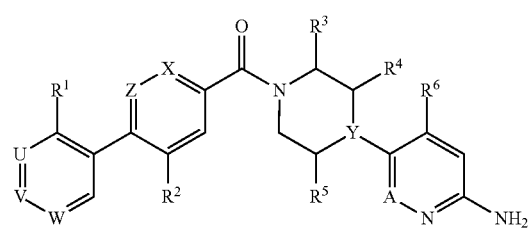

I wherein
A is $CR^7$ or N;
U is CH or N;
V is $CR^8$ or N;
W is $CR^9$ or N;
X is CH, $CC_{1-6}$alkyl, $COC_{1-6}$alkyl, or N;
Y is CH or N;
Z is CH, COH, $COC_{1-6}$alkyl or N;
$R^1$ is selected from the group consisting of H and halogen;
$R^2$ is selected from the group consisting of H, $C_{1-6}$alkyl, —CN, —$CF_3$, —$OCF_3$, $C_{3-6}$cycloalkyl, $OC_{1-6}$alkyl, and $OC_{3-6}$cycloalkyl;
  when Z is COH, $R^1$ may join with the hydroxyl group attached to the Z ring atom to form a central furanyl ring;
  $R^3$ is selected from the group consisting of
    H,
    $C_{1-6}$alkyl optionally substituted with one to three groups independently selected from the group consisting of halogen, hydroxy or methoxy, and
    $C_{3-6}$cycloalkyl;
$R^4$ is selected from the group consisting of H, $C_{1-6}$alkyl optionally substituted with hydroxyl, $C_{3-6}$cycloalkyl;
$R^5$ is H or $C_{1-6}$alkyl;
$R^3$ and $R^5$ can together form a bicyclic ring;

R$^6$ is selected from the group consisting of
H,
C$_{1-6}$alkyl,
—CN,
—CF$_3$,
OCF$_3$,
C$_{3-6}$cycloalkyl, and
OC$_{1-6}$alkyl optionally substituted one to three halogen;
R$^7$ is selected from the group consisting of H, C$_{1-6}$alkyl, and OC$_{1-6}$alkyl optionally substituted with one to three halogen;
R$^8$ is selected from the group consisting of
H,
C$_{1-6}$alkyl optionally substituted with C$_{3-6}$cycloalkyl or one to three halogen, halogen,
—CN,
—CF$_3$,
—NH$_2$,
phenyl,
C$_{3-6}$cycloalkyl,
OC$_{3-6}$cycloalkyl,
OC$_{1-6}$alkyl optionally substituted with one to three halogen or C$_{3-6}$cycloalkyl optionally substituted with one to three halogen, and
1-fluoromethyl-cyclopropylmethoxy;
R$^9$ is selected from the group consisting of
H,
C$_{1-6}$alkyl optionally substituted with one to three halogen, halogen,
—CN,
—CF$_3$,
OH,
C$_{3-6}$cycloalkyl,
OC$_{1-6}$alkyl optionally substituted with C$_{3-6}$cycloalkyl or one to three halogen, and
OC$_{3-6}$cycloalkyl;
when V is CR$^8$ and W is CR$^9$, R$^8$ and R$^9$ can together form a 5- to 6-membered fused heterocyclic ring;
and the pharmaceutically acceptable salts thereof.

In a second embodiment (embodiment two), the invention relates to a compound according to embodiment 1, wherein
R$^2$ is selected from the group consisting of H, C$_{1-6}$alkyl, and OC$_{1-6}$alkyl;
R$^3$ is selected from the group consisting of H and C$_{1-6}$alkyl optionally substituted with one to three groups independently selected from the group consisting of halogen and hydroxyl;
R$^4$ is selected from the group consisting of H and C$_{1-6}$alkyl optionally substituted with hydroxyl;
R$^5$ is H;
R$^6$ is selected from the group consisting of H, C$_{1-6}$alkyl, and OC$_{1-6}$alkyl optionally substituted with one to three halogen;
and the pharmaceutically acceptable salts thereof.

In a third embodiment (embodiment three), the invention relates to a compound according to embodiments one or two, wherein Z is CH and U, V, W, X, Y, and A are as defined in embodiments (a) to (o):

| Embodiment | A | U | V | W | X | Y | |
|---|---|---|---|---|---|---|---|
| (a) | N | CH | CR$^8$ | CR$^9$ | CH | CH | or, |
| (b) | N | CH | CR$^8$ | CR$^9$ | N | CH | or, |
| (c) | CR$^7$ | CH | CR$^8$ | CR$^9$ | N | N | or, |
| (d) | CR$^7$ | CH | CR$^8$ | CR$^9$ | N | CH | or, |
| (e) | CR$^7$ | CH | CR$^8$ | CR$^9$ | CH | N | or, |
| (f) | N | N | CR$^8$ | CR$^9$ | N | CH | or, |
| (g) | N | N | CR$^8$ | N | N | CH | or, |
| (h) | N | N | CR$^8$ | CR$^9$ | CH | CH | or, |
| (i) | N | CH | N | CR$^9$ | CH | CH | or, |
| (j) | CR$^7$ | N | CR$^8$ | CR$^9$ | N | N | or, |
| (k) | CR$^7$ | CH | CR$^8$ | CR$^9$ | N | N | or, |
| (l) | CR$^7$ | N | CR$^8$ | CR$^9$ | N | CH | or, |
| (m) | N | N | CR$^8$ | N | CH | CH | or, |
| (n) | N | CH | CR$^8$ | CR$^9$ | CH | N | or, |
| (o) | N | CH | CR$^8$ | CR$^9$ | N | N | . | and the pharmaceutically acceptable salts thereof.

In a fourth embodiment (embodiment four), the invention relates to a compound according to any one of embodiments one to three, wherein
U is N, V is CR$^8$, and W is CR$^9$,
X is CH or N,
and the pharmaceutically acceptable salts thereof.

In a fifth embodiment (embodiment five), the invention relates to a compound according to any one of embodiments one to four, wherein
A is N,
X is N,
Y is CH,
and the pharmaceutically acceptable salts thereof.

In a sixth embodiment (embodiment six), the invention relates to a compound according to any one of embodiments one to four, wherein
A is N,
X is CH,
Y is CH,
and the pharmaceutically acceptable salts thereof.

In a seventh embodiment (embodiment seven), the invention relates to a compound according to any one of embodiments one to four, wherein
A is CR$^7$,
X is N,
Y is N,
and the pharmaceutically acceptable salts thereof.

In an eighth embodiment (embodiment eight), the invention relates to a compound according to any one of embodiments one to four, wherein
A is CR$^7$,
X is N,
Y is CH,
and the pharmaceutically acceptable salts thereof.

In a ninth embodiment (embodiment nine), the invention relates to a compound according to any one of embodiments one to eight, wherein R$^8$ is selected from the group consisting H, F, CF$_3$, ethyl, methoxy, ethoxy, sec-butoxy, trifluoromethoxy, trifluoroethoxy, cyclopropyl, cyclopropylmethoxy, 1-cyclopropylethoxy, 1-methylcyclopropylmethoxy, 1-fluoromethylcyclopropylmethoxy, 2,2,2-trifluoroethoxy, 2,2,-dimethylcyclopropylmethoxy, 2,2,-diflurocyclopropylmethoxy, cyclopropoxy, and cyclobutoxy,
and the pharmaceutically acceptable salts thereof.

In a tenth embodiment (embodiment ten), the invention relates to a compound according to any one of embodiments one to nine, wherein R$^2$ is H or OCH$_3$, and the pharmaceutically acceptable salts thereof.

In an eleventh embodiment (embodiment eleven), the invention relates to a compound according to any one of embodiments one to ten, wherein
R$^3$, R$^4$, R$^5$ and R$^6$ are each H,
and the pharmaceutically acceptable salts thereof.

In a twelfth embodiment (embodiment twelve), the invention relates to a compound according to any one of embodiments one to eleven, wherein $R^2$ is $OCH_3$, and the pharmaceutically acceptable salts thereof.

In a thirteenth embodiment (embodiment thirteen), the invention relates to a compound according to any one of embodiments one to three, wherein
U is CH,
V is $CR^8$,
W is $CR^9$,
and the pharmaceutically acceptable salts thereof.

In a fourteenth embodiment (embodiment fourteen), the invention relates to a compound according to any one of embodiments one to three and thirteen, wherein
A is N,
X is CH,
Y is CH,
and the pharmaceutically acceptable salts thereof.

In a fifteenth embodiment (embodiment fifteen), the invention relates to a compound according to any one of embodiments one to three and thirteen, wherein
A is N,
X is N,
Y is CH,
and the pharmaceutically acceptable salts thereof.

In a sixteenth embodiment (embodiment sixteen), the invention relates to a compound according to any one of embodiments one to three and thirteen, wherein
A is CH,
X is N,
Y is N,
and the pharmaceutically acceptable salts thereof.

In a seventeenth embodiment (embodiment seventeen), the invention relates to a compound according to any one of embodiments one to three and thirteen, wherein
A is CH,
X is N,
Y is CH,
and the pharmaceutically acceptable salts thereof.

In an eighteenth embodiment (embodiment eighteen), the invention relates to a compound according to any one of embodiments one to three and thirteen, wherein
A is CH,
X is CH,
Y is N,
and the pharmaceutically acceptable salts thereof.

In a nineteenth embodiment (embodiment nineteen), the invention relates to a compound according to any one of embodiments one to three and thirteen, wherein
A is CH,
X is N,
Y is N,
and the pharmaceutically acceptable salts thereof.

In a twentieth embodiment (embodiment twenty), the invention relates to a compound according to any one of embodiments one to three and thirteen, wherein
A is N,
X is CH,
Y is N,
and the pharmaceutically acceptable salts thereof.

In a twenty first embodiment (embodiment twenty one), the invention relates to a compound according to any one of embodiments one to three and thirteen to twenty, wherein $R^8$ is selected from the group consisting of H, fluoro, chloro, $CF_3$, —CN, methyl, ethyl, isobutyl, tert-butyl, difluoromethyl, methoxy, difluoromethoxy, ethoxy, isopropoxy, trifluoromethoxy, 2,2,2-trifluoroethoxy, cyclopropylmethoxy, cyclopropoxy, and cyclopentoxy,
and the pharmaceutically acceptable salts thereof.

In a twenty second embodiment (embodiment twenty two), the invention relates to a compound according to any one of embodiments one to three and thirteen to twenty one, wherein $R^2$ is H or OCH3, and the pharmaceutically acceptable salts thereof.

In a twenty third embodiment (embodiment twenty three), the invention relates to a compound according to any one of embodiments one to three and thirteen to twenty two, wherein
$R^8$ is selected from the group consisting of H, chloro, $CF_3$, methyl, ethyl, isobutyl, tert-butyl, methoxy, isopropoxy, trifluoromethoxy, and 2,2,2-trifluoroethoxy; and
$R^9$ is selected from the group consisting of H, fluoro, chloro, and methoxy,
and the pharmaceutically acceptable salts thereof.

In a twenty fourth embodiment (embodiment twenty four), the invention relates to a compound according to any one of embodiments one to three and thirteen to twenty three, wherein $R^2$ is $OCH_3$, and the pharmaceutically acceptable salts thereof.

In a twenty fifth embodiment (embodiment twenty five), the invention relates to a compound according to any one of embodiments one to three and thirteen to twenty three, wherein $R^2$ is H, and the pharmaceutically acceptable salts thereof.

In a twenty sixth embodiment (embodiment twenty six), the invention relates to a compound according to any one of embodiments four to twenty five, wherein Z is CH, and the pharmaceutically acceptable salts thereof.

In a twenty seventh embodiment (embodiment twenty seven), the inventions relates to a compound of formula (I')

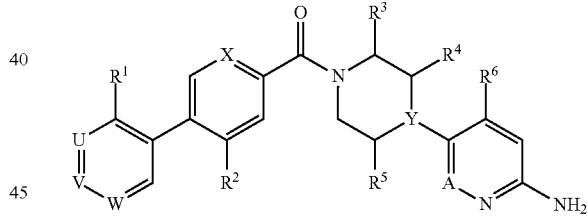

wherein
A is $CR^7$ or N;
U is CH or N;
V is $CR^9$ or N;
W is $CR^9$ or N;
X is CH or N;
Y is CH or N;
$R^1$ is selected from the group consisting of H and halogen;
$R^2$ is selected from the group consisting of H, $C_{1-6}$alkyl, —CN, —$CF_3$, —$OCF_3$, $C_{3-6}$cycloalkyl, $OC_{1-6}$alkyl, and $OC_{3-6}$cycloalkyl;
$R^3$ is selected from the group consisting of
H,
$C_{1-6}$alkyl optionally substituted with one to three groups independently selected from the group consisting of halogen, hydroxy or methoxy, and
$C_{3-6}$cycloalkyl;
$R^4$ is selected from the group consisting of H, $C_{1-6}$alkyl optionally substituted with hydroxyl, $C_{3-6}$cycloalkyl;
$R^5$ is H or $C_{1-6}$alkyl;
$R^3$ and $R^5$ can together form a bicyclic ring;

$R^6$ is selected from the group consisting of
H,
$C_{1-6}$alkyl,
—CN,
—$CF_3$,
—$OCF_3$,
$C_{3-6}$cycloalkyl, and
$OC_{1-6}$alkyl optionally substituted one to three halogen;
$R^7$ is selected from the group consisting of H, $C_{1-6}$alkyl, and $OC_{1-6}$alkyl optionally substituted with one to three halogen;
$R^8$ is selected from the group consisting of
H
$C_{1-6}$alkyl optionally substituted with $C_{3-6}$cycloalkyl or one to three halogen,
halogen,
—CN,
—$CF_3$,
—$NH_2$,
phenyl,
$C_{3-6}$cycloalkyl,
$OC_{3-6}$cycloalkyl, and
$OC_{1-6}$alkyl optionally substituted with one to three halogen or $C_{3-6}$cycloalkyl optionally substituted with one to three halogen;
$R^9$ is selected from the group consisting of
H,
$C_{1-6}$alkyl optionally substituted with one to three halogen,
halogen,
—CN,
—$CF_3$,
OH,
$C_{3-6}$cycloalkyl,
$OC_{1-6}$alkyl optionally substituted with $C_{3-6}$cycloalkyl or one to three halogen, and
$OC_{3-6}$cycloalkyl;
when V is $CR^8$ and W is $CR^9$, $R^8$ and $R^9$ can together form a 5- to 6-membered fused heterocyclic ring; or
when V is C-phenyl and W is C—OH, $R^8$ and $R^9$ can together form a 7- to 8-membered fused heterobicyclic ring;
and the pharmaceutically acceptable salts thereof.

In a twenty eighth embodiment (embodiment twenty eight), the invention relates to a pharmaceutical composition comprising a compound according to any one of embodiments one to twenty seven, or a pharmaceutically acceptable salt thereof, and a pharmaceutically acceptable excipient or carrier.

DETAILED DESCRIPTION OF THE INVENTION

Table 1.1 shows the compounds of the invention which can be made by the synthetic schemes and the examples shown in the Synthetic Examples section below.

TABLE 1.1

| Cpd No. | Structure | Structure Name |
| --- | --- | --- |
| 1 | 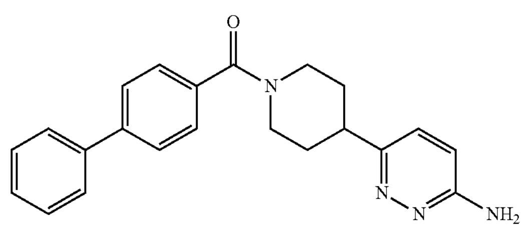 [SMILES: Nc1ccc(C2CCN(C(=O)c3ccc(-c4ccccc4)cc3)CC2)nn1] | [4-(6-Amino-pyridazin-3-yl)-piperidin-1-yl]-biphenyl-4-yl-methanone |
| 2 | 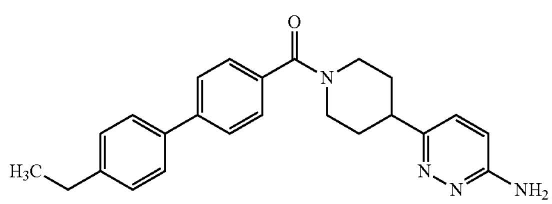 [SMILES: CCc1ccc(-c2ccc(C(=O)N3CCC(c4ccc(N)nn4)CC3)cc2)cc1] | [4-(6-Amino-pyridazin-3-yl)-piperidin-1-yl]-(4'-ethyl-biphenyl-4-yl)-methanone |
| 3 | 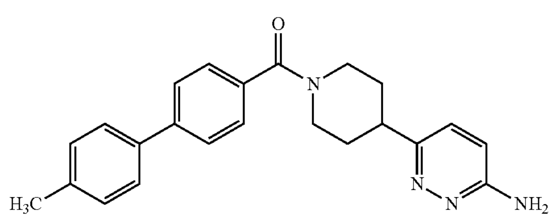 [SMILES: Cc1ccc(-c2ccc(C(=O)N3CCC(c4ccc(N)nn4)CC3)cc2)cc1] | [4-(6-Amino-pyridazin-3-yl)-piperidin-1-yl]-(4'-methyl-biphenyl-4-yl)-methanone |
| 4 | 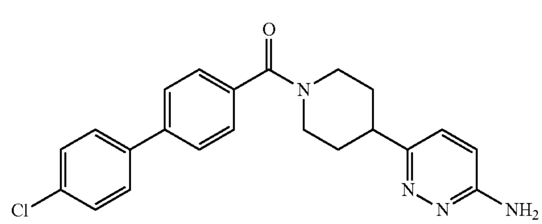 [SMILES: Nc1ccc(C2CCN(C(=O)c3ccc(-c4ccc(Cl)cc4)cc3)CC2)nn1] | [4-(6-Amino-pyridazin-3-yl)-piperidin-1-yl]-(4'-chloro-biphenyl-4-yl)-methanone |

TABLE 1.1-continued

| Cpd No. | Structure | Structure Name |
|---|---|---|
| 5 | 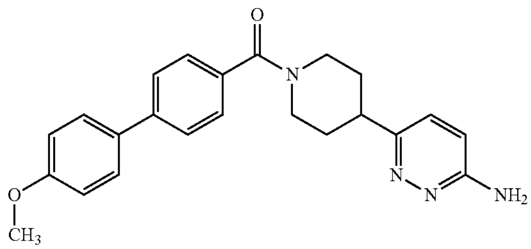 [SMILES: COc1ccc(-c2ccc(C(=O)N3CCC(c4ccc(N)nn4)CC3)cc2)cc1] | [4-(6-Amino-pyridazin-3-yl)-piperidin-1-yl]-(4'-methoxy-biphenyl-4-yl)-methanone |
| 6 | 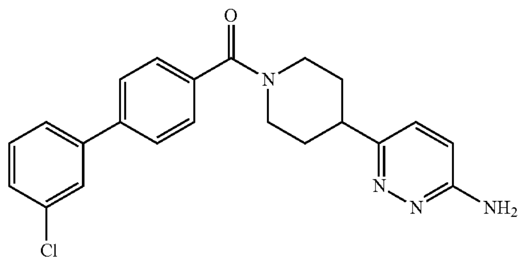 [SMILES: Nc1ccc(C2CCN(C(=O)c3ccc(-c4cccc(Cl)c4)cc3)CC2)nn1] | [4-(6-Amino-pyridazin-3-yl)-piperidin-1-yl]-(3'-chloro-biphenyl-4-yl)-methanone |
| 7 | 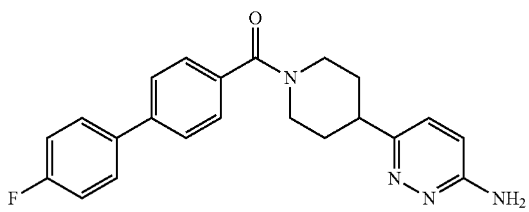 [SMILES: Nc1ccc(C2CCN(C(=O)c3ccc(-c4ccc(F)cc4)cc3)CC2)nn1] | [4-(6-Amino-pyridazin-3-yl)-piperidin-1-yl]-(4'-fluoro-biphenyl-4-yl)-methanone |
| 8 | 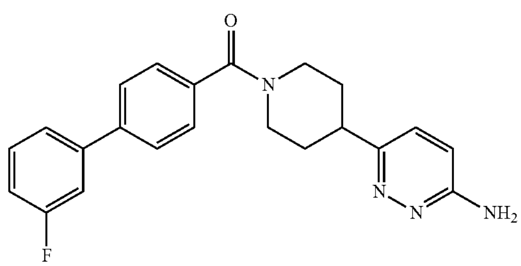 [SMILES: Nc1ccc(C2CCN(C(=O)c3ccc(-c4cccc(F)c4)cc3)CC2)nn1] | [4-(6-Amino-pyridazin-3-yl)-piperidin-1-yl]-(3'-fluoro-biphenyl-4-yl)-methanone |
| 9 | 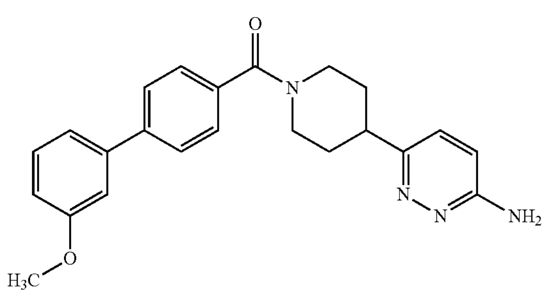 [SMILES: COc1cccc(-c2ccc(C(=O)N3CCC(c4ccc(N)nn4)CC3)cc2)c1] | [4-(6-Amino-pyridazin-3-yl)-piperidin-1-yl]-(3'-methoxy-biphenyl-4-yl)-methanone |
| 10 | 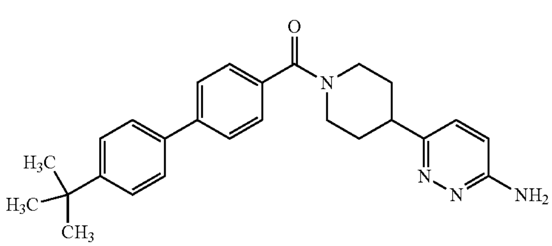 [SMILES: CC(C)(C)c1ccc(-c2ccc(C(=O)N3CCC(c4ccc(N)nn4)CC3)cc2)cc1] | [4-(6-Amino-pyridazin-3-yl)-piperidin-1-yl]-(4'-tert-butyl-biphenyl-4-yl)-methanone |

TABLE 1.1-continued

| Cpd No. | Structure | Structure Name |
| --- | --- | --- |
| 11 | 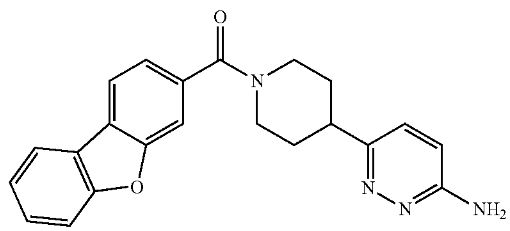 [SMILES: Nc1ccc(C2CCN(C(=O)c3ccc4c(c3)oc3ccccc34)CC2)nn1] | [4-(6-Amino-pyridazin-3-yl)-piperidin-1-yl]-dibenzofuran-3-yl-methanone |
| 12 | 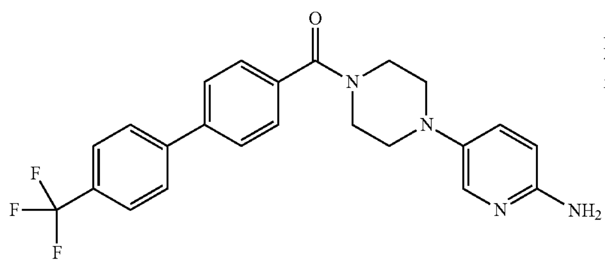 | [4-(6-Amino-pyridin-3-yl)-piperazin-1-yl]-(4'-trifluoromethyl-biphenyl-4-yl)-methanone |
| 13 | 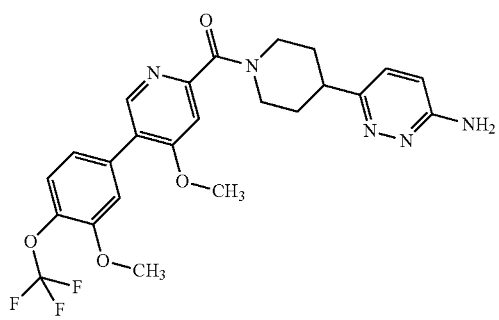 [SMILES: COc1cc(-c2cnc(C(=O)N3CCC(c4ccc(N)nn4)CC3)cc2OC)ccc1OC(F)(F)F] | [4-(6-Amino-pyridazin-3-yl)-piperidin-1-yl]-methoxy-5-(3-methoxy-4-trifluoromethoxy-phenyl)-pyridin-2-yl]-methanone |
| 14 | 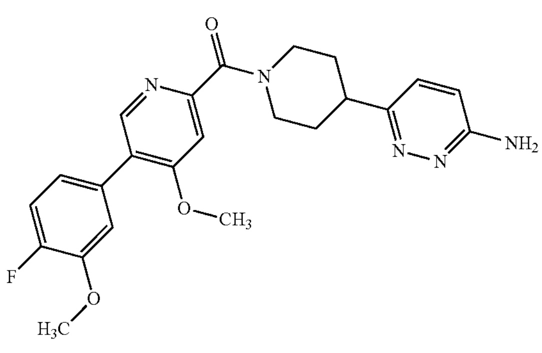 [SMILES: COc1cc(-c2cnc(C(=O)N3CCC(c4ccc(N)nn4)CC3)cc2OC)ccc1F] | [4-(6-Amino-pyridazin-3-yl)-piperidin-1-yl]-[5-(4-fluoro-3-methoxy-phenyl)-4-methoxy-pyridin-2-yl]-methanone |
| 15 | 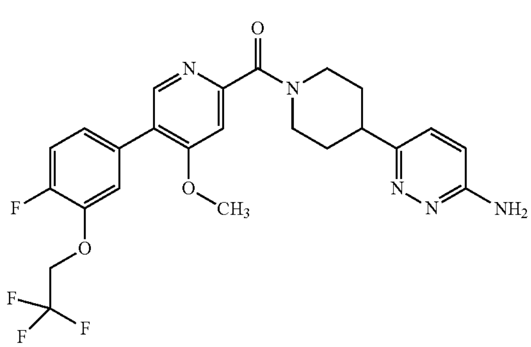 [SMILES: COc1cc(C(=O)N2CCC(c3ccc(N)nn3)CC2)ncc1-c1ccc(F)c(OCC(F)(F)F)c1] | [4-(6-Amino-pyridazin-3-yl)-piperidin-1-yl]-{5-(4-fluoro-3-(2,2,2-trifluoro-ethoxy)-phenyl]-4-methoxy-pyridin-2-yl}-methanone |

TABLE 1.1-continued

| Cpd No. | Structure | Structure Name |
| --- | --- | --- |
| 16 | 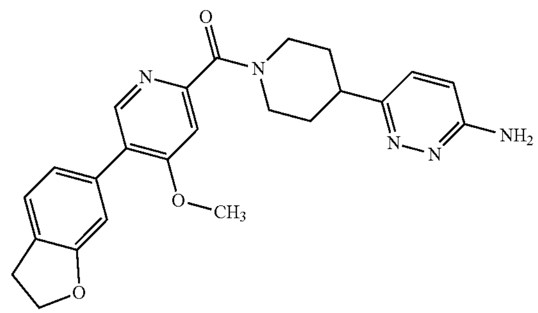 [SMILES: COc1cc(C(=O)N2CCC(c3ccc(N)nn3)CC2)ncc1-c1ccc2c(c1)OCC2] | [4-(6-Amino-pyridazin-3-yl)-piperidin-1-yl]-[5-(2,3-dihydro-benzofuran-6-yl)-4-methoxy-pyridin-2-yl]-methanone |
| 17 | 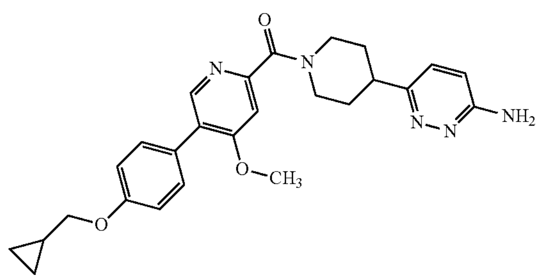 [SMILES: COc1cc(C(=O)N2CCC(c3ccc(N)nn3)CC2)ncc1-c1ccc(OCC2CC2)cc1] | [4-(6-Amino-pyridazin-3-yl)-piperidin-1-yl]-[5-(4-cyclopropylmethoxy-phenyl)-4-methoxy-pyridin-2-yl]-methanone |
| 18 | 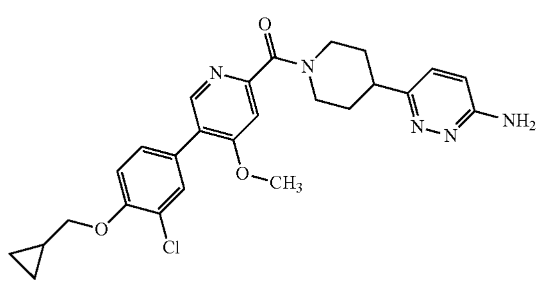 [SMILES: COc1cc(C(=O)N2CCC(c3ccc(N)nn3)CC2)ncc1-c1ccc(OCC2CC2)c(Cl)c1] | Amino-pyridazin-3-yl)-piperidin-1-yl]-[5-(3-chloro-4-cyclopropylmethoxy-phenyl)-4-methoxy-pyridin-2-yl]-methanone |
| 19 | 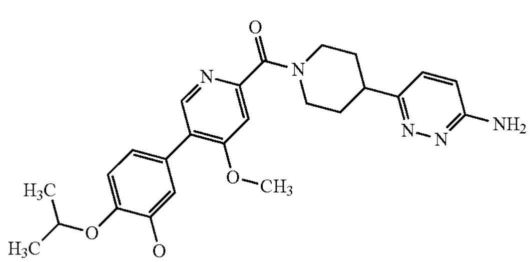 | [4-(6-Amino-pyridazin-3-yl)-piperidin-1-yl]-(3-chloro-4-isopropoxy-phenyl)-4-methoxy-pyridin-2-yl]-methanone |
| 20 | 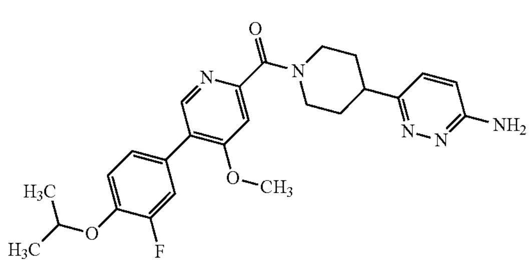 [SMILES: COc1cc(C(=O)N2CCC(c3ccc(N)nn3)CC2)ncc1-c1ccc(OC(C)C)c(O)c1] | [4-(6-Amino-pyridazin-3-yl)-piperidin-1-yl]-[5-(3-fluoro-4-isopropoxy-phenyl)-4-methoxy-pyridin-2-yl]-methanone |

TABLE 1.1-continued

| Cpd No. | Structure | Structure Name |
|---|---|---|
| 21 | 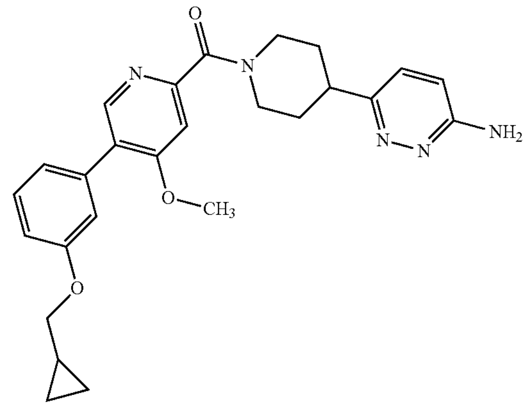 [SMILES: COc1cc(C(=O)N2CCC(c3ccc(N)nn3)CC2)ncc1-c1cccc(OCC2CC2)c1] | [4-(6-Amino-pyridazin-3-yl)-piperidin-1-yl]-[5-(3-cyclopropylmethoxy-phenyl)-4-methoxy-pyridin-2-yl]-methanone |
| 22 | 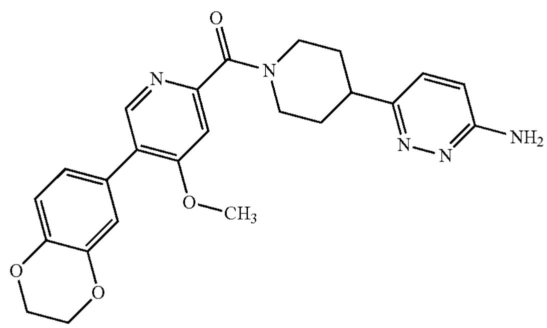 [SMILES: COc1cc(C(=O)N2CCC(c3ccc(N)nn3)CC2)ncc1-c1ccc2c(c1)OCCO2] | [4-(6-Amino-pyridazin-3-yl)-piperidin-1-yl]-[5-(2,3-dihydro-benzo[1,4]dioxin-6-yl)-4-methoxy-pyridin-2-yl]-methanone |
| 23 | 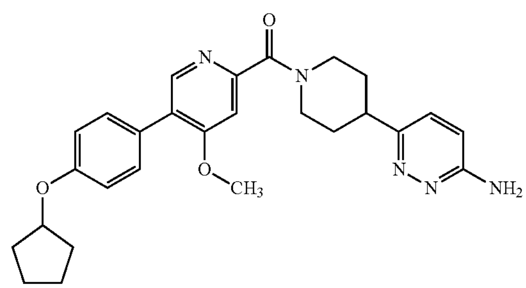 [SMILES: COc1cc(C(=O)N2CCC(c3ccc(N)nn3)CC2)ncc1-c1ccc(OC2CCCC2)cc1] | [4-(6-Amino-pyridazin-3-yl)-piperidin-1-yl]-[5-(4-cyclopentyloxy-phenyl)-4-methoxy-pyridin-2-yl]-methanone |
| 24 | 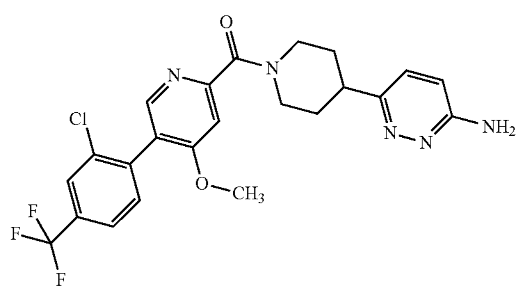 [SMILES: COc1cc(C(=O)N2CCC(c3ccc(N)nn3)CC2)ncc1-c1ccc(C(F)(F)F)cc1Cl] | [4-(6-Amino-pyridazin-3-yl)-piperidin-1-yl]-[5-(2-chloro-4-trifluoromethyl-phenyl)-4-methoxy-pyridin-2-yl]-methanone |
| 25 | 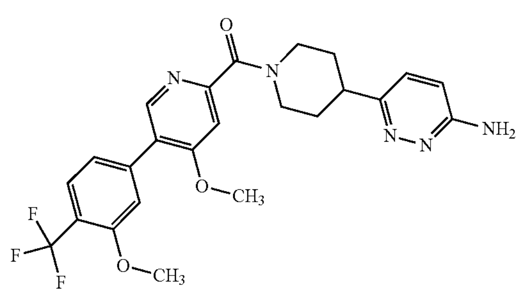 [SMILES: COc1cc(C(=O)N2CCC(c3ccc(N)nn3)CC2)ncc1-c1ccc(C(F)(F)F)c(OC)c1] | [4-(6-Amino-pyridazin-3-yl)-piperidin-1-yl]-methoxy-5-(3-methoxy-4-trifluoromethyl-phenyl)-pyridin-2-yl]-methanone |

TABLE 1.1-continued

| Cpd No. | Structure | Structure Name |
| --- | --- | --- |
| 26 | 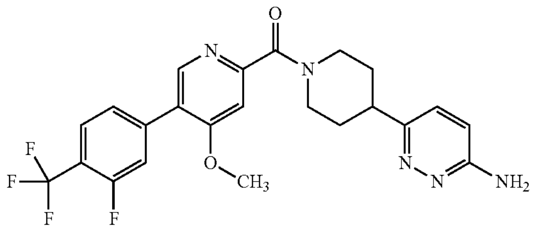 [SMILES: COc1cc(C(=O)N2CCC(c3ccc(N)nn3)CC2)ncc1-c1ccc(C(F)(F)F)c(F)c1] | [4-(6-Amino-pyridazin-3-yl)-piperidin-1-yl]-[5-(3-fluoro-4-trifluoromethyl-phenyl)-4-methoxy-pyridin-2-yl]-methanone |
| 27 | 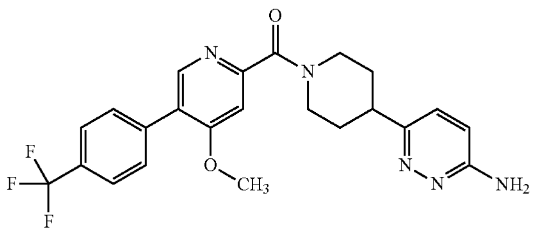 [SMILES: COc1cc(C(=O)N2CCC(c3ccc(N)nn3)CC2)ncc1-c1ccc(C(F)(F)F)cc1] | [4-(6-Amino-pyridazin-3-yl)-piperidin-1-yl]-[4-methoxy-5-(4-trifluoromethyl-phenyl)-pyridin-2-yl]-methanone |
| 28 | 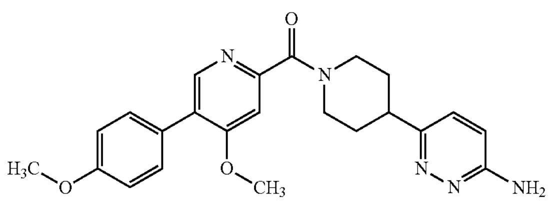 [SMILES: COc1ccc(-c2cnc(C(=O)N3CCC(c4ccc(N)nn4)CC3)cc2OC)cc1] | [4-(6-Amino-pyridazin-3-yl)-piperidin-1-yl]-[4-methoxy-5-(4-methoxy-phenyl)-pyridin-2-yl]-methanone |
| 29 | 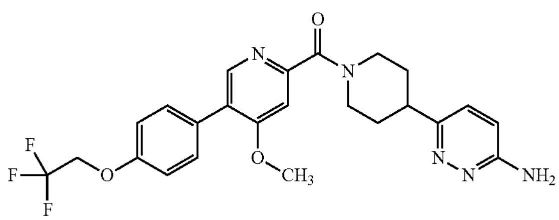 [SMILES: COc1cc(C(=O)N2CCC(c3ccc(N)nn3)CC2)ncc1-c1ccc(OCC(F)(F)F)cc1] | [4-(6-Amino-pyridazin-3-yl)-piperidin-1-yl]-{4-methoxy-5-[4-(2,2,2-trifluoro-ethoxy)-phenyl]-pyridin-2-yl}-methanone |
| 30 | 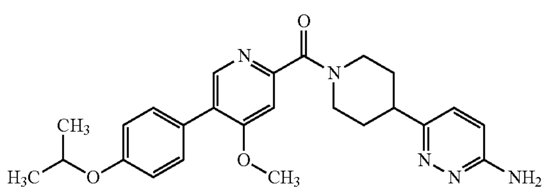 | [4-(6-Amino-pyridazin-3-yl)-piperidin-1-yl]-[5-(4-isopropoxy-phenyl)-4-methoxy-pyridin-2-yl]-methanone |
| 31 | 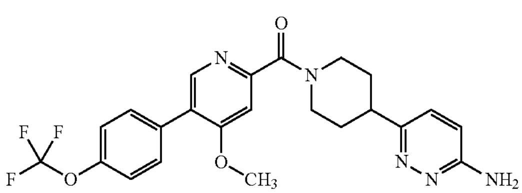 [SMILES: COc1cc(C(=O)N2CCC(c3ccc(N)nn3)CC2)ncc1-c1ccc(OC(F)(F)F)cc1] | [4-(6-Amino-pyridazin-3-yl)-piperidin-1-yl]-[4-methoxy-5-(4-trifluoromethoxy-phenyl)-pyridin-2-yl]-methanone |
| 32 | 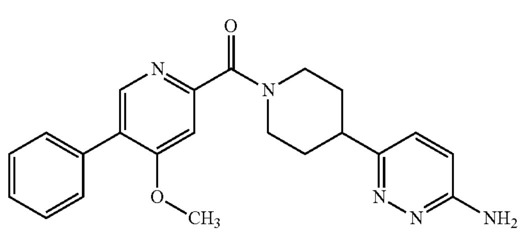 [SMILES: COc1cc(C(=O)N2CCC(c3ccc(N)nn3)CC2)ncc1-c1ccccc1] | [4-(6-Amino-pyridazin-3-yl)-piperidin-1-yl]-(4-methoxy-5-phenyl-pyridin-2-yl)-methanone |

TABLE 1.1-continued

| Cpd No. | Structure | Structure Name |
|---|---|---|
| 33 | 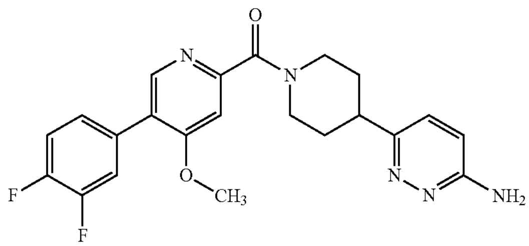 [SMILES: COc1cc(C(=O)N2CCC(c3ccc(N)nn3)CC2)ncc1-c1ccc(F)c(F)c1] | [4-(6-Amino-pyridazin-3-yl)-piperidin-1-yl]-[5-(3,4-difluoro-phenyl)-4-methoxy-pyridin-2-yl]-methanone |
| 34 | 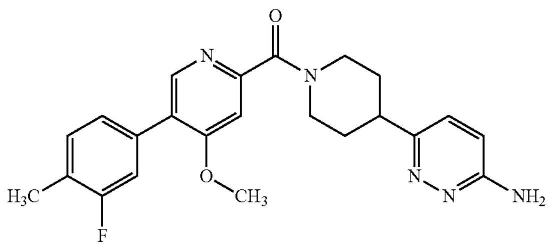 [SMILES: COc1cc(C(=O)N2CCC(c3ccc(N)nn3)CC2)ncc1-c1ccc(C)c(F)c1] | [4-(6-Amino-pyridazin-3-yl)-piperidin-1-yl]-[5-(3-fluoro-4-methyl-phenyl)-4-methoxy-pyridin-2-yl]-methanone |
| 35 | 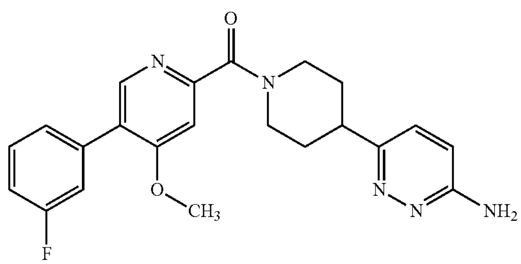 [SMILES: COc1cc(C(=O)N2CCC(c3ccc(N)nn3)CC2)ncc1-c1cccc(F)c1] | [4-(6-Amino-pyridazin-3-yl)-piperidin-1-yl]-[5-(3-fluoro-phenyl)-4-methoxy-pyridin-2-yl]-methanone |
| 36 | 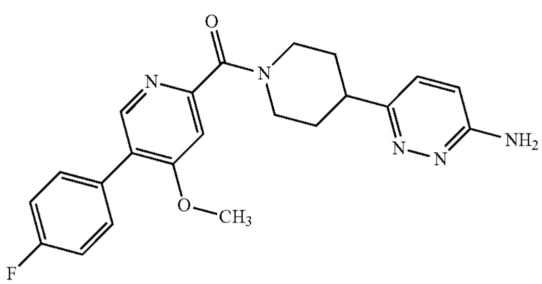 [SMILES: COc1cc(C(=O)N2CCC(c3ccc(N)nn3)CC2)ncc1-c1ccc(F)cc1] | [4-(6-Amino-pyridazin-3-yl)-piperidin-1-yl]-[5-(4-fluoro-phenyl)-4-methoxy-pyridin-2-yl]-methanone |
| 37 | 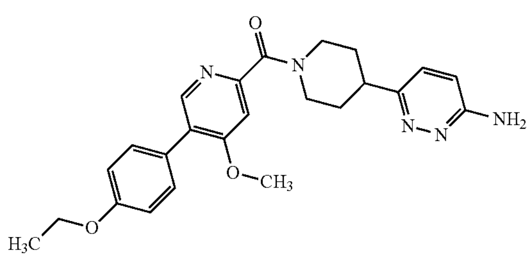 [SMILES: CCOc1ccc(-c2cnc(C(=O)N3CCC(c4ccc(N)nn4)CC3)cc2OC)cc1] | [4-(6-Amino-pyridazin-3-yl)-piperidin-1-yl]-[5-(4-ethoxy-phenyl)-4-methoxy-pyridin-2-yl]-methanone |
| 38 | 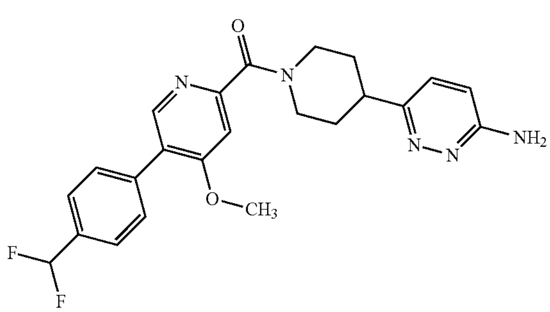 [SMILES: COc1cc(C(=O)N2CCC(c3ccc(N)nn3)CC2)ncc1-c1ccc(C(F)F)cc1] | [4-(6-Amino-pyridazin-3-yl)-piperidin-1-yl]-[5-(4-difluoromethyl-phenyl)-4-methoxy-pyridin-2-yl]-methanone |

TABLE 1.1-continued

| Cpd No. | Structure | Structure Name |
|---|---|---|
| 39 | 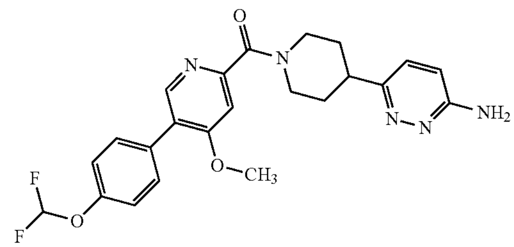 [SMILES: COc1cc(C(=O)N2CCC(c3ccc(N)nn3)CC2)ncc1-c1ccc(OC(F)F)cc1] | [4-(6-Amino-pyridazin-3-yl)-piperidin-1-yl]-[5-(4-difluoromethoxy-phenyl)-4-methoxy-pyridin-2-yl]-methanone |
| 40 | 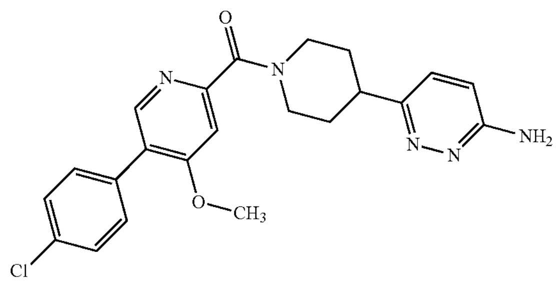 [SMILES: COc1cc(C(=O)N2CCC(c3ccc(N)nn3)CC2)ncc1-c1ccc(Cl)cc1] | [4-(6-Amino-pyridazin-3-yl)-piperidin-1-yl]-[5-(4-chloro-phenyl)-4-methoxy-pyridin-2-yl]-methanone |
| 41 | 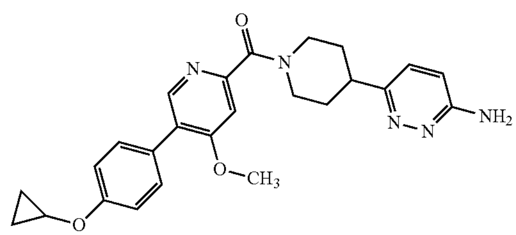 [SMILES: COc1cc(C(=O)N2CCC(c3ccc(N)nn3)CC2)ncc1-c1ccc(OC2CC2)cc1] | [4-(6-Amino-pyridazin-3-yl)-piperidin-1-yl]-[5-(4-cyclopropoxy-phenyl)-4-methoxy-pyridin-2-yl]-methanone |
| 42 | 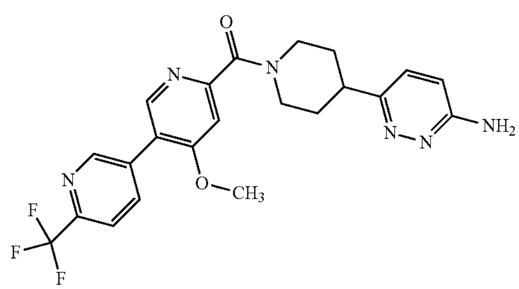 [SMILES: COc1cc(C(=O)N2CCC(c3ccc(N)nn3)CC2)ncc1-c1ccc(C(F)(F)F)nc1] | [4-(6-Amino-pyridazin-3-yl)-piperidin-1-yl]-[5-(4-methoxy-6'-trifluoromethyl-[3,3']bipyridinyl-6-yl)-methanone |
| 43 | 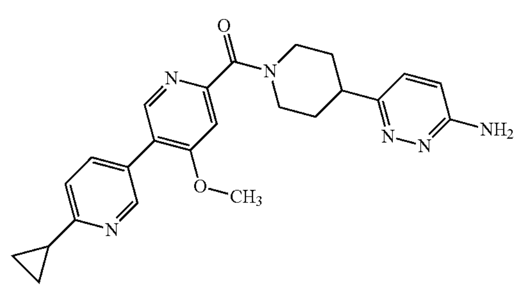 [SMILES: COc1cc(C(=O)N2CCC(c3ccc(N)nn3)CC2)ncc1-c1ccc(C2CC2)nc1] | [4-(6-Amino-pyridazin-3-yl)-piperidin-1-yl]-(6'-cyclopropyl-4-methoxy-[3,3']bipyridinyl-6-yl)-methanone |
| 44 | 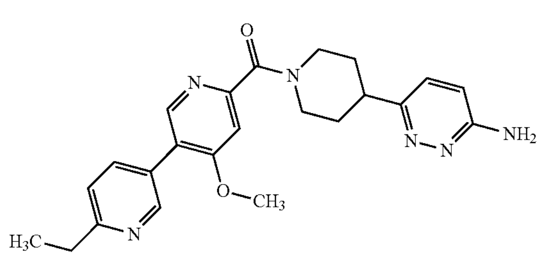 [SMILES: CCc1ccc(-c2cnc(C(=O)N3CCC(c4ccc(N)nn4)CC3)cc2OC)cn1] | [4-(6-Amino-pyridazin-3-yl)-piperidin-1-yl]-(6'-ethyl-4-methoxy-[3,3']bipyridinyl-6-yl)-methanone |

TABLE 1.1-continued

| Cpd No. | Structure | Structure Name |
| --- | --- | --- |
| 45 | 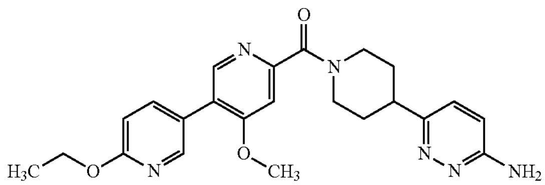 [SMILES: CCOc1ccc(-c2cnc(C(=O)N3CCC(c4ccc(N)nn4)CC3)cc2OC)cn1] | [4-(6-Amino-pyridazin-3-yl)-piperidin-1-yl]-(6'-ethoxy-4-methoxy-[3,3']bipyridinyl-6-yl)-methanone |
| 46 | 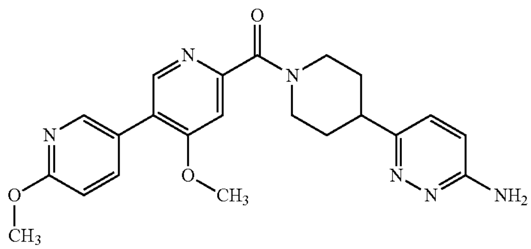 [SMILES: COc1ccc(-c2cnc(C(=O)N3CCC(c4ccc(N)nn4)CC3)cc2OC)cn1] | [4-(6-Amino-pyridazin-3-yl)-piperidin-1-yl]-(4,6'-dimethoxy-[3,3']bipyridinyl-6-yl)-methanone |
| 47 | 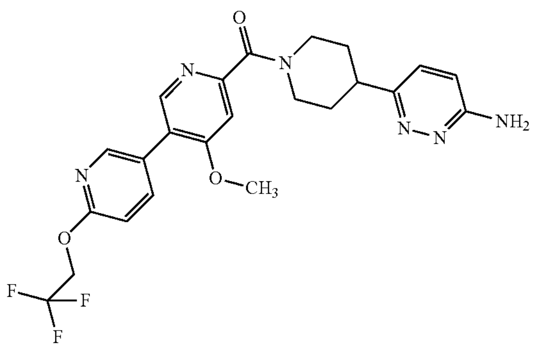 [SMILES: COc1cc(C(=O)N2CCC(c3ccc(N)nn3)CC2)ncc1-c1ccc(OCC(F)(F)F)nc1] | [4-(6-Amino-pyridazin-3-yl)-piperidin-1-yl]-[4-methoxy-6'-(2,2,2-trifluoro-ethoxy)-[3,3']bipyridinyl-6-yl]-methanone |
| 48 | 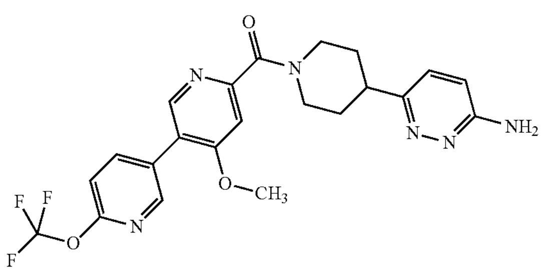 [SMILES: COc1cc(C(=O)N2CCC(c3ccc(N)nn3)CC2)ncc1-c1ccc(OC(F)(F)F)nc1] | [4-(6-Amino-pyridazin-3-yl)-piperidin-1-yl]-(4-methoxy-6'-trifluoromethoxy-[3,3']bipyridinyl-6-yl)-methanone |
| 49 | 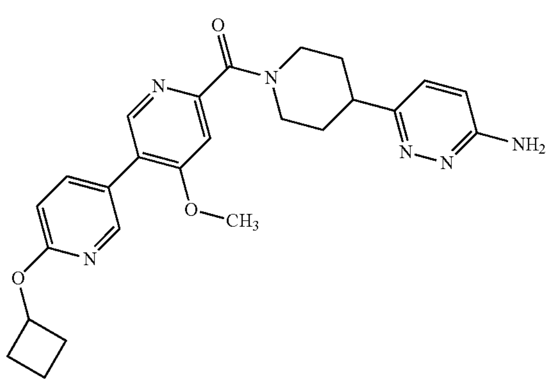 [SMILES: COc1cc(C(=O)N2CCC(c3ccc(N)nn3)CC2)ncc1-c1ccc(OC2CCC2)nc1] | [4-(6-Amino-pyridazin-3-yl)-piperidin-1-yl]-(6'-cyclobutoxy-4-methoxy-[3,3']bipyridinyl-6-yl)-methanone |

TABLE 1.1-continued

| Cpd No. | Structure | Structure Name |
| --- | --- | --- |
| 50 | 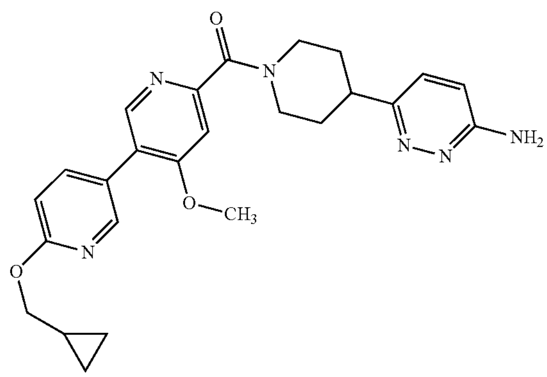 [SMILES: COc1cc(C(=O)N2CCC(c3ccc(N)nn3)CC2)ncc1-c1ccc(OCC2CC2)nc1] | [4-(6-Amino-pyridazin-3-yl)-piperidin-1-yl]-(6'-cyclopropylmethoxy-4-methoxy-[3,3']bipyridinyl-6-yl)-methanone |
| 51 | 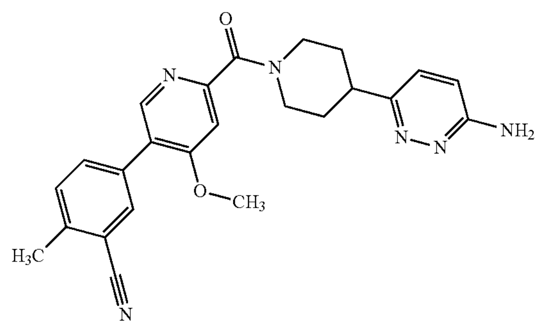 [SMILES: COc1cc(C(=O)N2CCC(c3ccc(N)nn3)CC2)ncc1-c1ccc(C)c(C#N)c1] | 5-{6-[4-(6-Amino-pyridazin-3-yl)-piperidine-1-carbonyl]-4-methoxy-pyridin-3-yl}-2-methyl-benzonitrile |
| 52 | 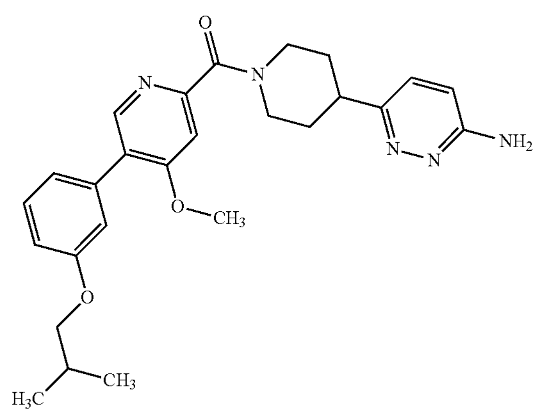 [SMILES: COc1cc(C(=O)N2CCC(c3ccc(N)nn3)CC2)ncc1-c1cccc(OCC(C)C)c1] | [4-(6-Amino-pyridazin-3-yl)-piperidin-1-yl]-[5-(3-isobutoxy-phenyl)-4-methoxy-pyridin-2-yl]-methanone |
| 53 | 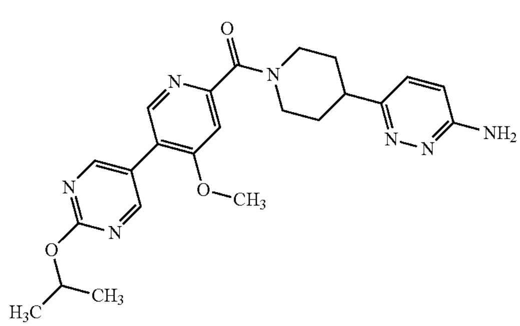 [SMILES: COc1cc(C(=O)N2CCC(c3ccc(N)nn3)CC2)ncc1-c1cnc(OC(C)C)nc1] | [4-(6-Amino-pyridazin-3-yl)-piperidin-1-yl]-[5-(2-isopropoxy-pyrimidin-5-yl)-4-methoxy-pyridin-2-yl]-methanone |

TABLE 1.1-continued

| Cpd No. | Structure | Structure Name |
|---|---|---|
| 54 | 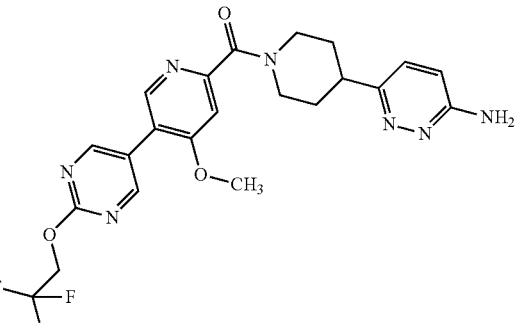 | [4-(6-Amino-pyridazin-3-yl)-piperidin-1-yl]-{4-methoxy-5-[2-(2,2,2-trifluoro-ethoxy)-pyrimidin-5-A-pyridin-2-yl}-methanone |
| 55 | 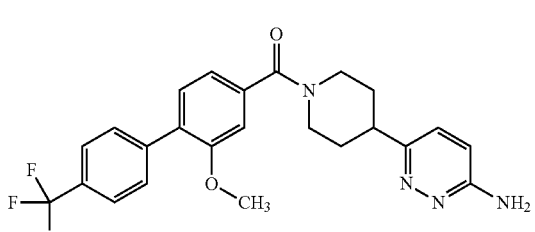 | [4-(6-Amino-pyridazin-3-yl)-piperidin-1-yl]-(2-methoxy-4'-trifluoromethyl-biphenyl-4-yl)-methanone |
| 56 | 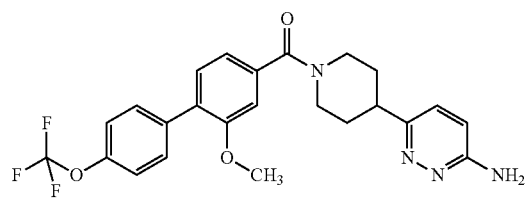 [SMILES: COc1cc(C(=O)N2CCC(c3ccc(N)nn3)CC2)ccc1-c1ccc(OC(F)(F)F)cc1] | [4-(6-Amino-pyridazin-3-yl)-piperidin-1-yl]-(2-methoxy-4'-trifluoromethoxy-biphenyl-4-yl)-methanone |
| 57 | 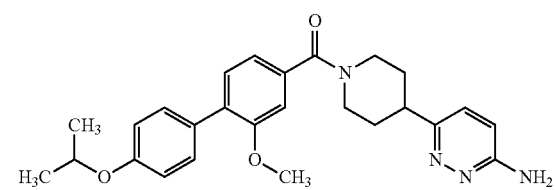 [SMILES: COc1cc(C(=O)N2CCC(c3ccc(N)nn3)CC2)ccc1-c1ccc(OC(C)C)cc1] | [4-(6-Amino-pyridazin-3-yl)-piperidin-1-yl]-(4'-isopropoxy-2-methoxy-biphenyl-4-yl)-methanone |
| 58 | 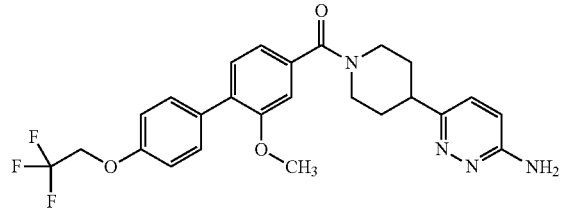 [SMILES: COc1cc(C(=O)N2CCC(c3ccc(N)nn3)CC2)ccc1-c1ccc(OCC(F)(F)F)cc1] | [4-(6-Amino-pyridazin-3-yl)-piperidin-1-yl]-[2-methoxy-4'-(2,2,2-trifluoro-ethoxy)-biphenyl-4-yl]-methanone |
| 59 | 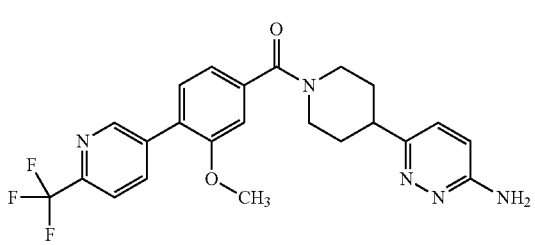 | [4-(6-Amino-pyridazin-3-yl)-piperidin-1-yl]-[3-methoxy-4-(6-trifluoromethyl-pyridin-3-yl)-phenyl]-methanone |

TABLE 1.1-continued

| Cpd No. | Structure | Structure Name |
|---|---|---|
| 60 | 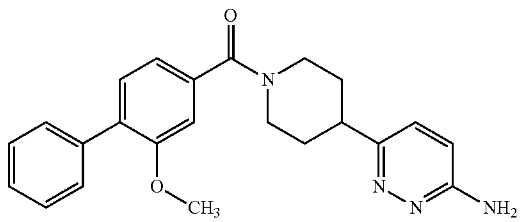 [SMILES: COc1cc(C(=O)N2CCC(c3ccc(N)nn3)CC2)ccc1-c1ccccc1] | [4-(6-Amino-pyridazin-3-yl)-piperidin-1-yl]-(2-methoxy-biphenyl-4-yl)-methanone |
| 61 | 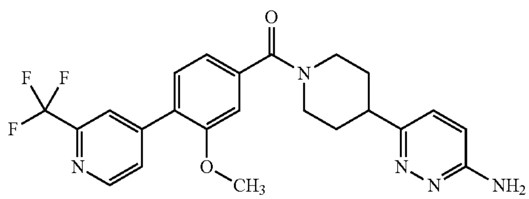 [SMILES: COc1cc(C(=O)N2CCC(c3ccc(N)nn3)CC2)ccc1-c1ccnc(C(F)(F)F)c1] | [4-(6-Amino-pyridazin-3-yl)-piperidin-1-yl]-[3-methoxy-4-(2-trifluoromethyl-pyridin-4-yl)-phenyl]-methanone |
| 62 | 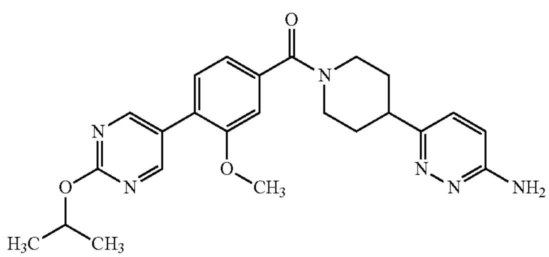 [SMILES: COc1cc(C(=O)N2CCC(c3ccc(N)nn3)CC2)ccc1-c1cnc(OC(C)C)nc1] | [4-(6-Amino-pyridazin-3-yl)-piperidin-1-yl]-[4-(2-isopropoxy-pyrimidin-5-yl)-3-methoxy-phenyl]-methanone |
| 63 | 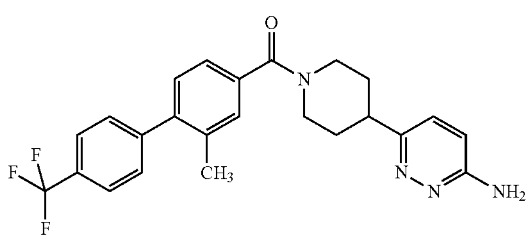 [SMILES: Cc1cc(C(=O)N2CCC(c3ccc(N)nn3)CC2)ccc1-c1ccc(C(F)(F)F)cc1] | [4-(6-Amino-pyridazin-3-yl)-piperidin-1-yl]-(2-methyl-4'-trifluoromethyl-biphenyl-4-yl)-methanone |
| 64 | 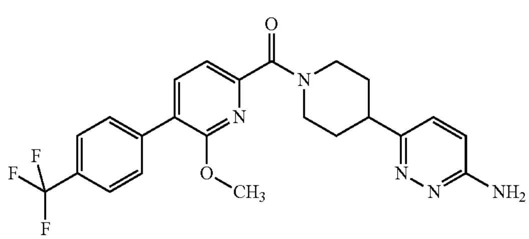 [SMILES: COc1nc(C(=O)N2CCC(c3ccc(N)nn3)CC2)ccc1-c1ccc(C(F)(F)F)cc1] | [4-(6-Amino-pyridazin-3-yl)-piperidin-1-yl]-[6-methoxy-5-(4-trifluoromethyl-phenyl)-pyridin-2-yl]-methanone |
| 65 | 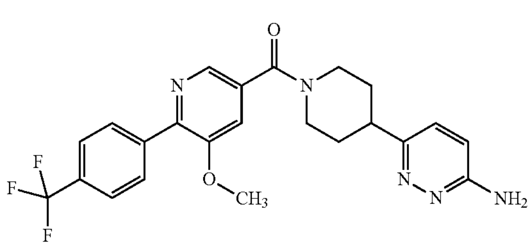 [SMILES: COc1cc(C(=O)N2CCC(c3ccc(N)nn3)CC2)cnc1-c1ccc(C(F)(F)F)cc1] | [4-(6-Amino-pyridazin-3-yl)-piperidin-1-yl]-[5-methoxy-6-(4-trifluoromethyl-phenyl)-pyridin-3-yl]-methanone |

TABLE 1.1-continued

| Cpd No. | Structure | Structure Name |
|---|---|---|
| 66 | 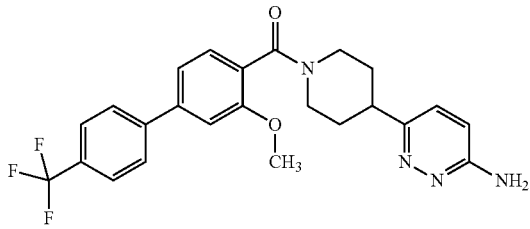 [SMILES: COc1cc(-c2ccc(C(F)(F)F)cc2)ccc1C(=O)N1CCC(c2ccc(N)nn2)CC1] | [4-(6-Amino-pyridazin-3-yl)-piperidin-1-yl]-(3-methoxy-4'-trifluoromethyl-biphenyl-4-yl)-methanone |
| 67 | 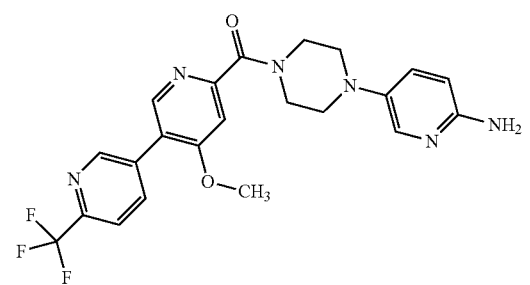 [SMILES: COc1cc(C(=O)N2CCN(c3ccc(N)nc3)CC2)ncc1-c1ccc(C(F)(F)F)nc1] | [4-(6-Amino-pyridin-3-yl)-piperazin-1-yl]-(4-methoxy-6'-trifluoromethyl-[3,3']bipyridinyl-6-yl)-methanone |
| 68 | 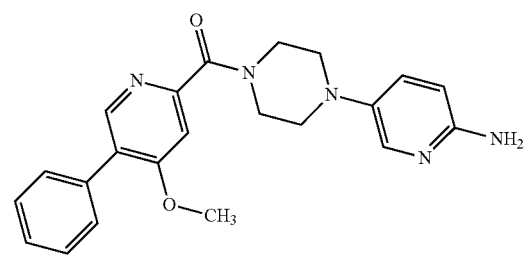 [SMILES: COc1cc(C(=O)N2CCN(c3ccc(N)nc3)CC2)ncc1-c1ccccc1] | [4-(6-Amino-pyridin-3-yl)-piperazin-1-yl]-(4-methoxy-5-phenyl-pyridin-2-yl)-methanone |
| 69 | 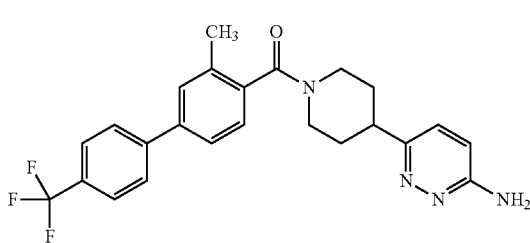 [SMILES: Cc1cc(-c2ccc(C(F)(F)F)cc2)ccc1C(=O)N1CCC(c2ccc(N)nn2)CC1] | [4-(6-Amino-pyridazin-3-yl)-piperidin-1-yl]-(3-methyl-4'-trifluoromethyl-biphenyl-4-yl)-methanone |
| 70 | 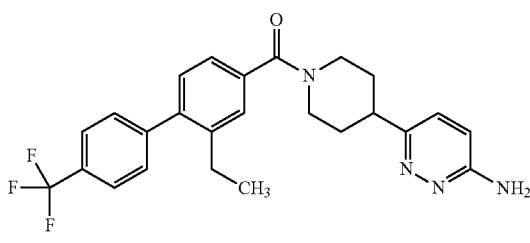 | [4-(6-Amino-pyridazin-3-yl)-piperidin-1-yl]-(2-ethyl-4'-trifluoromethyl-biphenyl-4-yl)-methanone |
| 71 | 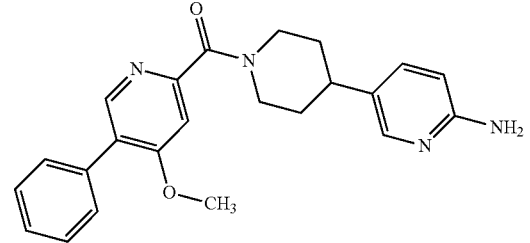 | (6-Amino-3',4',5',6'-tetrahydro-2'H-[3,4']bipyridinyl-1'-yl)-(4-methoxy-5-phenyl-pyridin-2-yl)-methanone |

TABLE 1.1-continued

| Cpd No. | Structure | Structure Name |
|---|---|---|
| 72 | 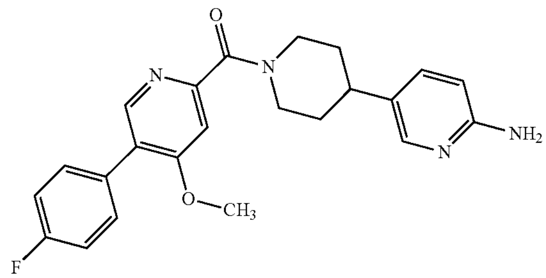 [SMILES: COc1cc(C(=O)N2CCC(c3ccc(N)nc3)CC2)ncc1-c1ccc(F)cc1] | (6-Amino-3',4',5',6'-tetrahydro-2'H-[3,4']bipyridinyl-1'-yl)-[5-(4-fluoro-phenyl)-4-methoxy-pyridin-2-yl]methanone |
| 73 | 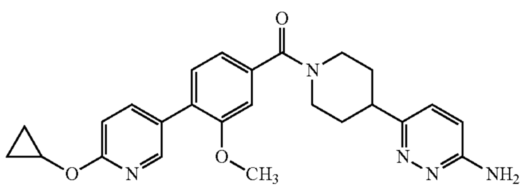 [SMILES: COc1cc(C(=O)N2CCC(c3ccc(N)nn3)CC2)ccc1-c1ccc(OC2CC2)nc1] | [4-(6-Amino-pyridazin-3-yl)-piperidin-1-yl]-[4-(6-cyclopropoxy-pyridin-3-yl)-3-methoxy-phenyl]-methanone |
| 74 | 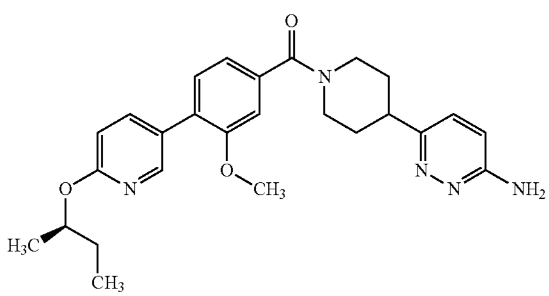 [SMILES: CC[C@@H](C)Oc1ccc(-c2ccc(C(=O)N3CCC(c4ccc(N)nn4)CC3)cc2OC)cn1] | [4-(6-Amino-pyridazin-3-yl)-piperidin-1-yl]-{4-[6-((R)-sec-butoxy)-pyridin-3-yl]-3-methoxy-phenyl}-methanone |
| 75 | 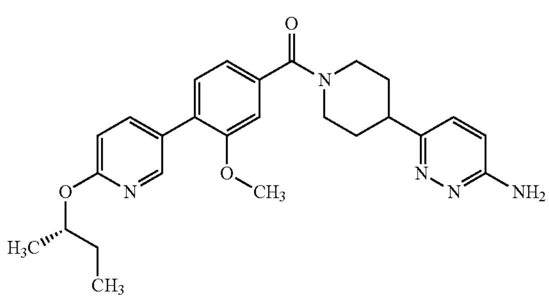 [SMILES: CC[C@H](C)Oc1ccc(-c2ccc(C(=O)N3CCC(c4ccc(N)nn4)CC3)cc2OC)cn1] | [4-(6-Amino-pyridazin-3-yl)-piperidin-1-yl]-{4-[6-((S)-sec-butoxy)-pyridin-3-yl]-3-methoxy-phenyl}-methanone |
| 76 | 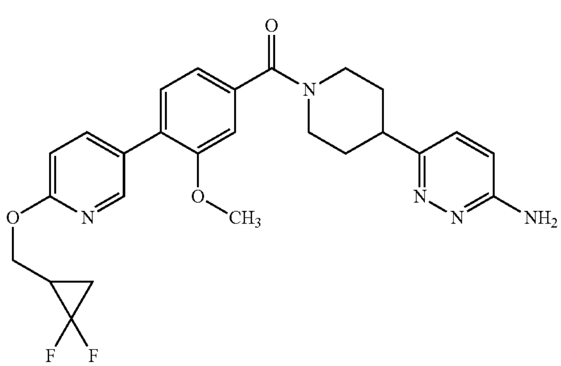 [SMILES: COc1cc(C(=O)N2CCC(c3ccc(N)nn3)CC2)ccc1-c1ccc(OCC2CC2(F)F)nc1] | [4-(6-Amino-pyridazin-3-yl)-piperidin-1-yl]{4-[6-(2,2-difluoro-cyclopropylmethoxy)-pyridin-3-yl]-3-methoxy-phenyl}-methanone |

TABLE 1.1-continued

| Cpd No. | Structure | Structure Name |
|---|---|---|
| 77 | 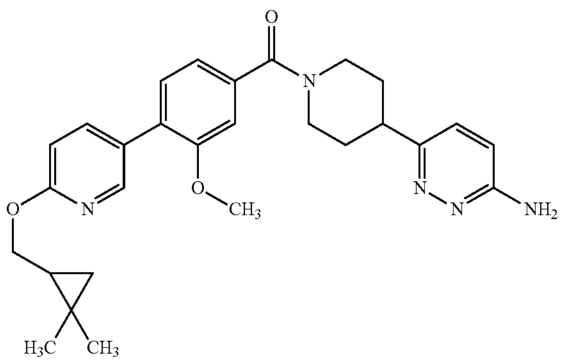 [SMILES: COc1cc(C(=O)N2CCC(c3ccc(N)nn3)CC2)ccc1-c1ccc(OCC2CC2(C)C)nc1] | [4-(6-Amino-pyridazin-3-yl)-piperidin-1-yl]-{4-[6-(2,2-dimethyl-cyclopropylmethoxy)-pyridin-3-yl]-3-methoxy-phenyl}-methanone |
| 78 | 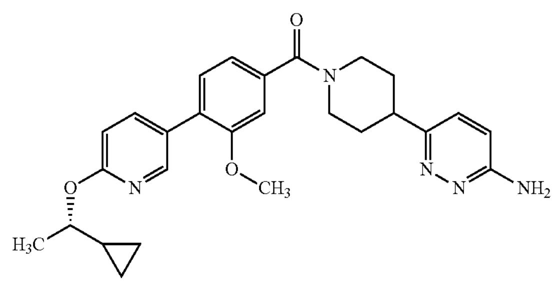 [SMILES: COc1cc(C(=O)N2CCC(c3ccc(N)nn3)CC2)ccc1-c1ccc(O[C@@H](C)C2CC2)nc1] | [4-(6-Amino-pyridazin-3-yl)-piperidin-1-yl]-{4-[6-((S)-1-cyclopropyl-ethoxy)-pyridin-3-yl]-3-methoxy-phenyl}-methanone |
| 79 | 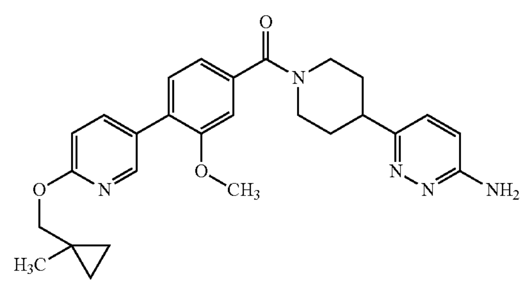 [SMILES: COc1cc(C(=O)N2CCC(c3ccc(N)nn3)CC2)ccc1-c1ccc(OCC2(C)CC2)nc1] | [4-(6-Amino-pyridazin-3-yl)-piperidin-1-yl]-{3-methoxy-4-[6-(1-methyl-cyclopropylmethoxy)-pyridin-3-yl]-phenyl}-methanone |
| 80 | 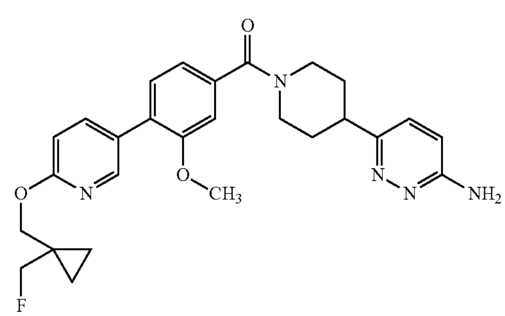 [SMILES: COc1cc(C(=O)N2CCC(c3ccc(N)nn3)CC2)ccc1-c1ccc(OCC2(CF)CC2)nc1] | [4-(6-Amino-pyridazin-3-yl)-piperidin-1-yl]-{4-[6-(1-fluoromethyl-cyclopropylmethoxy)-pyridin-3-yl]-3-methoxy-phenyl}-methanone |
| 81 | 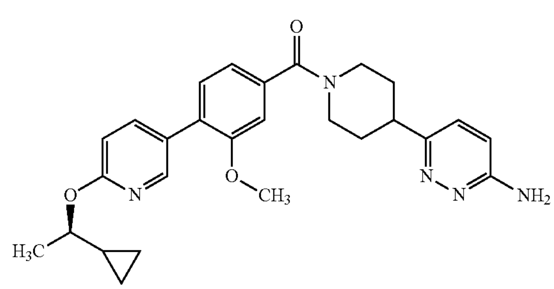 [SMILES: COc1cc(C(=O)N2CCC(c3ccc(N)nn3)CC2)ccc1-c1ccc(O[C@H](C)C2CC2)nc1] | [4-(6-Amino-pyridazin-3-yl)-piperidin-1-yl]-{4-[6-((R)-1-cyclopropyl-ethoxy)-pyridin-3-yl]-3-methoxy-phenyl}-methanone |

TABLE 1.1-continued

| Cpd No. | Structure | Structure Name |
|---|---|---|
| 82 | 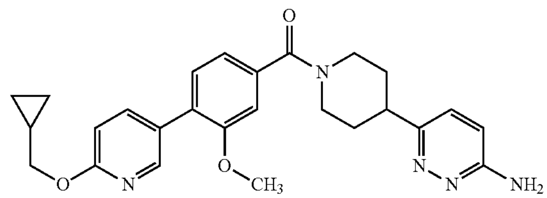 [SMILES: COc1cc(C(=O)N2CCC(c3ccc(N)nn3)CC2)ccc1-c1ccc(OCC2CC2)nc1] | [4-(6-Amino-pyridazin-3-yl)-piperidin-1-yl]-[4-(6-cyclopropylmethoxy-pyridin-3-yl)-3-methoxy-phenyl]-methanone |
| 83 | 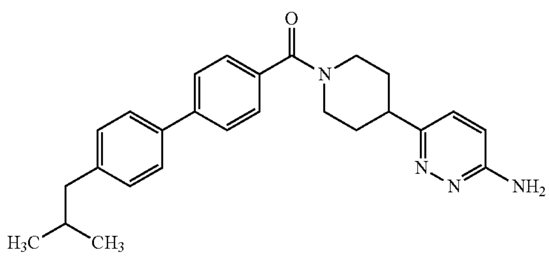 [SMILES: CC(C)Cc1ccc(-c2ccc(C(=O)N3CCC(c4ccc(N)nn4)CC3)cc2)cc1] | [4-(6-Amino-pyridazin-3-yl)-piperidin-1-yl]-(4'-isobutyl-biphenyl-4-yl)-methanone |
| 84 | 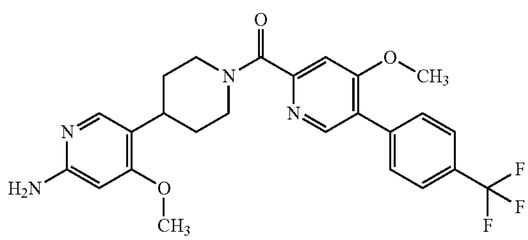 [SMILES: COc1cc(C(=O)N2CCC(c3cnc(N)cc3OC)CC2)ncc1-c1ccc(C(F)(F)F)cc1] | (6-Amino-4-methoxy-3',4',5',6'-tetrahydro-2'H-[3,4']bipyridinyl-1'-yl)-[4-methoxy-5-(4-trifluoromethyl-phenyl)-pyridin-2-yl]-methanone |
| 85 | 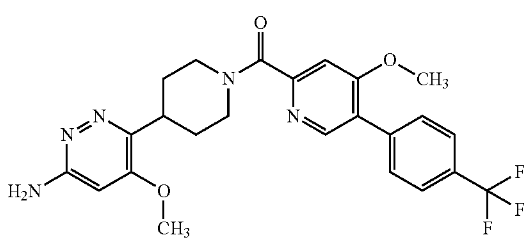 [SMILES: COc1cc(C(=O)N2CCC(c3nnc(N)cc3OC)CC2)ncc1-c1ccc(C(F)(F)F)cc1] | [4-(6-Amino-4-methoxy-pyridazin-3-yl)-piperidin-1-yl]-[4-methoxy-5-(4-trifluoromethyl-phenyl)-pyridin-2-yl]-methanone |
| 86 | 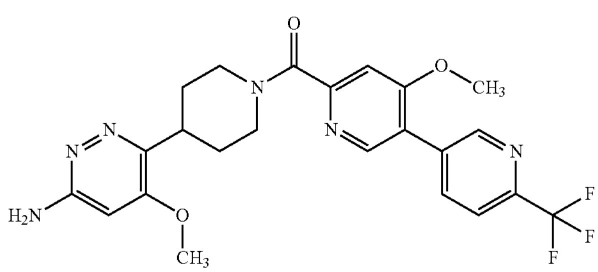 [SMILES: COc1cc(C(=O)N2CCC(c3nnc(N)cc3OC)CC2)ncc1-c1ccc(C(F)(F)F)nc1] | [4-(6-Amino-4-methoxy-pyridazin-3-yl)-piperidin-1-yl]-(4-methoxy-6'-trifluoromethyl-[3,3']bipyridinyl-6-yl)-methanone |
| 87 | 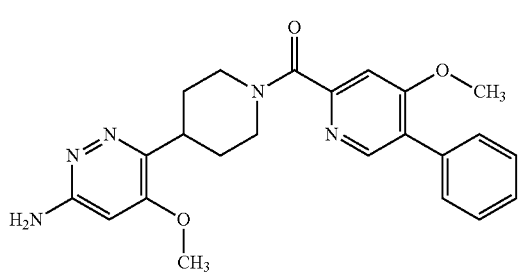 [SMILES: COc1cc(C(=O)N2CCC(c3nnc(N)cc3OC)CC2)ncc1-c1ccccc1] | [4-(6-Amino-4-methoxy-pyridazin-3-yl)-piperidin-1-yl]-(4-methoxy-5-phenyl-pyridin-2-yl)-methanone |

TABLE 1.1-continued

| Cpd No. | Structure | Structure Name |
|---|---|---|
| 88 | 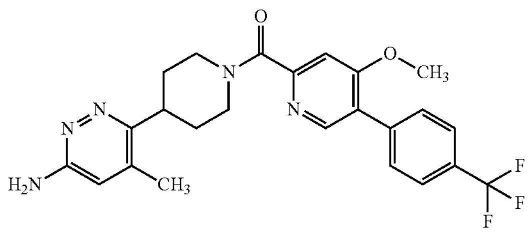 [SMILES: COc1cc(C(=O)N2CCC(c3nnc(N)cc3C)CC2)ncc1-c1ccc(C(F)(F)F)cc1] | [4-(6-Amino-4-methyl-pyridazin-3-yl)-piperidin-1-yl]-[4-methoxy-5-(4-trifluoromethyl-phenyl)-pyridin-2-yl]-methanone |
| 89 | 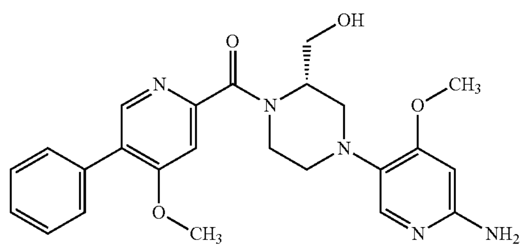 [SMILES: COc1cc(C(=O)N2CCN(c3cnc(N)cc3OC)C[C@H]2CO)ncc1-c1ccccc1] | [(S)-4-(6-Amino-4-methoxy-pyridin-3-yl)-2-hydroxymethyl-piperazin-1-yl]-(4-methoxy-5-phenyl-pyridin-2-yl)-methanone |
| 90 | 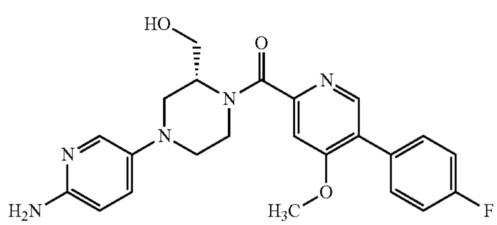 [SMILES: COc1cc(C(=O)N2CCN(c3ccc(N)nc3)C[C@@H]2CO)ncc1-c1ccc(F)cc1] | [(R)-4-(6-Amino-pyridin-3-yl)-2-hydroxymethyl-piperazin-1-yl]-[5-(4-fluoro-phenyl)-4-methoxy-pyridin-2-yl]-methanone |
| 91 | 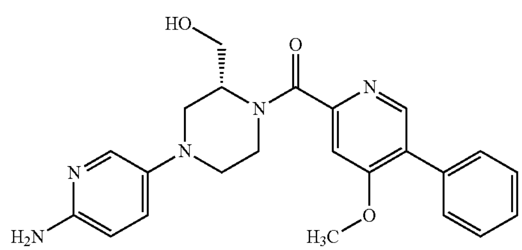 [SMILES: COc1cc(C(=O)N2CCN(c3ccc(N)nc3)C[C@@H]2CO)ncc1-c1ccccc1] | [(R)-4-(6-Amino-pyridin-3-yl)-2-hydroxymethyl-piperazin-1-yl]-(4-methoxy-5-phenyl-pyridin-2-yl)-methanone |
| 92 | 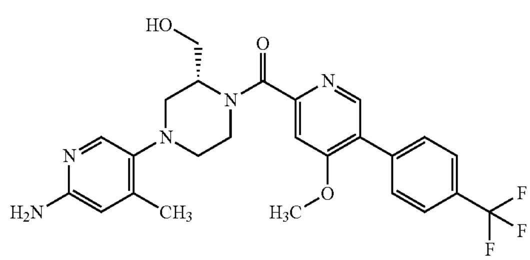 [SMILES: COc1cc(C(=O)N2CCN(c3cnc(N)cc3C)C[C@@H]2CO)ncc1-c1ccc(C(F)(F)F)cc1] | [(R)-4-(6-Amino-4-methyl-pyridin-3-yl)-2-hydroxymethyl-piperazin-1-yl]-[4-methoxy-5-(4-trifluoromethyl-phenyl)-pyridin-2-yl]-methanone |
| 93 | 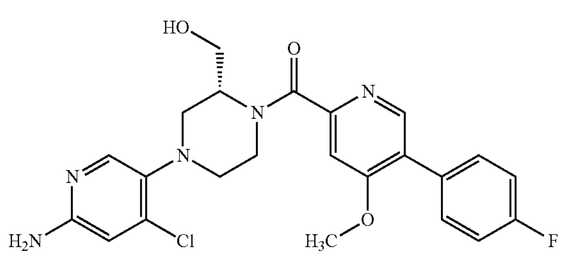 [SMILES: COc1cc(C(=O)N2CCN(c3cnc(N)cc3Cl)C[C@@H]2CO)ncc1-c1ccc(F)cc1] | [(R)-4-(6-Amino-4-methyl-pyridin-3-yl)-2-hydroxymethyl-piperazin-1-yl]-[5-(4-fluoro-phenyl)-4-methoxy-pyridin-2-yl]-methanone |

TABLE 1.1-continued

| Cpd No. | Structure | Structure Name |
|---|---|---|
| 94 | 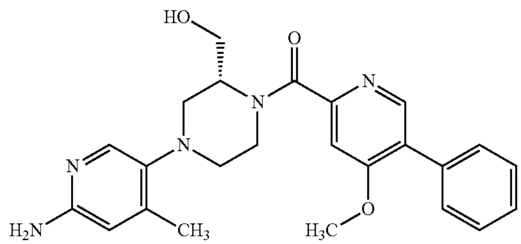 [SMILES: COc1cc(C(=O)N2CCN(c3cnc(N)cc3C)C[C@@H]2CO)ncc1-c1ccccc1] | [(R)-4-(6-Amino-4-methyl-pyridin-3-yl)-2-hydroxymethyl-piperazin-1-yl]-(4-methoxy-5-phenyl-pyridin-2-yl)-methanone |
| 95 | 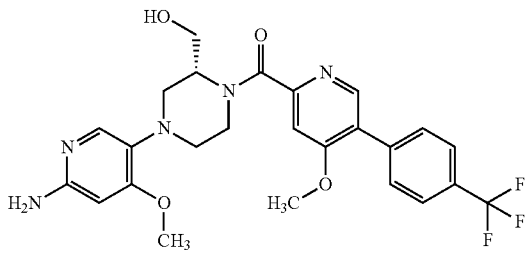 [SMILES: COc1cc(C(=O)N2CCN(c3cnc(N)cc3OC)C[C@@H]2CO)ncc1-c1ccc(C(F)(F)F)cc1] | [(R)-4-(6-Amino-4-methoxy-pyridin-3-yl)-2-hydroxymethyl-piperazin-1-yl]-[4-methoxy-5-(4-trifluoromethyl-phenyl)-pyridin-2-yl]-methanone |
| 96 | 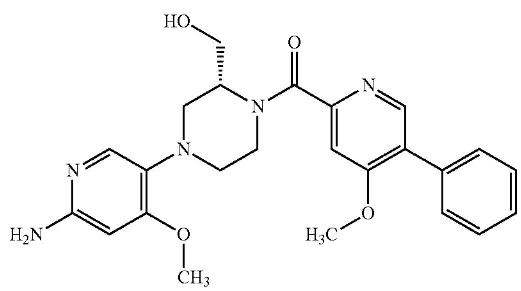 [SMILES: COc1cc(C(=O)N2CCN(c3cnc(N)cc3OC)C[C@@H]2CO)ncc1-c1ccccc1] | [(R)-4-(6-Amino-4-methoxy-pyridin-3-yl)-2-hydroxymethyl-piperazin-1-yl]-(4-methoxy-5-phenyl-pyridin-2-yl)-methanone |
| 97 | 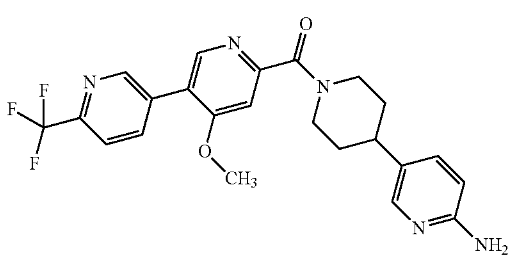 [SMILES: COc1cc(C(=O)N2CCC(c3ccc(N)nc3)CC2)ncc1-c1ccc(C(F)(F)F)nc1] | (6-Amino-3',4',5',6'-tetrahydro-2'H-[3,4']bipyridinyl-1'-yl)-(4-methoxy-6'-trifluoromethyl-[3,3']bipyridinyl-6-yl)-methanone |
| 98 | 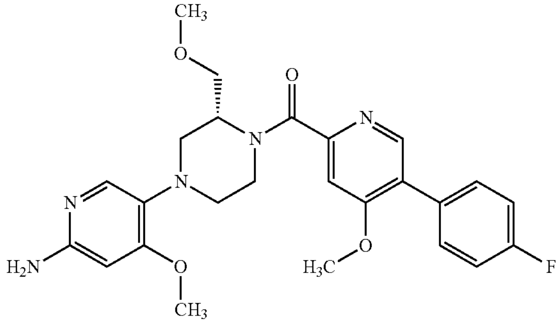 [SMILES: COC[C@H]1CN(c2cnc(N)cc2OC)CCN1C(=O)c1cc(OC)c(-c2ccc(F)cc2)cn1] | [(R)-4-(6-Amino-4-methoxy-pyridin-3-yl)-2-methoxymethyl-piperazin-1-yl]-[5-(4-fluoro-phenyl)-4-methoxy-pyridin-2-yl]-methanone |

TABLE 1.1-continued

| Cpd No. | Structure | Structure Name |
|---|---|---|
| 99 | 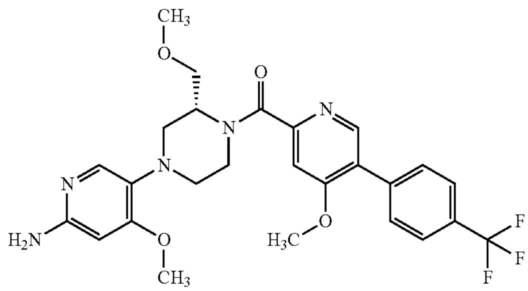 [SMILES: COC[C@H]1CN(c2cnc(N)cc2OC)CCN1C(=O)c1cc(OC)c(-c2ccc(C(F)(F)F)cc2)cn1] | [(R)-4-(6-Amino-4-methoxy-pyridin-3-yl)-2-methoxymethyl-piperazin-1-yl]-[4-methoxy-5-(4-trifluoromethyl-phenyl)-pyridin-2-yl]-methanone |
| 100 | 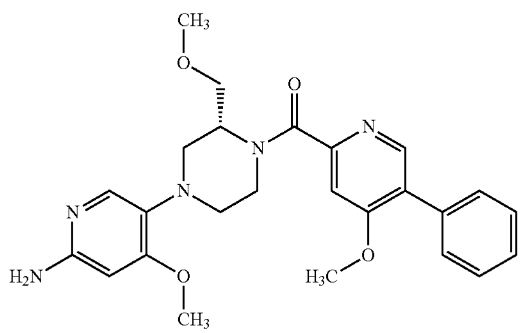 [SMILES: COC[C@H]1CN(c2cnc(N)cc2OC)CCN1C(=O)c1cc(OC)c(-c2ccccc2)cn1] | [(R)-4-(6-Amino-4-methoxy-pyridin-3-yl)-2-methoxymethyl-piperazin-1-yl]-(4-methoxy-5-phenyl-pyridin-2-yl)-methanone |
| 101 | 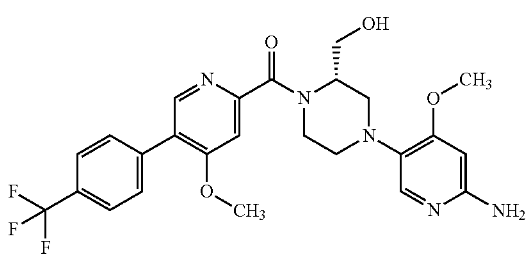 [SMILES: COc1cc(C(=O)N2CCN(c3cnc(N)cc3OC)C[C@H]2CO)ncc1-c1ccc(C(F)(F)F)cc1] | [(S)-4-(6-Amino-4-methoxy-pyridin-3-yl)-2-hydroxymethyl-piperazin-1-yl]-[4-methoxy-5-(4-trifluoromethyl-phenyl)-pyridin-2-yl]-methanone |
| 102 | 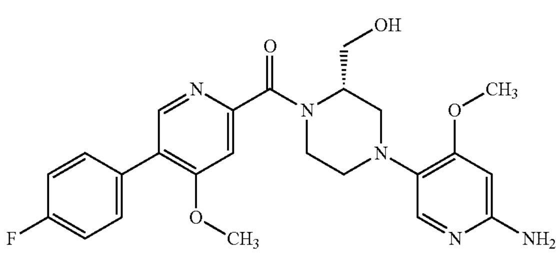 [SMILES: COc1cc(C(=O)N2CCN(c3cnc(N)cc3OC)C[C@H]2CO)ncc1-c1ccc(F)cc1] | [(S)-4-(6-Amino-4-methoxy-pyridin-3-yl)-2-hydroxymethyl-piperazin-1-yl]-[5-(4-fluoro-phenyl)-4-methoxy-pyridin-2-yl]-methanone |
| 103 | 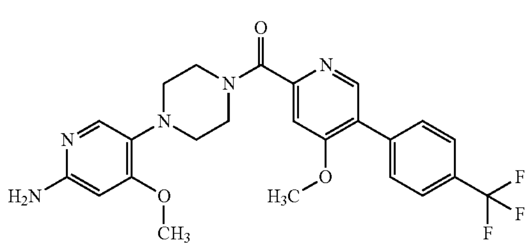 [SMILES: COc1cc(C(=O)N2CCN(c3cnc(N)cc3OC)CC2)ncc1-c1ccc(C(F)(F)F)cc1] | [4-(6-Amino-4-methoxy-pyridin-3-yl)-piperazin-1-yl]-[4-methoxy-5-(4-trifluoromethyl-phenyl)-pyridin-2-yl]-methanone |

TABLE 1.1-continued

| Cpd No. | Structure | Structure Name |
|---|---|---|
| 104 | 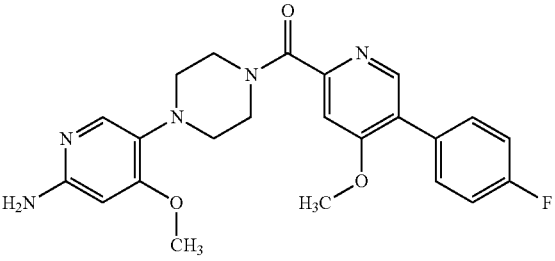 [SMILES: COc1cc(C(=O)N2CCN(c3cnc(N)cc3OC)CC2)ncc1-c1ccc(F)cc1] | [4-(6-Amino-4-methoxy-pyridin-3-yl)-piperazin-1-yl]-[5-(4-fluoro-phenyl)-4-methoxy-pyridin-2-yl]-methanone |
| 105 | 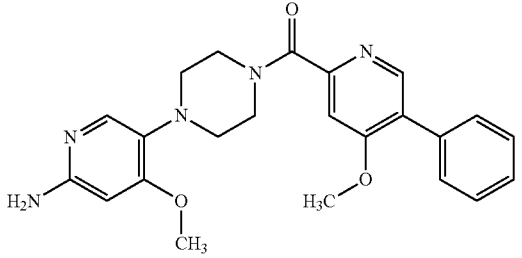 [SMILES: COc1cc(C(=O)N2CCN(c3cnc(N)cc3OC)CC2)ncc1-c1ccccc1] | [4-(6-Amino-4-methoxy-pyridin-3-yl)-piperazin-1-yl]-(4-methoxy-5-phenyl-pyridin-2-yl)-methanone |
| 106 | 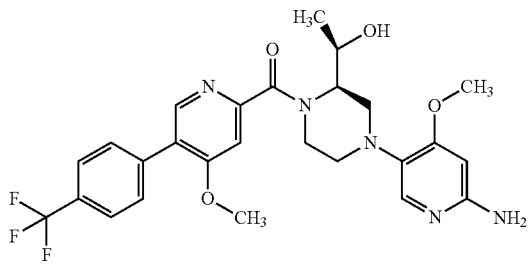 [SMILES: COc1cc(C(=O)N2CCN(c3cnc(N)cc3OC)C[C@@H]2[C@@H](C)O)ncc1-c1ccc(C(F)(F)F)cc1] | [(R)-4-(6-Amino-4-methoxy-pyridin-3-yl)-2-((R)-1-hydroxy-ethyl)piperazin-1-yl]-[4-methoxy-5-(4-trifluoromethyl-phenyl)-pyridin-2-yl]-methanone |
| 107 | 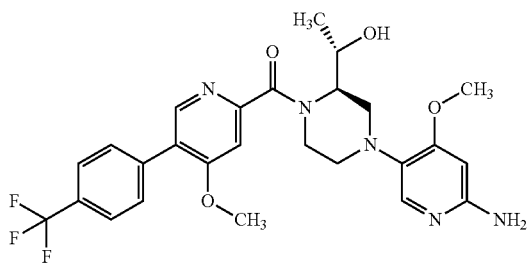 [SMILES: COc1cc(C(=O)N2CCN(c3cnc(N)cc3OC)C[C@@H]2[C@H](C)O)ncc1-c1ccc(C(F)(F)F)cc1] | [(R)-4-(6-Amino-4-methoxy-pyridin-3-yl)-2-((S)-1-hydroxy-ethyl)piperazin-1-yl]4-methoxy-5-(4-trifluoromethyl-phenyl)-pyridin-2-yl]-methanone |
| 108 | 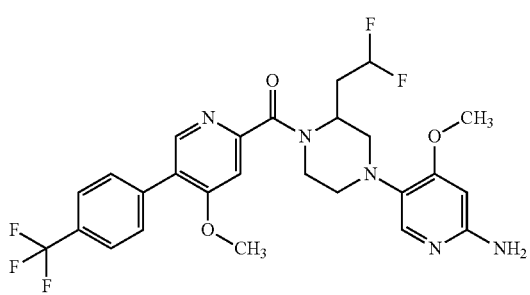 [SMILES: COc1cc(C(=O)N2CCN(c3cnc(N)cc3OC)CC2CC(F)F)ncc1-c1ccc(C(F)(F)F)cc1] | [4-(6-Amino-4-methoxy-pyridin-3-yl)-2-(2,2-difluoro-ethyl)-piperazin-1-yl]-[4-methoxy-5-(4-trifluoromethyl-phenyl)-pyridin-2-yl]-methanone |

TABLE 1.1-continued

| Cpd No. | Structure | Structure Name |
| --- | --- | --- |
| 109 | 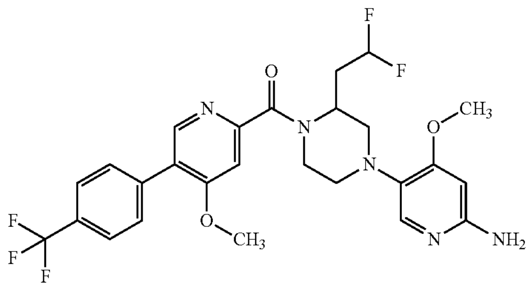 [SMILES: COc1cc(C(=O)N2CCN(c3cnc(N)cc3OC)CC2CC(F)F)ncc1-c1ccc(C(F)(F)F)cc1] | [(S)-4-(6-Amino-4-methoxy-pyridin-3-yl)-2-(2,2-difluoro-ethyl)-piperazin-1-yl]-[4-methoxy-5-(4-trifluoromethyl-phenyl)-pyridin-2-yl]-methanone |
| 110 | 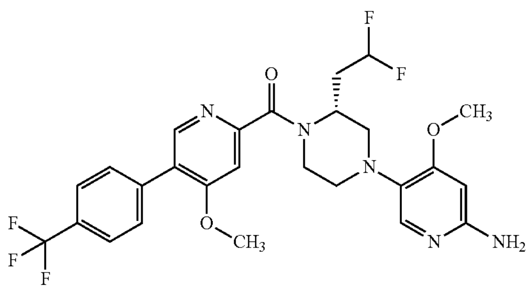 | [(R)-4-(6-Amino-4-methoxy-pyridin-3-yl)-2-(2,2-difluoro-ethyl)-piperazin-1-yl]-[4-methoxy-5-(4-trifluoromethyl-phenyl)-pyridin-2-yl]-methanone |
| 111 | 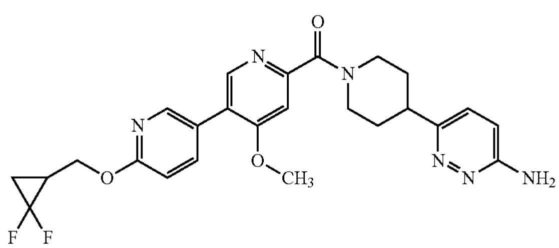 [SMILES: COc1cc(C(=O)N2CCC(c3ccc(N)nn3)CC2)ncc1-c1ccc(OCC2CC2(F)F)nc1] | [4-(6-Amino-pyridazin-3-yl)-piperidin-1-yl]-[6'-(2,2-difluoro-cyclopropylmethoxy)-4-methoxy-[3,3']bipyridinyl-6-yl]-methanone |
| 112 | 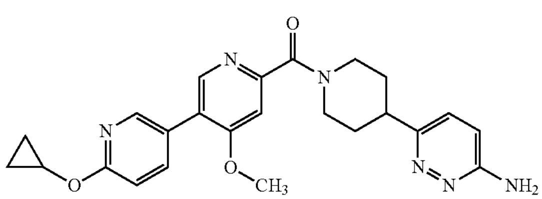 [SMILES: COc1cc(C(=O)N2CCC(c3ccc(N)nn3)CC2)ncc1-c1ccc(OC2CC2)nc1] | [4-(6-Amino-pyridazin-3-yl)-piperidin-1-yl]-(6'-cyclopropoxy-4-methoxy-[3,3']bipyridinyl-6-yl)-methanone |
| 113 | 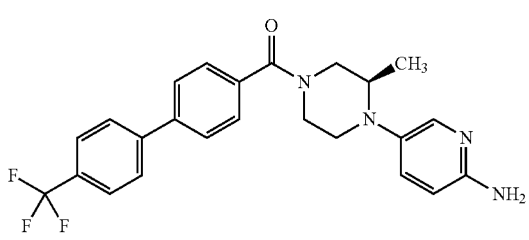 [SMILES: C[C@@H]1CN(C(=O)c2ccc(-c3ccc(C(F)(F)F)cc3)cc2)CCN1c1ccc(N)nc1] | [(R)-4-(6-Amino-pyridin-3-yl)-3-methyl-piperazin-1-yl]-(4'-trifluoromethyl-biphenyl-4-yl)-methanone |
| 114 | 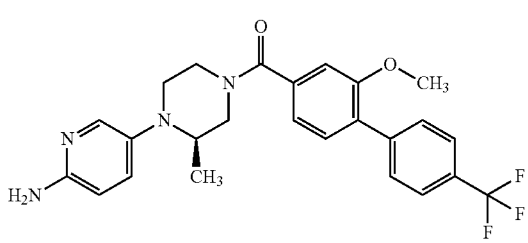 [SMILES: COc1cc(C(=O)N2CCN(c3ccc(N)nc3)[C@H](C)C2)ccc1-c1ccc(C(F)(F)F)cc1] | [(R)-4-(6-Amino-pyridin-3-yl)-3-methyl-piperazin-1-yl]-(2-methoxy-4'-trifluoromethyl-biphenyl-4-yl)-methanone |

TABLE 1.1-continued

| Cpd No. | Structure | Structure Name |
|---|---|---|
| 115 | H₂N-pyridazinyl-diazabicycloheptyl-C(O)-(2-methoxy-biphenyl-CF₃) structure | [(1S,4S)-5-(6-Amino-pyridazin-3-yl)-2,5-diaza-bicyclo[2.2.1]hept-2-yl]-(2-methoxy-4'-trifluoromethyl-biphenyl-4-yl)-methanone |
| 116 | H₂N-pyridazinyl-diazabicycloheptyl-C(O)-(methoxy-pyridinyl-phenyl-CF₃) structure | [(1S,4S)-5-(6-Amino-pyridazin-3-yl)-2,5-diaza-bicyclo[2.2.1]hept-2-yl]-[4-methoxy-5-(4-trifluoromethyl-phenyl)-pyridin-2-yl]-methanone |

In one embodiment, the invention relates to any of the compounds depicted in Table 1.1 above and the pharmaceutically acceptable salts thereof.

In another embodiment, the invention relates to a compound according to embodiment one described above, selected from the group consisting of compounds 1-116 from Table 1.1, and the pharmaceutically acceptable salts thereof.

The invention further relates to a pharmaceutical composition comprising any one of compounds 1 to 116 from Table 1.1, and the pharmaceutically acceptable salts thereof, and a pharmaceutically acceptable excipient or carrier.

In another embodiment, the invention relates to a to a pharmaceutical composition comprising a compound according to embodiment one described above, selected from the group consisting of compounds 1-116 from Table 1.1, and the pharmaceutically acceptable salts thereof, and a pharmaceutically acceptable excipient or carrier.

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, H₂N, (O)S, (O)₂S, NC (cyano), HOOC, F₃C or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

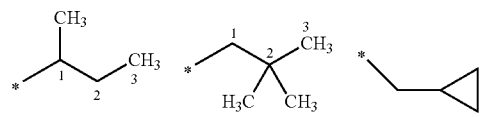

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio. As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term halogen generally denotes fluorine, chlorine, bromine and iodine

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

By the term "halo" added to an "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: $H_2FC-$, $HF_2C-$, $F_3C-$.

The term "carbocyclyl" as used either alone or in combination with another radical, means a mono- bi- or tricyclic ring structure consisting of 3 to 9 carbon atoms and optionally a heteroatom selected from the group consisting of N, O, and S. The term "carbocyclyl" refers to fully saturated ring systems and encompasses fused, bridged and spirocyclic systems.

Many of the terms given above may be used repeatedly in the definition of a formula or group and in each case have one of the meanings given above, independently of one another.

The present application provides compounds that can modulate TRPC6 function. Methods employing these compounds are also provided. Certain embodiments provide a method of modulating a TRPC6 function in a cell or animal comprising administering an effective amount of a compound that inhibits a TRPC6 function, wherein the compound inhibits a TRPC6-mediated ion flux. Certain embodiments provide a method of modulating a TRPC6 function in a cell or animal comprising administering an effective amount of a compound that inhibits a TRPC6 function, wherein the compound inhibits a TRPC6-mediated calcium influx. Certain embodiments provide a method of modulating a TRPC6 function in a cell or animal comprising administering an effective amount of a compound that inhibits a TRPC6 function, wherein the compound inhibits a TRPC6-mediated cytoskeletal reorganization or alteration in cell morphology. Certain embodiments provide a method of modulating a TRPC6 function in a cell comprising administering to the cell an effective amount of a compound that inhibits TRPC6 function, wherein the compound inhibits outward current mediated by TRPC6. Certain embodiments provide a method of modulating a TRPC6 function in a cell comprising administering to the cell an effective amount of a compound that inhibits TRPC6 function, wherein the compound inhibits inward current mediated by TRPC6. Certain embodiments provide a method of modulating a TRPC6 function in a cell comprising administering to the cell an effective amount of a compound that inhibits TRPC6 function, wherein the compound inhibits both the inward and outward currents mediated by TRPC6. Certain embodiments provide a method of modulating a TRPC6 function in a cell comprising administering to the cell an effective amount of a compound that inhibits TRPC6 function, wherein the compound inhibits TRPC6 mediated increases in intracellular calcium concentration. Certain embodiments provide a method of modulating a TRPC6 function in a cell comprising administering to the cell an effective amount of a compound that inhibits TRPC6 function, wherein the compound inhibits alterations in cell morphology. Certain embodiments also provide a method of preventing or treating a disease or condition related to TRPC6 function in a subject comprising administering to the subject a therapeutically effective amount of a compound that inhibits TRPC6 function, wherein the compound inhibits the inward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the outward current mediated by TRPC6. Certain embodiments also provide a method of preventing or treating a disease or condition related to TRPC6 function in a subject comprising administering to the subject a therapeutically effective amount of a compound that inhibits TRPC6 function, wherein the compound inhibits both the inward and outward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the ion flux mediated by TRPC6. Note that inhibition of a particular current refers to the ability of a compound to inhibit that current (e.g., inward and/or outward) in either an in vitro or an in vivo assay. Inhibition of a particular current in either an in vivo or an in vitro assay serves as a proxy for the particular functional activity of the particular compound.

The present invention provides methods of treating a TRPC6 mediated disorder in a subject, the method comprising administering an effective amount of a compound of the invention wherein each of the variables above are described herein, for example, in the detailed description below.

The present invention further provides a method for treating a TRPC6 mediated disorder in a subject, wherein the method comprises administering a composition comprising a compound of the invention and a pharmaceutically acceptable excipient, diluent or carrier.

The present invention further provides a method for treating a TRPC6 mediated disorder in a subject, wherein the method comprises administering a composition comprising a compound of the invention and a pharmaceutically acceptable excipient, diluent or carrier, and the TRPC6 mediated disorder is selected from sepsis, severe sepsis, septic shock, cardiac hypertrophy, ischemia, ischemic reperfusion injury, hypertension, pulmonary arterial hypertension, idiopathic pulmonary arterial hypertension, restenosis, chronic obstructive pulmonary disease, cystic fibrosis, Alzheimer's disease, Parkinson's disease, Huntington's disease, amyotrophic lateral sclerosis (ALS), trauma induced brain disorders, asthma, disease, rheumatoid arthritis, osteoarthritis, inflammatory bowel disease, multiple sclerosis, muscular dystrophy, Duchenne's muscular dystrophy, preeclampsia and pregnancy-induced hypertension, non-alcoholic steatohepatitis, minimal change disease, focal segmental glomerulosclerosis (FSGS), nephrotic syndrome, diabetic nephropathy or diabetic kidney disease (DKD), chronic kidney disease, renal insufficiency, end stage renal disease, ischemia or an ischemic reperfusion injury, cancer, diabetes, lung fibrosis, idiopathic pulmonary fibrosis (IPF), emphysema and acute respiratory disease syndrome (ARDS).

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds in Table 1.1 can exist in more than one tautomeric form. The invention includes methods for using all such tautomers.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (Also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The compounds of the invention are only those which are contemplated to be "chemically stable" as will be appreciated by those skilled in the art. For example, a compound which would have a "dangling valency", or a "carbanion" are not compounds contemplated by the inventive methods disclosed herein.

For all compounds disclosed herein above in this application, in the event the nomenclature is in conflict with the structure, it shall be understood that the compound is defined by the structure.

LIST OF ABBREVIATIONS

ACN or MeCN Acetonitrile
aq. Aqueous
BEH Ethylene Bridged Hybrid
Boc tert-Butyloxycarbonyl
° C. Degree celsius
CDI Di(imidazol-1-yl)methanone
CPhos-3G-Methanesulfonato(2-dicyclohexylphosphino-2',6'-palladacycle bis(dimethylamino)-1,1'-biphenyl)(2'-amino-1,1'-biphenyl-2-methane sulfonate yl)palladium (II)
DCM Dichloromethane
DIPEA N,N-diisopropylethylamine
DMF N,N-dimethylformamide
DMA N,N-dimethylacetamide
DMSO Dimethylsulfoxide
EDCl.HCl 1-Ethyl-3-(3-dimethylaminopropyl)carbodiimide hydrochloride
eq Equivalent
ESI-MS Electrospray ionisation mass spectrometry
Et$_2$O Diethylether
EtOAc or EE Ethyl acetate
h Hour
H$_2$ Hydrogen
HATU N,N,N',N'-tetramethyl-O-(7-azabenzotriazol-1-yl) uronium hexafluorophosphate
HCl Hydrochloric acid
HOBT 1-Hydroxybenzotriazole
HPLC High performance liquid chromatography
L Liter
LiOH Lithium hydroxide
MeI Methyl iodide
MeOH Methanol
min Minute
mL Milliliter
MS Mass spectrum
MTBE tert-Butyl methylether
m/z Mass-to-charge ratio
NaH Sodium hydride
NH$_3$ Ammonia
NH$_4$OH Solution of NH$_3$ in water
n-BuOH 1-Butanol
Pd$_2$(dba)$_3$ Tris(dibenzylideneacetone)dipalladium(0)
Pd/C Palladium on carbon
PdCl$_2$(dppf)CH$_2$Cl$_2$ [1,1'-Bis(diphenylphosphino)ferrocene]dichloropalladium(II) dichloromethane
PdCl$_2$(PPh$_3$)$_2$ Bis(triphenylphosphine)palladium(II) chloride
Pd(OH)$_2$ Palladium hydroxide
RP Reversed phase
RT or rt Room temperature (about 20° C.)
R$_t$ Retention time
RuPhos Pd G3 (2-Dicyclohexylphosphino-2',6'-diisopropoxy-1,1'-biphenyl)[2-(2'-amino-1,1'-biphenyl)]palladium(II) methanesulfonate
SFC Supercritical fluid chromatography
TBAF Tetrabutylammonium fluoride
TBTU Benzotriazolyl tetramethyluronium tetrafluoroborate
TEA Triethylamine
TetrakisPd Tetrakis(triphenylphosphine)palladium(0)
TF or TFA Trifluoroacetic acid
THF Tetrahydrofuran
TLC Thin-layer chromatography on SiO$_2$
XPhos 2-Dicyclohexylphosphino-2',4',6'-tri-i-propyl-1,1'-biphenyl
XPhos Pd G2 or
Xphos Pd 2$^{nd}$ Gen. Chloro(2-dicyclohexylphosphino-2',4',6'-triisopropyl-1,1'-biphenyl)[2-(2'-amino-1,1'-biphenyl)]palladium(II)
XantPhos 4,5-Bis(diphenylphosphino)-9,9-dimethylxanthene

SYNTHETIC EXAMPLES

The examples which follow are illustrative and, as recognized by one skilled in the art, particular reagents or conditions could be modified as needed for individual compounds without undue experimentation.

Intermediates and examples reported in the following bearing a basic or acidic group may be obtained as a corresponding salt or neutral compound depending on the purification method and conditions employed. Salts can be transformed into their neutral counterparts by standard procedures known to the one skilled in the art.

General Methods:

Unless noted otherwise, all reactions are run at room temperature (about 25° C.), under inert atmosphere (e.g., Argon, N$_2$), and under anhydrous conditions. All compounds are characterized by at least one of the following methods: $^1$H NMR, HPLC, HPLC-MS, or melting point.

Typically, reaction progress is monitored by thin layer chromatography (TLC) or HPLC-MS. Intermediates and products are purified using at least one of the following methods:

Flash chromatography on silica gel, Recrystallization, Super Critical Fluid (SFC) Chiral HPLC using a 3.0× 25.0 cm RegisPack column, eluting with an isocratic mixture of MeOH, isopropylamine (IPA), and super critical carbon dioxide at 125 bar; 80 mL/min, and/or Reversed phase HPLC using a C18 semi-preparative column eluting with a gradient of:
MeCN+0.1% TFA and H$_2$O+0.1% TFA,
MeCN+0.1% formic acid and H$_2$O+0.1% formic acid, or
MeCN and H$_2$O containing 2.5 mM NH$_4$HCO$_3$
MeCN and H$_2$O and 0.1% TFA, MeCN and H$_2$O and 0.1% NH$_3$ in water
MeCN and H$_2$O+0.1% TFA
MeCN and H$_2$O+0.1% NH$_3$ in water
MeOH and H$_2$O+0.1% TFA
MeOH and H$_2$O+0.1% NH$_3$ in water
MeCN+0.08% TFA and H$_2$O+0.1% TFA Analytical Data The reported mass spectrometry (MS) data is for observed mass (e.g., [M+H]$^+$). HPLC method used to characterize the compounds of the invention is described in Table 1.2.

TABLE 1.2.

HPLC Method

| Method | Mobile Phase A | Mobile Phase B | Gradient Time (min) | % A | % B | Flow (mL/min.) | Column |
|---|---|---|---|---|---|---|---|
| A | 0.1% Formic Acid in Water | 0.1% Formic Acid in MeCN | 0<br>1.0<br>1.3<br>1.4<br>1.7 | 95.0<br>5.0<br>5.0<br>95.0<br>95.0 | 5.0<br>95.0<br>95.0<br>5.0<br>5.0 | 0.8 | BEH 2.5 × 50 mm 018, 1.7 µm particle diameter |

HPLC Methods are described below.

Method 1
ESI+/− ion mode. Column: CSH C18 2.1×50 mm, 1.7 µm particle diameter. Gradient: 90% A to 100% B in 1.19 minutes hold at 100% B to 1.70 minutes. Flow rate 0.8 mL/min. A=(95% water+5% acetonitrile+0.05% formic acid) B=(acetonitrile+0.05% formic acid).

Method 2
ESI+/− ion mode. Column: BEH 2.1×50 mm C18, 1.7 µm particle diameter. Gradient: 90% A to 100% B in 4.45 minutes hold at 100% B to 4.58 minutes. Flow rate 0.8 mL/min. A=(95% water+5% acetonitrile+2.5 mM ammonium bicarbonate) B=(acetonitrile).

Method 3
ESI+/− ion mode. Column: BEH 2.1×50 mm C18, 1.7 µm particle diameter. Gradient: 90% A to 100% B in 1.7 minutes hold at 100% B to 1.19 minutes. Flow rate 0.8 mL/min. A=(95% water+5% acetonitrile+2.5 mM ammonium bicarbonate) B=(acetonitrile).

Method 4
ESI+/− ion mode. Column: HSS T3 2.1×100 mm, 1.8 µm particle diameter. Gradient:100% A hold for 1.00 minute, 100% A to 95% B in 4.50 minutes hold at 100% B to 4.91 minutes. Flow rate 0.6 mL/min. A=(95% water+5% acetonitrile+0.05% formic acid) B=(acetonitrile+0.05% formic acid).

Method 5
ESI+/− ion mode. Column: CSH C18 2.1×50 mm, 1.7 µm particle diameter: Gradient:90% A to 100% B in 4.45 minutes hold at 100% B to 4.58 minutes. Flow rate 0.8 mL/min. A=(95% water+5% acetonitrile+0.05% formic acid) B=(acetonitrile+0.05% formic acid).

Method 6
ESI+/− ion mode. Column: HSS T3 2.1×100 mm, 1.8 µm particle diameter. Gradient: 95% A to 100% B in 3.65 minutes, hold at 100% B to 4.95 minutes. Flow rate 0.6 mL/min. Column temperature 60 degrees C. A=(95% water+5% acetonitrile+0.05% formic acid) B=(acetonitrile+0.05% formic acid).

Method 7

| Method Name: | 7 |
| Device description: | Agilent 1200 with DA- and MS-Detector |
| Column: | Sunfire C18_3.0 × 30 mm_2.5 µm |
| Column producer: | Waters |

| Gradient/ Solvent Time [min] | % Sol [Water 0.1% TFA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Method 8

| Method Name: | 8 |
| Device description: | Waters ZQ2000 MS, Alliance 2695 PDA2996 210-500 nm, 2700 AS |
| Column: | Sunfire C18_4.6 × 50 mm_3.5 µm |
| Column producer: | Waters |

| Gradient/ Solvent Time [min] | % Sol [Water 0.1% TFA (v/v)] | % Sol [Methanol] | Flow [ml/min] | Temp [° C.] |
|---|---|---|---|---|
| 0.0 | 80.0 | 20.0 | 2.0 | 60.0 |
| 1.7 | 0.0 | 100.0 | 2.0 | 60.0 |
| 2.5 | 0.0 | 100.0 | 2.0 | 60.0 |
| 2.6 | 80.0 | 20.0 | 2.0 | 60.0 |

Method 9

| Method Name: | 9 |
| Device description: | Agilent 1200 with DA- and MS-Detector |
| Column: | XBridge C18_3.0 × 30 mm_2.5 µm |
| Column producer: | Waters |

| Gradient/ Solvent Time [min] | % Sol [Water 0.1% NH$_3$] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Method 10

| Method Name: | 10 |
| Device description: | Agilent 1200 with DA- and MS-Detector |
| Column: | XBridge C18_3.0 × 30 mm_2.5 µm |
| Column producer: | Waters |

| Gradient/ Solvent Time [min] | % Sol [Water 0.1% NH$_3$] | % Sol [Methanol] | Flow [ml/min] | Temp [° C.] |
|---|---|---|---|---|
| 0.0 | 95.0 | 5.0 | 2.2 | 60.0 |
| 0.05 | 95.0 | 5.0 | 2.2 | 60.0 |
| 1.4 | 0.0 | 100.0 | 2.2 | 60.0 |
| 1.8 | 0.0 | 100.0 | 2.2 | 60.0 |

Method 11

| Method Name: | 11 |
| Device description: | Waters Acquity with DA- and MS-Detector |
| Column: | XBridge BEH C18_2.1 × 30 mm_1.7 µm |
| Column producer: | Waters |

-continued

| Gradient/<br>Solvent Time<br>[min] | % Sol<br>[Water 0.1% NH$_3$] | % Sol<br>[Acetonitrile] | Flow<br>[ml/min] | Temp<br>[° C.] |
|---|---|---|---|---|
| 0.0 | 95.0 | 5.0 | 1.3 | 60.0 |
| 0.02 | 95.0 | 5.0 | 1.3 | 60.0 |
| 1.0 | 0.0 | 100.0 | 1.3 | 60.0 |
| 1.1 | 0.0 | 100.0 | 1.3 | 60.0 |

Method 12

| Method Name: | 12 |
|---|---|
| Device description: | Waters Acquity with DA- and MS-Detector |
| Column: | Sunfire C18__2.1 × 30 mm__2.5 μm |
| Column producer: | Waters |

| Gradient/<br>Solvent Time<br>[min] | % Sol<br>[Water 0.1%<br>TFA (v/v)] | % Sol<br>[Acetonitrile] | Flow<br>[ml/min] | Temp<br>[° C.] |
|---|---|---|---|---|
| 0.0 | 99.0 | 1.0 | 1.5 | 60.0 |
| 0.02 | 99.0 | 1.0 | 1.5 | 60.0 |
| 1.0 | 0.0 | 100.0 | 1.5 | 60.0 |
| 1.1 | 0.0 | 100.0 | 1.5 | 60.0 |

Method 13

| Method Name: | 13 |
|---|---|
| Device description: | Agilent 1200 with DA- and MS-Detector |
| Column: | Zorbax StableBond C18__3.0 × 30 mm__1.8 μm |
| Column producer: | Agilent |

| Gradient/<br>Solvent Time<br>[min] | % Sol<br>[Water 0.1%<br>TFA (v/v)] | % Sol<br>[Methanol] | Flow<br>[ml/min] | Temp<br>[° C.] |
|---|---|---|---|---|
| 0.0 | 95.0 | 5.0 | 2.2 | 60.0 |
| 0.05 | 95.0 | 5.0 | 2.2 | 60.0 |
| 1.4 | 0.0 | 100.0 | 2.2 | 60.0 |
| 1.8 | 0.0 | 100.0 | 2.2 | 60.0 |

Method 14

| Method Name: | 14 |
|---|---|
| Device description: | Agilent 1100 with DA- and MS-Detector |
| Column: | Zorbax StableBond C18__4.6 × 30 mm__3.5 μm |
| Column producer: | Agilent |

| Gradient/<br>Solvent Time<br>[min] | % Sol<br>[Water 0.1%<br>TFA (v/v)] | % Sol<br>[Acetonitrile] | Flow<br>[ml/min] | Temp<br>[° C.] |
|---|---|---|---|---|
| 0.0 | 95.0 | 5.0 | 4.0 | 60.0 |
| 0.15 | 95.0 | 5.0 | 4.0 | 60.0 |
| 1.7 | 0.0 | 100.0 | 4.0 | 60.0 |
| 2.25 | 0.0 | 100.0 | 4.0 | 60.0 |

Method 15

| Method Name: | 15 |
|---|---|
| Device description: | Agilent 1200 with DA and MS Detector |
| Column: | Zorbax StableBond C18__3.0 × 30 mm__1.8 μm |
| Column producer: | Agilent |

| Gradient/<br>Solvent Time<br>[min] | % Sol<br>[Water 0.1%<br>TFA (v/v)] | % Sol<br>[Acetonitrile] | Flow<br>[ml/min] | Temp<br>[° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Method 16

| Method Name: | 003_CA02 |
|---|---|
| Device description: | Waters Acquity, QDa Detector |
| Column: | Sunfire C18__3.0 × 30 mm__2.5 μm |
| Column producer: | Waters |

| Gradient/<br>Solvent Time<br>[min] | % Sol<br>[Water 0.1%<br>TFA (v/v)] | % Sol<br>[Acetonitrile<br>0.08% TFA (v/v)] | Flow<br>[ml/min] | Temp<br>[° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Synthetic Examples

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of invention.

Some of the intermediates described in the Synthetic Examples Section may be drawn for simplicity as free base, but according to the described reaction procedure those compounds may actually form a salt.

Preparation

The compounds according to the invention and their intermediates may be obtained using methods of synthesis which are known to one skilled in the art and described in the literature of organic synthesis for example using methods described in "Comprehensive Organic Transformations", 2$^{nd}$ Edition, Richard C. Larock, John Wiley & Sons, 2010 and "March's Advanced Organic Chemistry", 7$^{th}$ Edition, Michael B. Smith, John Wiley & Sons, 2013. Preferably the compounds are obtained analogously to the methods of preparation explained in more detail hereinafter, in particular as described in the experimental section. In some cases the sequences adopted in carrying out the reaction schemes may be varied. Variants of these reactions, that are known to a person skilled in the art, but are not described in detail here may also be used. The general processes for preparing the compounds according to the invention will become apparent to a person skilled in the art by studying the schemes that follow. Starting compounds are commercially available or may be prepared by methods that are described in the literature or herein, or may be prepared in an analogous or similar manner. Before the reaction is carried out, any functional groups in the starting compounds may be protected using conventional protecting groups. These protecting groups may be cleaved again at a suitable stage within the reaction sequence using methods familiar to the skilled person and described in the literature for example in "Protecting Groups", 3$^{rd}$ Edition, Philip J. Kocienski, Thieme, 2005 and "Protective Groups in Organic Synthesis", 4$^{th}$ Edition, Peter G. M. Wuts, Theodora W. Greene, John Wiley & Sons, 2006.

As depicted in Scheme 1 the compounds of the general formula (I) of the invention can be prepared by the reaction of a suitable carboxylic acid of formula INT-1 (either as a free acid or as a salt with a suitable metal cation such as Li$^+$, Na$^+$, K$^+$, etc.) and a suitable amine intermediate of the general formula INT-2 (either as a free amine or as a salt such as hydrochloride, hydrobromide, etc.) in a suitable solvent (e.g. N,N-dimethylformamide, N,N-dimethylacetamide, 1-methyl-2-pyrrolidinone, dichloromethane, tetrahydrofurane, 1,4-dioxane, etc.) in the presence of a suitable coupling agent (e.g. O-(7-azabenzotriazol-1-yl)-N,N,N',N'-tetramethyluronium hexafluorophosphate (HATU), O-(benzotriazol-1-yl)-N,N-N',N'-tetramethyl-uronium tetrafluoroborate (TBTU), (benzotriazol-1-yloxy)tripyrrolidinophosphonium hexafluorophosphate (PyBOP), carbodiimide reagents, etc.) and a base (e.g. trimethylamine, N,N-diisopropyl-ethylamine, pyridine, etc.) to form an amide bond. The groups/terms R$^1$ to R$^6$, A, U, V, W, X, Y and Z in scheme 1 have the meanings as defined hereinbefore and hereinafter.

ride or oxalyl chloride in dichloromethane) and coupled as such with amine INT-2 in the presence of a suited base (e.g. trimethylamine, N,N-diisopropyl-ethylamine, pyridine, etc.) in an appropriate solvent. Alternatively the carboxylic acid INT-1 can be activated with di(imidazole-1-yl)methanone (CDI) and coupled as such with an amine INT-2 in the presence of a suited base (e.g. trimethylamine, N,N-diisopropyl-ethylamine, etc.) in an appropriate solvent (e.g. N,N-dimethylformamide, N,N-dimethylacetamid, etc.). Intermediates INT-1 and INT-2 are known in the art or can be prepared by the methods described below.

A depicted further below in Scheme 2 compound (I) of the invention can alternatively be prepared from a boronic acid derivative of formula INT-3 and a halogen containing derivative of formula INT-4 by a transition metal catalyzed coupling reaction under appropriate conditions. The groups/terms R$^1$ to R$^6$, A, U, V, W, X, Y and Z in scheme 2 have the meanings as defined hereinbefore and hereinafter. The reaction is preferably performed with a palladium derived catalyst, e.g. [1,1'-bis(diphenylphosphino)-ferrocene]-dichloropalladium(II)—CH$_2$Cl$_2$-complex (PdCl$_2$(dppf)*CH$_2$Cl$_2$) in the presence of a base (e.g. potassium phosphate, sodium carbonate, etc.) in an appropriate solvent (water/tetrahydrofurane, water/1,4-dioxane, 1,4 dioxane or N,N-dimethylformamide, etc.) at 40° C. to 120° C.

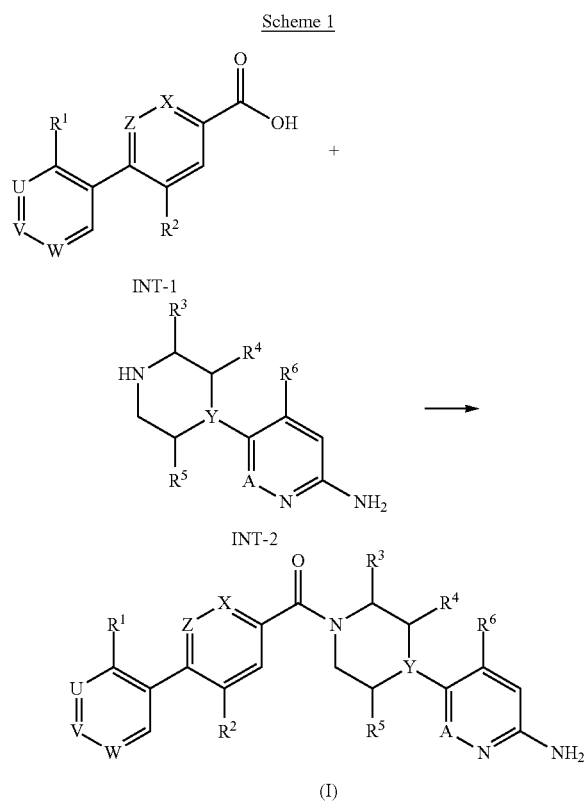

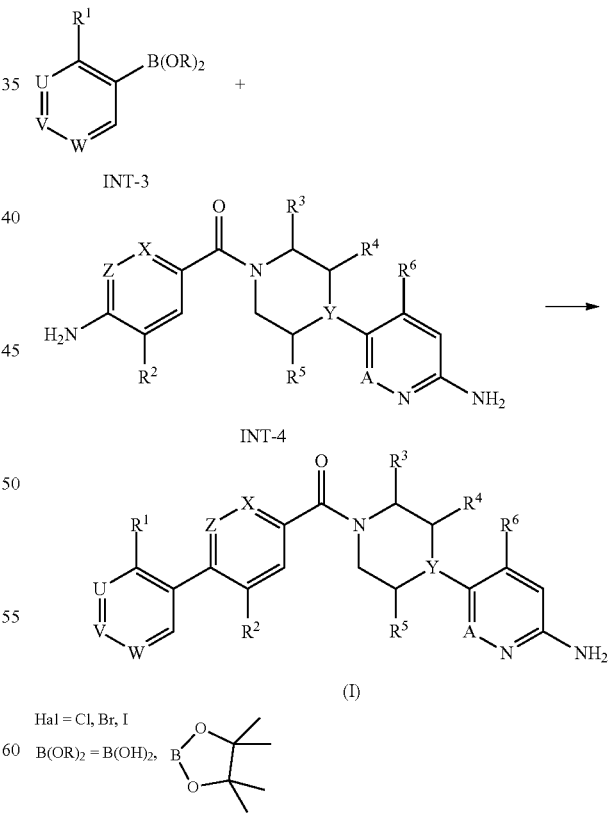

The carboxylic acid INT-1 can alternatively be transformed into a carboxylic chloride (using e.g. thionyl chlo- Intermediates INT-3 and INT-4 are known in the art or commercially available or can be prepared by the methods described below.

As depicted below in Scheme 3 compounds of the general formula (I) of the invention can alternatively be prepared by reacting a halogen containing derivative of formula INT-5 with a boronic acid derivative of formula INT-6 by a transition metal catalyzed coupling reaction under appropriate conditions. The groups/terms $R^1$ to $R^6$, A, U, V, W, X, Y and Z in scheme 3 have the meanings as defined hereinbefore and hereinafter. The reaction is preferably performed with a palladium derived catalyst, e.g. [1,1'-bis(diphenylphosphino)-ferrocene]-dichloropalladium(II)—CH$_2$Cl$_2$-complex (PdCl$_2$(dppf)*CH$_2$Cl$_2$) in the presence of a base (e.g. potassium phosphate, sodium carbonate, etc.) in an appropriate solvent (water/tetrahydrofurane, water/1,4-dioxane, 1,4 dioxane or N,N-dimethylformamide, etc.) at 40° C. to 120° C. The reaction can optionally be performed in a microwave.

derivative of formula INT-5 with a metallated derivative of formula INT-7 under appropriate conditions as depicted below in Scheme 4. The groups/terms $R^1$ to $R^6$, A, U, V, W, X, Y and Z in scheme 4 have the meanings as defined hereinbefore and hereinafter. The reaction is performed with a catalyst preferably with a Palladium catalyst (e.g. tetrakis(triphenylphosphine)palladium) in an appropriate solvent (e.g. 1,4-dioxane, etc.) at 100° C. to 150° C.

Alternatively the reaction is performed with a catalyst preferably with a Palladium catalyst (e.g. tetrakis(triphenylphosphine)palladium, Pd$_2$(dba)$_3$, etc) in the presence of a base (e.g. cesium fluoride, etc.) and a copper-(I) derivative (e.g. CuBr or CuI) in an appropriate solvent (e.g. N,N-dimethylformamide, etc.) at 40° C. to 120° C. An additional ligand can be added (e.g. P(o-McC$_6$H$_4$)$_3$).

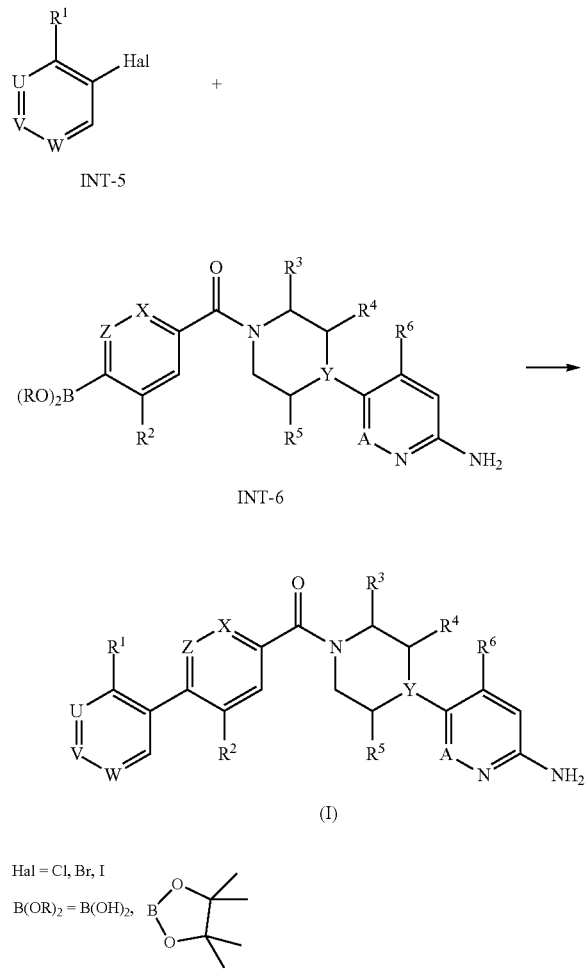

Scheme 3

Hal = Cl, Br, I
B(OR)$_2$ = B(OH)$_2$, pinacol boronate

Intermediates INT-5 and INT-6 are known in the art or commercially available or can be prepared by the methods described below.

Alternatively compounds of the general formula (I) of the invention can be prepared by reacting a halogen containing

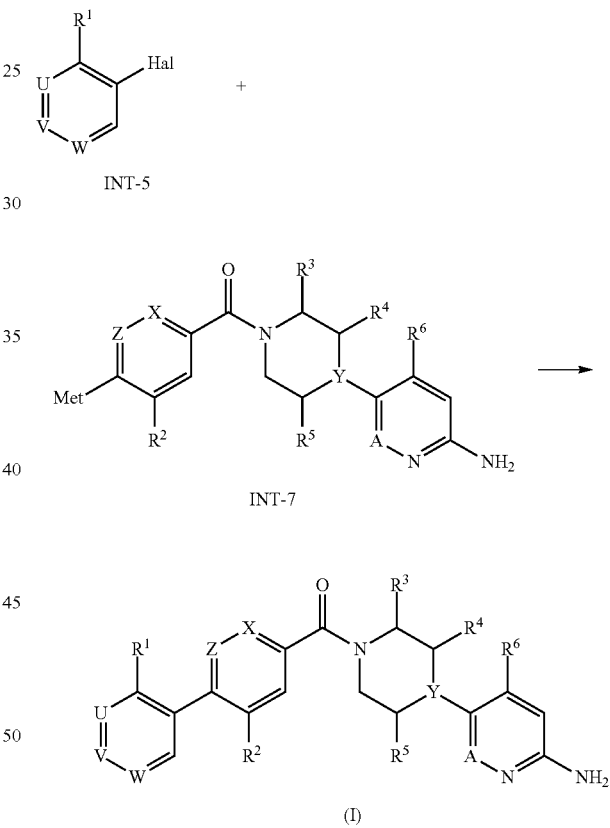

Scheme 4

Hal = Cl, Br, I
Met = (CH$_3$)$_3$Sn, (n-butyl)$_3$Sn

Intermediates INT-5 and INT-7 are known in the art or can be prepared by the methods described below.

The intermediates of the general formula INT-2 shown in scheme 1 can be prepared according to scheme 5. The groups/terms $R^3$ to $R^6$, A and Y=CH in scheme 5 have the meanings as defined hereinbefore and hereinafter.

Intermediate INT-10 can be prepared from boronic acid derivative INT-8 and a halogen containing heteroaromatic derivative INT-9. The reaction is performed with a palladium catalyst (e.g. 1,1'-bis(diphenylphosphino)-ferrocene]-dichloropalladium(II)—$CH_2Cl_2$-complex ($PdCl_2$(dppf)* $CH_2Cl_2$), chloro(2-dicyclohexylphosphino-2',4',6'-triisopropyl-1,1'-biphenyl)[2-(2'-amino-1,1'-biphenyl)]palladium(II) (XPhos Pd $2^{nd}$ generation catalyst), tris(dibenzylideneacetone)-dipalladium $Pd_2$(dba)$_3$ with additional XPhos as ligand, etc.) in the presence of a base (e.g. potassium phosphate, sodium carbonate, etc.) in an appropriate solvent (water/tetrahydrofurane, water/1,4-dioxane, water/n-butanol, 1,4 dioxane or N,N-dimethylformamide, etc.) at elevated temperature e.g. 80° C. to 150° C. The reaction might optionally be performed in a microwave.

In case a heteroaromatic intermediate INT-9 is employed with a protected or masked amino group ($NL_2$ is not $NH_2$) this group can be transformed afterwards into the $NH_2$ group by cleaving off the protective group applying standard procedures reported in the literature of organic chemistry. A tert.-butyl carbonyl group (such as a Boc protecting group) is preferably cleaved under acidic conditions with e.g. trifluoroacetic acid or hydrochloric acid, in a solvent such as dichloromethane, 1,4-dioxane, isopropanol, HCl in 1,4-dioxane or ethyl acetate, etc. A benzyl group can be removed by using hydrogen in the presence of a transition metal such as palladium on carbon. Benzyl groups bearing electron donating groups such as methoxy on the aromatic ring may also be removed under acidic conditions (e.g. with trifluoroacetic acid or hydrochloric acid). The 2,5-dimethylpyrrol ring can be cleaved to release the amino-functionality by hydroxylamine hydrochloride and trimethylamine in an appropriate solvent like a mixture of ethanol and water at elevated temperature preferably 80° C.

The nitrogen-atom of the piperidene ring of the intermediate INT-8 is protected with an appropriate protecting group PG1 (e.g. tert-butyl-oxycarbonyl (Boc), benzyl-oxycarbonyl (Cbz), benzyl (Bn), etc.). The protecting group PG1 can be introduced by methods known to a person skilled in the art.

The position of the double bond in the piperidene-ring of intermediate INT-8 may depend on the substituents $R^3$, $R^4$ and $R^5$. The substituents $R^3$ and $R^4$ of the intermediate INT-8 may contain functional groups which may also bear appropriate protecting groups. In particular hydroxy groups can be protected with appropriate silyl-containing protecting groups (e.g. triethylsilyl, tert.-butyl-dimethylsilyl, etc.). Protecting groups for functional groups at $R^3$ and $R^4$ can be selected in a way, that the protecting groups can be removed without removing PG1 to allow further modifications at $R^3$ and $R^4$. Silyl protecting group can be cleaved e.g. with a fluoride source (e.g. tetra-n-butylammonium fluoride) in a suited solvent (e.g. tetrahydrofuran) at ambient temperature or under acidic conditions (e.g. hydrochloric acid in 1,4-dioxane, HCl in 1,4-dioxane, etc at elevated temperature).

The position of the resulting double bond in the piperidene-ring of intermediate INT-10 may depend on the substituents $R^3$, $R^4$, $R^5$ and $R^6$. The double bond in the piperidene-ring of intermediate INT-10 can be hydrogenated by using hydrogen in the presence of a transition metal, preferably palladium (or Pd(OH)$_2$, etc) on carbon in a solvent such as methanol, ethanol, tetrahydrofuran, 1,4-dioxane, methanol/acetic acid, etc. Preferably hydrogen is applied at 1 to 5 bar pressure and the reaction is performed at room temperature up to 50° C. In case heteroaromatic intermediate INT-10 is employed with a protected or masked amino group ($NL_2$ is not $NH_2$) this group can be transformed into the $NH_2$-group as reported in the literature of organic chemistry or mentioned earlier in this paragraph.

Removal of the protecting group PG1 can be performed as reported in the literature of organic chemistry. A tert.-butyl carbonyl group (Boc) is preferably cleaved under acidic conditions with e.g. trifluoroacetic acid or hydrochloric acid, in a solvent such as dichloromethane, 1,4-dioxane, isopropanol, HCl in 1,4-dioxane or ethyl acetate, etc. A benzyl (Bn) group or a benzyloxycarbonyl (Cbz) group can be removed by using hydrogen in the presence of a transition metal such as palladium on carbon. Benzyl groups bearing electron donating groups such as methoxy on the aromatic ring may also be removed under acidic conditions (e.g. with trifluoroacetic acid or hydrochloric acid). Depending on the reaction conditions the intermediate INT-2 can be obtained either as a free base or as a salt such as hydrochloride, trifluoroacetate, hydrobromide, etc.). The salt of the intermediate INT-2 can be transformed into their neutral counterparts by standard procedures known to the one skilled in the art.

Scheme 5

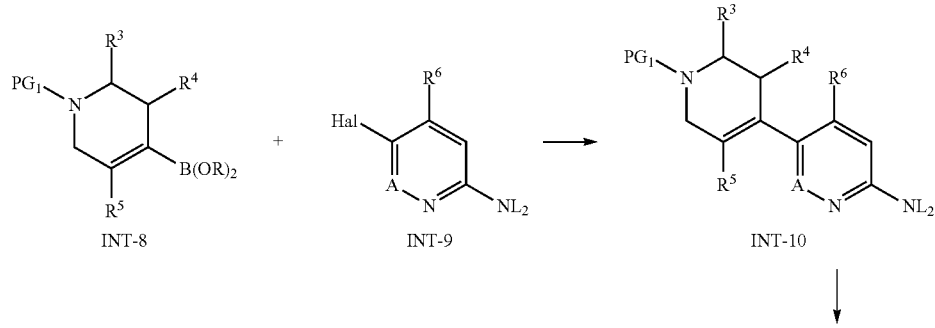

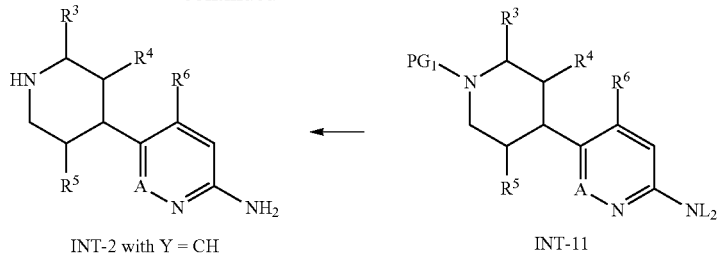

INT-2 with Y = CH    INT-11

Hal, Cl, Br, I

PG₁ = Boc, Cbz or benzyl

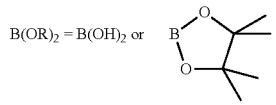

B(OR)₂ = B(OH)₂ or

NL₂ = NH₂ or protected or masked NH2 such as NH—Bn, NH—Boc or

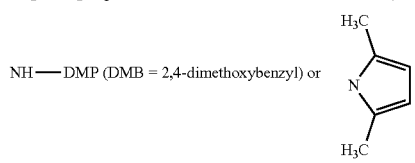

NH—DMP (DMB = 2,4-dimethoxybenzyl) or

The compounds of the general formula INT-2 shown in scheme 1 can be prepared according to scheme 6, if Y=N. The groups/terms $R^3$ to $R^6$, A, and Y=N in scheme 6 have the meanings as defined hereinbefore and hereinafter. The substituents $R^3$ and $R^4$ of the intermediate INT-12 may contain functional groups which may also bear appropriate protecting groups. In particular hydroxy groups can be protected with appropriate silyl-containing protecting groups (e.g. triethylsilyl, tert.-butyl-dimethylsilyl, etc.). Protecting groups for functional groups at $R^3$ and $R^4$ can be selected in a way, that the protecting groups can be removed without removing PG1 to allow further modifications at $R^3$ and $R^4$. Silyl protecting groups can be cleaved e.g. with a fluoride source (e.g. tetra-n-butylammonium fluoride) in a suited solvent (e.g. tetrahydrofuran) at ambient temperature or under acidic conditions (e.g. hydrochloric acid in 1,4-dioxane, HCl in 1,4-dioxane) at elevated temperature.

INT-9 in scheme 6 can be coupled directly with the N-containing heterocycle INT-12 to form the carbon-nitrogen bond to provide intermediate INT-13. The groups/terms $R^3$ to $R^6$, A, and Y=N in scheme 6 have the meanings as defined hereinbefore and hereinafter. The reaction is preferably conducted with a palladium derived catalyst (e.g. 2-(2'-di-tert-butylphosphine)-biphenyl palladium (II) acetate, (2-dicyclohexylphosphino-2',6'-diisopropoxy-1,1-biphenyl)[2-(2'-amino-1,1-biphenyl)]-palladium(II) methanesulfonate (RuPhos Pd 3$^{rd}$ generation), CPhos-3G-palladacycle methane sulfonate, etc.) in the presence of a base (e.g. sodium tert-butoxide, cesium carbonate, etc.) in a suited solvent (e.g. toluene, tetrahydrofuran, 1,4-dioxane, etc.) at 40 to 120° C.

In case the heteroaromatic intermediate INT-9 is employed with a protected or masked amino group (NL₂ is not NH₂) this group can be transformed afterwards into the NH₂ group by cleaving off the protective group applying standard procedures reported in the literature of organic chemistry or as described hereinbefore. This transformation into the NH₂-group may be performed at different stages (e.g. to provide intermediate INT-14 or intermediate INT-2 with Y=N) within the overall synthesis of intermediate INT2 with Y=N as shown in scheme 6 depending on the overall synthesis strategy and overall protecting group strategy.

Scheme 6

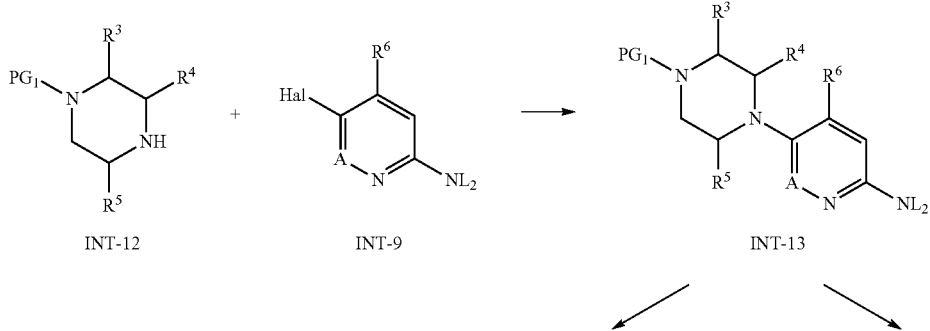

INT-12    INT-9    INT-13

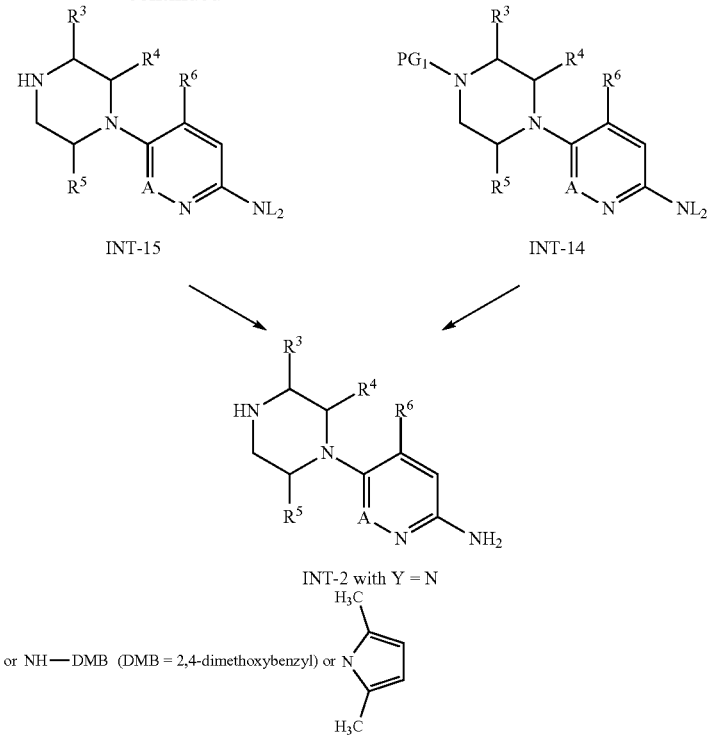

INT-15

INT-14

INT-2 with Y = N

Hal = Cl, Br, I
NL₂ = NH₂ or protected or masked NH₂ such as NH—Bn or NH—DMB (DMB = 2,4-dimethoxybenzyl) or pyrrole
PG₁ = Boc, Cbz or benzyl Removal of the protecting group PG1 can be performed as reported in the literature of organic chemistry or hereinbefore. A tert.-butyl carbonyl group (Boc) is preferably cleaved under acidic conditions with e.g. trifluoroacetic acid or hydrochloric acid, in a solvent such as dichloromethane, 1,4-dioxane, isopropanol, or ethyl acetate. A benzyl (Bn) group or a benzyloxycarbonyl (Cbz) group can be removed by using hydrogen in the presence of a transition metal such as palladium on carbon. Benzyl groups bearing electron donating groups such as methoxy on the aromatic ring may also be removed under acidic conditions (e.g. with trifluoroacetic acid or hydrochloric acid).

Depending on the reaction conditions and the overall deprotection strategy the intermediate INT-2 with Y=N can be obtained either as a free base or as a salt such as hydrochloride, trifluoroacetate, hydrobromide, etc.). Salts can be transformed into their neutral counterparts by standard procedures known to the one skilled in the art. Removal of the protecting group PG1 can be performed at various steps during the overall synthesis of intermediate INT-2 with Y=N (e.g. removal of protecting group PG1 from intermediate INT-13 or intermediate INT-14 as shown in scheme 6) depending on the overall synthesis strategy and deprotection strategy.

The intermediate of the general formula INT-14 can alternatively be prepared according to scheme 7. The groups/terms $R^1$ to $R^6$, A, U, V, W, X and Z in scheme 7 have the meanings as defined hereinbefore and hereinafter and Y=N.

In intermediate INT-16 $NO_n$ represents either a nitro-group (n=2) or a nitroso-group (n=1). Intermediates of the general formula INT-17 can be prepared via a nucleophilic substitution on a electron-poor heteroaromatic derivative of the formula INT-16 bearing either a nitro or nitroso group and a suitable piperazine derivative of formula INT-12 in a suitable solvent (e.g. ethanol) and in the presence of a suitable base (e.g. diisopropyl-ethyl-amine, etc). Alternatively intermediate INT-17 can be prepared by a transition metal catalyzed coupling reaction of a suitable piperazine derivative of formula INT-12 and a heteroaromatic derivative of the formula INT-16 bearing a nitro group (n=2) in the presence of a catalyst preferably a palladium catalyst (e.g. tri(dibenzylideneacetone)dipalladium $Pd_2(dba)_3$, etc.) and a suitable ligand preferably XantPhos (4,5-bis(diphenylphosphino)-9,9-dimethylxanthene) in a suitable solvent (e.g. 1,4-dioxane, etc.) and in the presence of a suitable base (e.g. cesium carbonate, etc.) at higher temperature e.g. 80-120° C.

Intermediate INT-14 can also be synthesized according to scheme 7. The nitroso (n=1) or nitro (n=2) groups of INT-17 can be transformed into an amino group by methods known to a person skilled in the art. Preferably the hydrogenation of INT-17 is performed in a hydrogen atmosphere (e.g. at 1 to 5 bar) and in the presence of a transition metal, preferably palladium on carbon in a solvent such as methanol, ethanol, tetrahydrofuran, 1,4-dioxane, etc. Compound of the general formula (I) can be synthesized from INT-14 according to scheme 7. The reaction from intermediate INT-14 to intermediate INT-2 with Y=N can be performed using the same reaction conditions as described in scheme 6. The reaction from intermediate INT-2 with Y=N to compound of the general formula (I) can be performed using the same reaction conditions as described in scheme 1.

Intermediates of the formula INT-19 can be prepared from compound INT-18 and a carboxylic acid INT-1 as described in scheme 1. Compound of the general formula (I) can be synthesized from INT-19 via conversion of the nitroso (n=1) or nitro (n=2) group to the amino group in analogy to procedures reported in the literature of organic chemistry preferably in a hydrogen atmosphere in the presence of palladium on carbon in a suitable solvent (e.g. methanol, ethanol, etc.).

Scheme 7

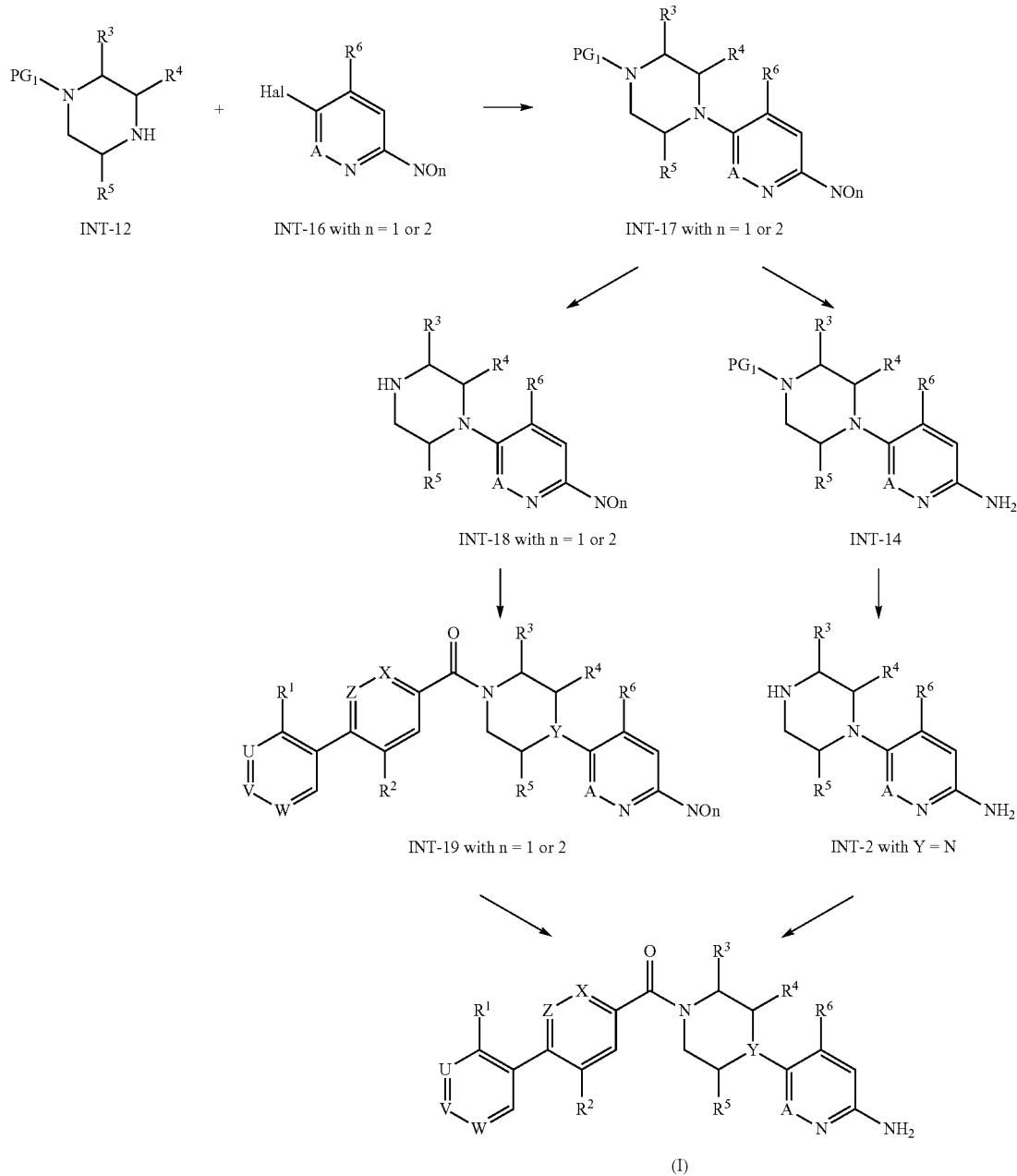

Hal = F, Cl, Br
PG$_1$ = Boc, Cbz or Benzyl
NOn = NO or NO$_2$

As shown in scheme 8 carboxylic acids of formula INT-1, wherein the groups/terms R$^1$ to R$^2$, U, V, W, X and Z have the meanings as defined hereinbefore and hereinafter, are preferably prepared from the corresponding ester of the general formula INT-21 by hydrolysis or hydrogenolysis depending on the nature of the protecting group PG2. If the protecting group PG2 represents lower alkyl group esters such as ethyl or methyl esters, those are preferably cleaved by hydrolysis with a hydroxide base such as NaOH, LiOH or KOH in a mixture of water and a suitable miscible solvent (e.g. tetrahydrofuran, methanol, ethanol, 1,4-dioxane, etc. or mixtures of these), with heating if necessary. The acid INT-1 may be isolated either as a salt with the metal cation or as a free acid. The tert.-butyl ester is preferably cleaved by treatment with an acid (e.g. hydrochloric acid or trifluoro-acetic acid) in a suitable solvent (e.g. dichloromethane, 1,4-dioxane, methanol, ethanol, tetrahydrofuran, water or mixtures of these). A benzyl ester is preferably cleaved by hydrogenolysis with a suitable catalyst (e.g. palladium on carbon, etc) in a suitable solvent (e.g. ethanol, methanol, tetrahydrofuran, dichloromethane, ethylacetate) under an atmosphere of hydrogen (preferably 1 to 5 bar) The ester of the general formula INT-21 can be prepared according to scheme 8 via transition metal catalyzed coupling reaction. A transition metal catalyzed coupling reaction is preferably carried out in analogy to procedures reported in the literature of organic chemistry referred to Suzuki coupling reactions using suitable palladium catalysts, ligands, bases and solvents. The groups/terms $R^1$ to $R^2$, U, V, W, X and Z in scheme 8 have the meanings as defined hereinbefore and hereinafter. The reaction of a boronic acid derivative INT-3 and a halogen containing heteroaromat INT-20 is preferably performed with a palladium derived catalyst, e.g. [chloro(2-dicyclohexylphosphino-2',4',6'-triisopropyl-1,1'-biphenyl)[2-(2'-amino-1,1'-biphenyl)]palladium(II) (XPhos Pd $2^{nd}$ Gen), 1,1'-bis(diphenylphosphino)-ferrocene]-dichloropalladium(II)—$CH_2Cl_2$-complex ($PdCl_2(dppf)*CH_2Cl_2$) in the presence of a base (e.g. potassium phosphate, sodium carbonate, etc.) in an appropriate solvent (water/tetrahydrofuran, water/1,4-dioxane, 1,4 dioxane or N,N-dimethylformamide, etc.) at 40° C. to 120° C.

dium derived catalyst, e.g. [chloro(2-dicyclohexylphosphino-2',4',6'-triisopropyl-1,1'-biphenyl)[2-(2'-amino-1,1'-biphenyl)]palladium(II) (XPhos Pd $2^{nd}$ Gen), 1,1'-bis(diphenylphosphino)-ferrocene]-dichloropalladium(II)—$CH_2Cl_2$-complex ($PdCl_2(dppf)*CH_2Cl_2$) in the presence of a base (e.g. potassium phosphate, sodium carbonate, etc.) in an appropriate solvent (water/tetrahydrofurane, water/1,4-dioxane, 1,4 dioxane or N,N-dimethylformamide, etc.) at 40° C. to 120° C. The reaction might optionally be performed in a microwave.

Scheme 9

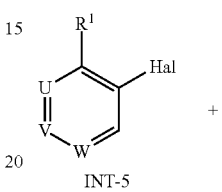

INT-5

Scheme 8

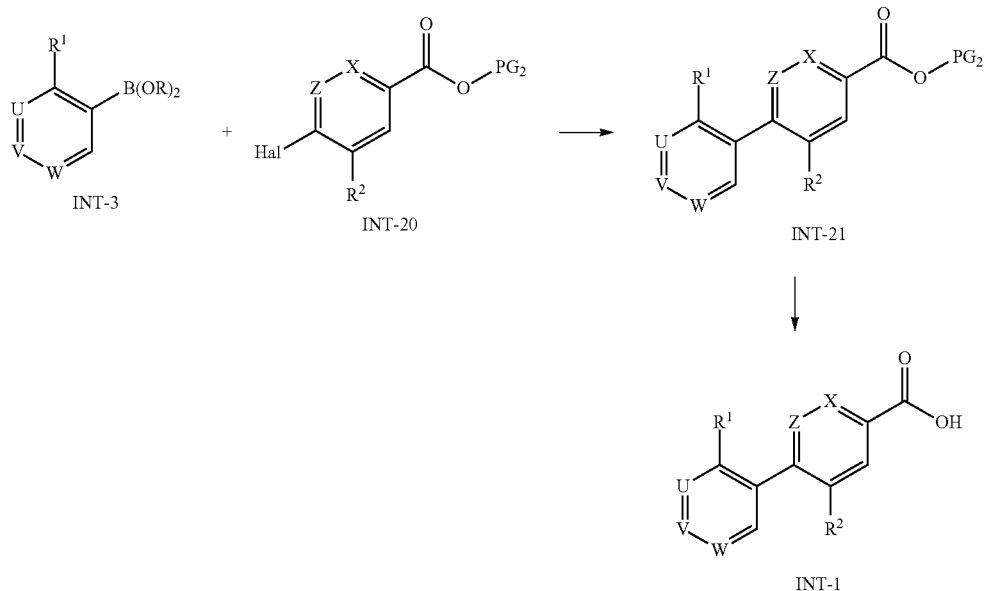

Hal = Cl, Br, I

PG$_2$ = Methyl, ethyl, tert.-butyl, benzyl

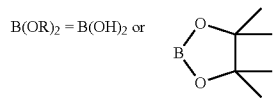

Alternatively the ester of the general formula INT-21 can be synthesized according to scheme 9 via transition metal catalyzed coupling reaction. The groups/terms $R^1$ to $R^2$, U, V, W, X and Z in scheme 9 have the meanings as defined hereinbefore and hereinafter. A transition metal catalyzed coupling reaction is preferably carried out in analogy to procedures reported in the literature of organic chemistry referred to Suzuki coupling reactions using suitable palladium catalysts, ligands, bases and solvents. The reaction of a boronic acid derivative INT-22 and a halogen containing heteroaromat INT-5 is preferably performed with a palla- -continued

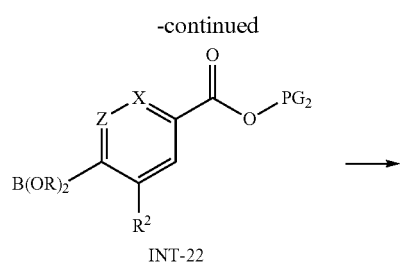

INT-22

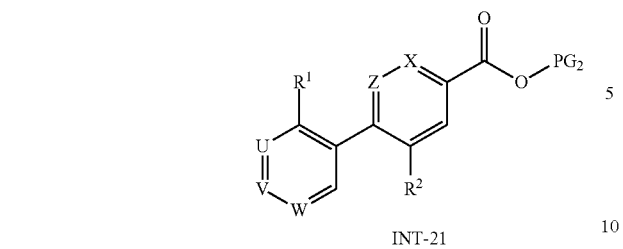

INT-21

Hal = Cl, Br, I

PG$_2$ = methyl, ethyl, tert.-butyl, benzyl

B(OR)$_2$ = B(OH)$_2$ or 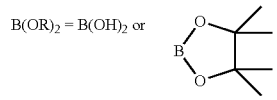

As depicted in Scheme 10 compounds of the general formula INT-6 can be prepared by the reaction of a suitable carboxylic acid INT-23 (either as a free acid or as a salt with a suitable metal cation such as Li$^+$, Na$^+$, etc.) and a suitable amine INT-2 (either a free amine or as salt such as hydrochloride, hydrobromide, etc.) as described for scheme 1. The groups/terms R$^2$ to R$^6$, A, X, Y and Z in scheme 10 have the meanings as defined hereinbefore and hereinafter.

Scheme 10

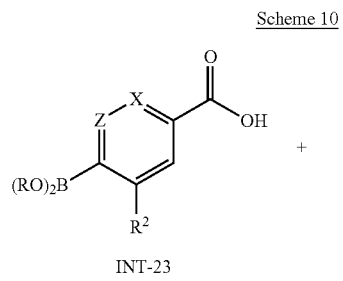

INT-23

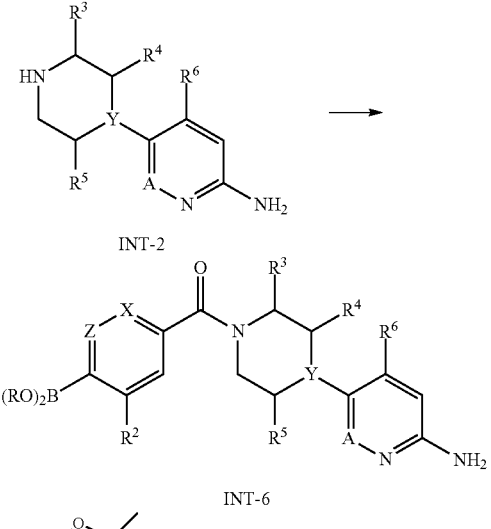

INT-2

INT-6

B(OR)$_2$ = B(OH)$_2$, 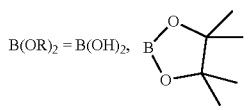

As depicted in Scheme 11 compounds of the general formula INT-4 can be prepared by the reaction of a suitable carboxylic acid INT-24 (either as a free acid or as a salt with a suitable metal cation such as Li$^+$, Na$^+$, etc.) and a suitable amine INT-2 (either a free amine or as salt such as hydrochloride, hydrobromide, etc.) as described for scheme 1. The groups/terms R$^2$ to R$^6$, A, X, Y and Z in scheme 11 have the meanings as defined hereinbefore and hereinafter.

As depicted in scheme 11 intermediate INT-7 can be synthesized via palladium catalyst (e.g. tetrakis(triphenylphosphin palladium, etc.) mediated reaction of an appropriate intermediate INT-4 and a suited stannane derivative (e.g. 1,1,1,2,2,2-hexamethyl-distannane) in a suited solvent (e.g. 1,4-dioxane/dimethylformamide, etc.) at elevated temperature (e.g. 100° C.).

Scheme 11

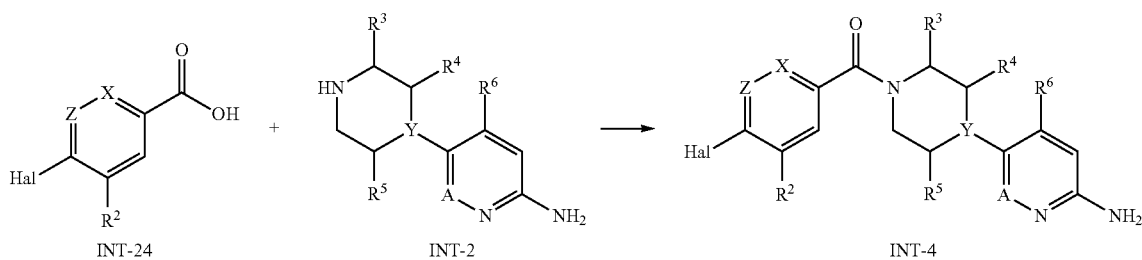

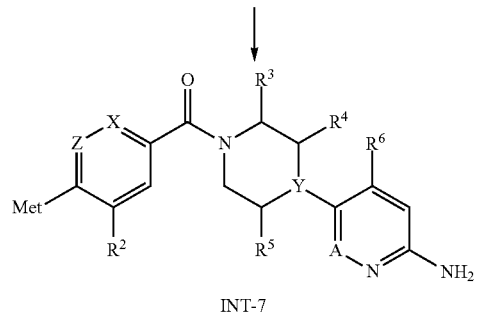

INT-7

Hal = Cl, Br, I
Met = (CH$_3$)$_3$Sn, (n-butyl)$_3$Sn

Synthesis of Intermediates

4-(6-Amino-pyridazin-3-yl)-3,6-dihydro-2H-pyridine-1-carboxylic acid tert-butyl ester

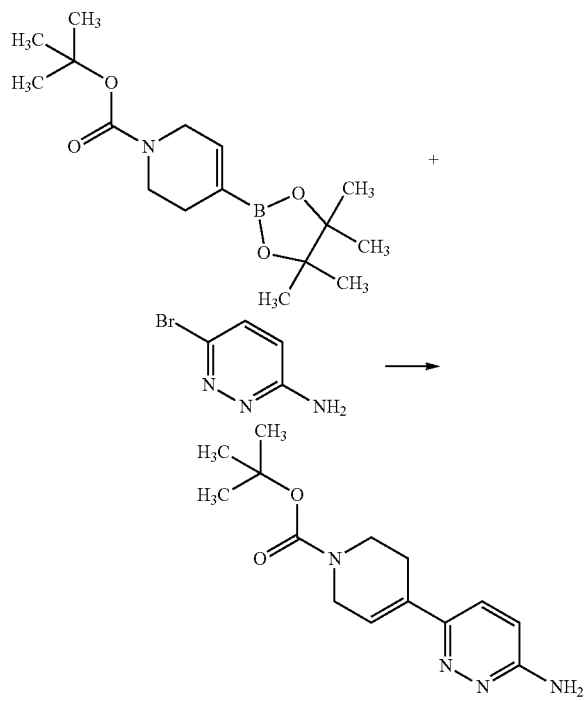

To 4-(4,4,5,5-tetramethyl-[1,3,2]dioxaborolan-2-yl)-3,6-dihydro-2H-pyridine-1-carboxylic acid tert-butyl ester (26.7 g, 86.2 mmol) and 6-bromo-pyridazin-3-ylamine (15.0 g, 86.2 mmol) in n-BuOH/H$_2$O (306 mL/70 mL) is added K$_3$PO$_4$ (64.0 g, 301 mmol) and degassed with argon for 5 min. Then XPhos (4.11 g, 8.62 mmol) and tris(dibenzylideneacetone) dipalladium (3.95 g, 4.31 mmol) is added. The resultant mixture is stirred at 115° C. for 15 h. The reaction mixture is diluted with water and extracted with EtOAc. The combined organic layers are washed with water, brine, dried over Na$_2$SO$_4$, filtered and concentrated under reduced pressure. The crude mixture is purified by column chromatography (MeOH/DCM) to provide the title compound.

Yield: 23.1 g (97%) ESI-MS: m/z=277 (M+H)$^+$ R$_t$(HPLC): 0.44 min (Method 1)

4-(6-Amino-pyridazin-3-yl)-piperidine-1-carboxylic acid tert-butyl ester

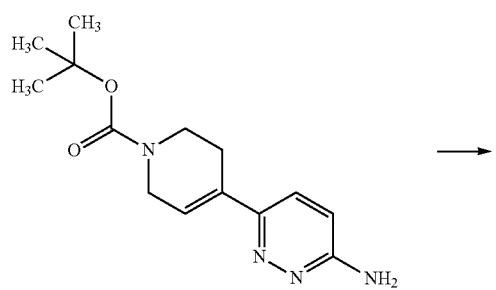

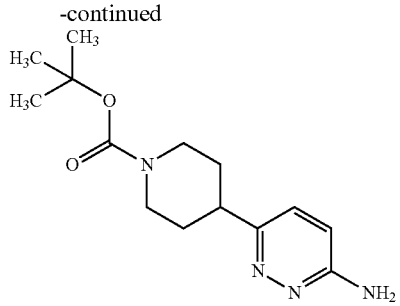

To 4-(6-amino-pyridazin-3-yl)-3,6-dihydro-2H-pyridine-1-carboxylic acid tert-butyl ester (20.0 g, 72.3 mmol) in ethanol (400 mL) is added Pd(OH)$_2$ on carbon (2.03 g, 14.4 mmol) under nitrogen atmosphere and then the reaction mixture is stirred at 60 PSI hydrogen pressure in a PARR Shaker for 16 h. The reaction mixture is filtered through Celite®. The filtrate is evaporated under reduced pressure, and the resulting crude material is purified by column chromatography using silica gel to provide the title compound.

Yield: 10.6 g (53%) ESI-MS: m/z=279 (M+H)$^+$ R$_t$(HPLC): 0.38 min (Method 1)

6-Piperidin-4-yl-pyridazin-3-ylamine dihydrochloride

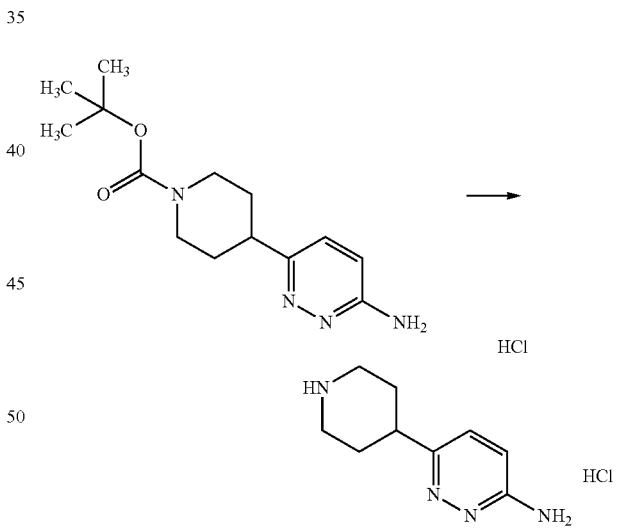

To 4-(6-amino-pyridazin-3-yl)-piperidine-1-carboxylic acid tert-butyl ester (10.0 g, 35.9 mmol) in 1,4-dioxane (35 mL) is added 4M hydrogen chloride solution in dioxane (45 mL, 179.6 mmol). The reaction mixture is stirred for 3 h at ambient temperature. All volatiles are removed under reduced pressure, and the resulting crude material is washed with hexane to afford the title compound.

Yield: 8.0 g (89%) ESI-MS: m/z=179 (M+H)$^+$ R$_t$(HPLC): 0.34 min (Method 4)

6-Piperidin-4-yl-pyridazin-3-ylamine

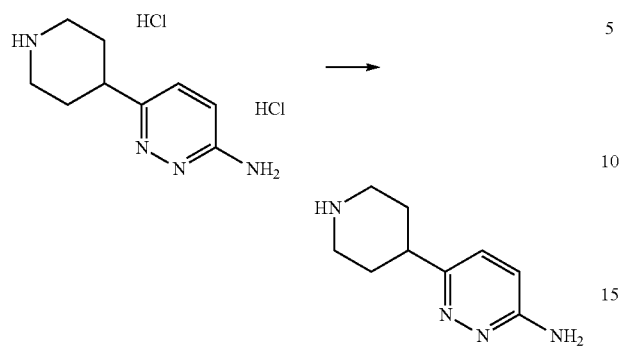

6-Piperidin-4-yl-pyridazin-3-ylamine dihydrochloride is dissolved in an appropriate volume of methanol and purified by HPLC (basic conditions, XBridge, gradient: ACN/water+ NH$_3$) to obtain the corresponding free base.

Alternatively the free base can be obtained in the following reaction step by adding two additional equivalents of base to the reaction mixture.

ESI-MS: m/z=179 (M+H)$^+$ R$_t$(HPLC): 0.31 min (Method 9)

5-Bromo-4-methoxy-pyridine-2-carboxylic acid

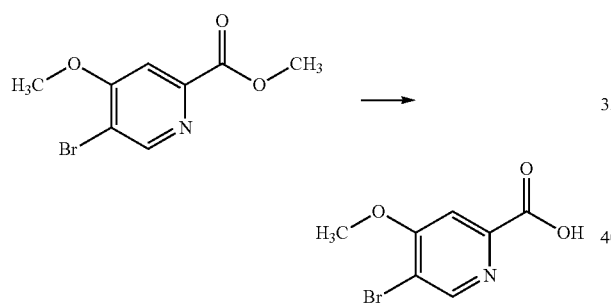

To 5-bromo-4-methoxy-pyridine-2-carboxylic acid methyl ester (1.0 g, 4.06 mmol) in MeOH/water/THF 1/1/1 (10 mL) is added LiOH (325 mg, 8.13 mmol) and stirred for 16 h at rt. All volatiles are removed under reduced pressure. The crude product is dissolved in water (10 mL) and washed with EtOAc (10 mL). The aqueous layer is acidified with 1N HCl up to neutral pH. The precipitate is collected and dried to provide the title compound.

Yield: 863 mg (92%)

[4-(6-Amino-pyridazin-3-yl)-piperidin-1-yl]-(5-bromo-4-methoxy-pyridin-2-yl)-methanone

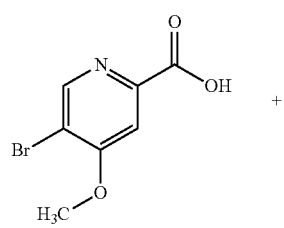

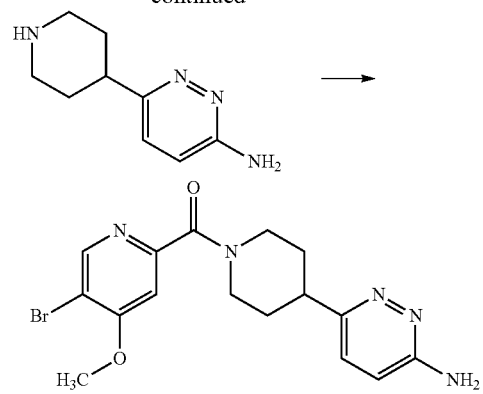

To 5-bromo-4-methoxy-pyridine-2-carboxylic acid (0.40 g, 1.72 mmol), TBTU (0.55 g, 1.72 mmol) and triethylamine (0.72 mL, 5.17 mmol) in DMF (1 mL) is added 6-piperidin-4-yl-pyridazin-3-ylamine (307 mg, 1.72 mmol). The reaction mixture is stirred for 2 h at rt and purified by silica gel chromatography to afford the title compound.

Yield: 588 mg (87%) ESI-MS: m/z=394 (M+H)$^+$

[4-(6-Amino-pyridazin-3-yl)-piperidin-1-yl]-(4-bromo-3-methoxy-phenyl)-methanone

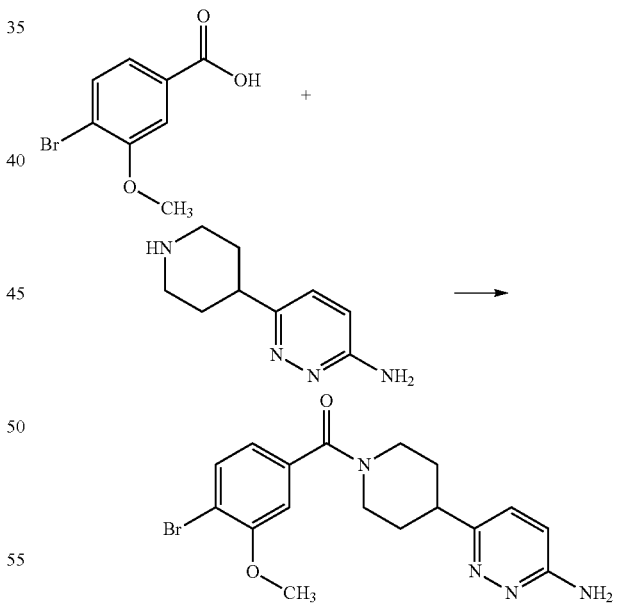

To 4-bromo-3-methoxy-benzoic acid (100 mg, 0.42 mmol) in DMF (1 mL) is added triethylamine (180 μL, 1.30 mmol), TBTU (139 mg, 0.43 mmol) and piperidin-4-yl-pyridazin-3-ylamine (77.0 mg, 0.43 mmol). The reaction mixture is stirred for 2 h at rt and purified by HPLC to provide the title compound.

Yield: 63.0 mg (37%) ESI-MS: m/z=393 (M+H)$^+$

[4-(6-Amino-pyridazin-3-yl)-piperidin-1-yl]-(4-bromo-3-methyl-phenyl)-methanone

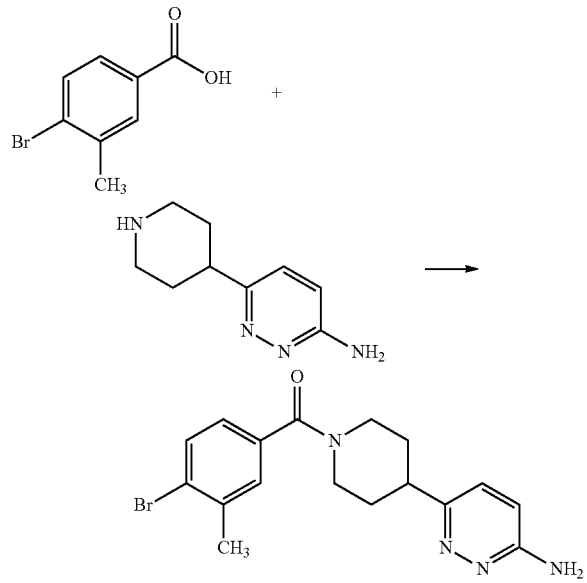

The title compound is synthesized from 4-bromo-3-methyl-benzoic acid (100 mg, 0.47 mmol) and piperidin-4-yl-pyridazin-3-ylamine (83.0 mg, 0.47 mmol) according to the procedure described for the synthesis of the intermediate [4-(6-amino-pyridazin-3-yl)-piperidin-1-yl]-(4-bromo-3-methoxy-phenyl)-methanone.

Yield: 112 mg (64%) [4-(6-Amino-pyridazin-3-yl)-piperidin-1-yl]-(5-bromo-6-methoxy-pyridin-2-yl)-methanone

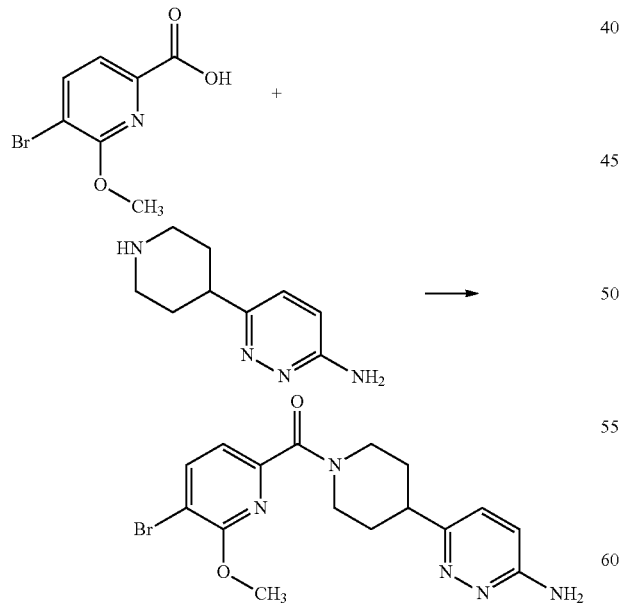

The title compound is synthesized from 5-bromo-6-methoxy-pyridine-2-carboxylic acid (100 mg, 0.43 mmol) and piperidin-4-yl-pyridazin-3-ylamine (77.0 mg, 0.43 mmol) according to the procedure described for the synthe-sis of the intermediate [4-(6-amino-pyridazin-3-yl)-piperidin-1-yl]-(4-bromo-3-methoxy-phenyl)-methanone.

Yield: 149 mg (88%) [4-(6-Amino-pyridazin-3-yl)-piperidin-1-yl]-(6-bromo-5-methoxy-pyridin-3-yl)-methanone

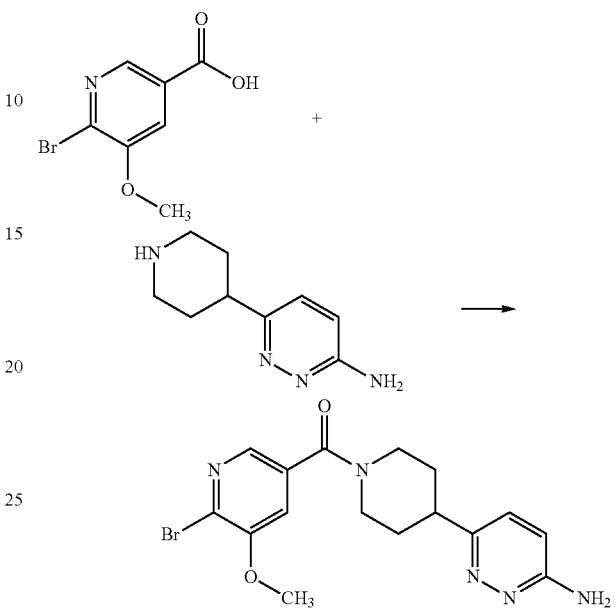

The title compound is synthesized from 6-bromo-5-methoxy-nicotinic acid (250 mg, 1.08 mmol) and piperidin-4-yl-pyridazin-3-ylamine (192 mg, 1.08 mmol) according to the procedure described for the synthesis of the intermediate [4-(6-amino-pyridazin-3-yl)-piperidin-1-yl]-(4-bromo-3-methoxy-phenyl)-methanone.

Yield: 368 mg (87%)

{4-[4-(6-Aminopyridazin-3-yl)piperidine-1-carbonyl]-2-methoxphenylboronic acid

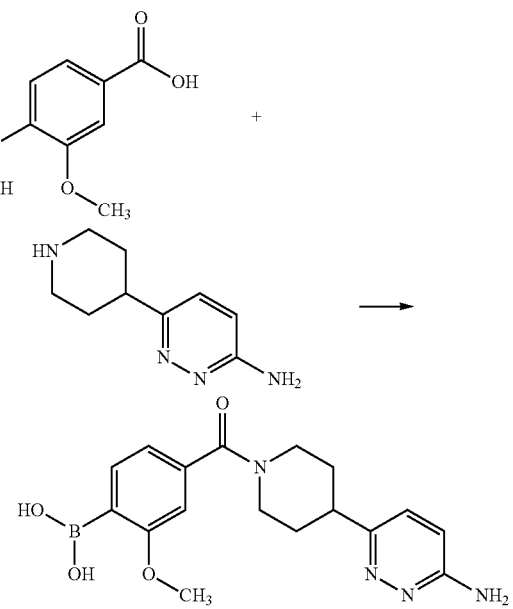

The title compound is synthesized from 4-borono-3-methoxybenzoic acid (1.0 g, 5.10 mmol) and piperidin-4-yl-pyridazin-3-ylamine (1.64 g, 7.65 mmol) according to the procedure described for the synthesis of the intermediate [4-(6-amino-pyridazin-3-yl)-piperidin-1-yl]-(4-bromo-3-methoxy-phenyl)-methanone. The purification of the product is done by column chromatography using silica gel (DCM/MeOH with 1% aqueous NH$_4$OH).

Yield: 335 mg (18%)

[4-(6-Amino-pyridazin-3-yl)-piperidin-1-yl]-(4-bromo-2-methoxy-phenyl)-methanone

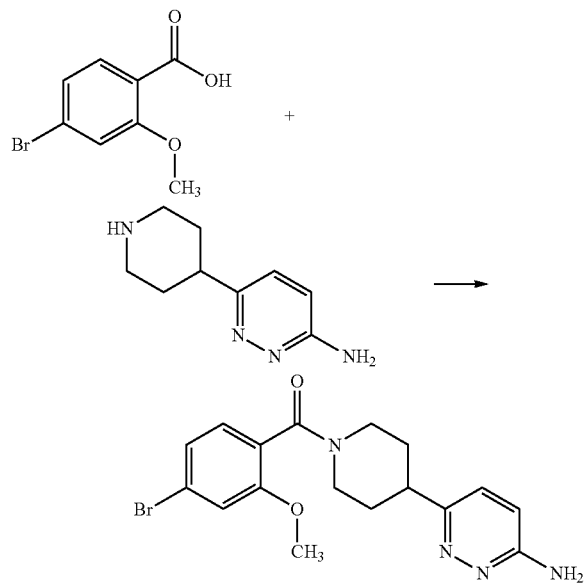

The title compound is synthesized from 4-bromo-2-methoxy-benzoic acid (250 mg, 1.08 mmol) and piperidin-4-yl-pyridazin-3-ylamine (192 mg, 1.08 mmol) according to the procedure described for the synthesis of the intermediate [4-(6-amino-pyridazin-3-yl)-piperidin-1-yl]-(4-bromo-3-methoxy-phenyl)-methanone.

Yield: 313 mg (74%)

6-[1-(4-bromo-3-ethylbenzoyl)piperidin-4-yl]pyridazin-3-amine

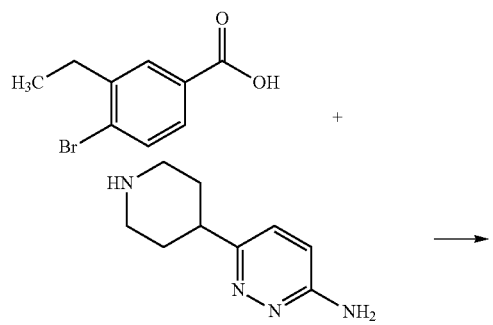

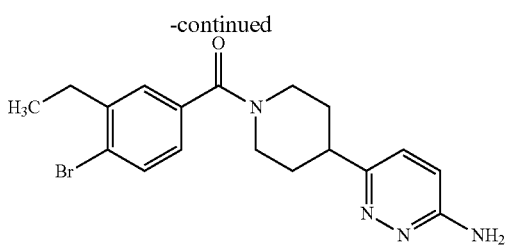

Piperidin-4-yl-pyridazin-3-ylamine (351 mg, 1.64 mmol) is added to 4-bromo-3-ethylbenzoic acid (250 mg, 1.09 mmol) and TBTU (1.05 g, 3.27 mmol) in DMA. Triethylamine (760 µL, 5.46 mmol) is added to the reaction mixture. The reaction mixture is stirred for 24 h at RT. The volatiles are removed under reduced pressure and the residue is purified by column chromatography using silica gel (DCM/MeOH with 1% aqueous NH$_4$OH) to obtain the desired product.

Yield: 334 mg (79%)

4-(6-Nitro-pyridin-3-yl)-piperazine-1-carboxylic acid tert-butyl ester

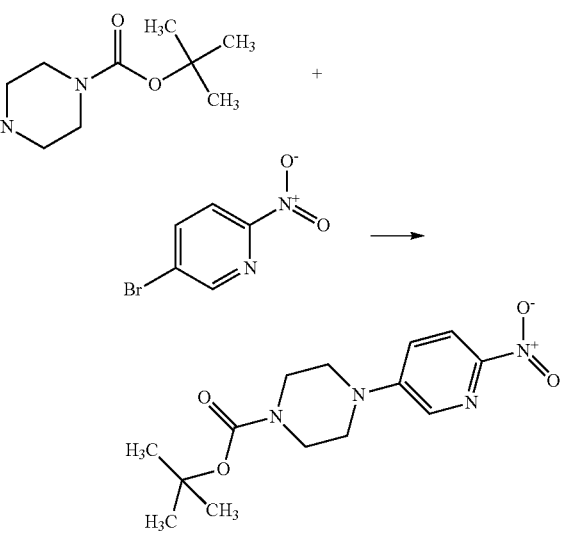

Piperazine-1-carboxylic acid tert-butyl ester (3.0 g, 16.11 mmol), 5-bromo-2-nitro-pyridine (3.3 g, 16.11 mmol) and DIPEA (6.2 g, 48.32 mmol) in ethanol (30 mL) are stirred at rt for 20 h. The reaction mixture is concentrated under reduces pressure and the residue is diluted with ethyl acetate and water. The organic layer is washed with water, brine, dried over MgSO$_4$, filtered and concentrated under reduces pressure. The residue is purified with column chromatography using silica gel (EtOAc/heptane) to afford the title compound.

Yield: 1.34 g (27%) ESI-MS: m/z=309 (M+H)$^+$
R$_t$(HPLC): 0.89 min (Method 1)

4-(6-Amino-pyridin-3-yl)-piperazine-1-carboxylic acid tert-butyl ester

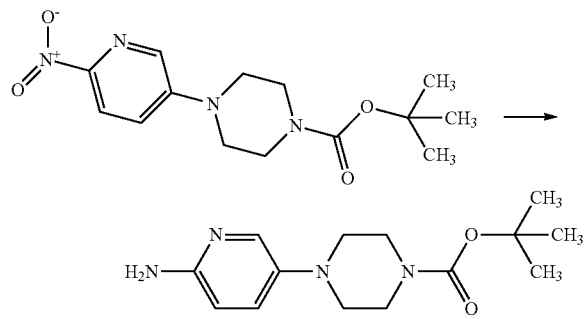

To 4-(6-nitro-pyridin-3-yl)-piperazine-1-carboxylic acid tert-butyl ester (2.0 g, 6.43 mmol) in EtOH (15 mL) is added Pd/C (200 mg) under a hydrogen atmosphere maintained by a $H_2$ balloon for 3 h. The reaction mixture is filtered and the filtrate is concentrated under reduced pressure to afford the crude title compound.
Yield: 1.90 g (quantitative)

5-Piperazin-1-yl-pyridin-2-ylamine dihydrochloride

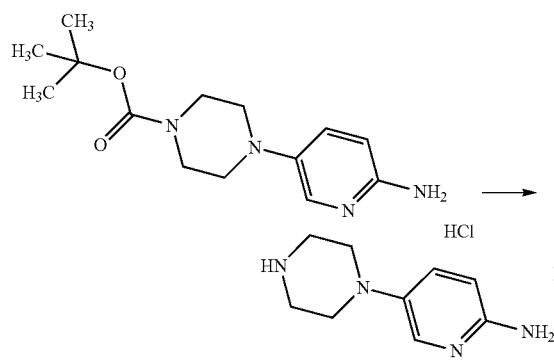

The title compound is synthesized from 4-(6-amino-pyridin-3-yl)-piperazine-1-carboxylic acid tert-butyl ester (1.00 g, 3.59 mmol) according to the procedure described for the synthesis of the intermediate 6-piperidin-4-yl-pyridazin-3-ylamine dihydrochloride.
Yield: 590 mg (92%)

5-Piperazin-1-yl-pyridin-2-ylamine

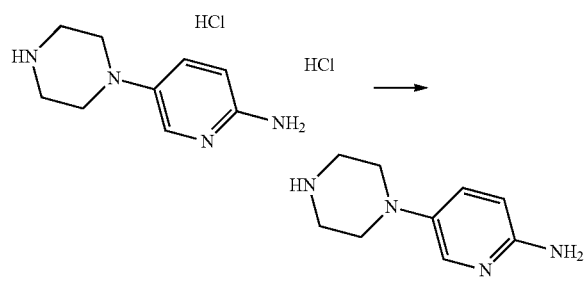

The title compound can be synthesized from 5-piperazin-1-yl-pyridin-2-ylamine dihydrochloride analog to the procedure described for 6-piperidin-4-yl-pyridazin-3-ylamine. Alternatively the free base can be obtained in the following reaction step by adding two additional equivalents of base to the reaction mixture.

6-Amino-3',4',5',6'-tetrahydro-2'H-[3,4']bipyridinyl-1'-carboxylic acid tert-butyl ester

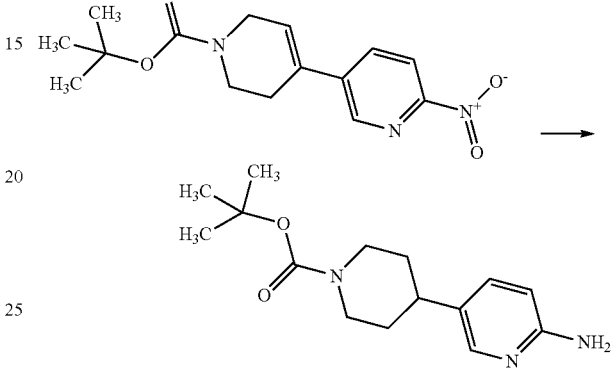

To 6-nitro-3',6'-dihydro-2'H-[3,4']bipyridinyl-1'-carboxylic acid tert-butyl ester (10.0 g, 36.3 mmol) in ethanol (250 mL) is added $Pd(OH)_2$ on carbon (255 mg, 1.82 mmol) under a nitrogen atmosphere and the reaction mixture is stirred at 30 psi $H_2$ pressure in a PARR Shaker for 16 h. The reaction mixture is filtered through Celite®, the filtrate is evaporated under reduced pressure, and the resulting crude material is purified by column chromatography using silica gel to afford the title compound.
Yield: 4.90 g (49%)

5-(Piperidin-4-yl)pyridin-2-amine dihydrochloride

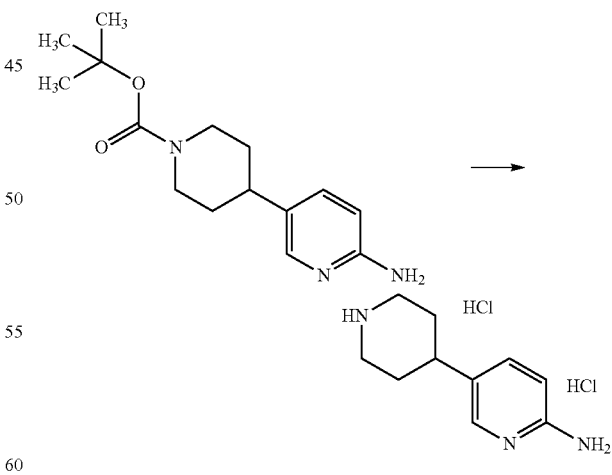

6-amino-3',4',5',6'-tetrahydro-2'H-[3,4']bipyridinyl-1-carboxylic acid tert-butyl ester (0.8 g, 2.88 mmol) in dichloromethane (8 mL) is added 4N HCl in dioxane (7.2 mL, 28.8 mmol). The reaction mixture is stirred for 4 h at RT. The reaction mixture is concentrated under reduced pressure. The desired product is used without further purification.
Yield: 694 mg (96%)

91

5-(Piperidin-4-yl)pyridin-2-amine

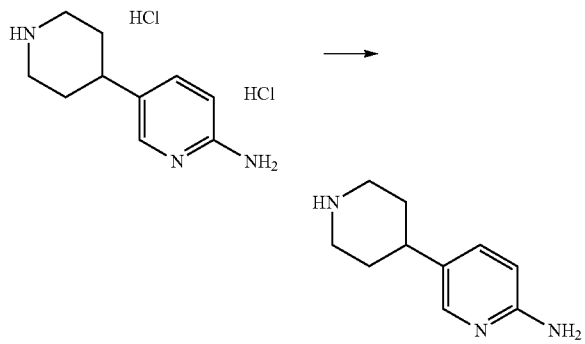

5-(Piperidin-4-yl)pyridin-2-amine can be obtained from 5-(piperidin-4-yl)pyridin-2-amine dihydrochloride in an analogous procedure as described for 6-piperidin-4-yl-pyridazin-3-ylamine. Alternatively the free base can be obtained in the following reaction step by adding two additional equivalents of base to the reaction mixture.

[4-(6-Amino-pyridazin-3-yl)-piperidin-1-yl]-(5-bromo-4-methoxy-pyridin-2-yl)-methanone

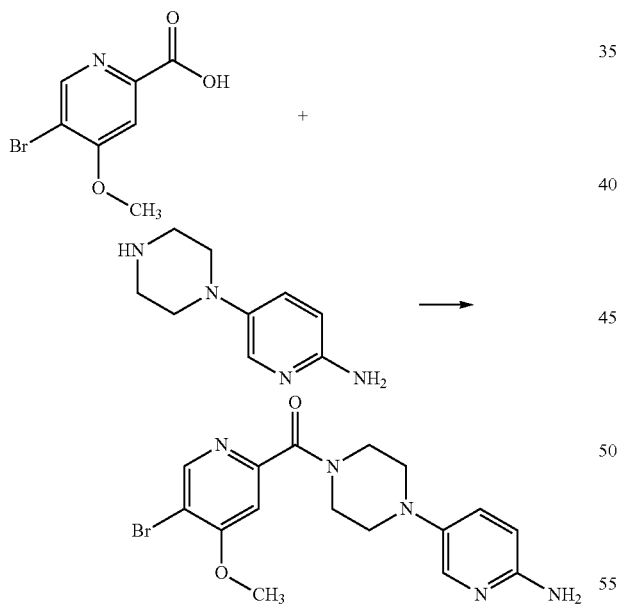

The title compound is synthesized from 5-bromo-4-methoxy-pyridine-2-carboxylic acid (200 mg, 0.86 mmol) and 6-piperidin-4-yl-pyridazin-3-ylamine (154 mg, 0.86 mmol) according to the procedure described for the synthesis of the intermediate [4-(6-amino-pyridazin-3-yl)-piperidin-1-yl]-(4-bromo-3-methoxy-phenyl)-methanone. The purification is done by silica gel chromatography.

Yield: 118 mg (35%)

92

{4-[4-(6-Aminopyridazin-3-yl)piperidine-1-carbonyl]phenyl}boronic acid

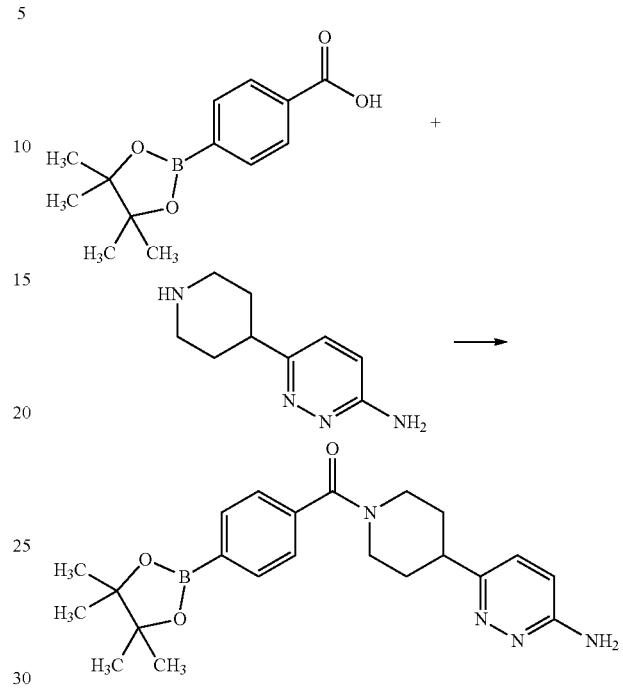

The title compound is synthesized from 4-(4,4,5,5-tetramethyl-[1,3,2]dioxaborolan-2-yl)-benzoic acid (500 mg, 2.02 mmol) and 6-piperidin-4-yl-pyridazin-3-ylamine (359 mg, 2.02 mmol) according to the procedure described for the synthesis of the intermediate [4-(6-amino-pyridazin-3-yl)-piperidin-1-yl]-(4-bromo-3-methoxy-phenyl)-methanone.

Yield: 411 mg (50%)

[4-(6-Amino-pyridazin-3-yl)-piperidin-1-yl]-(4-bromo-2-methyl-phenyl)-methanone

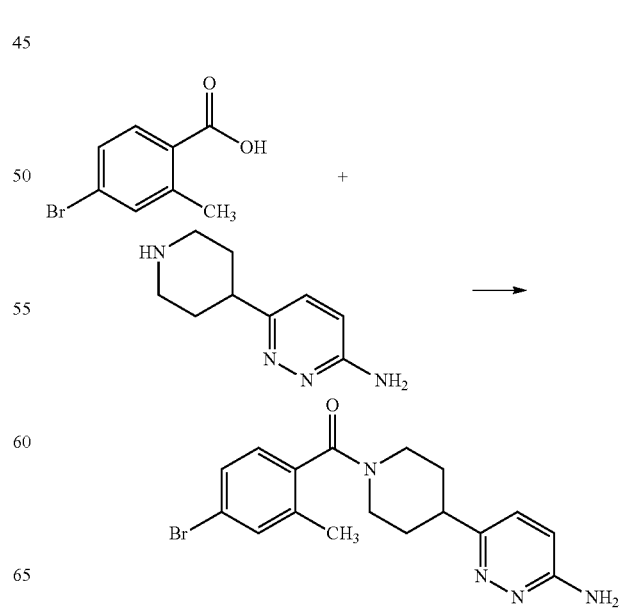

The title compound is synthesized from 4-bromo-2-methyl-benzoic acid (250 mg, 1.16 mmol) and 6-piperidin-4-yl-pyridazin-3-ylamine (207 mg, 1.16 mmol) according to the procedure described for the synthesis of the intermediate [4-(6-amino-pyridazin-3-yl)-piperidin-1-yl]-(4-bromo-3-methoxy-phenyl)-methanone.

Yield: 393 mg (90%)

5-[1-(5-Bromo-4-methoxypyridine-2-carbonyl)piperidin-4-yl]pyridin-2-amine

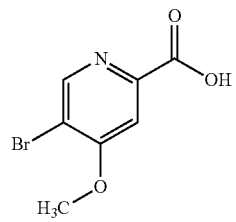

5-Bromo-4-methoxy-pyridine-2-carboxylic acid (500 mg, 2.16 mmol), CDI (1.05 g, 6.47 mmol) and diisopropylethylamine (6.47 mmol) in an appropriate volume of DMA (3 mL) are stirred for 30 min at RT. 5-(Piperidin-4-yl)pyridin-2-amine dihydrochloride (552 mg, 2.21 mmol) is added and the reaction mixture is stirred for 24 h at RT. The volatiles are removed under reduced pressure and the residue is dissolved in EtOAc and 10% aqueous NaHCO₃ solution. The layers are separated and the aqueous phase is extracted with EtOAc (2 times). The combined organic layers are washed with brine, dried, filtered and concentrated under reduced pressure. The residue is purified by column chromatography on silica gel (DCM/MeOH).

Yield: 0.55 g (63%)

Synthesis of Compounds

General Procedure I

The carboxylic acid (1 eq.) (intermediate 2 in the following table 2) and TBTU (1 eq.) in an appropriate volume of DMF (approximately 0.5 mL DMF per 0.4 mmol intermediate 1) is stirred for 15 min at RT and added to an amine (1 eq.) (intermediate 1 in the following table 2) and triethylamine (3 eq.) in an appropriate volume of DMF (approximately 0.5 mL DMF per 0.4 mmol intermediate 1). The reaction mixture is stirred at rt for 2 h. The crude reaction mixture is purified using reversed phase HPLC (acidic or basic conditions) to afford the product.

TABLE 2

Compounds of the invention 1-12.

| Cpd | Amine intermediate (intermediate 1) | Carboxylic acid (intermediate 2) | Yield % | ESI-MS m/z [M + H]⁺ | HPLC R_t (min.) | HPLC Method |
|---|---|---|---|---|---|---|
| 1 | 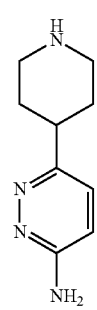 | 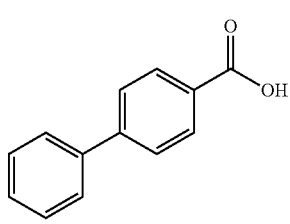 [SMILES: O=C(O)c1ccc(-c2ccccc2)cc1] | 42 | 359 | 0.59 | 16 |

TABLE 2-continued

Compounds of the invention 1-12.

| Cpd | Amine intermediate (intermediate 1) | Carboxylic acid (intermediate 2) | Yield % | ESI-MS m/z [M + H]+ | HPLC R$_t$ (min.) | HPLC Method |
|---|---|---|---|---|---|---|
| 2 | 4-(6-aminopyridazin-3-yl)piperidine | 4'-ethyl-[1,1'-biphenyl]-4-carboxylic acid | 7 | 387 | 0.70 | 16 |
| 3 | 4-(6-aminopyridazin-3-yl)piperidine | 4'-methyl-[1,1'-biphenyl]-4-carboxylic acid | 11 | 373 | 0.65 | 16 |
| 4 | 4-(6-aminopyridazin-3-yl)piperidine | 4'-chloro-[1,1'-biphenyl]-4-carboxylic acid | 30 | 393 | 0.67 | 16 |
| 5 | 4-(6-aminopyridazin-3-yl)piperidine | 4'-methoxy-[1,1'-biphenyl]-4-carboxylic acid | 6 | 389 | 0.58 | 16 |
| 6 | 4-(6-aminopyridazin-3-yl)piperidine | 3'-chloro-[1,1'-biphenyl]-4-carboxylic acid | 30 | 393 | 0.63 | 16 |

TABLE 2-continued

Compounds of the invention 1-12.

| Cpd | Amine intermediate (intermediate 1) | Carboxylic acid (intermediate 2) | Yield % | ESI-MS m/z [M + H]+ | HPLC R$_t$ (min.) | HPLC Method |
|---|---|---|---|---|---|---|
| 7 | piperidin-4-yl-pyridazin-3-amine | 4'-fluoro-[1,1'-biphenyl]-4-carboxylic acid | 8 | 377 | 0.61 | 16 |
| 8 | piperidin-4-yl-pyridazin-3-amine | 3'-fluoro-[1,1'-biphenyl]-4-carboxylic acid | 9 | 377 | 0.61 | 16 |
| 9 | piperidin-4-yl-pyridazin-3-amine | 3'-methoxy-[1,1'-biphenyl]-4-carboxylic acid | 8 | 390 | 0.59 | 16 |
| 10 | piperidin-4-yl-pyridazin-3-amine | 4'-tert-butyl-[1,1'-biphenyl]-4-carboxylic acid | 37 | 415 | 0.77 | 16 |
| 11 | piperidin-4-yl-pyridazin-3-amine | dibenzofuran-3-carboxylic acid | 11 | 374 | 0.58 | 16 |

TABLE 2-continued

Compounds of the invention 1-12.

| Cpd | Amine intermediate (intermediate 1) | Carboxylic acid (intermediate 2) | Yield % | ESI-MS m/z [M + H]+ | HPLC R$_t$ (min.) | HPLC Method |
|---|---|---|---|---|---|---|
| 12 | piperazine-pyridin-2-amine | 4'-(trifluoromethyl)-[1,1'-biphenyl]-4-carboxylic acid | 39 | 427 | 0.70 | 16 |

General Procedure II

To the Br-intermediate (1 eq.) (intermediate 1 in the following table 3) in an appropriate volume of water and 1,4-dioxane (water/dioxane approximately 0.25 mL/2.0 mL per 0.06 mmol up to 2.5 mmol intermediate 1) is added $K_3PO_4$ (2 eq.) and boronic acid (1 eq. up to 1.5 eq.) (intermediate 2 in the following table 3) and degassed with argon for 5 min. Then $PdCl_2(dppf)*CH_2Cl_2$ (0.2 eq.) is added and degassed with argon for 5 min again. The resultant mixture is stirred at 120° C. for 10 min or until reaction is completed (60 min or overnight). Afterwards the reaction mixture is filtered and purified by reversed phase HPLC (acidic or basic conditions).

TABLE 3

Compounds of the invention 13-72.

| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 13 | aminopyridazine-piperidine-(5-bromo-4-methoxypyridin-2-yl)methanone | (4-(trifluoromethoxy)-3-methoxyphenyl)boronic acid | 40 | 504.5 | 0.98 | 5 |
| 14 | aminopyridazine-piperidine-(5-bromo-4-methoxypyridin-2-yl)methanone | (4-fluoro-3-methoxyphenyl)boronic acid | 37 | 438 | 0.55 | 5 |

TABLE 3-continued

Compounds of the invention 13-72.

| Cpd | Br-Intermediate (Intermediate 1) | Boronic acid (intermediate 2) | Yield % | ESI-MS m/z [M + H]⁺ | HPLC R$_t$ (min.) | HPLC Method |
|---|---|---|---|---|---|---|
| 15 | [structure] | [structure] | 21 | 506.5 | 0.93 | 5 |
| 16 | [structure] | [structure] | 9 | 432 | 0.48 | 5 |
| 17 | [structure] | [structure] | 20 | 461 | 0.56 | 16 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 18 | (structure) | (structure) | 20 | 494 | 1.16 | 5 |
| 19 | (structure) | (structure) | 15 | 482 | 1.12 | 5 |
| 20 | (structure) | (structure) | 15 | 466.5 | 0.93 | 5 |

TABLE 3-continued
Compounds of the invention 13-72.
| Cpd | Br-Intermediate (Intermediate 1) | Boronic acid (intermediate 2) | Yield % | ESI-MS m/z [M + H]$^+$ | HPLC R$_t$ (min.) | HPLC Method |
|---|---|---|---|---|---|---|
| 21 | 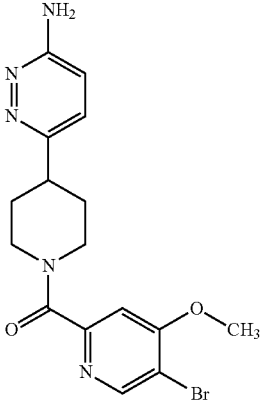 [SMILES: COc1cc(C(=O)N2CCC(c3ccc(N)nn3)CC2)ncc1Br] | 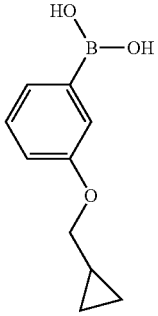 [SMILES: OB(O)c1cccc(OCC2CC2)c1] | 11 | 460 | 0.58 | 16 |
| 22 | 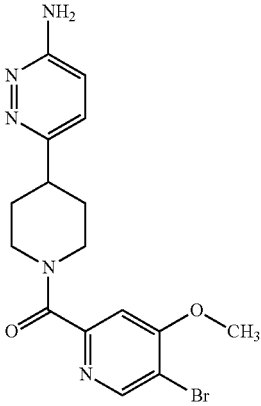 [SMILES: COc1cc(C(=O)N2CCC(c3ccc(N)nn3)CC2)ncc1Br] | 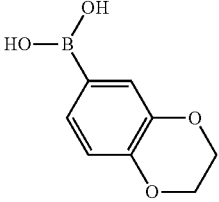 [SMILES: OB(O)c1ccc2c(c1)OCCO2] | 49 | 448 | 0.45 | 16 |
| 23 | 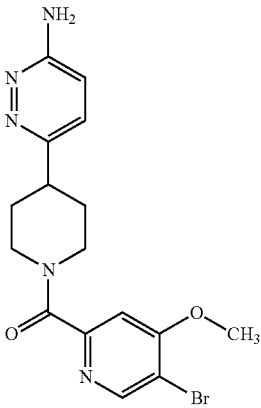 [SMILES: COc1cc(C(=O)N2CCC(c3ccc(N)nn3)CC2)ncc1Br] | 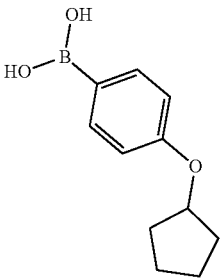 [SMILES: OB(O)c1ccc(OC2CCCC2)cc1] | 18 | 474 | 0.63 | 16 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 24 | (structure) | (structure) | 8 | 492/494 | 0.66 | 16 |
| 25 | (structure) | (structure) | 13 | 488 | 0.63 | 16 |
| 26 | (structure) | (structure) | 65 | 476 | 2.09 | 6 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R_t (min.) | HPLC Method |
|---|---|---|---|---|---|---|
| 27 | | | 43 | 458 | 0.60 | 16 |
| 28 | | | 16 | 420 | | |
| 29 | | | 14 | 488 | 0.57 | 16 |

TABLE 3-continued

Compounds of the invention 13-72.

| Cpd | Br-Intermediate (Intermediate 1) | Boronic acid (intermediate 2) | Yield % | ESI-MS m/z [M + H]⁺ | HPLC R$_t$ (min.) | HPLC Method |
|---|---|---|---|---|---|---|
| 30 | (structure) | 4-isopropoxyphenylboronic acid | 16 | 448 | 0.55 | 16 |
| 31 | (structure) | 4-(trifluoromethoxy)phenylboronic acid | 11 | 474 | | |
| 32 | (structure) | phenylboronic acid | 42 | 390 | 1.34 | 6 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 33 | | | 10 | 426 | 0.53 | 16 |
| 34 | | | 10 | 422 | 0.55 | 16 |
| 35 | | | 10 | 408 | 0.50 | 16 |

TABLE 3-continued
Compounds of the invention 13-72.
| Cpd | Br-Intermediate (Intermediate 1) | Boronic acid (intermediate 2) | Yield % | ESI-MS m/z [M + H]⁺ | HPLC R$_t$ (min.) | HPLC Method |
|---|---|---|---|---|---|---|
| 36 | 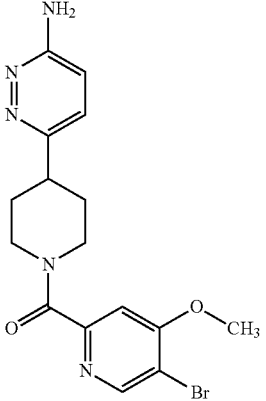 [SMILES: COc1cc(C(=O)N2CCC(c3ccc(N)nn3)CC2)ncc1Br] | 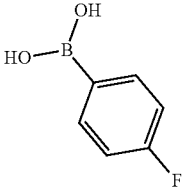 | 27 | 408 | 0.49 | 16 |
| 37 | 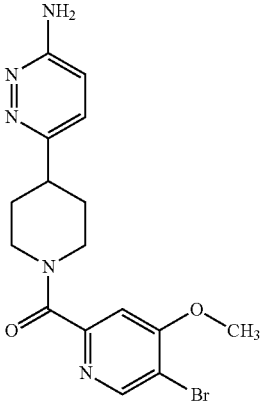 [SMILES: COc1cc(C(=O)N2CCC(c3ccc(N)nn3)CC2)ncc1Br] | 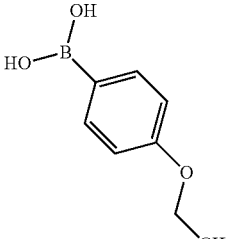 | 7 | 434 | 0.51 | 16 |
| 38 | 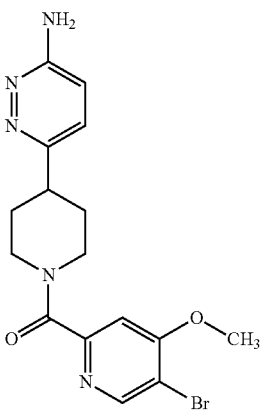 [SMILES: COc1cc(C(=O)N2CCC(c3ccc(N)nn3)CC2)ncc1Br] | 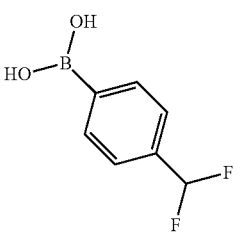 [SMILES: OB(O)c1ccc(C(F)F)cc1] | 6 | 439 | 0.52 | 16 |

TABLE 3-continued
Compounds of the invention 13-72.
| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 39 | 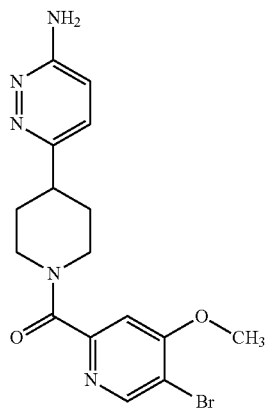 [SMILES: COc1cc(C(=O)N2CCC(c3ccc(N)nn3)CC2)ncc1Br] | 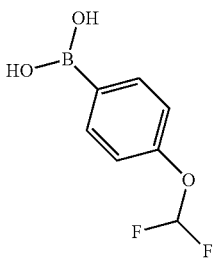 [SMILES: OB(O)c1ccc(OC(F)F)cc1] | 74 | 455 | | |
| 40 | 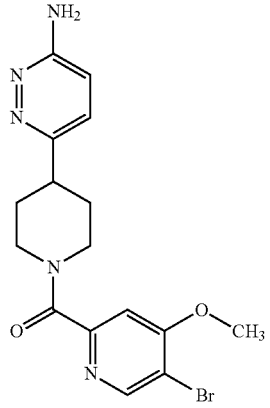 [SMILES: COc1cc(C(=O)N2CCC(c3ccc(N)nn3)CC2)ncc1Br] | 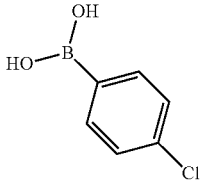 | 10 | 423 | | |
| 41 | 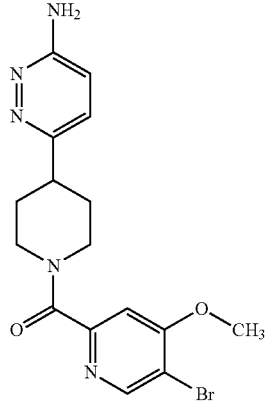 [SMILES: COc1cc(C(=O)N2CCC(c3ccc(N)nn3)CC2)ncc1Br] | 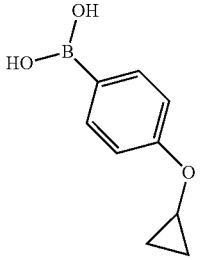 | 8 | 446 | | |

TABLE 3-continued

Compounds of the invention 13-72.

| Cpd | Br-Intermediate (Intermediate 1) | Boronic acid (intermediate 2) | Yield % | ESI-MS m/z [M + H]⁺ | HPLC R$_t$ (min.) | HPLC Method |
|---|---|---|---|---|---|---|
| 42 | (structure) | (structure) | 76 | 458 | | |
| 43 | (structure) | (structure) | 16 | 431.5 | 1.22 | 2 |
| 44 | (structure) | (structure) | 12 | 419 | 1.01 | 2 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 45 | | | 36 | 435 | 0.46 | 16 |
| 46 | | | 8 | 421 | 0.55 | 5 |
| 47 | | | 5 | 489 | 1.67 | 2 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 48 | | | 7 | 475 | 1.50 | 2 |
| 49 | | | 2 | 461 | 1.67 | 2 |
| 50 | | | 17 | 461.5 | 1.62 | 2 |

TABLE 3-continued
Compounds of the invention 13-72.
| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 51 | 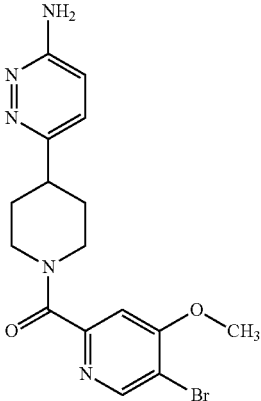 [SMILES: COc1cc(C(=O)N2CCC(c3ccc(N)nn3)CC2)ncc1Br] | 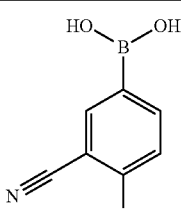 | 6 | 429 | 1.38 | 2 |
| 52 | 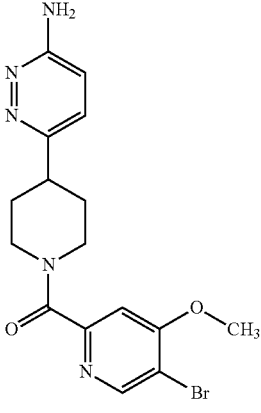 [SMILES: COc1cc(C(=O)N2CCC(c3ccc(N)nn3)CC2)ncc1Br] | 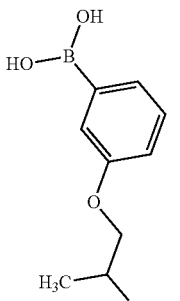 | 4 | 462.5 | 2.08 | 2 |
| 53 | 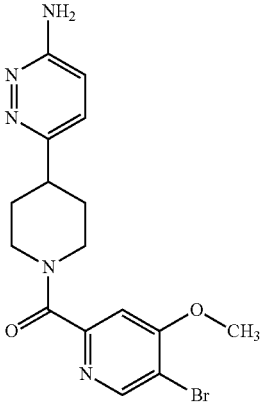 [SMILES: COc1cc(C(=O)N2CCC(c3ccc(N)nn3)CC2)ncc1Br] | 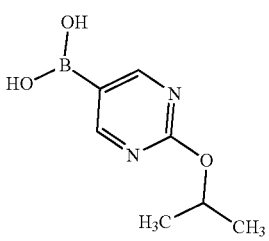 | 20 | 450.5 | 0.68 | 5 |

TABLE 3-continued
Compounds of the invention 13-72.
| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 54 | 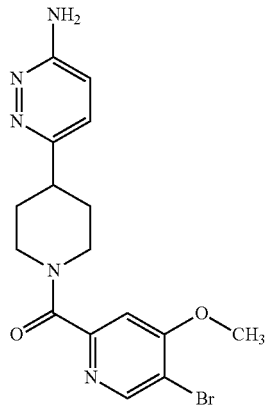 [SMILES: COc1cc(C(=O)N2CCC(c3ccc(N)nn3)CC2)ncc1Br] | 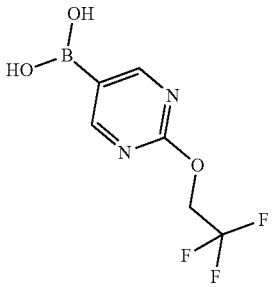 [SMILES: OB(O)c1cnc(OCC(F)(F)F)nc1] | 24 | 490 | 0.56 | 5 |
| 55 | 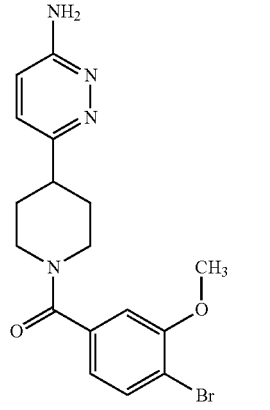 [SMILES: COc1cc(C(=O)N2CCC(c3ccc(N)nn3)CC2)ccc1Br] | 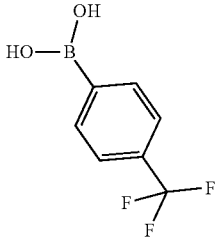 [SMILES: OB(O)c1ccc(C(F)(F)F)cc1] | 65 | 458 | 0.70 | 16 |
| 56 | 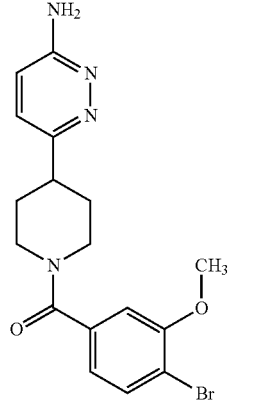 [SMILES: COc1cc(C(=O)N2CCC(c3ccc(N)nn3)CC2)ccc1Br] | 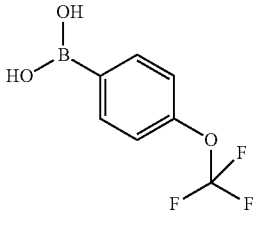 [SMILES: OB(O)c1ccc(OC(F)(F)F)cc1] | 46 | 473 | 0.73 | 16 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R_t (min.) | HPLC Method |
|---|---|---|---|---|---|---|
| 57 | (structure) | (structure) | 30 | 447 | 0.69 | 16 |
| 58 | (structure) | (structure) | 24 | 487 | 0.70 | 16 |
| 59 | (structure) | (structure) | 29 | 458 | 0.62 | 16 |

TABLE 3-continued
Compounds of the invention 13-72.
| Cpd | Br-Intermediate (Intermediate 1) | Boronic acid (intermediate 2) | Yield % | ESI-MS m/z [M + H]+ | HPLC R_t (min.) | HPLC Method |
|---|---|---|---|---|---|---|
| 60 | 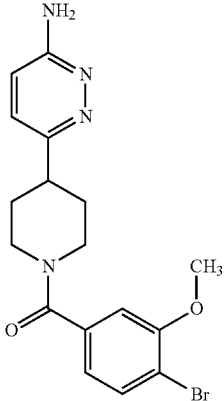 [SMILES: COc1cc(C(=O)N2CCC(c3ccc(N)nn3)CC2)ccc1Br] | 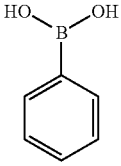 | 48 | 389 | 0.61 | 16 |
| 61 | 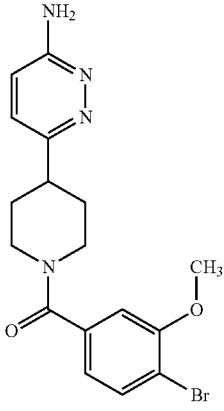 [SMILES: COc1cc(C(=O)N2CCC(c3ccc(N)nn3)CC2)ccc1Br] | 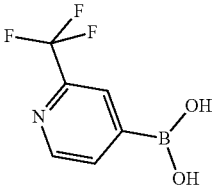 [SMILES: OB(O)c1ccnc(C(F)(F)F)c1] | 34 | 458 | 0.60 | 16 |
| 62 | 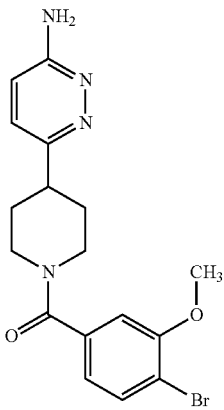 [SMILES: COc1cc(C(=O)N2CCC(c3ccc(N)nn3)CC2)ccc1Br] | 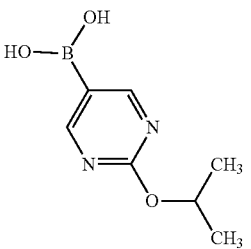 | 29 | 449 | 0.57 | 16 |

TABLE 3-continued

Compounds of the invention 13-72.

| Cpd | Br-Intermediate (Intermediate 1) | Boronic acid (intermediate 2) | Yield % | ESI-MS m/z [M + H]⁺ | HPLC R_t (min.) | HPLC Method |
|---|---|---|---|---|---|---|
| 63 | | | 50 | 440.7 | 0.73 | 16 |
| 64 | | | 32 | 458 | 0.70 | 16 |
| 65 | | | 19 | 459 | 0.65 | 16 |

TABLE 3-continued
Compounds of the invention 13-72.
| Cpd | Br-Intermediate (Intermediate 1) | Boronic acid (intermediate 2) | Yield % | ESI-MS m/z [M + H]+ | HPLC R$_t$ (min.) | HPLC Method |
|---|---|---|---|---|---|---|
| 66 | 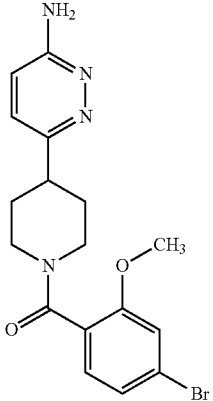 [SMILES: COc1cc(Br)ccc1C(=O)N1CCC(c2ccc(N)nn2)CC1] | | 10 | 457 | 0.70 | 16 |
| 67 | | | 9 | 459 | 0.54 | 16 |
| 68 |  | 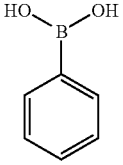 | 11 | 390 | 0.47 | 16 |

TABLE 3-continued
Compounds of the invention 13-72.
| Cpd | Br-Intermediate (Intermediate 1) | Boronic acid (intermediate 2) | Yield % | ESI-MS m/z [M + H]+ | HPLC R_t (min.) | HPLC Method |
|---|---|---|---|---|---|---|
| 69 | 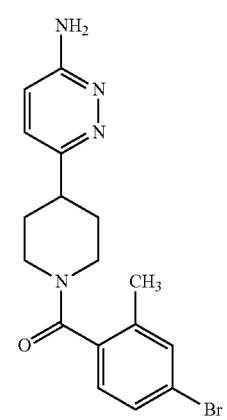 [SMILES: Cc1cc(Br)ccc1C(=O)N1CCC(c2ccc(N)nn2)CC1] | 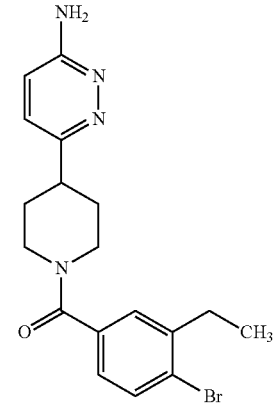 [SMILES: CCc1cc(C(=O)N2CCC(c3ccc(N)nn3)CC2)ccc1Br] | 20 | 442 | 0.72 | 16 |
| 70 | 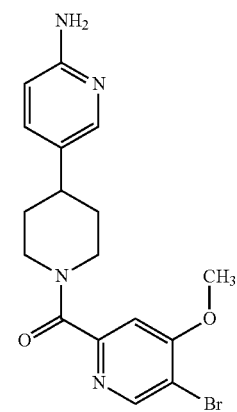 [SMILES: COc1cc(C(=O)N2CCC(c3ccc(N)nc3)CC2)ncc1Br] | | 58 | 455 | 0.76 | 16 |
| 71 | | | 11 | 389 | 0.47 | 16 |

TABLE 3-continued

Compounds of the invention 13-72.

| Cpd | Br-Intermediate (Intermediate 1) | Boronic acid (intermediate 2) | Yield % | ESI-MS m/z [M + H]+ | HPLC R_t (min.) | HPLC Method |
|---|---|---|---|---|---|---|
| 72 | 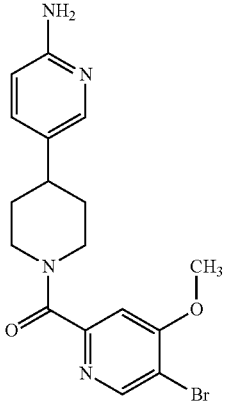 [SMILES: COc1cc(C(=O)N2CCC(c3ccc(N)nc3)CC2)ncc1Br] | 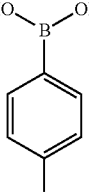 | 11 | 407 | 0.50 | 16 |

Synthesis of Intermediates

5-Bromo-2-cyclopropylmethoxy-pyridine

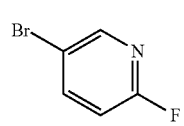 + 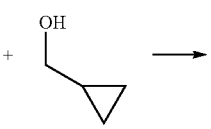 →

5-Bromo-2-fluoro-pyridine (250 mg, 1.42 mmol), cyclopropyl-methanol (154 mg, 2.13 mmol) and potassium tert-butoxide (287 mg, 2.56 mmol) are combined in THF (5 mL). The reaction mixture is stirred for 24 h at rt. The reaction mixture is diluted with EtOAc and water. The aqueous phase is separated and extracted two more times with EtOAc. The organic layers are combined, washed with brine, dried over Na$_2$SO$_4$, filtered and concentrated under reduced pressure. The residue is purified by SiO$_2$ flash chromatography (EtOAc/heptane) to afford the title product.

Yield: 298 mg (92%) ESI-MS: m/z=228/230 (M+H)+ R$_t$(HPLC): 1.14 min (Method 10)

5-Bromo-2-cyclopropoxy-pyridine

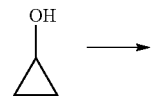

The title compound is synthesized from 5-bromo-2-fluoro-pyridine (250 mg, 1.42 mmol) and cyclopropanol (124 mg, 2.13 mmol) according to the procedure described for the synthesis of the intermediate 5-bromo-2-cyclopropylmethoxy-pyridine.

Yield: 272 mg (89%)

5-Bromo-2-((R)-sec-butoxy)-pyridine

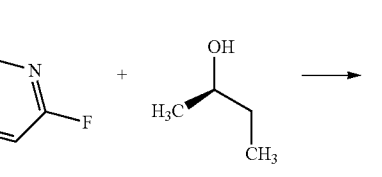

The title compound is synthesized from 5-bromo-2-fluoro-pyridine (250 mg, 1.42 mmol) and (R)-butan-2-ol (158 mg, 2.13 mmol) according to the procedure described for the synthesis of the intermediate 5-bromo-2-cyclopropylmethoxy-pyridine.

Yield: 263 mg (81%)

5-Bromo-2-((S)-sec-butoxy)-pyridine

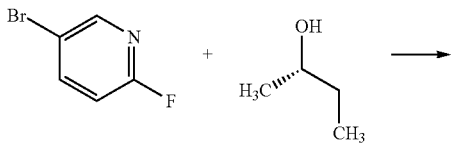

-continued

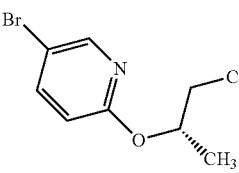

The title compound is synthesized from 5-bromo-2-fluoro-pyridine (250 mg, 1.42 mmol) and (S)-butan-2-ol (158 mg, 2.13 mmol) according to the procedure described for the synthesis of the intermediate 5-bromo-2-cyclopropylmethoxy-pyridine.

Yield: 252 mg (77%)

5-Bromo-2-(2,2-difluoro-cyclopropylmethoxy)-pyridine

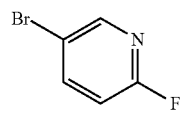

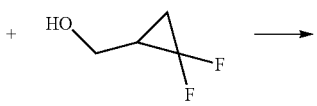

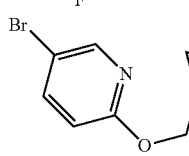

The title compound is synthesized from 5-bromo-2-fluoro-pyridine (250 mg, 1.42 mmol) and (2,2-difluoro-cyclopropyl)-methanol (230 mg, 2.13 mmol) according to the procedure described for the synthesis of the intermediate 5-bromo-2-cyclopropylmethoxy-pyridine.

Yield: 349 mg (93%) ESI-MS: m/z=264/266 (M+H)⁺ R$_t$(HPLC): 1.27 min (Method 13)

5-Bromo-2-(2,2-dimethyl-cyclopropylmethoxy)-pyridine

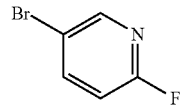

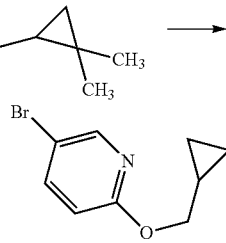

The title compound is synthesized from 5-bromo-2-fluoro-pyridine (250 mg, 1.42 mmol) and (2,2-dimethyl-cyclopropyl)-methanol (213 mg, 2.13 mmol) according to the procedure described for the synthesis of the intermediate 5-bromo-2-cyclopropylmethoxy-pyridine.

Yield: 320 mg (88%)

5-Bromo-2-((S)-1-cyclopropyl-ethoxy)-pyridine

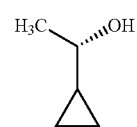

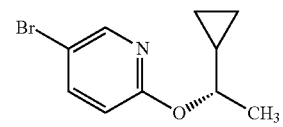

The title compound is synthesized from 5-bromo-2-fluoro-pyridine (250 mg, 1.42 mmol) and (S)-1-cyclopropyl-ethanol (183 mg, 2.13 mmol) according to the procedure described for the synthesis of the intermediate 5-bromo-2-cyclopropylmethoxy-pyridine.

Yield: 240 mg (70%)

5-Bromo-2-((R)-1-cyclopropyl-ethoxy)-pyridine

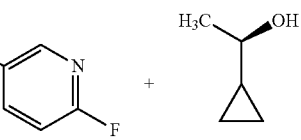

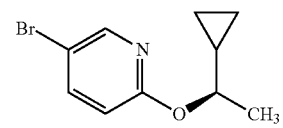

The title compound is synthesized from 5-bromo-2-fluoro-pyridine (250 mg, 1.42 mmol) and (R)-1-cyclopropyl-ethanol (183 mg, 2.13 mmol) according to the procedure described for the synthesis of the intermediate 5-bromo-2-cyclopropylmethoxy-pyridine.

Yield: 230 mg (67%)

5-Bromo-2-(1-methyl-cyclopropylmethoxy)-pyridine

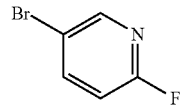

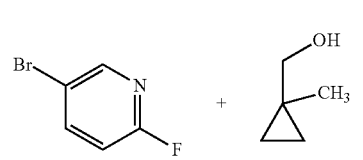

The title compound is synthesized from 5-bromo-2-fluoro-pyridine (250 mg, 1.42 mmol) and (1-methyl-cyclopropyl)-methanol (183 mg, 2.13 mmol) according to the procedure described for the synthesis of the intermediate 5-bromo-2-cyclopropylmethoxy-pyridine.

Yield: 229 mg (67%)

5-Bromo-2-(1-fluoromethyl-cyclopropylmethoxy)-pyridine

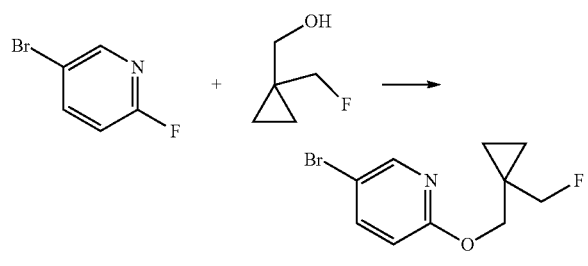

The title compound is synthesized from 5-bromo-2-fluoro-pyridine (250 mg, 1.42 mmol) and (1-fluoromethyl-cyclopropyl)-methanol (222 mg, 2.13 mmol) according to the procedure described for the synthesis of the intermediate 5-bromo-2-cyclopropylmethoxy-pyridine.

Yield: 280 mg (76%)

General Procedure III

To aryl bromide (1 eq.) (intermediate 2 in the following table 4) in an appropriate volume of water and 1,4-dioxane (water/1,4-dioxane approximately 0.25 mL/2.0 mL per 0.07 mmol up to 0.14 mmol intermediate 1 in Table 4) is added $K_3PO_4$ (2 eq.) and boronic acid (1 eq.) (intermediate 1 in the following Table 4) and degassed with argon for 5 min. Then $PdCl_2(dppf)*CH_2Cl_2$ (0.2 eq.) is added and degassed with argon for 5 min again. The reaction mixture is stirred at 120° C. for 60 min in a microwave. The volatiles are removed under reduced pressure and the resultant residue is dissolved in DMF and purified by reversed phase HPLC to afford the desired product.

TABLE 4

Compounds of the invention 73-83.

| Cpd | Intermediate 1 | Aryl bromide (intermediate 2) | Yield % | ESI-MS m/z M + H⁺ | HPLC $R_t$ (min.) | HPLC Method |
|---|---|---|---|---|---|---|
| 73 | 6-amino-3-(1-{[3-methoxy-4-(dihydroxyboranyl)phenyl]carbonyl}piperidin-4-yl)pyridazine | 5-bromo-2-(cyclopropyloxy)pyridine | 81 | 446 | 0.52 | 16 |
| 74 | 6-amino-3-(1-{[3-methoxy-4-(dihydroxyboranyl)phenyl]carbonyl}piperidin-4-yl)pyridazine | 5-bromo-2-[(propan-2-yl)oxy]pyridine | 58 | 463 | 0.62 | 16 |

TABLE 4-continued
Compounds of the invention 73-83.
| Cpd | Intermediate 1 | Aryl bromide (intermediate 2) | Yield % | ESI-MS m/z M + H⁺ | HPLC R$_t$ (min.) | HPLC Method |
|---|---|---|---|---|---|---|
| 75 | 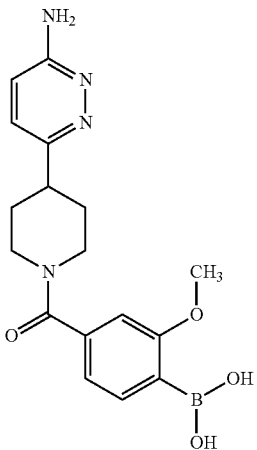 [SMILES: COc1cc(C(=O)N2CCC(c3ccc(N)nn3)CC2)ccc1B(O)O] | 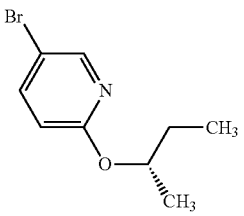 | 33 | 462 | 0.61 | 16 |
| 76 | 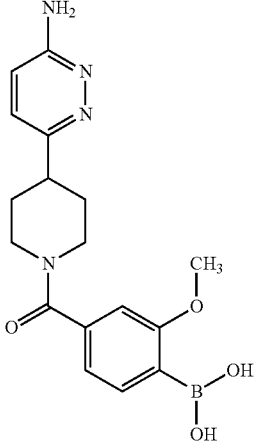 [SMILES: COc1cc(C(=O)N2CCC(c3ccc(N)nn3)CC2)ccc1B(O)O] | 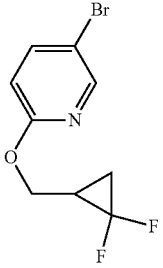 | 31 | 496.5 | 0.65 | 16 |
| 77 | 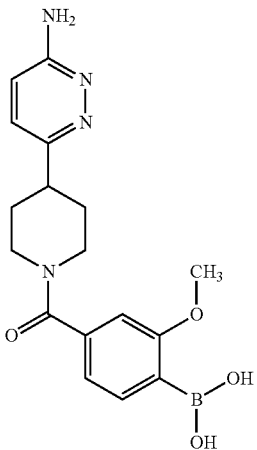 [SMILES: COc1cc(C(=O)N2CCC(c3ccc(N)nn3)CC2)ccc1B(O)O] | 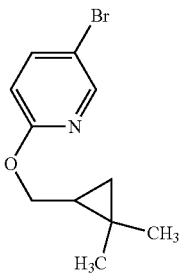 | 18 | 488.5 | 0.70 | 16 |

TABLE 4-continued
Compounds of the invention 73-83.
| Cpd | Intermediate 1 | Aryl bromide (intermediate 2) | Yield % | ESI-MS m/z M + H⁺ | HPLC R_t (min.) | HPLC Method |
|---|---|---|---|---|---|---|
| 78 | 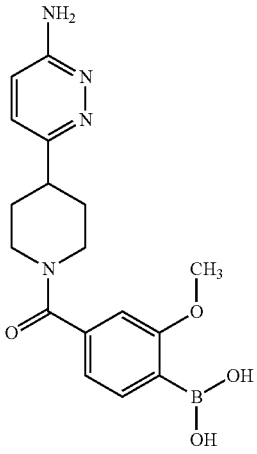 [SMILES: COc1cc(C(=O)N2CCC(c3ccc(N)nn3)CC2)ccc1B(O)O] | 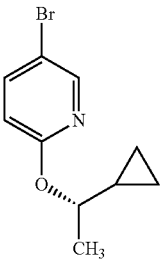 | 10 | 474 | 0.92 | 4 |
| 79 | 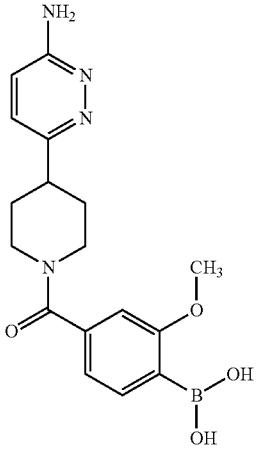 [SMILES: COc1cc(C(=O)N2CCC(c3ccc(N)nn3)CC2)ccc1B(O)O] | 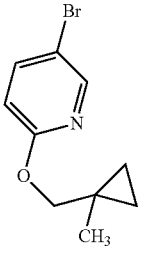 | 29 | 474.6 | 0.66 | 16 |
| 80 | 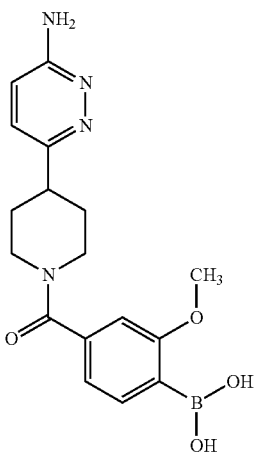 [SMILES: COc1cc(C(=O)N2CCC(c3ccc(N)nn3)CC2)ccc1B(O)O] | 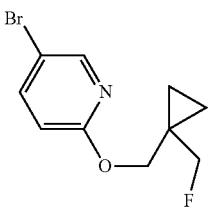 [SMILES: FCC1(COc2ccc(Br)cn2)CC1] | 37 | 492 | 0.62 | 16 |

TABLE 4-continued

Compounds of the invention 73-83.

| Cpd | Intermediate 1 | Aryl bromide (intermediate 2) | Yield % | ESI-MS m/z M + H⁺ | HPLC R_t (min.) | HPLC Method |
|---|---|---|---|---|---|---|
| 81 | | | 19 | 474 | 0.91 | 4 |
| 82 | | | 14 | 460 | 0.60 | 16 |
| 83 | | | 50 | 415 | 0.79 | 16 |

Synthesis of Intermediate

2-Methoxy-4'-trifluoromethyl-biphenyl-4-carboxylic acid

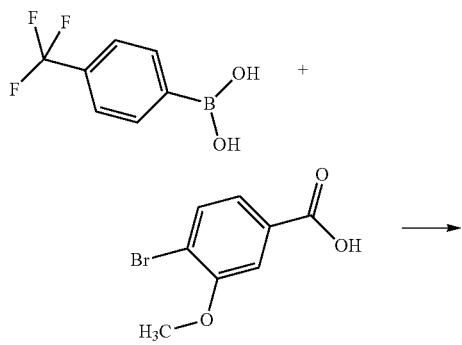

To 4-bromo-3-methoxy-benzoic acid (300 mg, 1.23 mmol) in water (250 µL) and 1,4-dioxane (2 mL) is added K$_3$PO$_4$ (551 mg, 2.60 mmol) and [4-(trifluoromethyl)phenyl]boronic acid (247 mg, 1.30 mmol) and degassed with argon for 5 min. Then PdCl$_2$(dppf)*CH$_2$Cl$_2$ (212 mg, 0.26 mmol) is added and degassed with argon for 5 min again. The reaction mixture is stirred in the microwave at 130° C. for 30 min. Ethyl acetate and water are added and the layers are separated. The aqueous layer is extracted with ethyl acetate and the combined organic layers are washed with brine, dried with MgSO$_4$, filtered and concentrated under reduced pressure. The crude product is purified by silica gel chromatography (EtOAc/heptane) to afford the title product.

Yield: 217 mg (56%) ESI-MS: m/z=295 (M−H)$^-$ R$_t$(HPLC): 2.57 min (Method 5)

4-Methoxy-5-(4-trifluoromethyl-phenyl)-pyridine-2-carboxylic acid methyl ester

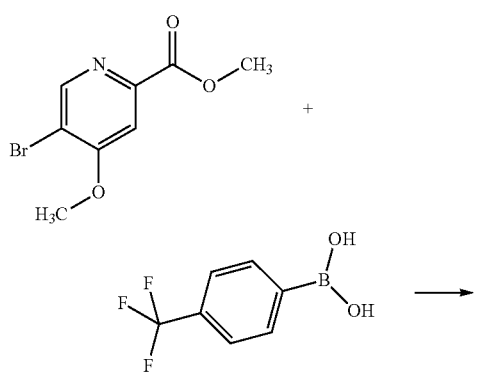

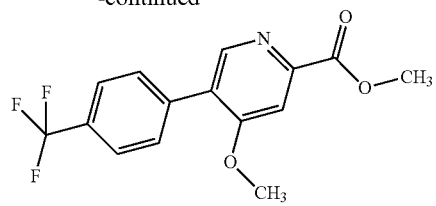

To 5-bromo-4-methoxy-pyridine-2-carboxylic acid methyl ester (5.0 g, 20.3 mmol) in water (4 mL) and 1,4-dioxane (16 mL) is added K$_3$PO$_4$ (8.6 g, 40.6 mmol) and [4-(trifluoromethyl)-phenyl]boronic acid (3.9 g, 20.3 mmol) and degassed with argon for 5 min. Then PdCl$_2$(dppf)* CH$_2$Cl$_2$ (3.3 g, 4.01 mmol) is added and degassed with argon for 5 min again. The reaction mixture is stirred at 100° C. for 30 min. The volatiles are removed under reduced pressure and the resulting residue is purified by silica gel chromatography (EtOAc/heptane) to afford the title product.

Yield: 2.5 g (40%)

4-Methoxy-5-(4-trifluoromethyl-phenyl)-pyridine-2-carboxylic acid

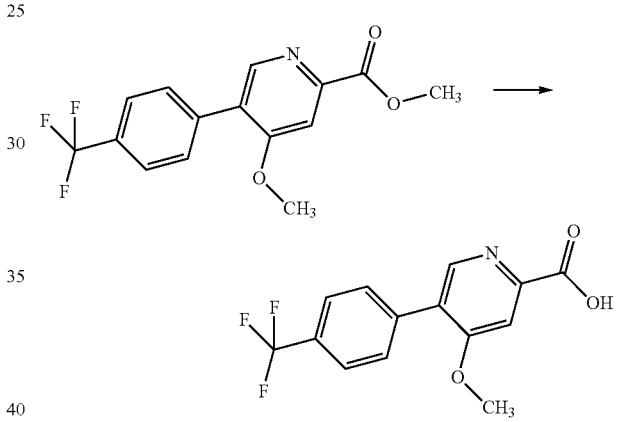

To 4-methoxy-5-(4-trifluoromethyl-phenyl)-pyridine-2-carboxylic acid methyl ester (2.5 g, 8.03 mmol) in an appropriate volume of THF/MeOH/H$_2$O (1/1/1 ratio, approximately 30 mL) is added LiOH (769 mg, 32.1 mmol) and the reaction mixture is stirred at rt for 4 h. The volatiles are removed under reduced pressure and the residue is dissolved in H$_2$O. To the mixture is added, drop wise, aqueous conc. HCl to bring the mixture to pH 2. The resulting precipitate is isolated by filtration and dried under vacuum at 80° C. for 8 h to provide the title compound.

Yield: 2.1 g (88%)

4-Methoxy-5-phenyl-pyridine-2-carboxylic acid methyl ester

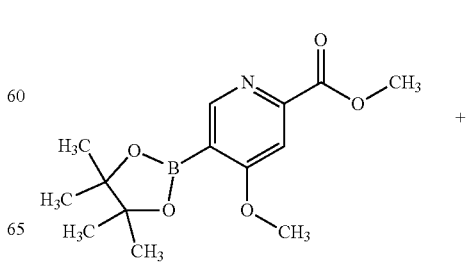

-continued

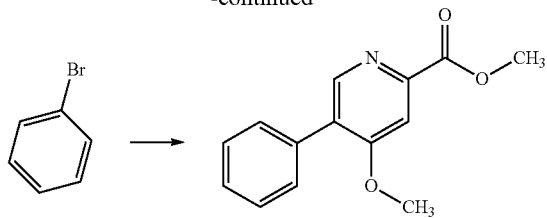

To bromobenzene (401 mg, 2.56 mmol) in water (0.25 mL) and 1,4-dioxane (2 mL) is added $K_3PO_4$ (724 mg, 3.41 mmol) and 4-methoxy-5-(4,4,5,5-tetramethyl-[1,3,2]dioxaborolan-2-yl)-pyridine-2-carboxylic acid methyl ester (500 mg, 1.71 mmol) and degassed with argon for 5 min. Then $PdCl_2(dppf)*CH_2Cl_2$ (278 mg, 0.34 mmol) is added and degassed with argon for 5 min again. The reaction mixture is stirred at 120° C. for 15 min in a microwave. The volatiles are removed under reduced pressure and the resulting residue is purified by silica gel chromatography to afford the title product.

Yield: 335 mg (81%)

4-Methoxy-5-phenyl-pyridine-2-carboxylic acid

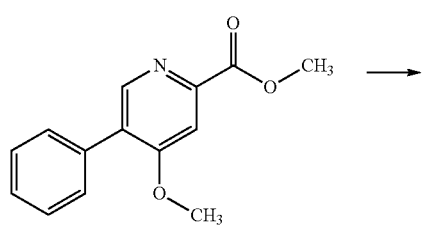

To 4-methoxy-5-phenyl-pyridine-2-carboxylic acid methyl ester (335 mg, 1.38 mmol) in an appropriate volume of THF/MeOH/$H_2O$ (approximately 4 mL/2 mL/1 mL) is added LiOH (132 mg, 5.51 mmol) and the reaction mixture is stirred at rt for 48 h. The volatiles are removed under reduced pressure and the residue is dissolved in $H_2O$. To the mixture is added, drop wise, aqueous conc. HCl to bring the mixture to pH 2. The resulting precipitate is isolated by filtration and dried under vacuum at 80° C. for 8 h to provide the title compound.

Yield: 283 mg (90%)

5-(4-Fluoro-phenyl)-4-methoxy-pyridine-2-carboxylic acid methyl ester

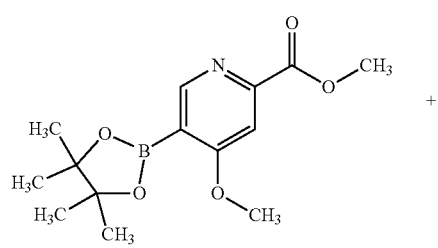

-continued

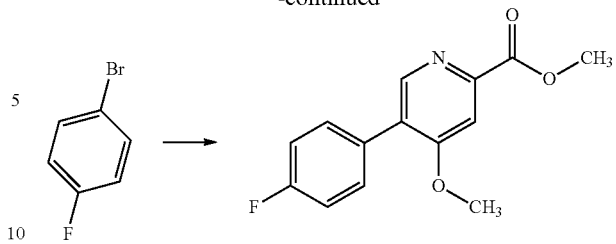

To 1-bromo-4-fluoro-benzene (149 mg, 0.85 mmol) in water (0.25 mL) and 1,4-dioxane (2 mL) is added $K_3PO_4$ (362 mg, 1.70 mmol) and 4-methoxy-5-(4,4,5,5-tetramethyl-[1,3,2]dioxaborolan-2-yl)-pyridine-2-carboxylic acid methyl ester (250 mg, 0.85 mmol, commercially available MFCD18727245) and degassed with argon for 5 min. Then $PdCl_2(dppf).CH_2Cl_2$ (139 mg, 0.17 mmol) is added and degassed with argon for 5 min again. The reaction mixture is stirred at 120° C. for 18 h. The volatiles are removed under reduced pressure and the resulting residue is purified by silica gel chromatography to afford the title product.

Yield: 131 mg (59%)

5-(4-Fluoro-phenyl)-4-methoxy-pyridine-2-carboxylic acid

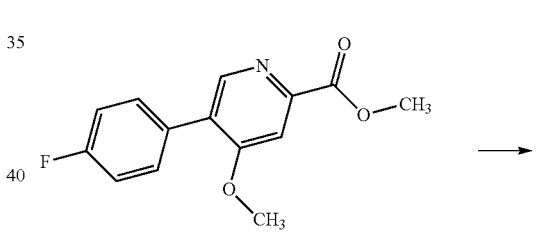

To 5-(4-fluoro-phenyl)-4-methoxy-pyridine-2-carboxylic acid methyl ester (3.5 g, 13.4 mmol) in an appropriate volume of THF/MeOH (180 mL/20 mL) is added an aqueous 1M LiOH solution (54 mL, 53.6 mmol) and the reaction mixture is stirred at rt for 2 h. The volatiles are removed under reduced pressure and the residue is dissolved in $H_2O$. To the mixture is added, dropwise, aqueous 6N HCl to bring the mixture to pH 2. The resulting precipitate is isolated by filtration and dried under vacuum at 80° C. for 8 h to provide the title compound.

Yield: 2.6 g (78%)

4-Methoxy-6'-trifluoromethyl-[3,3']bipyridinyl-6-carboxylic acid methyl ester

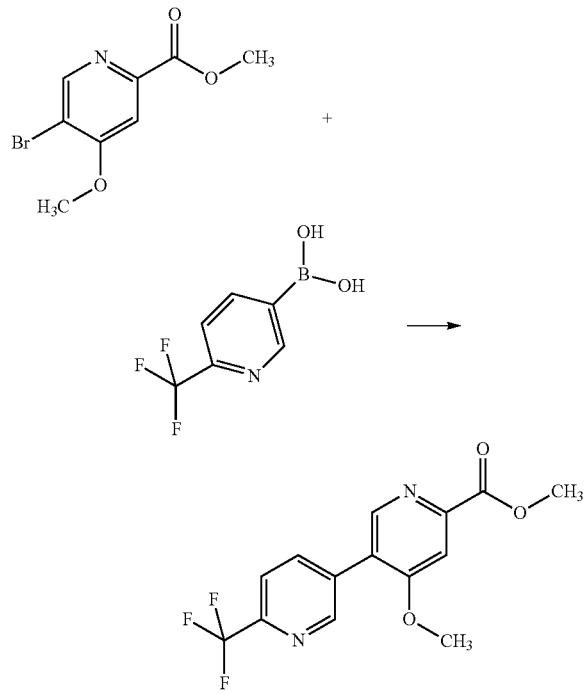

To 5-bromo-4-methoxy-pyridine-2-carboxylic acid methyl ester (4.5 g, 18.3 mmol) in water (10 mL) and 1,4-dioxane (100 mL) is added K$_3$PO$_4$ (7.8 g, 36.6 mmol) and [6-(trifluoro-methyl)-pyridin-3-yl]boronic acid (5.3 g, 27.4 mmol) and degassed with argon for 5 min. Then PdCl$_2$(dppf).CH$_2$Cl$_2$ (747 mg, 0.91 mmol) is added and degassed with argon for 5 min again. The reaction mixture is stirred at 90° C. for overnight. The reaction mixture is filtered through Celite®. The organic volatiles are removed under reduced pressure and the resulting residue taken up in water and EtOAc. The aqueous layer is extracted three times with EtOAc. The combined organic layers are dried over Na$_2$SO$_4$, filtered and concentrated under reduced pressure. The residue is purified by silica gel chromatography (EtOAc/hexane) to afford the title product.

Yield: 2.8 g (49%)

4-Methoxy-6'-trifluoromethyl-[3,3']bipyridinyl-6-carboxylic acid

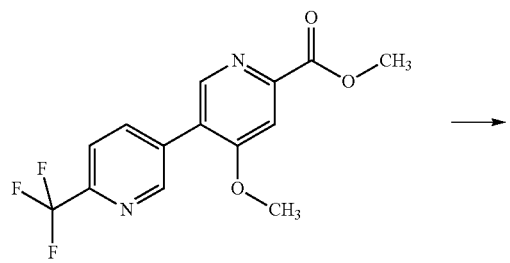

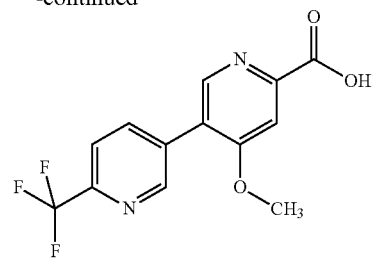

To 4-methoxy-6'-trifluoromethyl-[3,3']bipyridinyl-6-carboxylic acid methyl ester (3.0 g, 9.61 mmol) in THF (50 mL) is added aqueous 1 M LiOH solution (19 mL, 19.0 mmol) at 0° C. and the reaction mixture is stirred at rt for overnight. The volatiles are removed under reduced pressure and the residue is dissolved in H$_2$O. To the mixture is added, dropwise, conc. HCl to bring the mixture to pH 2. The resulting precipitate is isolated by filtration to provide the title compound.

Yield: 2.7 g (94%) ESI-MS: m/z=299 (M+H)$^+$ R$_t$(HPLC): 0.74 min (Method 7)

(R)-3-Methyl-4-(6-nitro-pyridin-3-yl)-piperazine-1-carboxylic acid tert-butyl ester

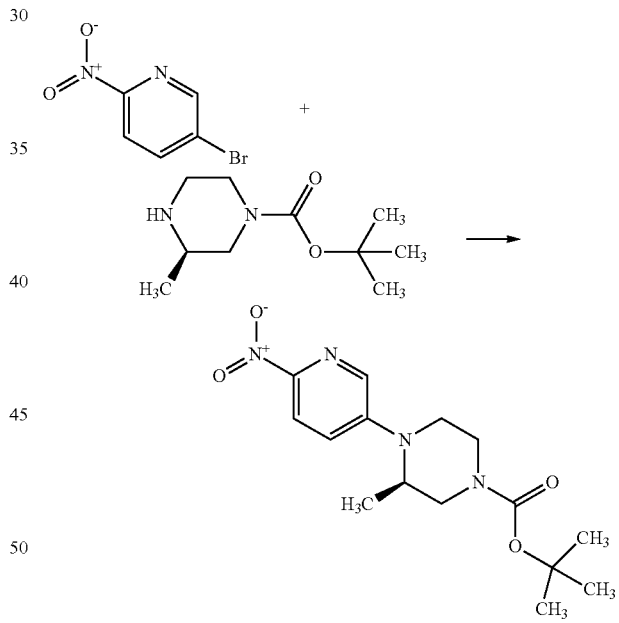

To 5-bromo-2-nitro-pyridine (500 mg, 2.46 mmol) and (R)-3-methyl-piperazine-1-carboxylic acid tert-butyl ester (592 mg, 2.96 mmol) in 1,4-dioxane is added Cs$_2$CO$_3$ (963 mg, 2.96 mmol) and XantPhos (71.3 mg, 0.12 mmol). The mixture is degassed for 5 min. Pd$_2$(dba)$_3$ (123 mg, 0.12 mmol) is added, degassed for 5 min. and stirred for 15 h at reflux. The reaction mixture is filtered through Celite® and washed with DCM (50 mL×2). The combined organic layers are washed with brine, dried with Na$_2$SO$_4$, filtered and concentrated under reduced pressure. The resulting residue is purified by silica gel chromatography (EtOAc/hexane) to afford the title product.

Yield: 400 mg (50%)

(R)-2-Methyl-1-(6-nitro-pyridin-3-yl)-piperazine hydrochloride

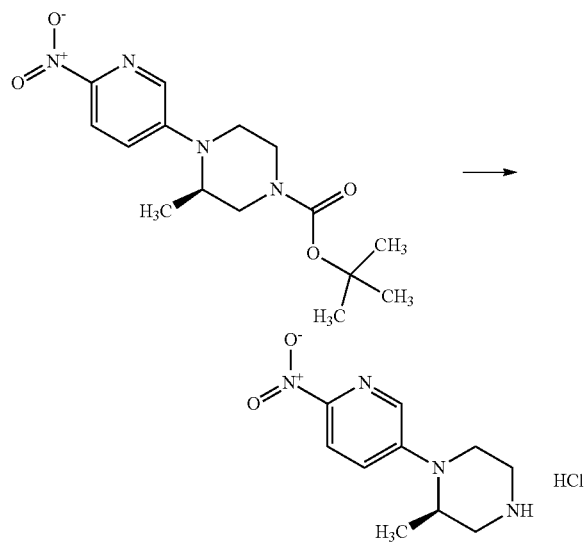

To (R)-3-methyl-4-(6-nitro-pyridin-3-yl)piperazine-1-carboxylic acid tert-butyl ester (3.0 g, 9.30 mmol) in DCM (40 mL) is added at 0° C. 4M HCl in 1,4-dioxane (20 mL) and stirred at rt for 5 h. 1,4 Dioxane and DCM are removed under reduced pressure and the residue is washed with 30% EtOAc in hexane. The resulting precipitate is isolated by decantation of the solvent and dried under reduced pressure to afford the title product.

Yield: 2.1 g (87%) ESI-MS: m/z=223 (M+H)$^+$

(1S,4S)-5-(6-Nitroso-pyridazin-3-yl)-2,5-diaza-bicyclo[2.2.1]heptane-2-carboxylic acid tert-butyl ester

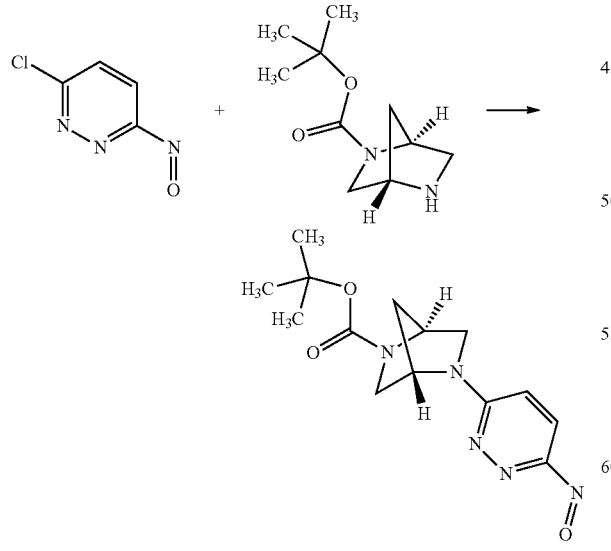

3-Chloro-6-nitroso-pyridazine (2.0 g, 13.9 mmol), (1S, 4S)-2,5-diaza-bicyclo[2.2.1]heptane-2-carboxylic acid tert-butyl ester (3.3 g, 16.7 mmol) and DIPEA (7.2 mL, 41.8 mmol) in ethanol (12 mL) are stirred at rt for 2.5 days. The resulting precipitate is collected to afford the title compound.

Yield: 1.8 g (42%) ESI-MS: m/z=282 (M+H)$^+$ R$_t$(HPLC): 0.69 min (Method 1)

(1S,4S)-2-(6-Nitroso-pyridazin-3-yl)-2,5-diaza-bicyclo[2.2.1]heptane hydrochloride

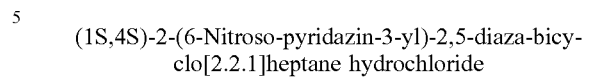

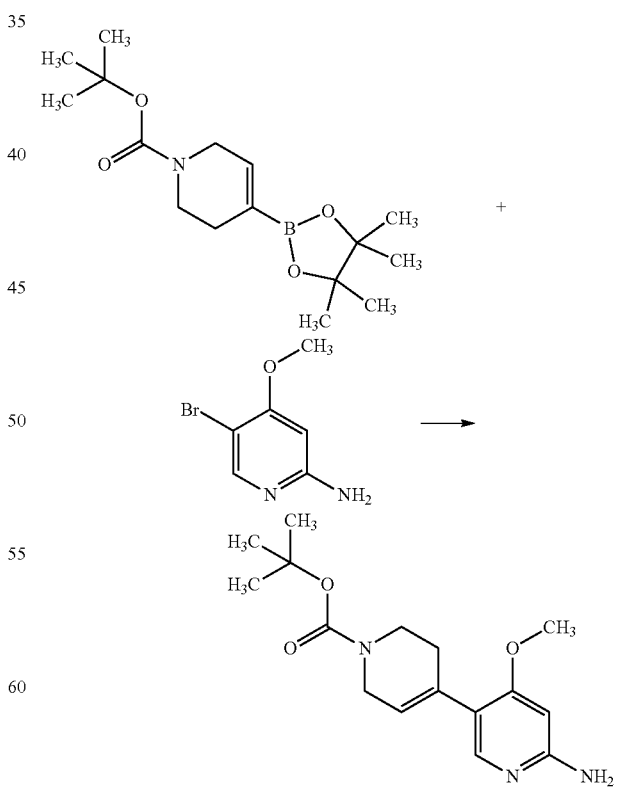

(1S,4S)-5-(6-Nitroso-pyridazin-3-yl)-2,5-diaza-bicyclo [2.2.1]heptane-2-carboxylic acid tert-butyl ester (175 mg, 0.57 mmol) in 4M HCl in 1,4-dioxane (1.5 mL) is stirred for 1 h at rt. The solvent is removed under reduced pressure and ether is added. The resulting precipitate is collected to afford the title compound.

Yield: 120 mg (quantitative)

6-Amino-4-methoxy-3',6'-dihydro-2'H-[3,4']bipyridinyl-V-carboxylic acid tert-butylester To 4-(4,4,5,5-tetramethyl-[1,3,2]dioxaborolan-2-yl)-3,6-dihydro-2H-pyridine-1-carboxylic acid tert-butyl ester (5.02 g, 16.3 mmol) and 5-bromo-4-methoxy-pyridin-2-ylamine (3.30 g, 16.3 mmol) in 1,4-dioxane (15 mL) is added 2M aqueous Na$_2$CO$_3$ solution (3.5 mL) and degassed with argon for 5 min. Pd(dppf)Cl$_2$*CH$_2$Cl$_2$ (1.32 g, 1.63 mmol) is added. The reaction mixture is stirred at 115° C. for 45 min. The reaction mixture is diluted with water and extracted with EtOAc. The combined organic layers are washed with water, brine, dried over Na$_2$SO$_4$, filtered and concentrated under reduced pressure. The residue is purified by silica gel chromatography (DCM/MeOH).

Yield: 2.88 g (97%) ESI-MS: m/z=306 (M+H)$^+$ R$_t$(HPLC): 0.75 min (Method 5)

6-Amino-4-methoxy-3',4',5',6'tetrahydro-2'H-[3,4']bipyridinyl-1'-carboxylic acid tert-butyl ester

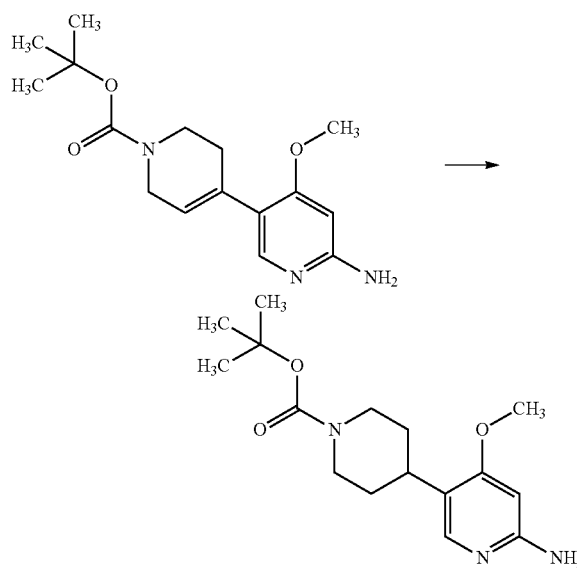

To 6-amino-4-methoxy-3',6'-dihydro-2'H-[3,4']bipyridinyl-1'-carboxylic acid tert-butyl ester (0.75 g, 2.46 mmol) in methanol (25 mL) is added Pd/C (0.26 g, 0.25 mmol) under nitrogen atmosphere and then subjected to a balloon of H$_2$. The reaction mixture is stirred at rt for 2 days. The reaction mixture is filtered and evaporated under reduced pressure. The residue is purified by silica gel chromatography (DCM/MeOH).

Yield: 715 mg (94%) ESI-MS: m/z=308 (M+H)$^+$ R$_t$(HPLC): 0.88 min (Method 5)

4-Methoxy-5-(piperidin-4-yl)pyridin-2-amine dihydrochloride

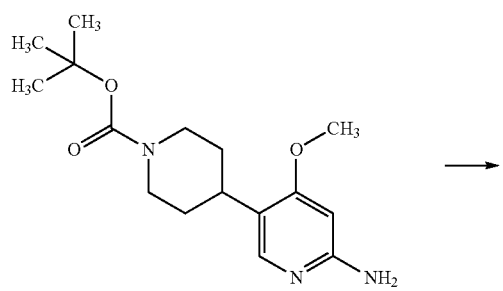

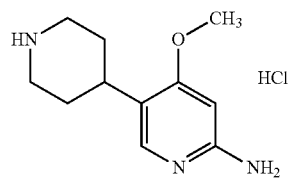

To 6-amino-4-methoxy-3',4',5',6'-tetrahydro-2'H-[3,4']bipyridinyl-1'-carboxylic acid tert-butyl ester (4.98 g, 16.2 mmol) in DCM (66 mL) is added 4M HCl in 1,4-dioxane (17 mL). The reaction mixture is stirred for 16 h at an ambient temperature. The reaction mixture is evaporated under reduced pressure. The residue is washed with ether to afford the title compound.

Yield: 4.0 g (quantitative) ESI-MS: m/z=208 (M+H)$^+$ R$_t$(HPLC): 0.39 min (Method 4)

4-(6-Amino-4-methoxy-pyridazin-3-yl)-3,6-dihydro-2H-pyridine-1-carboxylic acid tert-butyl ester

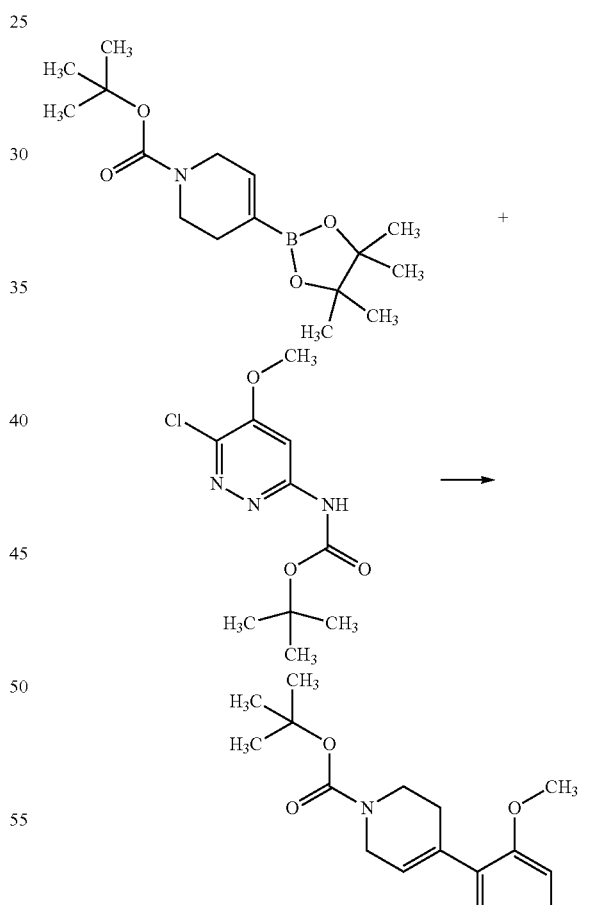

The title compound is synthesized from (6-chloro-5-methoxy-pyridazin-3-yl)-carbamic acid tert-butyl ester (595 mg, 1.93 mmol) and 4-(4,4,5,5-tetramethyl-[1,3,2]dioxaborolan-2-yl)-3,6-dihydro-2H-pyridine-1-carboxylic acid tert-butyl ester (500 mg, 1.93 mmol) according to the procedure described for the synthesis of the intermediate 6-amino-4-methoxy-3',6'-dihydro-2'H-[3,4']bipyridinyl-1'-carboxylic acid tert-butyl ester.

Yield: 78.0 mg (13%) ESI-MS: m/z=307 (M+H)+
$R_t$(HPLC): 0.63 min (Method 5)

4-(6-Amino-4-methoxy-pyridazin-3-yl)-piperidine-1-carboxylic acid tert-butyl ester

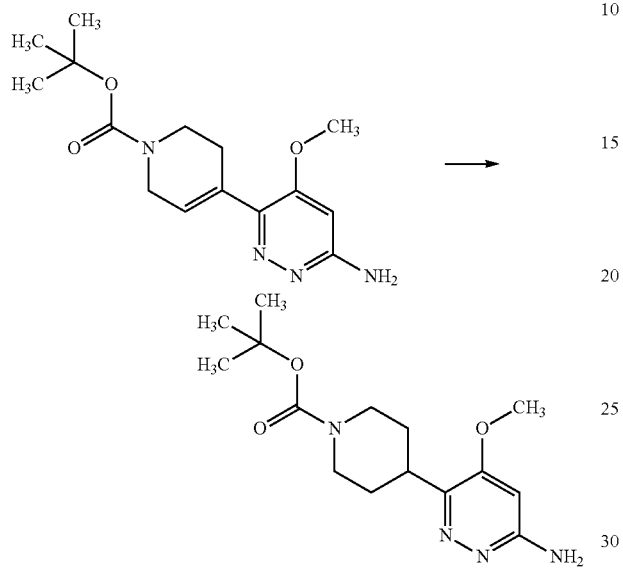

The title compound is synthesized from 4-(6-amino-4-methoxy-pyridazin-3-yl)-3,6-dihydro-2H-pyridine-1-carboxylic acid tert-butyl ester (650 mg, 2.12 mmol) according to the procedure described for the synthesis of the intermediate 6-amino-4-methoxy-3',4',5',6'-tetrahydro-2'H-[3,4']bipyridinyl-1'-carboxylic acid tert-butyl ester.

Yield: 498 mg (76%) ESI-MS: m/z=309 (M+H)+
$R_t$(HPLC): 1.56 min (Method 2)

5-Methoxy-6-piperidin-4-yl-pyridazin-3-ylamine dihydrochloride

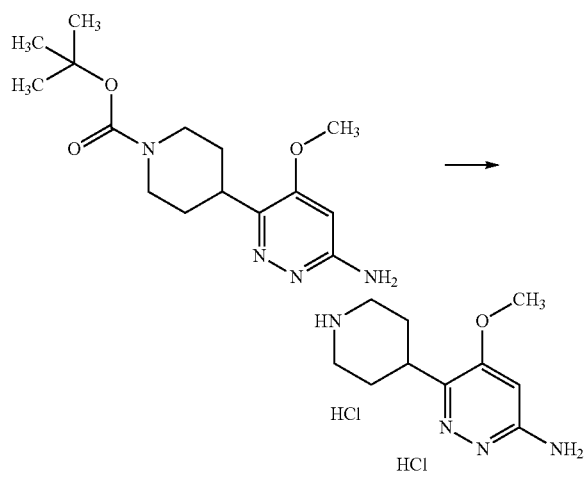

The title compound is synthesized from 4-(6-amino-4-methoxy-pyridazin-3-yl)-piperidine-1-carboxylic acid tert-butyl ester (388 mg, 1.26 mmol) according to the procedure described for the synthesis of the intermediate 4-methoxy-5-(piperidin-4-yl)pyridin-2-amine dihydrochloride.

Yield: 232 mg (66%) ESI-MS: m/z=209 (M+H)+
$R_t$(HPLC): 0.15 min (Method 5)

4-(6-Amino-4-methyl-pyridazin-3-yl)-3,6-dihydro-2H-pyridine-1-carboxylic acid tert-butyl ester

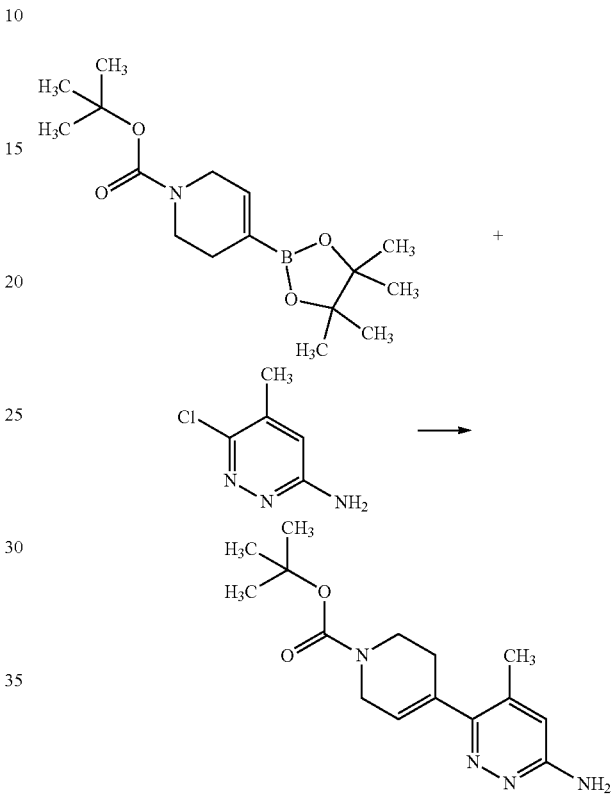

The title compound is synthesized from 6-chloro-5-methyl-pyridazin-3-ylamine (250 mg, 1.74 mmol) and 4-(4,4,5,5-tetramethyl-[1,3,2]dioxaborolan-2-yl)-3,6-dihydro-2H-pyridine-1-carboxylic acid tert-butyl ester (538 mg, 1.74 mmol) according to the procedure described for the synthesis of the intermediate 6-amino-4-methoxy-3',6'-dihydro-2'H-[3,4']bipyridinyl-1'-carboxylic acid tert-butyl ester.

Yield: 326 mg (65%) ESI-MS: m/z=292 (M+H)+
$R_t$(HPLC): 0.51 min (Method 5)

4-(6-Amino-4-methyl-pyridazin-3-yl)-piperidine-1-carboxylic acid tert-butyl ester

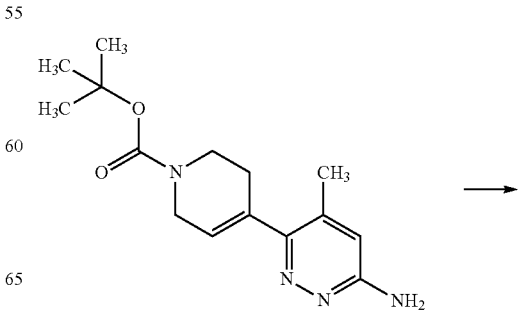

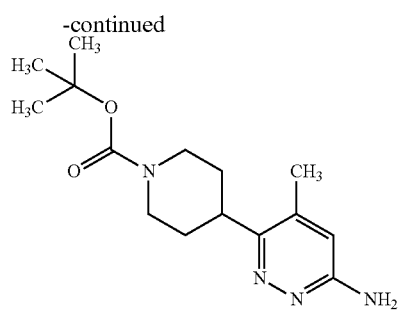

The title compound is synthesized from 4-(6-amino-4-methyl-pyridazin-3-yl)-3,6-dihydro-2H-pyridine-1-carboxylic acid tert-butyl ester (500 mg, 1.72 mmol) according to the procedure described for the synthesis of the intermediate 6-amino-4-methoxy-3',4',5',6'-tetrahydro-2'H-[3,4']-bipyridinyl-1'-carboxylic acid tert-butyl ester.

Yield: 176 mg (35%) ESI-MS: m/z=293 (M+H)+
$R_t$(HPLC): 1.38 min (Method 2)

5-Methyl-6-piperidin-4-yl-pyridazin-3-ylamine dihydrochoride

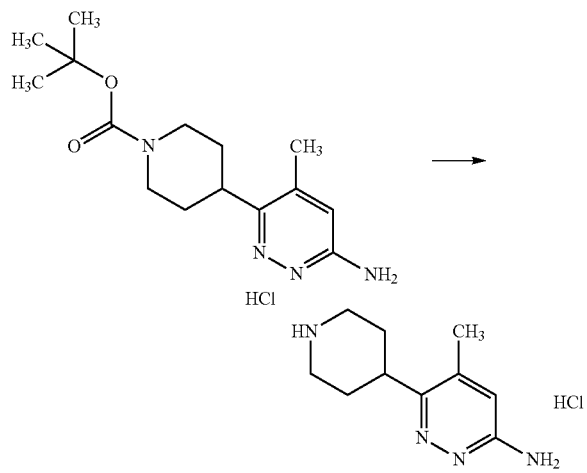

The title compound is synthesized from 4-(6-amino-4-methyl-pyridazin-3-yl)-piperidine-1-carboxylic acid tert-butyl ester (289 mg, 0.99 mmol) according to the procedure described for the synthesis of the intermediate 4-methoxy-5-(piperidin-4-yl)pyridin-2-amine dihydrochloride.

Yield: 243 mg (93%) ESI-MS: m/z=193 (M+H)+
$R_t$(HPLC): 0.14 min (Method 5)

6-Nitro-3',6'-dihydro-2'H-[3,4']bipyridinyl-1'-carboxylic acid tert-butyl ester

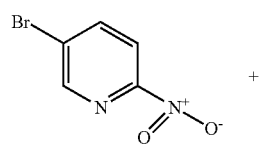 +

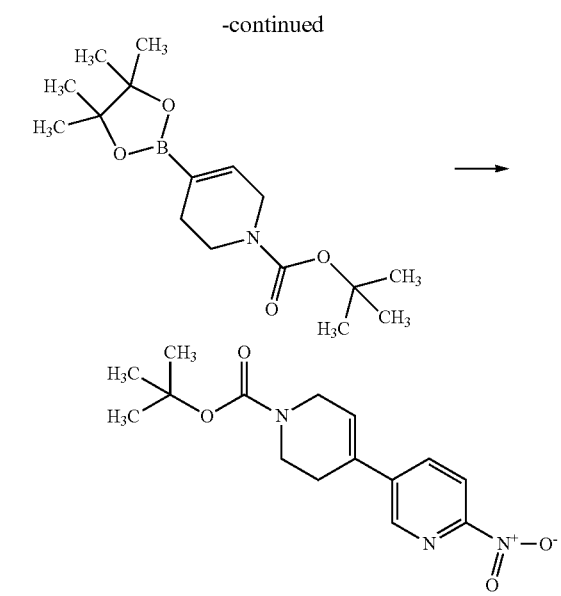

To 4-(4,4,5,5-tetramethyl-[1,3,2]dioxaborolan-2-yl)-3,6-dihydro-2H-pyridine-1-carboxylic acid tert-butyl ester (8.81 g, 43.4 mmol) and 5-bromo-2-nitro-pyridine (13.8 g, 44.7 mmol) in 1,4-dioxane/H₂O (90 mL/22.5 mL) is added K₂CO₃ (18.0 g, 130 mmol) and degassed with argon for 5 min. Then PdCl₂(PPh₃)₂ (152 mg, 0.22 mmol) is added. The reaction mixture is stirred at 90° C. for 3 h. The reaction mixture is diluted with water (70 mL) and 1,4-dioxane is distilled off to 130 g. Subsequently it is charged with MTBE (22.5 mL) and heptane (90 mL) and stirred for 30 min. The precipitate is filtered. The cake is washed with water, 1:4 MTBE/heptane and dried under vacuum.

Yield: 13.2 g (quantitative) ESI-MS: m/z=306 (M+H)+

5-Bromo-2-(2,5-dimethyl-pyrrol-1-yl)-4-methyl-pyridine

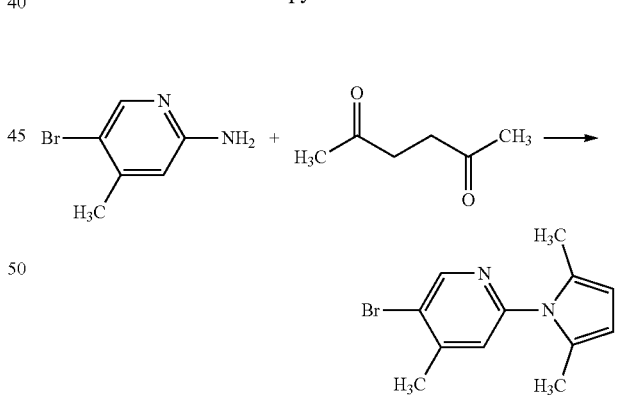

To 5-bromo-4-methyl-pyridin-2-ylamine (2.00 g, 10.7 mmol) and hexane-2,5-dione (1.47 g, 12.8 mmol) in toluene (50 mL) is added para toluene sulfonic acid (61.0 mg, 0.32 mmol) and the reaction mixture is stirred for 18 h at 140° C. The reaction mixture is poured into water and diluted in EtOAc. The separated organic layer is washed with brine and dried over MgSO₄, filtered and concentrated under reduced pressure. The residue is purified by silica gel column chromatography (ethyl acetate/heptane) to afford the title compound.

Yield: 2.68 g (95%)

5-Bromo-2-(2,5-dimethyl-pyrrol-1-yl)-4-methoxy-pyridine

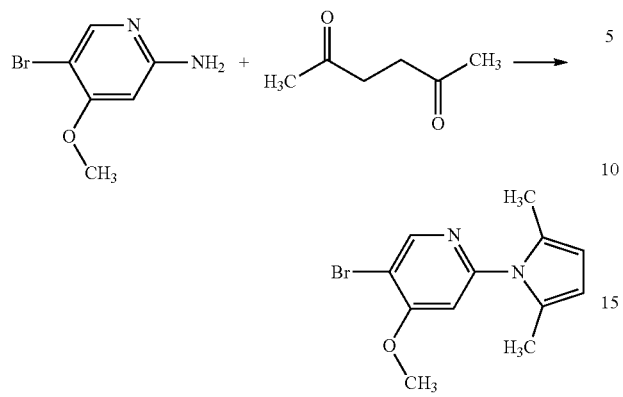

The title compound is synthesized from 5-bromo-4-methoxy-pyridin-2-ylamine (10.6 g, 52.1 mmol) according to the procedure described for the synthesis of the intermediate 5-bromo-2-(2,5-dimethyl-pyrrol-1-yl)-4-methyl-pyridine.

Yield: 14.0 g (96%) ESI-MS: m/z=283 (M+H)$^+$
R$_t$(HPLC): 0.93 min (Method 3)

(R)-2-(tert-Butyl-dimethyl-silanyloxymethyl)-4-[6-(2,5-dimethyl-pyrrol-1-yl)-4-methoxy-pyridin-3-yl]-piperazine-1-carboxylic acid tert-butyl ester

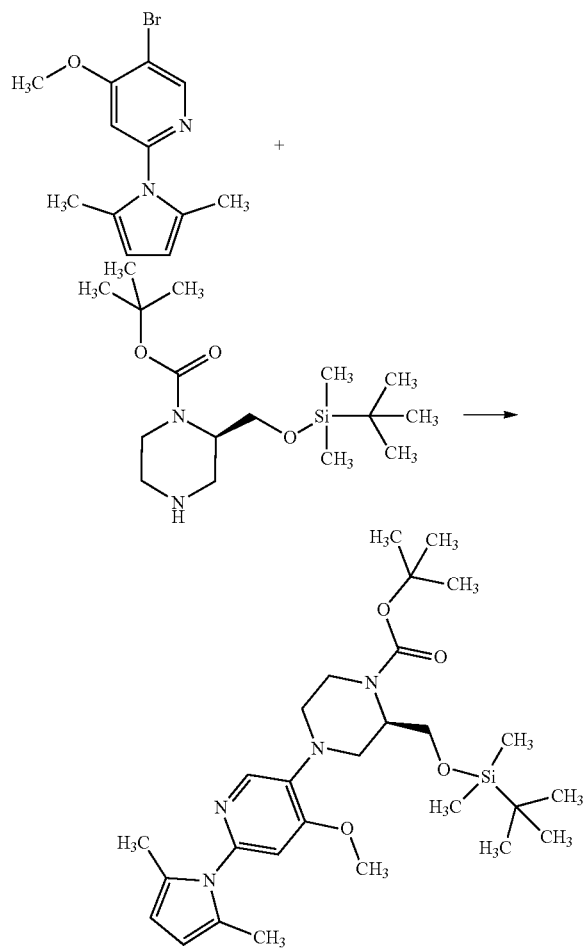

To 5-bromo-2-(2,5-dimethyl-pyrrol-1-yl)-4-methoxy-pyridine (5.48 g, 19.5 mmol), (R)-2-(tert-butyl-dimethyl-silanyloxymethyl)-piperazine-1-carboxylic acid tert-butyl ester (6.75 g, 20.4 mmol) and sodium tert-butylate (3.75 g, 39.0 mmol) in THF (75 mL) is added RuPhos Pd G3 (815 mg, 0.98 mmol) and degassed with N$_2$ for 5 min. The reaction mixture is stirred for 18 h at 85° C. The reaction mixture is filtered through Celite®, washed with EtOAc and concentrated. The residue is purified by HPLC (basic conditions, C-18 column) to afford the title product.

Yield: 4.8 g (37%) ESI-MS: m/z=531 (M+H)$^+$

(R)-4-(6-Amino-4-methoxy-pyridin-3-yl)-2-hydroxymethyl-piperazine-1-carboxylic acid tert-butyl ester

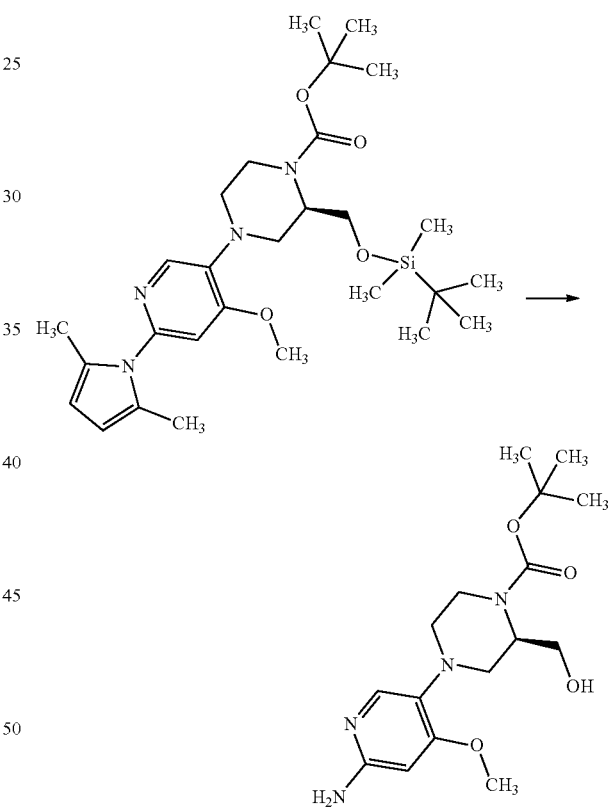

(R)-2-(tert-Butyl-dimethyl-silanyloxymethyl)-4-[6-(2,5-dimethyl-pyrrol-1-yl)-4-methoxy-pyridin-3-yl]-piperazine-1-carboxylic acid tert-butyl ester (1.29 g, 2.07 mmol), hydroxylamine hydrochloride (718 mg, 10.3 mmol) and triethylamine (0.29 mL, 2.07 mmol) in ethanol (6 mL) and water (3 mL) are stirred at 80° C. for 18 h. The reaction mixture is concentrated under reduced pressure and purified by silica gel column chromatography (DCM/MeOH) to afford the title product.

Yield: 369 mg (53%) ESI-MS: m/z=339 (M+H)$^+$

167

[(R)-4-(6-Amino-4-methoxy-pyridin-3-yl)-piperazin-2-yl]-methanol hydrochloride

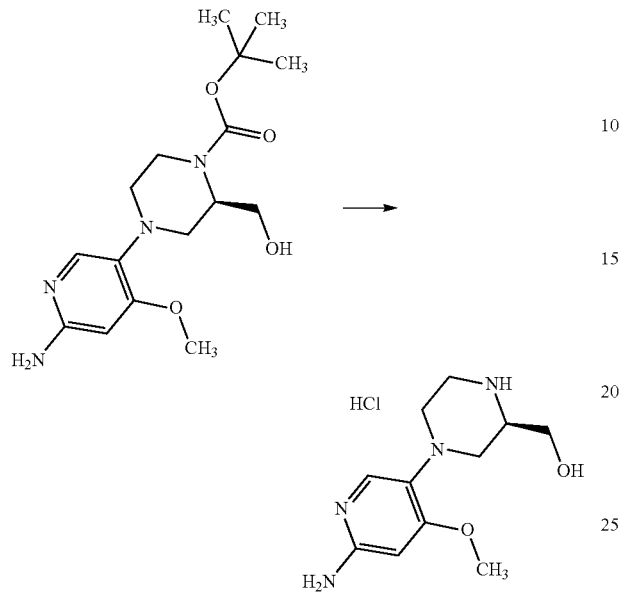

To (R)-4-(6-amino-4-methoxy-pyridin-3-yl)-2-hydroxymethyl-piperazine-1-carboxylic acid tert-butyl ester (45 mg, 0.13 mmol) in DCM (0.5 mL) is added 4M hydrogen chloride in 1,4-dioxane (0.17 mL, 0.67 mmol). The reaction mixture is stirred for 2 h at ambient temperature. All volatiles are evaporated under reduced pressure. Ether is added to the residue and filtered to afford the title compound.

Yield: 30 mg (82%) ESI-MS: m/z=239 (M+H)+
$R_t$(HPLC): 0.23 min (Method 9)

(S)-2-(tert-Butyl-dimethyl-silanyloxymethyl)-piperazine-1-carboxylic acid tert-butyl ester

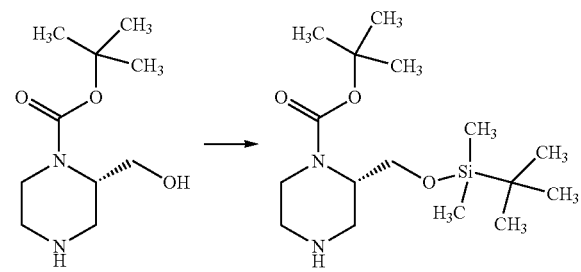 [SMILES: CC(C)(C)OC(=O)N1CCNC[C@H]1CO ; CC(C)(C)OC(=O)N1CCNC[C@H]1CO[Si](C)(C)C(C)(C)C]

To (S)-2-hydroxymethyl-piperazine-1-carboxylic acid tert-butyl ester (2.00 g, 9.25 mmol) in DMA (10 mL) is added tert-butyl-chloro-dimethyl-silane (2.09 g, 13.9 mmol) and imidazole (1.89 g, 27.7 mmol). The reaction mixture is stirred for 24 h at rt. The reaction mixture is diluted with NH₄Cl-solution and extracted with EtOAc. The organic layer is washed with water and brine, dried over Na₂SO₄, filtered and concentrated under reduced pressure. The residue is purified by silica gel column chromatography to afford the title compound.

Yield: 2.80 g (92%)

168

(S)-2-(tert-Butyl)-dimethyl-silanyloxymethyl)-4-[6-(2,5-dimethyl-pyrrol-1-yl)-4-methoxy-pyridin-3-yl]-piperazine-1-carboxylic acid tert-butylester

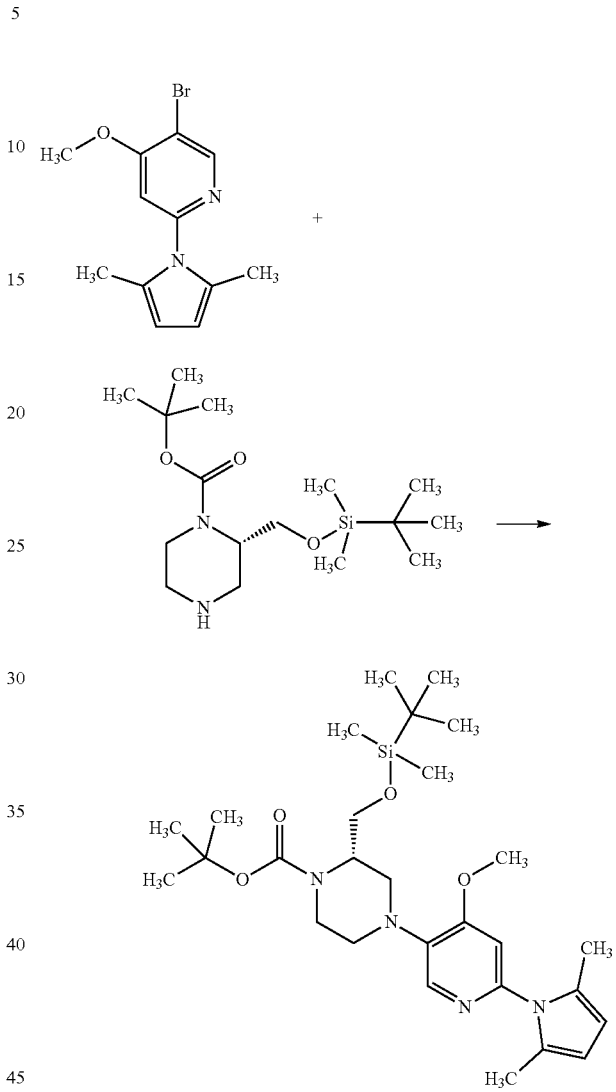

A pressure vessel is charged with 5-bromo-2-(2,5-dimethyl-pyrrol-1-yl)-4-methoxy-pyridine (3.25 g, 11.6 mmol), CPhos-3G-palladacycle methane sulfonate (0.47 g, 0.58 mmol) and (S)-2-(tert-butyl-dimethyl-silanyloxymethyl)-piperazine-1-carboxylic acid tert-butyl ester (3.82 g, 11.6 mmol) in 1,4 dioxane (40 mL). Sodium tert-butoxide (3.3 g, 34.7 mmol) is added and the vessel is flushed with argon, sealed and stirred at 100° C. overnight. The reaction mixture is cooled to room temperature, diluted with water and EtOAc and filtered through Celite®. The organic layer is separated and washed with brine, dried, filtered and concentrated under reduced pressure. The residue is purified by silica gel column chromatography (EtOAc/heptane) to provide the desired compound.

Yield: 4.94 g (73%) ESI-MS: m/z=531 (M+H)+
$R_t$(HPLC): 1.49 min (Method 3)

(S)-4-(6-Amino-4-methoxy-pyridin-3-yl)-2-hydroxymethyl-piperazine-1-cart tert-butyl ester

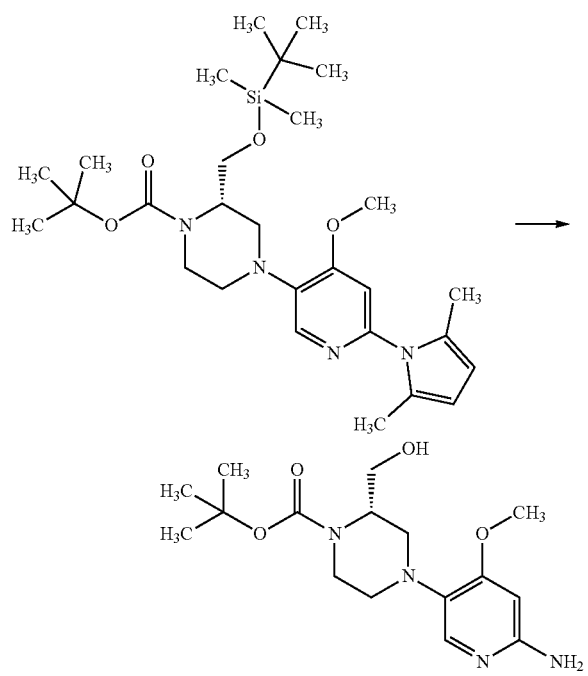

(S)-2-(tert-Butyl-dimethyl-silanyloxymethyl)-4-[6-(2,5-dimethyl-pyrrol-1-yl)-4-methoxypyrid in-3-yl]-piperazine-1-carboxylic acid tert-butyl ester (5.9 g, 11.2 mmol), hydroxylamine hydrochloride (3.89 g, 56.0 mmol) and triethylamine (1.6 mL, 11.2 mmol) in ethanol (30 mL) and water (15 mL) are stirred for 18 h at 80° C. Additional triethylamine (7.8 mL, 56.0 mmol) is added. The reaction mixture is concentrated under reduced pressure and the residue is purified by silica gel chromatography (MeOH/DCM) to afford the title compound.

Yield: 2.57 g (68%)

(S)-4-(6-Amino-4-methoxy-pyridin-3-yl)-piperazin-2-yl]-methanol hydrochloride

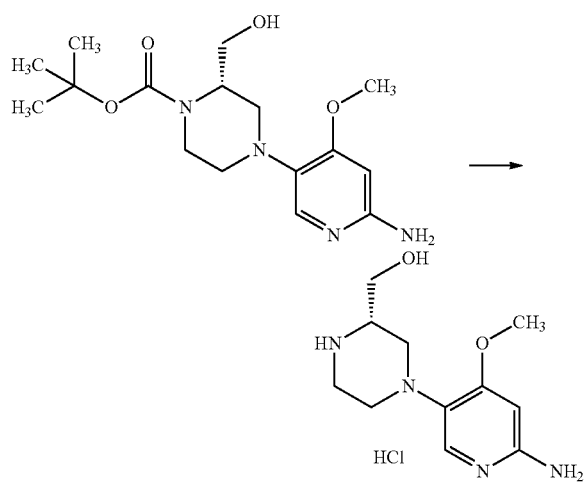

To (S)-4-(6-amino-4-methoxy-pyridin-3-yl)-2-hydroxymethyl-piperazine-1-carboxylic acid tert-butyl ester (264 mg, 0.58 mmol) in dichloromethane (1 mL) is added 4N HCl in dioxane (0.73 mL, 2.92 mmol). The reaction mixture is stirred at RT until reaction shows completion. The reaction mixture is evaporated under reduced pressure. The residue is used without further purification.

Yield: 160 mg (quantitative)

(R)-2-(tert-Butyl-dimethyl-silanyloxymethyl)-4-[6-(2,5-dimethyl-pyrrol-1-yl)-4-methyl-pyridin-3-yl]-piperazine-1-carboxylic acid tert-butyl ester

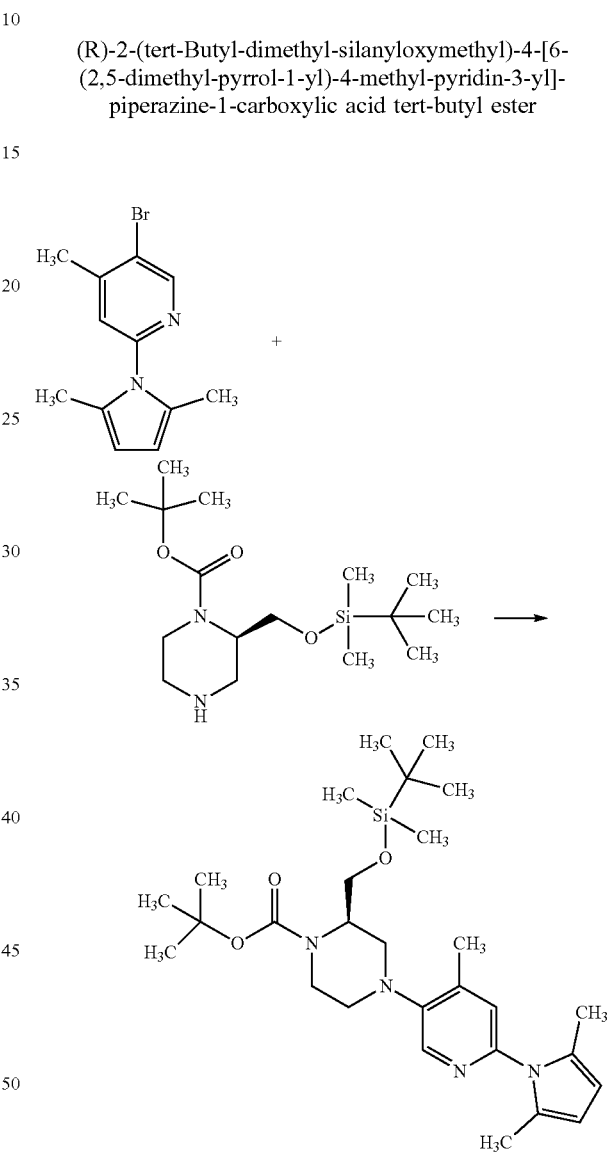

To 5-bromo-2-(2,5-dimethyl-pyrrol-1-yl)-4-methyl-pyridine (1.00 g, 3.77 mmol) and (R)-2-(tert-butyl-dimethyl-silanyloxymethyl)-piperazine-1-carboxylic acid tert-butyl ester (1.25 g, 3.77 mmol) in 1,4-dioxane (13 mL) is added sodium tert-butoxide (1.09 g, 11.3 mmol) and CPhos-G3-palladacycle methansulfonate (152 mg, 0.19 mmol). The mixture is degassed with nitrogen for 5 min, and stirred for 18 h at 100° C. The reaction mixture is filtered through a pad of silica gel and eluting with EtOAc. The filtrate is concentrated under reduced pressure to afford the title compound.

Yield: 1.67 g (86%) ESI-MS: m/z=515 (M+H)$^+$
$R_t$(HPLC): 1.56 min (Method 1)

(R)-4-(6-Amino-4-methyl-pyridin-3-yl)-2-hydroxymethyl-piperazine-1-carboxylic acid tert-butyl ester

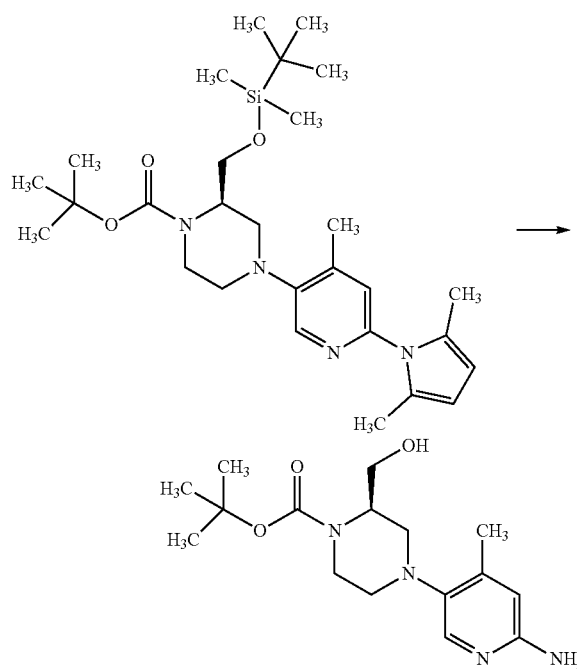

(R)-2-(tert-Butyl-dimethyl-silanyloxymethyl)-4-[6-(2,5-dimethyl-pyrrol-1-yl)-4-methyl-pyridin-3-yl]-piperazine-1-carboxylic acid tert-butyl ester (1.67 g, 3.24 mmol), hydroxylamine hydrochloride (1.13 g, 16.2 mmol) and triethylamine (452 µl, 3.24 mmol) in ethanol (10 mL) and water (5 mL) is stirred for 18 h at 80° C. The reaction mixture is concentrated under reduced pressure and the residue is purified by reversed phase chromatography to afford the title compound.

Yield: 0.5 g (47%) ESI-MS: m/z=323 (M+H)$^+$ R$_t$(HPLC): 0.66 min (Method 3)

[(R)-4-(6-Amino-4-methyl-pyridin-3-yl)-piperazin-2-yl]-methanol dihydrochloride

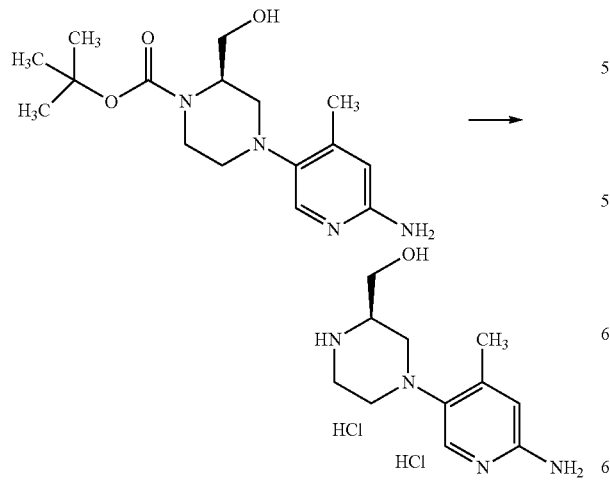

To (R)-4-(6-amino-4-methyl-pyridin-3-yl)-2-hydroxymethyl-piperazine-1-carboxylic acid tert-butyl ester (450 mg, 1.40 mmol) in dichloromethane (2 mL) is added 4N HCl in dioxane (2 mL, 8.0 mmol) and the reaction mixture is stirred 4 h at RT. The reaction mixture is concentrated under reduced pressure. The residue is used without further purification.

Yield: 412 mg (quantitative)

(R)-4-[6-(2,5-Dimethyl-pyrrol-1-yl)-4-methoxy-pyridin-3-yl]-2-hydroxymethyl-piperazine-1-carboxylic acid tert-butyl ester

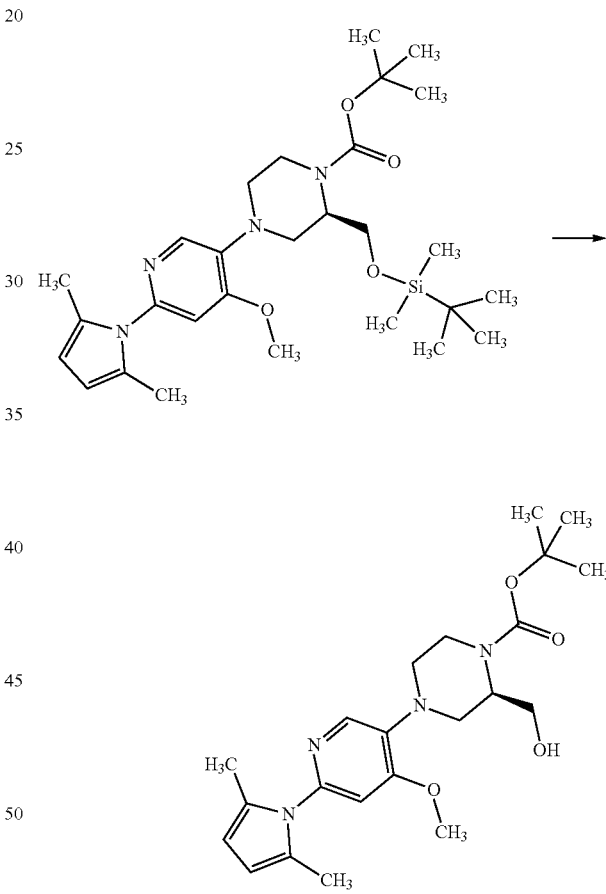

To (R)-2-(tert-butyl-dimethyl-silanyloxymethyl)-4-[6-(2,5-dimethyl-pyrrol-1-yl)-4-methoxy-pyridin-3-yl]-piperazine-1-carboxylic acid tert-butyl ester (8.56 g, 16.1 mmol) in THF (100 mL) is added TBAF (1 M in THF, 16.1 mL, 16.1 mmol). The reaction mixture is stirred for 2.5 h at rt. The reaction mixture is concentrated under reduced pressure and the residue is purified by silica chromatography (EtOAc/heptane) to afford the title product.

Yield: 6.1 g (91%) ESI-MS: m/z=417 (M+H)$^+$ R$_t$(HPLC): 0.98 min (Method 1)

(R)-4-[6-(2,5-Dimethyl-pyrrol-1-yl)-4-methoxy-pyridin-3-yl]-2-methoxymethyl-piperazine-1-carboxylic acid tert-butyl ester

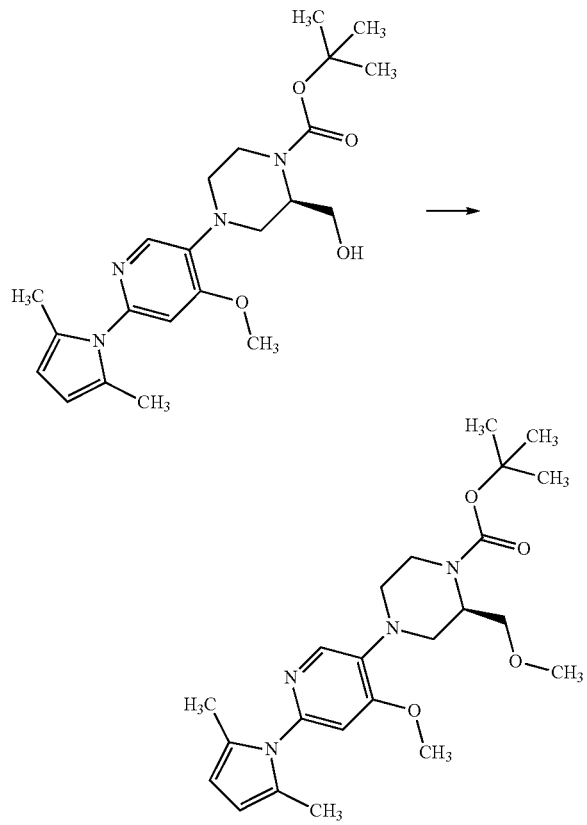

NaH (60%, 230 mg, 9.58 mmol) is added to (R)-4-[6-(2,5-dimethyl-pyrrol-1-yl)-4-methoxy-pyridin-3-yl]-2-hydroxymethyl-piperazine-1-carboxylic acid tert-butyl ester (2.0 g, 4.80 mmol) and MeI (401 µL, 7.20 mmol) in DMA (20 mL). The reaction mixture is stirred for 2 h at rt. Water is added and the reaction mixture is extracted with EtOAc (3 times). The combined organic layers are washed with brine, dried over MgSO$_4$, filtered and concentrated under reduced pressure. The residue is purified by normal phase chromatography (ethyl acetate/heptane).

Yield: 1.8 g (87%) ESI-MS: m/z=431 (M+H)$^+$ R$_t$(HPLC): 1.11 min (Method 1)

(R)-4-(6-Amino-4-methoxy-pyridin-3-yl)-2-methoxymethyl-piperazine-1-carboxylic acid tert-butyl ester

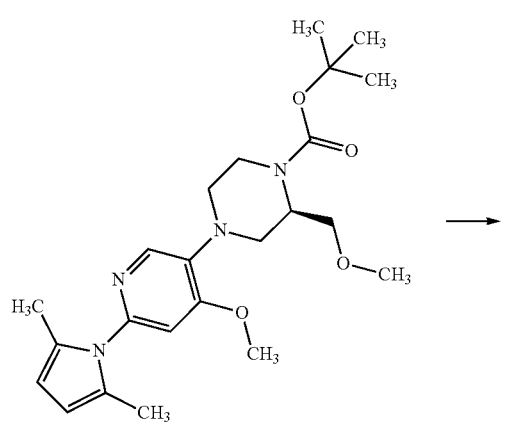

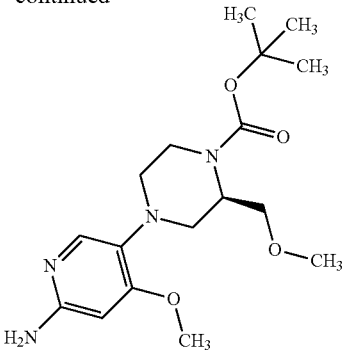

(R)-4-[6-(2,5-Dimethyl-pyrrol-1-yl)-4-methoxy-pyridin-3-yl]-2-methoxymethyl-piperazine-1-carboxylic acid tert-butyl ester (1.8 g, 4.18 mmol), hydroxylamine hydrochloride (1.45 g, 20.9 mmol) and triethylamine (0.58 mL, 4.18 mmol) in ethanol (10 mL) and water (5 mL) are stirred at 80° C. for 18 h. The reaction mixture is concentrated under reduced pressure, slurried in DCM, filtered to remove salts and concentrated again under reduced pressure. The residue is purified by normal phase column chromatography to afford the title product.

Yield: 440 mg (30%) ESI-MS: m/z=353 (M+H)$^+$ R$_t$(HPLC): 0.44 min (Method 1)

4-Methoxy-5-((R)-3-methoxymethyl-piperazin-1-yl)-pyridin-2-ylamine dihydrochloride

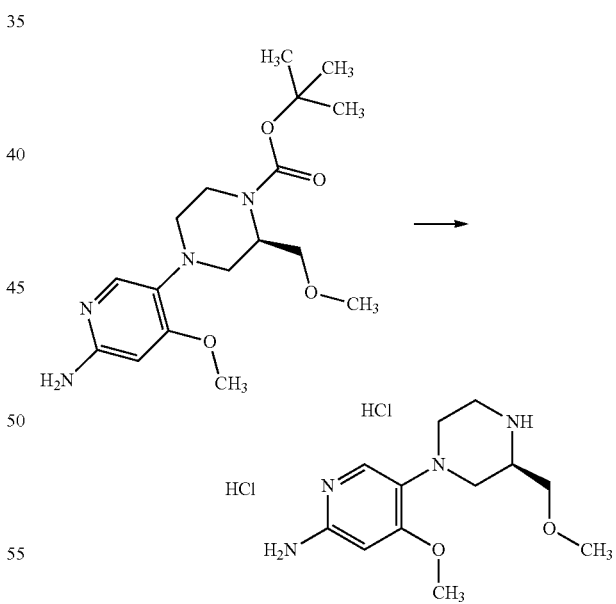

(R)-4-(6-amino-4-methoxy-pyridin-3-yl)-2-methoxymethyl-piperazine-1-carboxylic acid tert-butyl ester (440 mg, 1.25 mmol) is dissolved in dichloromethane (2 mL) and 4N HCl in dioxane (1.56 mL) is added. The reaction mixture is stirred at rt for 4 h. The reaction mixture is concentrated under reduced pressure. The residue is used without further purification.

Yield: 406 mg (quantitative)

4-[6-(2,5-Dimethyl-pyrrol-1-yl)-4-methoxy-pyridin-3-yl]-piperazine-1-carboxylic acid tert-butyl ester

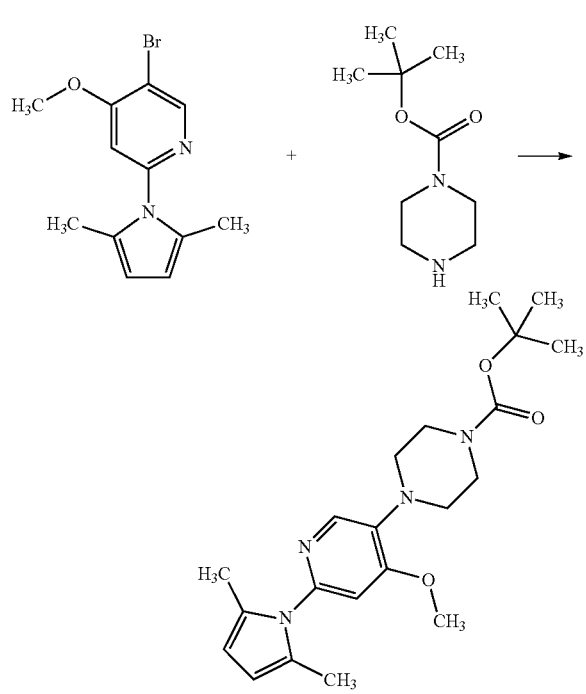

5-bromo-2-(2,5-dimethyl-pyrrol-1-yl)-4-methoxy-pyridine (1.5 g, 5.37 mmol), piperazine-1-carboxylic acid tert-butyl ester (1.0 g, 5.37 mmol), CPhos-3G-palladacycle methane sulfonate (0.2 g, 0.27 mmol) and sodium tert-butoxide (1.55 g, 16.1 mmol) in 1,4-dioxane (15 mL) are sparged with nitrogen for 5 min and then heated to 100° C. for 10 h. The reaction mixture is cooled to room temperature, filtered through a pad of silica, eluting with ethyl acetate and concentrated under reduced pressure. The residue is purified by silica gel column chromatography.

Yield: 2.1 g (87%) ESI-MS: m/z=387 (M+H)⁺ Rt(HPLC): 1.15 min (Method 1)

4-(6-Amino-4-methoxy-pyridin-3-yl)-piperazine-1-carboxylic acid tert-butyl ester

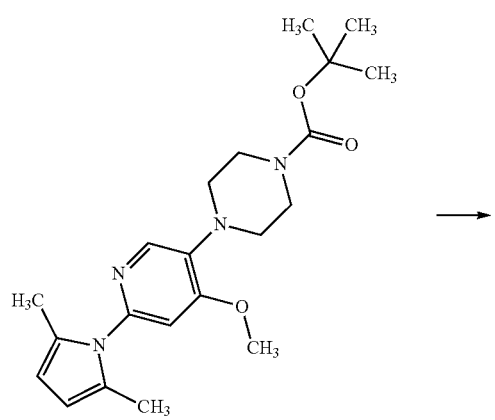

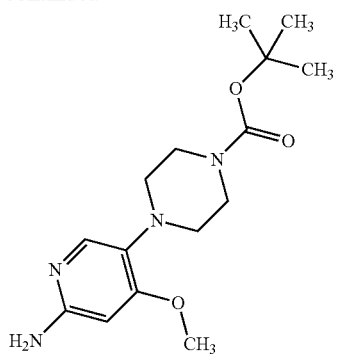

The title compound is synthesized from 4-[6-(2,5-dimethyl-pyrrol-1-yl)-4-methoxy-pyridin-3-yl]-piperazine-1-carboxylic acid tert-butyl ester (2.1 g, 4.73 mmol) according to the procedure described for the synthesis of the intermediate (R)-4-(6-amino-4-methoxy-pyridin-3-yl)-2-hydroxymethyl-piperazine-1-carboxylic acid tert-butyl ester.

Yield: 1.07 g (73%)

4-Methoxy-5-piperazin-1-yl-pyridin-2-ylamine dihydrochloride

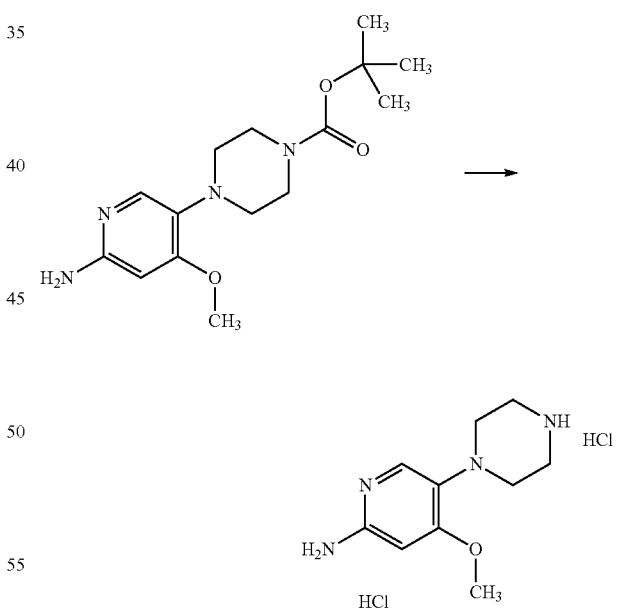

The title compound is synthesized from 4-(6-amino-4-methoxy-pyridin-3-yl)-piperazine-1-carboxylic acid tert-butyl ester (1.07 g, 3.47 mmol) according to the procedure described for the synthesis of the intermediate [(R)-4-(6-amino-4-methoxy-pyridin-3-yl)-piperazin-2-yl]-methanol hydrochloride.

Yield: 976 mg (quantitative) ESI-MS: m/z=209 (M+H)⁺

2-(2,2-Difluoro-ethyl)-4-[6-(2,5-dimethyl-pyrrol-1-yl)-4-methoxy-pyridin-3-yl]-piperazine-1-carboxylic acid tert-butyl ester

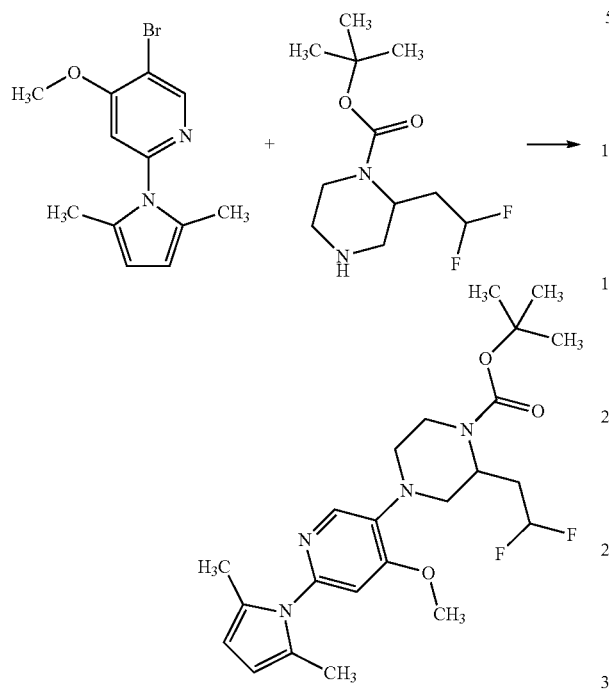

A pressure vessel equipped with a Teflon stir bar is charged with 5-bromo-2-(2,5-dimethyl-pyrrol-1-yl)-4-methoxy-pyridine (360 mg, 1.28 mmol) and CPhos-3G-palladacycle methane sulfonate (51.6 mg, 0.06 mmol). 2-(2,2-difluoro-ethyl)-piperazine-1-carboxylic acid tert-butyl ester (320 mg, 1.28 mmol) is added in 1,4 dioxane (6 mL). Cesium carbonate (1.25 g, 3.84 mmol) is added and the vessel is flushed with argon, sealed and stirred at 80° C. overnight. The reaction mixture is cooled to room temperature, diluted with EtOAc and water and filtered through Celite®. The aqueous layer is removed and the organic layer is washed with brine, dried over MgSO$_4$, filtered and concentrated. The residue is purified by silica gel column chromatography (EtOAc/heptane).

Yield: 477 mg (83%) ESI-MS: m/z=451 (M+H)$^+$
R$_t$(HPLC): 1.18 min (method 3)

4-(6-Amino-4-methoxy-pyridin-3-yl)-2-(2,2-difluoro-ethyl)-piperazine-1-carboxylic acid tert-butyl ester

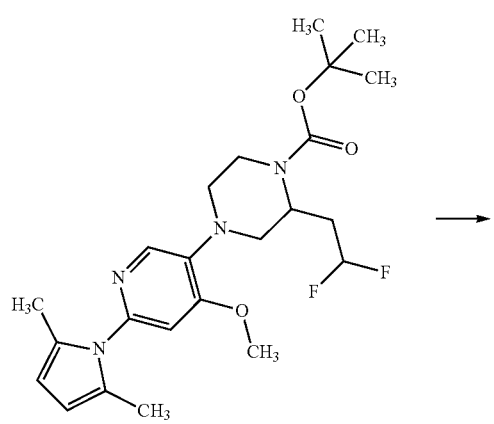

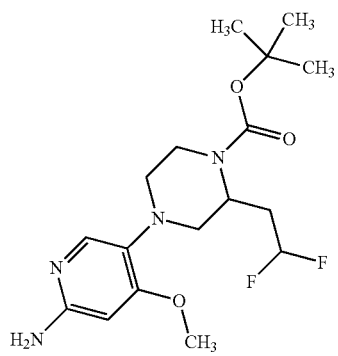

The title compound is synthesized from 2-(2,2-difluoro-ethyl)-4-[6-(2,5-dimethyl-pyrrol-1-yl)-4-methoxy-pyridin-3-yl]-piperazine-1-carboxylic acid tert-butyl ester (477 mg, 1.06 mmol) according to the procedure described for the synthesis of the intermediate (R)-4-(6-amino-4-methoxy-pyridin-3-yl)-2-hydroxymethyl-piperazine-1-carboxylic acid tert-butyl ester.

Yield: 0.40 g (quant.) ESI-MS: m/z=373 (M+H)$^+$
R$_t$(HPLC): 0.82 min (Method 3)

5-[3-(2,2-Difluoro-ethyl)-piperazin-1-yl]-4-methoxy-pyridin-2-ylamine hydrochloride

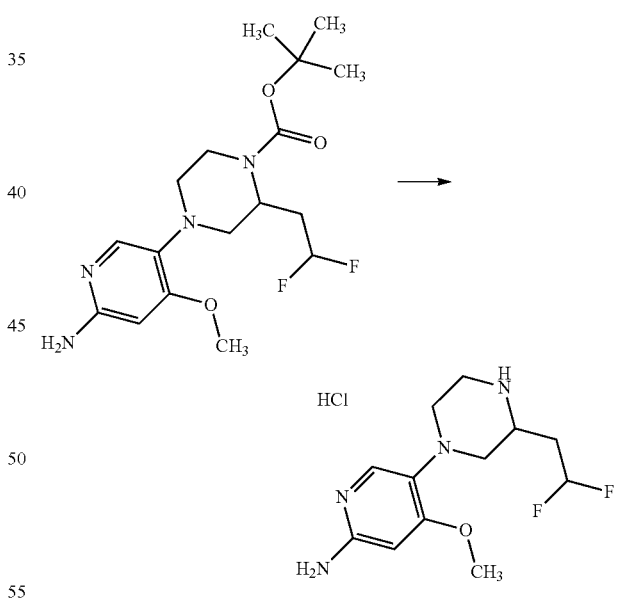

The title compound is synthesized from 4-(6-amino-4-methoxy-pyridin-3-yl)-2-(2,2-difluoro-ethyl)-piperazine-1-carboxylic acid tert-butyl ester (395 mg, 1.06 mmol) according to the procedure described for the synthesis of the intermediate [(R)-4-(6-amino-4-methoxy-pyridin-3-yl)-piperazin-2-yl]-methanol hydrochloride. After 2 hours reaction time, additional dioxane (5 mL) is added. The reaction mixture is stirred at RT overnight. The reaction mixture is concentrated under reduced pressure.

Yield: 327 mg (quantitative)

4-Benzyl 1-tert-butyl (2R)-2-methoxy(methyl)carbamoyl)piperazine-1,4-dicarboxylate

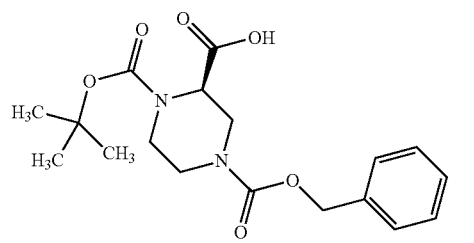

(2R)-4-[(benzyloxy)carbonyl]-1-[(tert-butoxy)carbonyl]piperazine-2-carboxylic acid (4.00 g, 11.0 mmol), DIPEA (5.1 mL, 27.4 mmol), HATU (5.01 g, 13.2 mmol) and N,O-dimethylhydroxylamine hydrochloride (1.29 g, 13.2 mmol) in DMA (40 mL) are stirred at rt over the weekend. The reaction mixture is diluted with EtOAc, and washed with water and brine. The organic layer is dried over MgSO$_4$, filtered, and concentrated under reduced pressure. The residue is purified by silica gel column chromatography (EtOAc/heptane) to afford the title compound.

Yield: 4.44 g (99%) ESI-MS: m/z=408 (M+H)$^+$

4-Benzyl 1-tert-butyl (2R)-2-acetylpiperazine-1,4-dicarboxylate

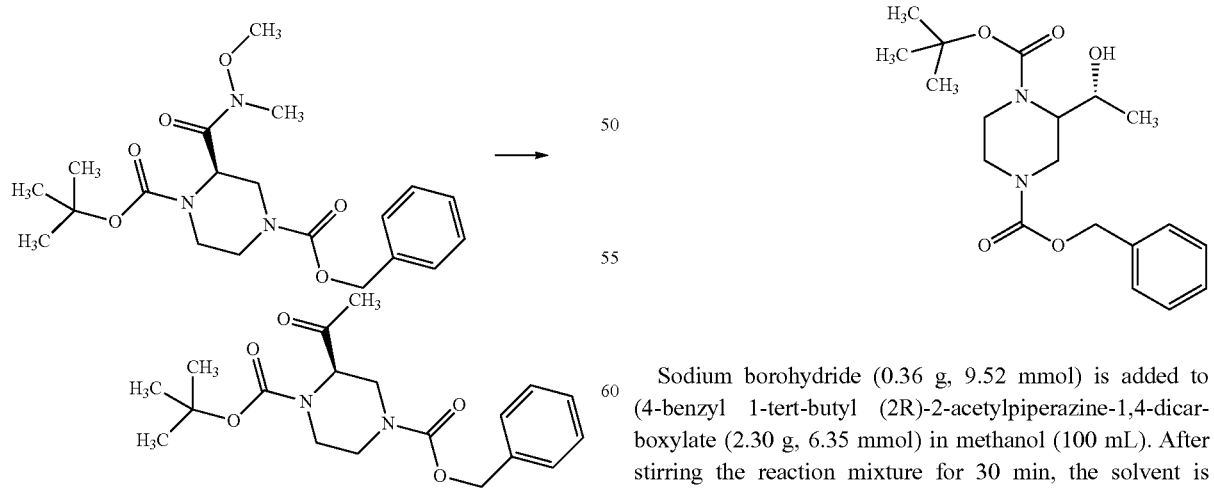

To a −20° C. cooled mixture of 4-benzyl 1-tert-butyl (2R)-2-[methoxy(methyl)carbamoyl]-piperazine-1,4-dicarboxylate (4.40 g, 10.80 mmol) in THF (25 mL) is added dropwise methyl magnesium bromide (5.40 mL, 16.20 mmol) and stirred at −20° C. for 30 min. The reaction mixture is quenched with saturated, aqueous NH$_4$Cl solution, diluted with EtOAc, washed with water+1N HCl and brine. The organic layer is dried over MgSO$_4$, filtered and concentrated under reduced pressure. The residue is purified by silica gel chromatography (EtOAc/heptane) to afford the desired product. Further purification is done by chiral HPLC to afford the pure R enantiomer.

Yield: 2.38 g (61%) ESI-MS: m/z=363 (M+H)$^+$ R$_t$(HPLC): 1.01 min (Method 1)

4-Benzyl 1-tert-butyl (2R)-2-(1-hydroxyethyl)piperazine-1,4-dicarboxylate

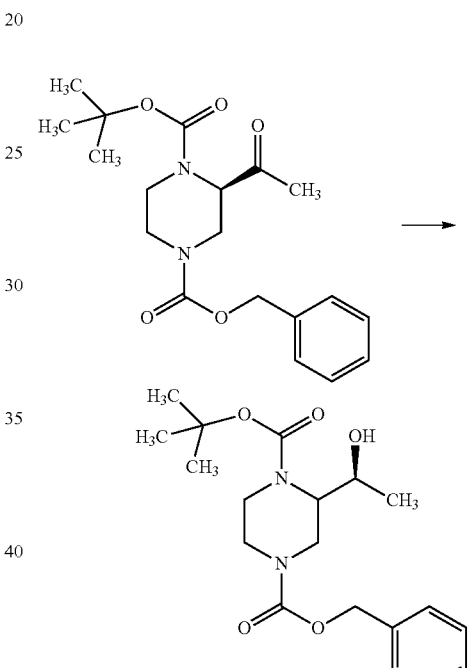

Sodium borohydride (0.36 g, 9.52 mmol) is added to (4-benzyl 1-tert-butyl (2R)-2-acetylpiperazine-1,4-dicarboxylate (2.30 g, 6.35 mmol) in methanol (100 mL). After stirring the reaction mixture for 30 min, the solvent is removed under reduced pressure. The residue is purified by silica gel chromatography (ethyl acetate/heptane).

Yield: 2.10 g (91%)

181

4-Benzyl 1-tert-butyl (2R)-2-{1-[(tert-butyldimethylsilyl)oxy]ethyl}piperazine-1,4-dicarboxylate

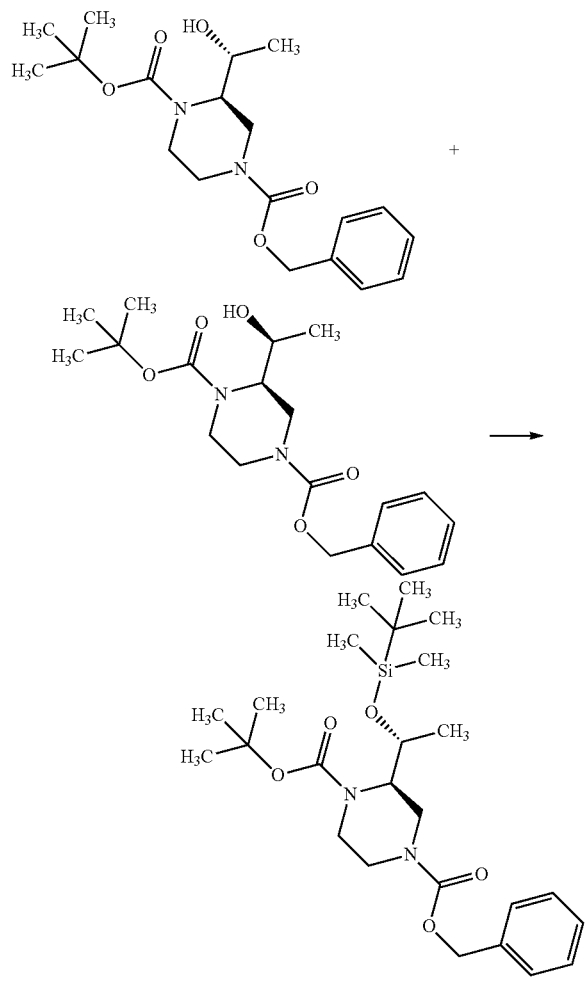

182

-continued

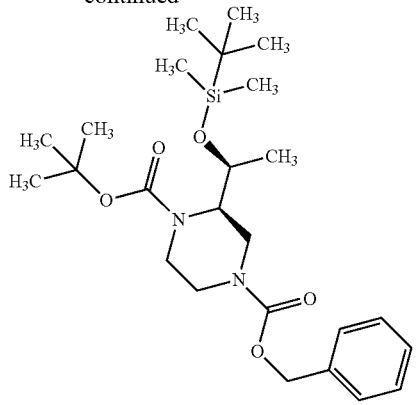

tert-Butyl(chloro)dimethylsilane (1.30 g, 8.64 mmol) is added to 4-benzyl 1-tert-butyl (2R)-2-(1-hydroxyethyl)piperazine-1,4-dicarboxylate (2.10 g, 5.76 mmol) and imidazole (1.18 g, 17.29 mmol) in dichloromethane (15 mL). The reaction mixture is stirred overnight. After adding water (10 mL), the aqueous layer is extracted with dichloromethane (2×25 mL). The combined organic layers are washed with brine. The organic layer is dried, filtered, and concentrated under reduced pressure. The residue is purified by silica chromatography (ethyl acetate/heptane).

Yield: 2.75 g (99.7%)

tert-Butyl (2R)-2-{1-[(tert-butyldimethyl)silyl)oxy]ethyl}piperazine-1-carboxylate

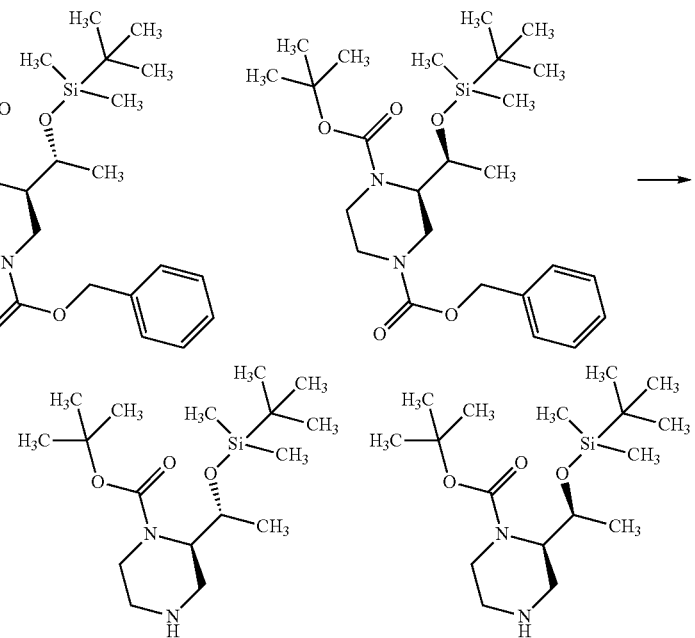

Under a hydrogen atmosphere (balloon) 4-benzyl 1-tert-butyl (2R)-2-{1-[(tert-butyldimethylsilyl)-oxy]ethyl}piperazine-1,4-dicarboxylate (2.75 g, 5.75 mmol) and Pd/C (0.20 g) is stirred at room temperature in ethanol (50 mL) for 2 h. After removal of the catalyst by filtering through Celite®, the solvent is removed under reduced pressure. The residue is filtered through silica eluting with 10% MeOH/dichloromethane.

Yield: 1.89 g (96%)

(tert-Butyl (2R)-2-{1-[(tert-butyldimethyl)silyl)oxy]ethyl}-4-[6-(2,5-dimethyl-1H-pyrrol-1-yl)-4-methoxypyridin-3-yl]piperazine-1-carboxylate

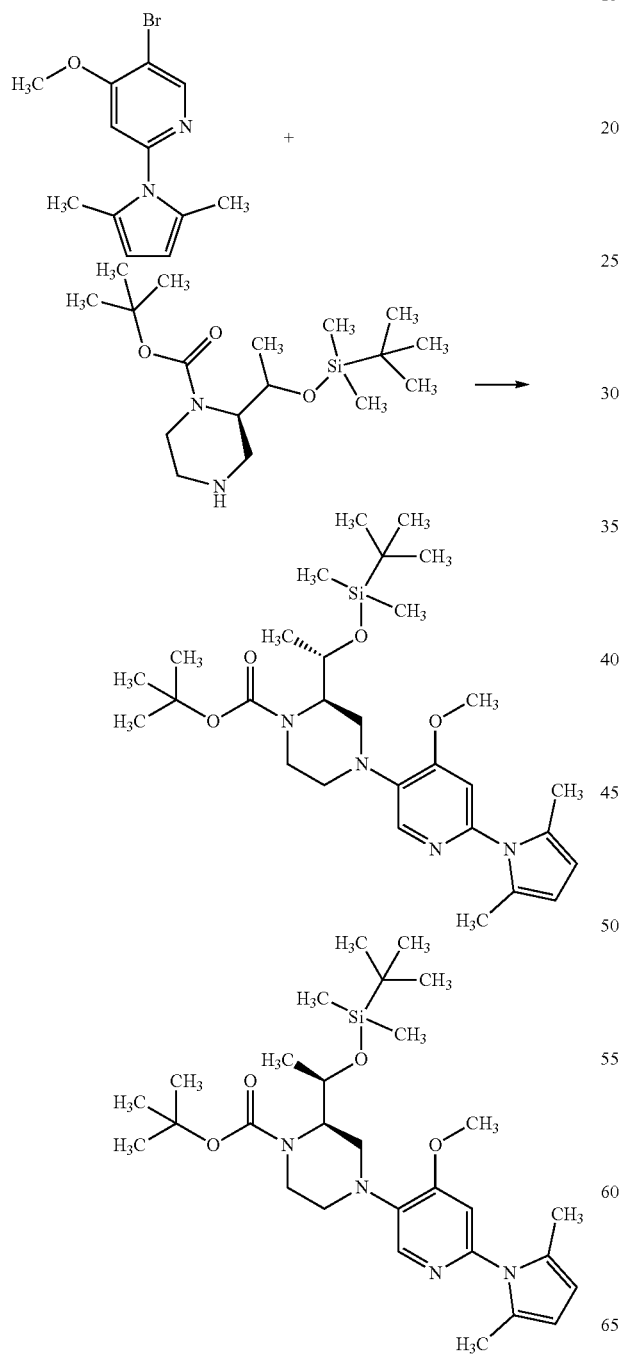

To tert-butyl (2R)-2-{1-[(tert-butyldimethylsilyl)oxy]ethyl}piperazine-1-carboxylate (1.89 g, 5.49 mmol) and 5-bromo-2-(2,5-dimethyl-pyrrol-1-yl)-4-methoxy-pyridine (1.54 g, 5.49 mmol) in 1,4-dioxane (20 mL) is added CPhos-3G-palladacycle methane sulfonate (0.22 g) and sodium tert-butoxide (1.58 g, 16.5 mmol) and sparged with nitrogen. The reaction mixture is stirred at 100° C. for 10 h. The reaction mixture is filtered through a pad of silica eluting with EtOAc and concentrated. The residue is purified twice by silica chromatography (ethyl acetate/heptane) to afford the title compounds.

Yield: (tert-butyl (2R)-2-[(1S)-1-[(tert-butyldimethylsilyl)oxy]ethyl]-4-[6-(2,5-dimethyl-1H-pyrrol-1-yl)-4-methoxypyridin-3-yl]piperazine-1-carboxylate): 0.57 g (19%) and ((tert-butyl (2R)-2-[(1R)-1-[(tert-butyldimethylsilyl)oxy]ethyl]-4-[6-(2,5-dimethyl-1H-pyrrol-1-yl)-4-methoxypyridin-3-yl]piperazine-1-carboxylate)): 0.78 g (26%)

tert-Butyl (2R)-4-(6-amino-4-methoxypyridin-3-yl)-2-[(1R)-1-hydroxyethyl]piperazine-1-carboxylate

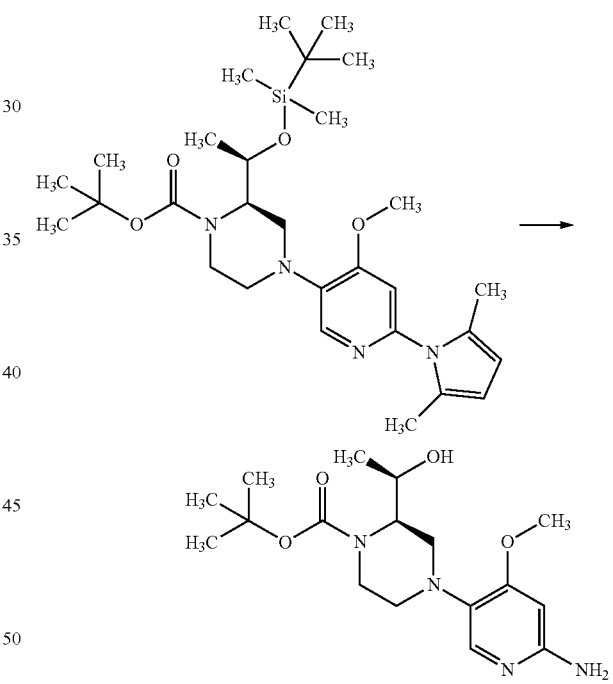

tert-Butyl (2R)-2-[(1R)-1-[(tert-butyldimethylsilyl)oxy]ethyl]-4-[6-(2,5-dimethyl-1H-pyrrol-1-yl)-4-methoxypyridin-3-yl]piperazine-1-carboxylate (0.87 g, 1.60 mmol), hydroxylamine hydrochloride (0.56 g, 7.99 mmol) and triethylamine (0.22 mL, 1.60 mmol) in ethanol (8 mL) and water (4 mL) is heated at 80° C. for 42 h. An additional amount of hydroxylamine hydrochloride (0.22 g, 3.19 mmol) is added and the reaction mixture is stirred at 80° C. overnight. The reaction mixture is concentrated under reduced pressure, taken up in dichloromethane and filtered. The desired compound is purified by silica chromatography (MeOH/DCM).

Yield: 0.20 g (36%)

(1R)-1-[(2R)-4-(6-Amino-4-methoxypyridin-3-yl) piperazin-2-yl]ethan-1-ol dihydrochloride

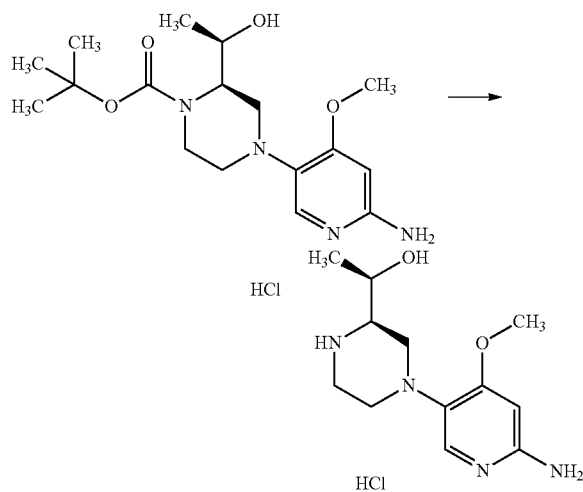

4N HCl in dioxane (0.71 mL, 2.84 mmol) is added to tert-butyl (2R)-4-(6-amino-4-methoxypyridin-3-yl)-2-[(1R)-1-hydroxyethyl]piperazine-1-carboxylate (0.20 g, 0.57 mmol) in dichloromethane (5 mL) and stirred at RT for 2 h. Additional 1 mL of 4N HCl in dioxane is added and stirred 1 h at RT. The reaction mixture is concentrated under reduced pressure. The residue is used without further purification.

Yield: 0.18 g (quantitative)

tert-Butyl (2R)-4-(6-amino-4-methoxypyridin-3-yl)-2-[(1S)-1-hydroxyethyl]piperazine-1-carboxylate

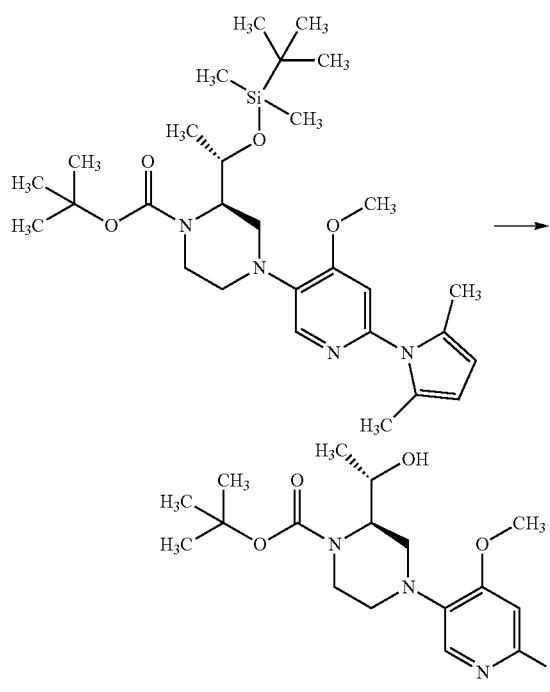

din-3-yl]piperazine-1-carboxylate (0.57 g, 1.04 mmol), hydroxylamine hydrochloride (0.36 g, 5.21 mmol) and trimethylamine (0.15 mL, 1.04 mmol) in ethanol (4 mL) and water (2 mL) is heated at 80° C. for 42 h. Additional amount of hydroxylamine hydrochloride (0.15 g, 2.09 mmol) is added and the reaction mixture is stirred at 80° C. overnight. The reaction mixture is concentrated under reduced pressure, taken up in dichloromethane and filtered. The desired compound is purified by silica chromatography (ethyl acetate/heptane) and repurified by HPLC.

Yield: 0.12 g (33%)

(1S)-1-[(2R)-4-(6-Amino-4-methoxypyridin-3-yl) piperazin-2-yl]ethan-1-ol dihydrochloride

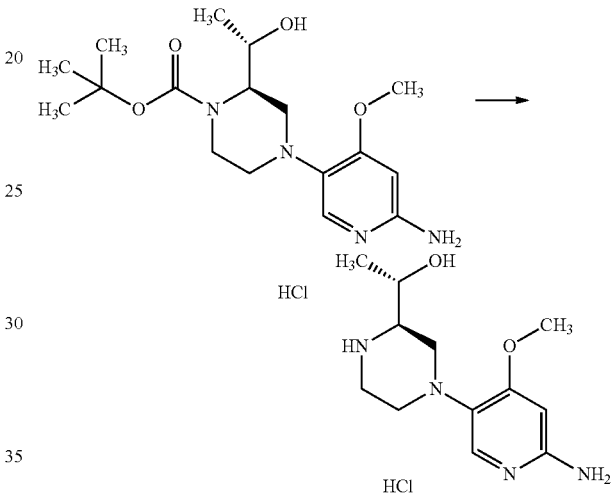

4N HCl in dioxane (0.50 mL, 2.00 mmol) is added to tert-butyl (2R)-4-(6-amino-4-methoxypyridin-3-yl)-2-[(1S)-1-hydroxyethyl]piperazine-1-carboxylate (0.12 g, 0.34 mmol) in dichloromethane (1 mL) and stirred at RT for 1 h. The reaction mixture is concentrated under reduced pressure. The residue is used without further purification.

Yield: quantitative

[4-(6-Amino-pyridazin-3-yl)-piperidin-1-yl]-(4-methoxy-5-trimethylstannanyl-pyridin-2-yl)-methanone

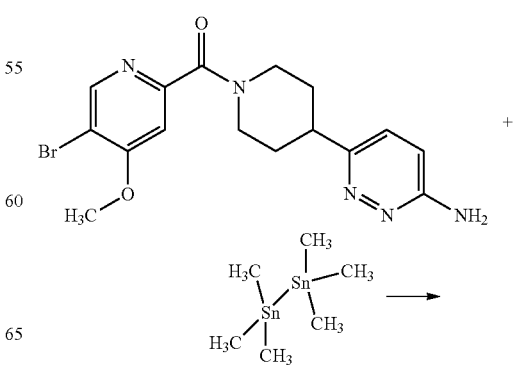

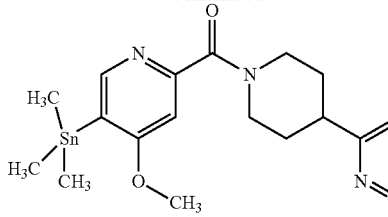

[4-(6-Amino-pyridazin-3-yl)-piperidin-1-yl]-(5-bromo-4-methoxy-pyridin-2-yl)-methanone (1.0 g, 2.55 mmol), 1,1,1,2,2,2-hexamethyl-distannane (1.0 g, 3.06 mmol) and Tetrakis Pd (295 mg, 0.26 mmol) in 1,4-dioxane/DMA are stirred for 4 h at 100° C. The volatiles are removed under reduced pressure. EtOAc is added and the mixture is poured into 10% NaHCO₃ (aq). The aqueous phase is separated and extracted two times with EtOAc. The combined organic layers are dried over Na₂SO₄, filtered and concentrated under reduced pressure. The residue is purified by flash chromatography (MeOH/DCM).

Yield: 454 mg (37%))

[(R)-3-Methyl-4-(6-nitro-pyridin-3-yl)-piperazin-1-yl]-(4'-trifluoromethyl-biphenyl-4-yl)-methanone

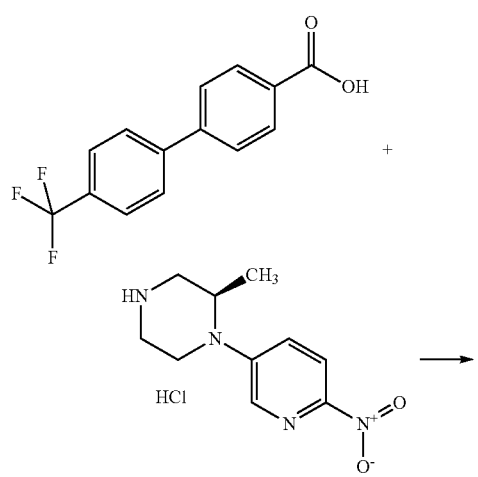

4'-Trifluoromethyl-biphenyl-4-carboxylic acid (100 mg, 0.38 mmol) is stirred for 2 h at rt with TBTU (120 mg, 0.37 mmol), (R)-2-methyl-1-(6-nitro-pyridin-3-yl)-piperazine hydrochloride (0.096, 0.37 mmol) and triethylamine (157 µl, 1.13 mmol) in DMF (1 mL). The reaction mixture is purified by HPLC.

Yield: 99 mg (56%) ESI-MS: m/z=501 (M+H)⁺ R$_t$(HPLC): 2.56 min (Method 5)

(2-Methoxy-4'-trifluoromethyl-biphenyl-4-yl)-[(R)-3-methyl-4-(6-nitro-pyridin-3-yl)-piperazin-1-yl]-methanone

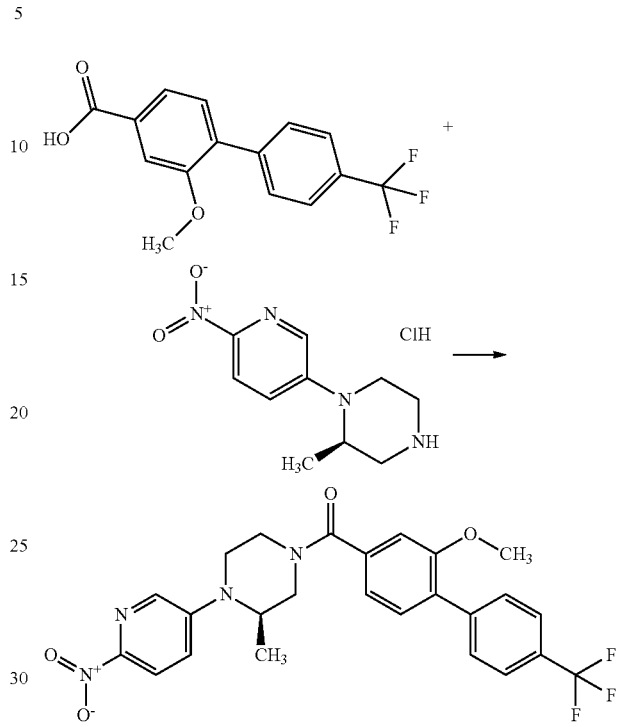

2-Methoxy-4'-trifluoromethyl-biphenyl-4-carboxylic acid (50.0 mg 0.17 mmol) and HATU (77.0 mg, 0.20 mmol) in DMA (1.5 mL) is added to (R)-2-methyl-1-(6-nitro-pyridin-3-yl)-piperazine hydrochloride (48.0 mg, 0.19 mmol) and DIPEA (152 µl, 0.84 mmol). The reaction mixture is stirred at rt for 18 h and purified by silica gel chromatography (EtOAc/heptane) to obtain the desired product.

Yield: 84.0 mg (99%) ESI-MS: m/z=501 (M+H)⁺ Rt(HPLC): 2.56 min (Method 5)

[4-Methoxy-5-(4-trifluoromethyl-phenyl)-pyridin-2-yl]-[(1S,4S)-5-(6-nitroso-pyridazin-3-yl)-2,5-diaza-bicyclo[2.2.1]hept-2-yl]-methanone

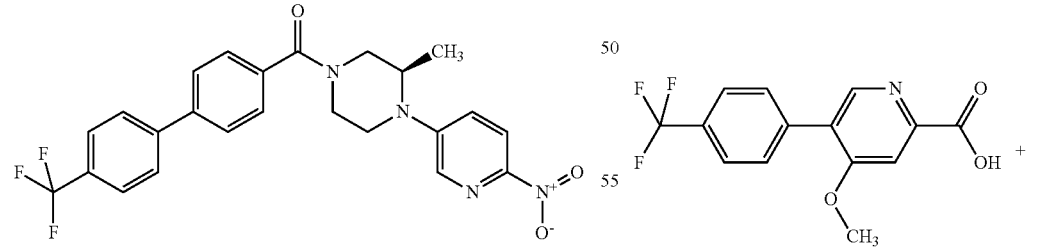

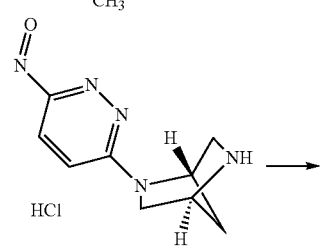

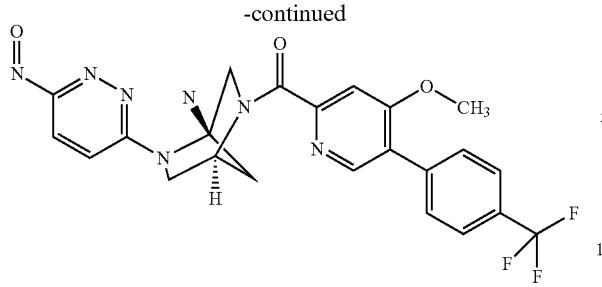

The title compound is synthesized from 4-methoxy-5-(4-trifluoromethyl-phenyl)-pyridine-2-carboxylic acid (88.0 mg, 0.30 mmol) and (1S,4S)-2-(6-nitroso-pyridazin-3-yl)-2,5-diaza-bicyclo[2.2.1]heptane hydrochloride (71.6 mg, 0.30 mmol) according to the procedure described for the synthesis of the intermediate (2-methoxy-4'-trifluoromethyl-biphenyl-4-yl)-[(R)-3-methyl-4-(6-nitro-pyridin-3-yl)-piperazin-1-yl]-methanone.

Yield: 110 mg (77%)

(2-Methoxy-4'-trifluoromethyl-biphenyl-4-yl)-[(1S,4S)-5-(6-nitroso-pyridazin-3-yl)-2,5-diaza-bicyclo[2.2.1]hept-2-yl]-methanone

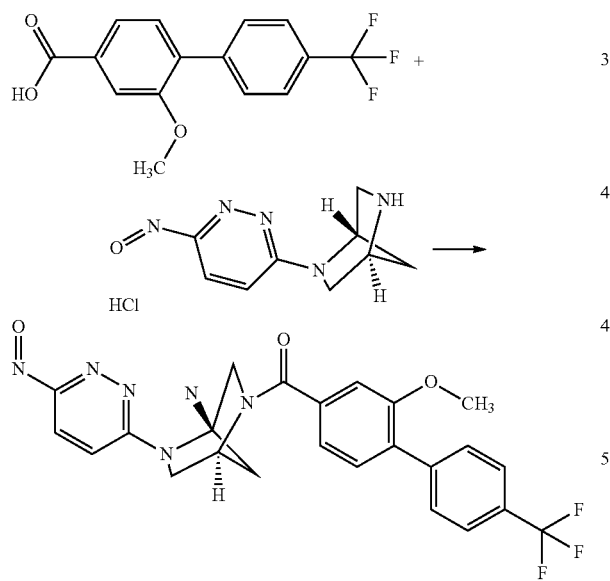

The title compound is synthesized from 2-methoxy-4'-trifluoromethyl-biphenyl-4-carboxylic acid (65.0 mg, 0.22 mmol) and (1S,4S)-2-(6-nitroso-pyridazin-3-yl)-2,5-diaza-bicyclo[2.2.1]heptane hydrochloride (53.0 mg, 0.22 mmol) according to the procedure described for the synthesis of the intermediate (2-methoxy-4'-trifluoromethyl-biphenyl-4-yl)-[(R)-3-methyl-4-(6-nitro-pyridin-3-yl)-piperazin-1-yl]methanone.

Yield: 105 mg (99%) Rt(HPLC): 2.13 min (Method 5)

(R)-2-(tert-Butyl-dimethyl-silanyloxymethyl)-4-(6-nitro-pyridin-3-yl)-piperazine-1-carboxylic acid tert-butyl ester

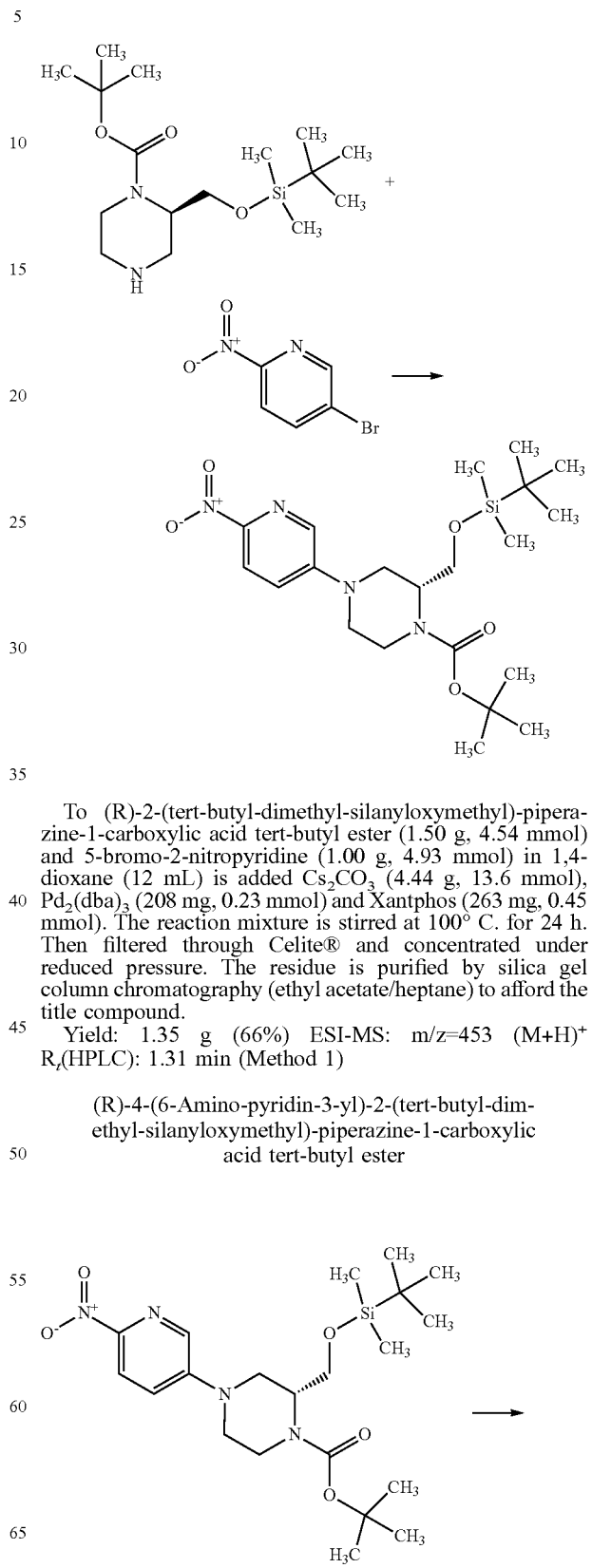

To (R)-2-(tert-butyl-dimethyl-silanyloxymethyl)-piperazine-1-carboxylic acid tert-butyl ester (1.50 g, 4.54 mmol) and 5-bromo-2-nitropyridine (1.00 g, 4.93 mmol) in 1,4-dioxane (12 mL) is added $Cs_2CO_3$ (4.44 g, 13.6 mmol), $Pd_2(dba)_3$ (208 mg, 0.23 mmol) and Xantphos (263 mg, 0.45 mmol). The reaction mixture is stirred at 100° C. for 24 h. Then filtered through Celite® and concentrated under reduced pressure. The residue is purified by silica gel column chromatography (ethyl acetate/heptane) to afford the title compound.

Yield: 1.35 g (66%) ESI-MS: m/z=453 (M+H)+
R$_t$(HPLC): 1.31 min (Method 1)

(R)-4-(6-Amino-pyridin-3-yl)-2-(tert-butyl-dimethyl-silanyloxymethyl)-piperazine-1-carboxylic acid tert-butyl ester -continued

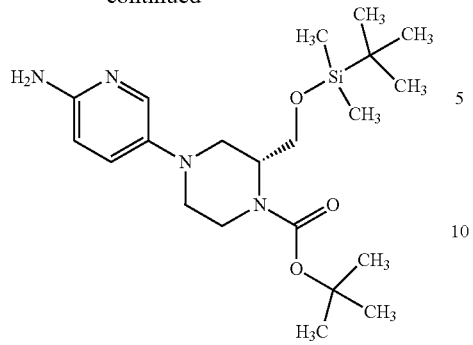

(R)-2-(tert-Butyl-dimethyl-silanyloxymethyl)-4-(6-nitro-pyridin-3-yl)-piperazine-1-carboxylic acid tert-butyl ester (1.35 g, 2.98 mmol) and Pd/C (317 mg, 0.15 mmol) in methanol (20 mL) is stirred with an $H_2$ balloon for 24 h. The reaction mixture is filtered through Celite®, washed with methanol and the filtrate is concentrated under reduced pressure.

Yield: 1.26 g (quantitative)

[(R)-4-(6-Amino-pyridin-3-yl)-piperazin-2-yl]-methanol dihydrochloride

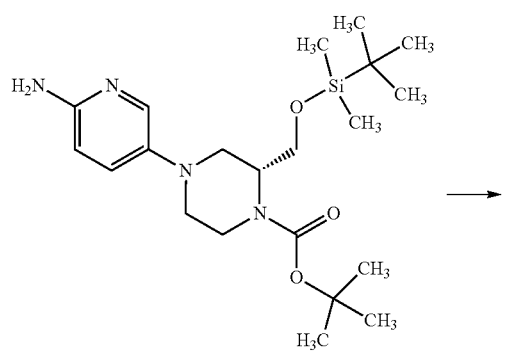

-continued (R)-4-(6-Amino-pyridin-3-yl)-2-(tert-butyl-dimethyl-silanyloxymethyl)-piperazine-1-carboxylic acid tert-butyl ester (1.26 g, 2.98 mmol) in DCM (10 mL) and 4M HCl in 1,4-dioxane (7.5 mL, 30.0 mmol) is stirred for 1 h at rt. The reaction mixture is concentrated under reduced pressure, slurried in ether, filtered and washed with ether to afford the title compound.

Yield: 838 mg (quantitative)

Synthesis of Compounds

General Procedure IV

The carboxylic acid (1.0 eq.) (intermediate 2 in the following table 5) and HATU (1.2 eq.) in an appropriate volume of DMA (approximately 0.5 mL up to 1 mL DMA per 0.18 mmol intermediate 1) is stirred for 15 min and added to an amine (1 eq.) (intermediate 1 in the following table 5) and DIPEA (5 eq.) in an appropriate volume of DMA (approximately 0.5 mL up to 1 mL DMA per 0.18 mmol intermediate 1). The reaction mixture is stirred at rt for 18 h. The crude reaction mixture is purified using a reversed phase HPLC (0-18 column, acidic or basic conditions) to afford the desired product.

General Procedure V

The carboxylic acid (1.0 eq.) (intermediate 2 in the following table 5) and CDI (1.3 eq.) in an appropriate volume of DMA (approximately 2 mL DMA per 0.25 mmol intermediate 1) is stirred for 30 min and to which amine (1.0 eq.) (intermediate 1 in the following table 5) and DIPEA (2 eq.) are added. The reaction mixture is stirred at rt for 18 h. The crude reaction mixture is purified using a reversed phase HPLC (0-18 column, acidic or basic conditions) to afford the desired product.

TABLE 5

Compounds of the invention 84-110.

| Cpd | Amine (intermediate 1) | Carboxylic acid (intermediate 2) | Yield % | gen. proce- dure | ESI- MS m/z M + H⁺ | HPLC R$_t$ (min.) | HPLC method |
|---|---|---|---|---|---|---|---|
| 84 | HCl ... NH₂ | ... CF₃ | 53 | IV | 487 | 1.13 | 5 |

TABLE 5-continued

Compounds of the invention 84-110.

| Cpd | Amine (intermediate 1) | Carboxylic acid (intermediate 2) | Yield % | gen. proce- dure | ESI- MS m/z M + H+ | HPLC R$_t$ (min.) | HPLC method |
|---|---|---|---|---|---|---|---|
| 85 | HCl, piperidine-pyridazine-OCH$_3$-NH$_2$·HCl | 5-(4-trifluoromethylphenyl)-4-methoxy-pyridine-2-carboxylic acid | 63 | V | 488 | 0.64 | 16 |
| 86 | HCl, piperidine-pyridazine-OCH$_3$-NH$_2$·HCl | 5-(6-trifluoromethylpyridin-3-yl)-4-methoxy-pyridine-2-carboxylic acid | 26 | V | 489 | 0.56 | 16 |
| 87 | HCl, piperidine-pyridazine-OCH$_3$-NH$_2$·HCl | 5-phenyl-4-methoxy-pyridine-2-carboxylic acid | 18 | V | 420.5 | 1.53 | 2 |
| 88 | HCl, piperidine-pyridazine-CH$_3$-NH$_2$·HCl | 5-(4-trifluoromethylphenyl)-4-methoxy-pyridine-2-carboxylic acid | 35 | V | 472.5 | 1.90 | 2 |

TABLE 5-continued
Compounds of the invention 84-110.
| Cpd | Amine (intermediate 1) | Carboxylic acid (intermediate 2) | Yield % | gen. proce- dure | ESI- MS m/z M + H⁺ | HPLC R$_t$ (min.) | HPLC method |
|---|---|---|---|---|---|---|---|
| 89 | 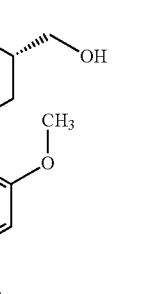 | 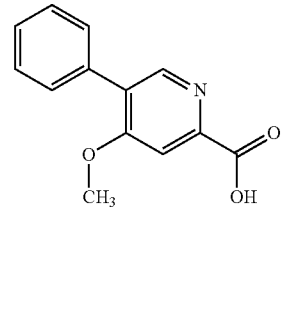 [SMILES: COc1cc(C(=O)O)ncc1-c1ccccc1] | 32 | IV | 450 | 0.69 | 3 |
| 90 | 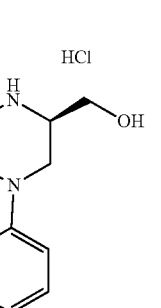 | 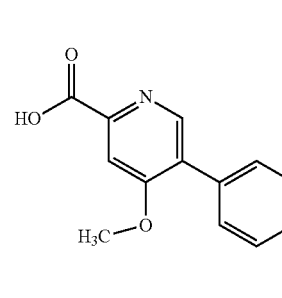 | 22 | IV | 438 | 0.45 | 1 |
| 91 | 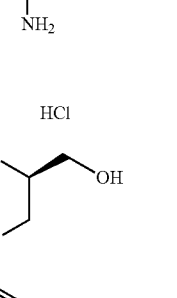 | 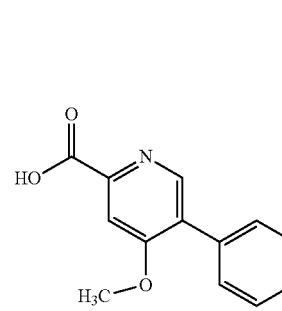 | 16 | IV | 420 | 0.43 | 1 |
| 92 | 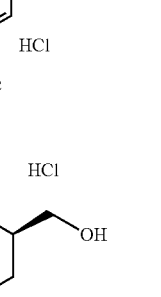 | 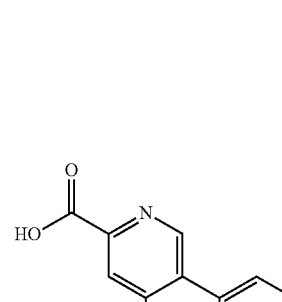 | 64 | IV | 502.5 | 0.55 | 1 |

TABLE 5-continued
Compounds of the invention 84-110.
| Cpd | Amine (intermediate 1) | Carboxylic acid (intermediate 2) | Yield % | gen. procedure | ESI-MS m/z M + H⁺ | HPLC R$_t$ (min.) | HPLC method |
|---|---|---|---|---|---|---|---|
| 93 | 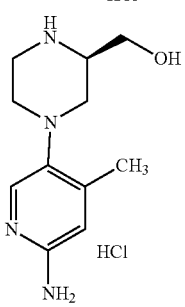 | 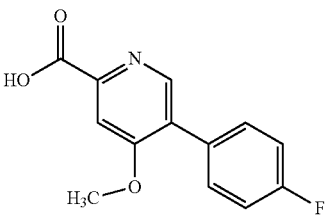 [SMILES: COc1cc(C(=O)O)ncc1-c1ccc(F)cc1] | 60 | IV | 452.5 | 0.44 | 1 |
| 94 | 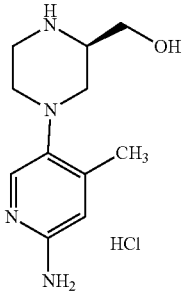 | 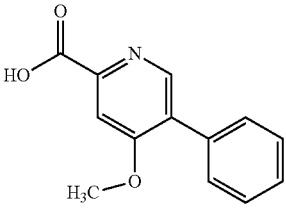 [SMILES: COc1cc(C(=O)O)ncc1-c1ccccc1] | 63 | IV | 434.5 | 0.42 | 1 |
| 95 | 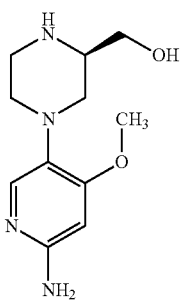 | 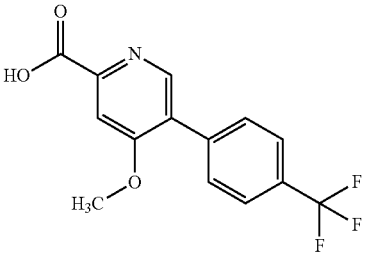 [SMILES: COc1cc(C(=O)O)ncc1-c1ccc(C(F)(F)F)cc1] | 38 | IV | 518 | 0.60 | 16 |
| 96 | 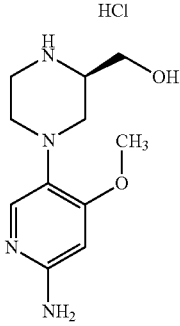 | 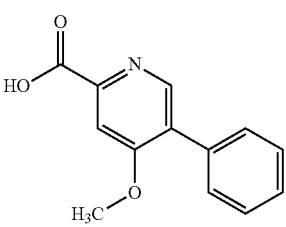 | 33 | IV | 450 | 0.45 | 16 |

TABLE 5-continued

Compounds of the invention 84-110.

| Cpd | Amine (intermediate 1) | Carboxylic acid (intermediate 2) | Yield % | gen. proce- dure | ESI- MS m/z M + H$^+$ | HPLC R$_t$ (min.) | HPLC method |
|---|---|---|---|---|---|---|---|
| 97 | | | 65 | V | 458 | 2.87 | 4 |
| 98 | | | 52 | IV | 482.5 | 0.52 | 1 |
| 99 | | | 64 | IV | 532.5 | 0.61 | 1 |
| 100 | | | 66 | IV | 464 | 0.51 | 16 |

TABLE 5-continued

Compounds of the invention 84-110.

| Cpd | Amine (intermediate 1) | Carboxylic acid (intermediate 2) | Yield % | gen. proce- dure | ESI- MS m/z M + H+ | HPLC R$_t$ (min.) | HPLC method |
|---|---|---|---|---|---|---|---|
| 101 | HCl salt of piperazine with hydroxymethyl substituent, linked to methoxy-aminopyridine | 5-(4-trifluoromethylphenyl)-4-methoxy-pyridine-2-carboxylic acid | 31 | IV | 518 | 0.82 | 3 |
| 102 | HCl salt of piperazine with hydroxymethyl substituent, linked to methoxy-aminopyridine | 5-(4-fluorophenyl)-4-methoxy-pyridine-2-carboxylic acid | 25 | IV | 468 | 0.70 | 3 |
| 103 | di-HCl salt of piperazine linked to methoxy-aminopyridine | 5-(4-trifluoromethylphenyl)-4-methoxy-pyridine-2-carboxylic acid | 76 | IV | 488.5 | 0.58 | 1 |
| 104 | di-HCl salt of piperazine linked to methoxy-aminopyridine | 5-(4-fluorophenyl)-4-methoxy-pyridine-2-carboxylic acid | 74 | IV | 438 | 0.47 | 1 |

TABLE 5-continued

Compounds of the invention 84-110.

| Cpd | Amine (intermediate 1) | Carboxylic acid (intermediate 2) | Yield % | gen. procedure | ESI-MS m/z M + H$^+$ | HPLC R$_t$ (min.) | HPLC method |
|---|---|---|---|---|---|---|---|
| 105 | | | 73 | IV | 420 | 0.44 | 1 |
| 106 | | | 46 | IV | 532 | 0.59 | 1 |
| 107 | | | 68 | IV | 532 | 0.60 | 1 |
| 108 | | | 45 | IV | 552 | 0.72 | 16 |

TABLE 5-continued

Compounds of the invention 84-110.

| Cpd | Amine (intermediate 1) | Carboxylic acid (intermediate 2) | Yield % | gen. procedure | ESI-MS m/z M + H⁺ | HPLC R$_t$ (min.) | HPLC method |
|---|---|---|---|---|---|---|---|
| 109 | chiral separation method 1 for compound 108 stereochemistry has been randomly asigned | (structure) | 31 | | 552 | 1.36 | chiral analytical method 1 |
| 110 | chiral separation method 1 for compound 108 stereochemistry has been randomly asigned | (structure) | 32 | | 552 | 2.46 | chiral analytical method 1 |

Chiral Separation Method 1:

| | |
|---|---|
| Column | 2.1 × 25.0 cm Chiralpak AD-H from Chiral Technologies (West Chester, PA) |
| Solvent | CO₂ Co-solvent (Solvent A) Isopropanol with 0.25% Isopropylamine (Solvent B) |
| Isocratic Method | 40% Co-solvent at 70 g/min |
| System Pressure | 120 bar |
| Column Temperature | 25° C. |
| Sample Diluent | 3:1 Isopropanol/Methanol |

Chiral Analytical Method 1:

| | |
|---|---|
| Column | 4.6 × 100 mm Chiralpak AD-H from Chiral Technologies (West Chester, PA) |
| Solvent | CO₂ Co-solvent (Solvent B) Isopropanol with 0.1% Isopropylamine |
| Isocratic Method | 35% Co-solvent at 4 mL/min |
| System Pressure | 125 bar |
| Column Temperature | 40° C. |
| Sample Diluent | Methanol |

Synthesis of Compounds

General Procedure VI 4-(6-Amino-pyridazin-3-yl)-piperidin-1-yl]-(4-methoxy-5-trimethylstannanyl-pyridin-2-yl)-methanone (1.0 eq.) (intermediate 2 in the following table 6), bromo compound (1.3 eq.) (intermediate 1 in the following table 6) and Tetrakis Pd (0.1 eq.) are heated in a degassed, appropriate volume of 1,4-dioxane for 2 h at 50° C. up to 150° C. in a sealed tube. The reaction mixture is filtered and the product is purified by reversed phase column chromatography or by silica gel chromatography

TABLE 6

Compounds of the invention 111-112.

| Cpd | Intermediate 1 | Intermediate 2 | Yield % | ESI-MS m/z M + H⁺ | HPLC R$_t$ (min.) | HPLC method |
|---|---|---|---|---|---|---|
| 111 | *(structure: 5-bromo-2-((2,2-difluorocyclopropyl)methoxy)pyridine)* | *(structure: trimethylstannyl-methoxypyridine carbonyl piperidinyl aminopyridazine)* | 4 | 497.5 | 1.08 | 5 |
| 112 | *(structure: 5-bromo-2-(cyclopropyloxy)pyridine)* | *(structure: trimethylstannyl-methoxypyridine carbonyl piperidinyl aminopyridazine)* | 18 | 447.5 | 2.64 | 4 |

Synthesis of Compounds

General Procedure VII

To the nitro derivative (intermediate 1 of the following table 7) (1.0 eq.) in glacial acetic acid (approximately 1.0 mL glacial acetic acid per 0.2 mmol intermediate 1) and an appropriate volume of ethanol (approximately 1.0 mL ethanol per 0.2 mmol intermediate 1) is added zinc metal (10 eq.). The reaction mixture is stirred at rt for 2 h. The reaction mixture is filtered through Celite®, washed with ethanol and concentrated under reduced pressure. The residue is subsequently purified by silica gel chromatography (MeOH/DCM) and then by reversed phase HPLC.

General Procedure VIII

To the nitroso derivative (intermediate 1 of the following table 7) (1 eq.) in an appropriate volume of ethanol (approximately 1.0 mL ethanol per 0.2 mmol intermediate 1) is added Pd/C (0.1 eq.) and a balloon filled with hydrogen. The reaction is stirred for 4 h at rt. The reaction mixture is filtered through Celite®, washed with methanol and concentrated under reduced pressure. The residue is purified by reversed phase HPLC.

TABLE 7

Compounds of the invention 113-116

| Cpd | Nitro/Nitroso compound (intermediate 1) | Yield % | proc. | ESI-MS m/z M + H⁺ | HPLC R$_t$ (min.) | HPLC method |
|---|---|---|---|---|---|---|
| 113 | *(structure: 4'-(trifluoromethyl)biphenyl-4-carbonyl-(3-methylpiperazin-1-yl)-(6-nitropyridin-3-yl))* | 35 | VII | 441 | 0.71 | 16 |

TABLE 7-continued
Compounds of the invention 113-116
| Cpd | Nitro/Nitroso compound (intermediate 1) | Yield % | proc. | ESI-MS m/z M + H⁺ | HPLC R_t (min.) | HPLC method |
|---|---|---|---|---|---|---|
| 114 | | 61 | VII | 471 | 1.29 | 5 |
| 115 | | 17 | VIII | 470 | 1.16 | 5 |
| 116 | | 32 | VIII | 471 | 0.64 | 16 |
Alternative Synthesis of 4-(6-amino-4-methoxy-pyridazin-3-yl)-3,6-dihydro-2H-pyridine-1-carboxylic acid tert-butyl ester
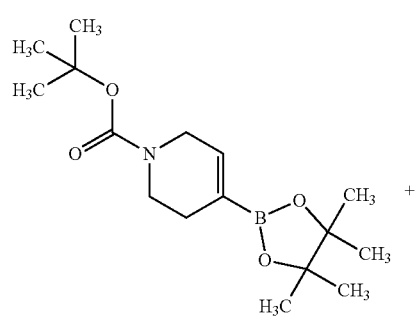
+
-continued
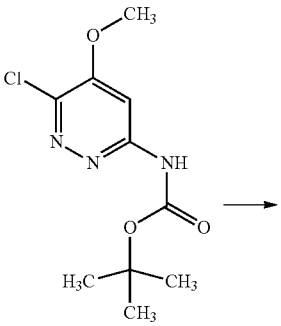
→

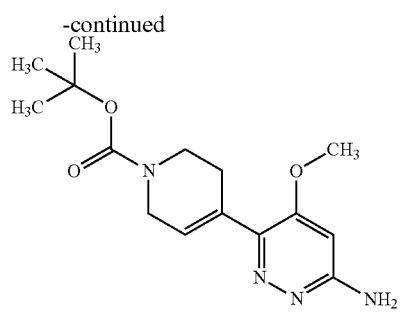

4-(4,4,5,5-tetramethyl-[1,3,2]dioxaborolan-2-yl)-3,6-dihydro-2H-pyridine-1-carboxylic acid tert-butyl ester (1.24 g, 4.00 mmol), (6-chloro-5-methoxy-pyridazin-3-yl)-carbamic acid tert-butyl ester (1.04 g, 4.00 mmol) and PdCl$_2$(dppf)*CH$_2$Cl$_2$ (0.33 g, 0.40 mmol) in 1,4-dioxane (10 mL) and 2M aqueous Na$_2$CO$_3$ solution (4.0 mL, 8.0 mmol) is sparged with nitrogen for 5 min and then heated in a microwave at 150° C. for 30 min. The reaction mixture is diluted with ethyl acetate (10 mL) and water (10 mL) and the layers are separated. The aqueous fraction is extracted with ethyl acetate (10 mL). The combined organic fractions are washed with brine (25 mL), dried over Na$_2$SO$_4$, filtered and concentrated. The residue is purified by silica gel chromatography (DCM/MeOH).

Yield: 0.11 g (9%) ESI-MS: m/z=307 (M+H)$^+$ R$_f$(HPLC): 0.65 min (Method 5)

Alternative Synthesis of 4-(6-amino-4-methoxy-pyridazin-3-yl)-piperidine-1-carboxylic acid tert-butyl ester

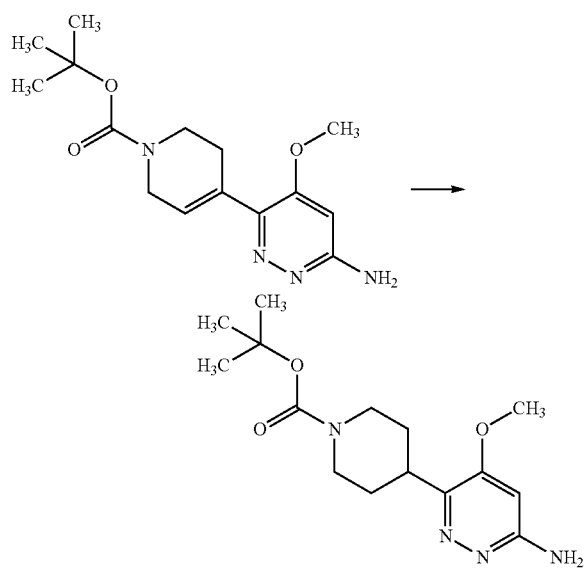

Under a nitrogen atmosphere Pd/C (0.14 g, 0.13 mmol) is added to 4-(6-amino-4-methoxy-pyridazin-3-yl)-3,6-dihydro-2H-pyridine-1-carboxylic acid tert-butyl ester (405 mg, 1.32 mmol) in MeOH (10 mL) and acetic acid (1 mL). The reaction mixture is degassed and subjected to a balloon of Hydrogen. The reaction mixture is stirred at RT until the reaction is completed. The reaction is filtered and concentrated. The residue is subjected to silica gel chromatography (DCM/MeOH).

Yield: 0.39 mg (95%) ESI-MS: m/z=309 (M+H)$^+$ R$_f$(HPLC): 0.73 min (Method 5)

Ethyl 2-(N-benzyl-2-{[(tert-butoxy)carbonyl]amino}-4,4-difluorobutanamido)acetate

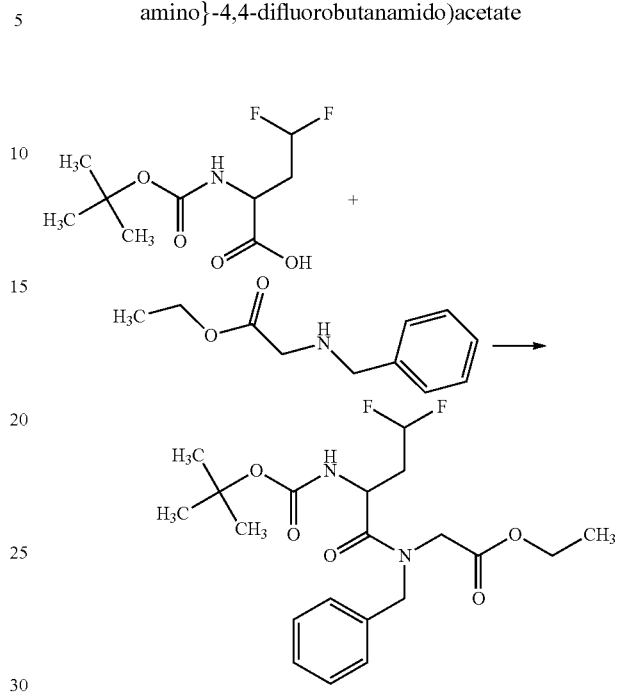

2-{[(tert-Butoxy)carbonyl]amino}-4,4-difluorobutanoic acid (0.50 g; 2.09 mmol) and N,N'-dicyclohexylcarbodiimide (0.43 g; 2.09 mmol) in DCM (14 mL) are stirred at RT for 5 minutes. Ethyl 2-(benzylamino)acetate (0.39 mL; 2.09 mmol) is added and the reaction mixture is stirred at RT overnight. The reaction mixture is concentrated under reduced pressure and used without further purification.

Yield: quantitative ESI-MS: m/z=415 (M+H)$^+$ R$_f$(HPLC): 1.07 min (method 3)

1-Benzyl-3-(2,2-difluoroethyl)piperazine-2,5-dione

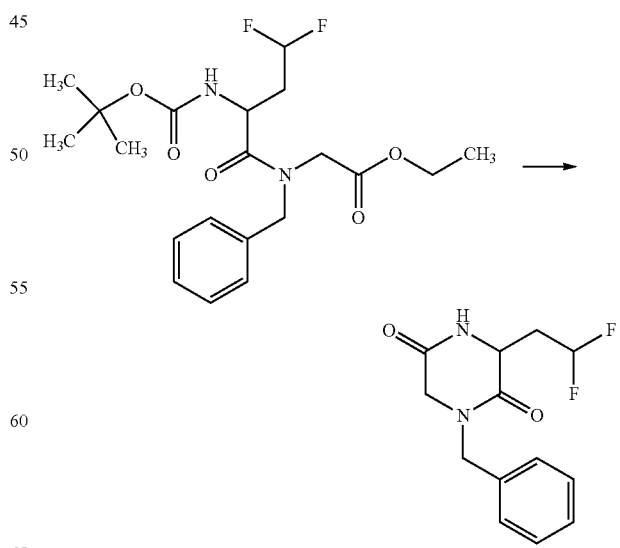

Ethyl 2-(N-benzyl-2-{[(tert-butoxy)carbonyl]amino}-4,4-difluorobutanamido)acetate (2.60 g; 6.27 mmol) and TFA (33 mL; 0.43 mol) in DCM (33 mL) are stirred at RT for 1.5 hours. The solvent is evaporated under reduced pressure and the residue is taken up in EtOH (30 mL) and triethylamine (4.4 mL; 31.35 mmol). After stirring at reflux for 1.5 hours the reaction mixture is concentrated under reduced pressure. The residue is purified by silica gel chromatography (MeOH/DCM).

Yield: 1.65 g (98%) ESI-MS: m/z=269 (M+H)$^+$ R$_t$(HPLC): 0.58 min (method 3)

1-Benzyl-3-(2,2-difluoroethyl)piperazine

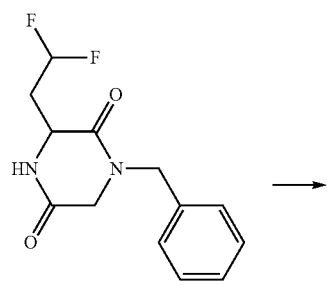

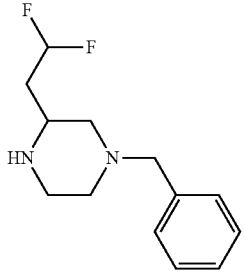

1-Benzyl-3-(2,2-difluoroethyl)piperazine-2,5-dione (1.65 g; 6.15 mmol) and Lithiumaluminiumhydride (1 mol/L; solution in THF; 24.60 mL; 24.60 mmol) in THF (36 mL) are stirred at reflux for 2 hours. After cooling down to RT the reaction mixture is diluted with diethyl ether and cooled to 0° C. Water (1 mL) is added slowly, followed by NaOH (15%; solution in water, 1 mL) and water (3 mL). MgSO$_4$ is added to the mixture and stirred over night at RT. The mixture is filtered through Celite® and concentrated under reduced pressure. The residue is used without further purification.

Yield: 1.00 g (68%) ESI-MS: m/z=241 (M+H)$^+$ R$_t$(HPLC): 0.76 min (method 3)

tert-Butyl 4-benzyl-2-(2,2-difluoroethyl)piperazine-1-carboxylate

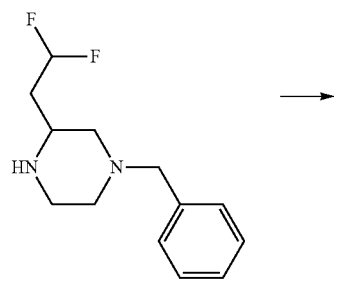

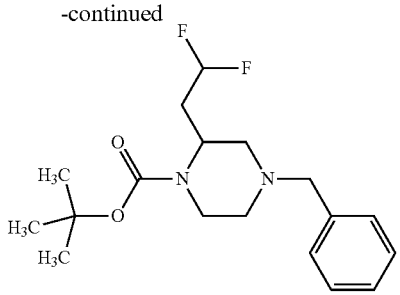

1-Benzyl-3-(2,2-difluoroethyl)piperazine (0.43 g; 1.80 mmol), di-tert-butyl dicarbonate (0.51 g; 2.34 mmol) and triethylamine (0.50 mL; 3.60 mmol) in DCM (18 mL) are stirred at RT over night. The reaction mixture is diluted with DCM and washed with water and brine. The organic layer is separated, dried over MgSO$_4$, filtered, and concentrated under reduced pressure. The residue is purified by silica gel chromatography (EtOAc/hexane).

Yield: 0.46 g (75%) ESI-MS: m/z=341 (M+H)$^+$ R$_t$(HPLC): 1.25 min (method 3)

tert-Butyl 2-(2,2-difluoroethyl)piperazine-1-carboxylate

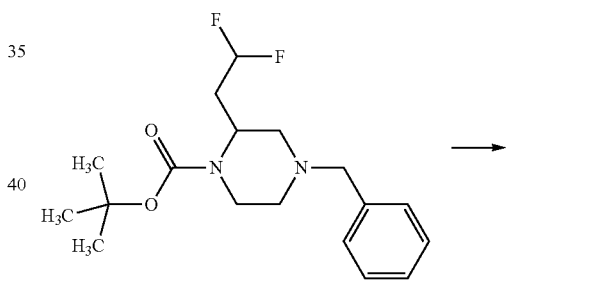

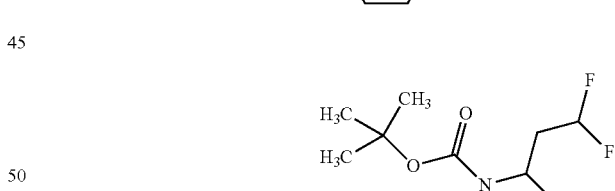

tert-Butyl 4-benzyl-2-(2,2-difluoroethyl)piperazine-1-carboxylate (0.46 g; 1.35 mmol) in acetic acid (27.09 mL; 1.35 mmol) is passed through a H-Cube hydrogenation cartridge (1.0 mL/min; 80 bar; 80° C.). The solvent is evaporated and the residue is taken up in DCM and neutralized with NaHCO$_3$ (saturated aq. solution). The organic layer is passed through a phase separator and concentrated under reduced pressure. The residue is used without further purification.

Yield: 0.32 g (94%)

Alternative Preparation of Compound 71

5-[1-(4-Methoxy-5-phenylpyridine-2-carbonyl)piperidin-4-yl]pyridin-2-amine

Methyl 4-methoxy-5-phenylpyridine-2-carboxylate

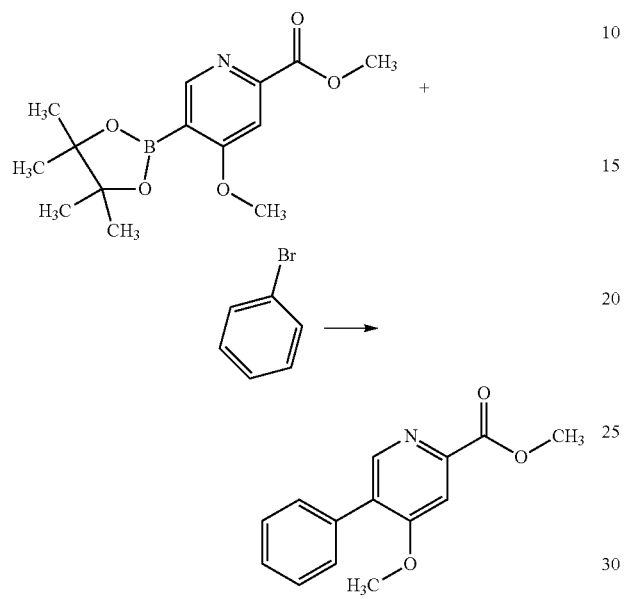

Methyl 4-methoxy-5-(4,4,5,5-tetramethyl-1,3,2-dioxaborolan-2-yl)pyridine-2-carboxylate (0.25 g; 0.85 mmol, commercially available MFCD18727245), PdCl$_2$(dppf)*CH$_2$Cl$_2$ (0.14 g; 0.17 mmol), K$_3$PO$_4$ (0.36 g; 1.71 mmol) and bromobenzene (0.13 g; 0.85 mmol) in 1,4-dioxane (2 mL) and water (0.25 ml) are purged with argon. The reaction mixture is stirred at 120° C. for 60 minutes in a microwave. The reaction mixture is concentrated under reduced pressure and further used as crude product without purification.

Yield: 0.21 g (quantitative)

4-Methoxy-5-phenylpyridine-2-carboxylic acid

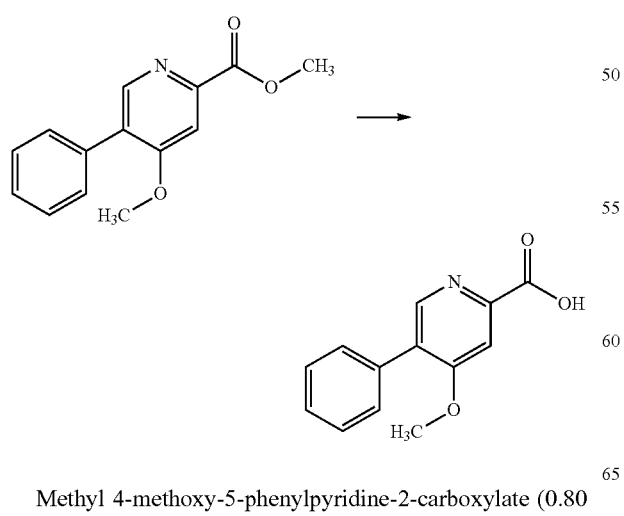

Methyl 4-methoxy-5-phenylpyridine-2-carboxylate (0.80 g; 3.29 mmol) and LiOH (0.16 g; 6.58 mmol in 1 mL water) in THF/MeOH (4 mL/2 mL) are stirred at RT for 2 hours. The reaction mixture is concentrated under reduced pressure. The residue is taken up in water and acidified using aqueous, conc. HCl. The product is isolated via lyophilyzation.

Yield: 0.75 g (quantitative) ESI-MS: m/z=230 (M+H)$^+$
R$_t$(HPLC): 0.56 min (Method 2)

5-[1-(4-Methoxy-5-phenylpyridine-2-carbonyl)piperidin-4-yl]pyridin-2-amine trifluoroacetic acid

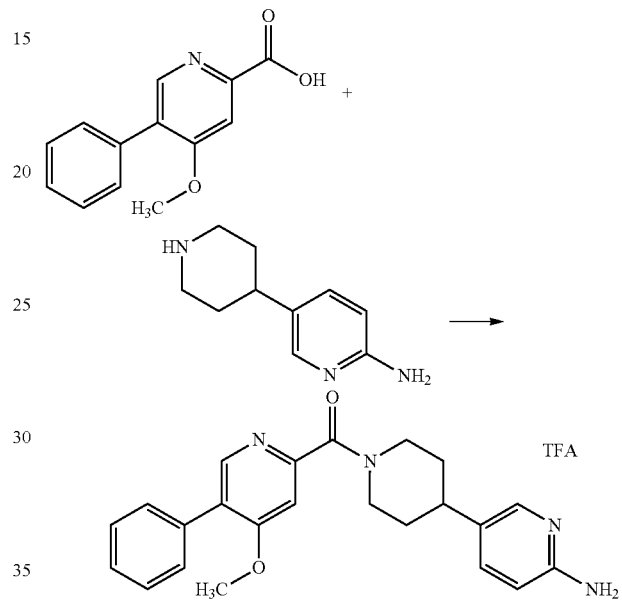

4-Methoxy-5-phenylpyridine-2-carboxylic acid (55.0 mg; 0.24 mmol), HATU (110.0 mg; 0.29 mmol) and DIPEA (105.0 µL; 0.61 mmol) in DMF (3 mL) are stirred at RT for 30 minutes. 5-(piperidin-4-yl)pyridin-2-amine (50.0 mg; 0.28 mmol) is added. After stirring over night at RT the reaction mixture is purified by RP-HPLC (ACN/water+TFA).

Yield: 75.0 mg (71%) ESI-MS: m/z=389 (M+H)$^+$
R$_t$(HPLC): 0.74 min (Method 7)

Alternative Preparation of Compound 105

4-Methoxy-5-[4-(4-methoxy-5-phenylpyridine-2-carbonyl)piperazin-1-yl]pyridin-2-amine 5-Bromo-2-(2,5-dimethyl-1H-pyrrol-1-yl)-4-methoxypyridine

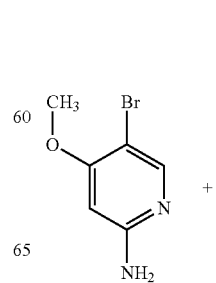

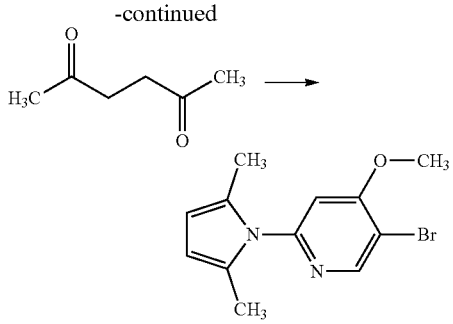

5-Bromo-4-methoxypyridin-2-amine (9.50 g; 46.79 mmol), hexane-2,5-dione (7.1 mL; 60.83 mmol) and p-toluenesulfonic acid (0.81 g; 4.68 mmol) in toluene (80 mL) are stirred in a Dean-Stark-apparatus over night at 120° C. The reaction mixture is concentrated under reduced pressure and purified by silica gel chromatography (DCM).

Yield: 7.60 g (58%) ESI-MS: m/z=281/283 (M+H)$^+$ R$_t$(HPLC): 1.13 min (Method 7)

1-[6-(2,5-Dimethyl-1H-pyrrol-1-yl)-4-methoxypyridin-3-yl]piperazine bis-trifluoracetic acid

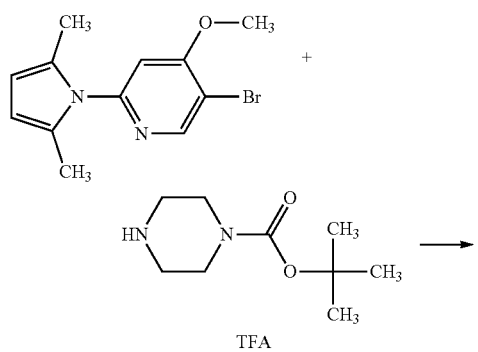

Step 1:

The reaction is performed under an argon atmosphere. 5-Bromo-2-(2,5-dimethyl-1H-pyrrol-1-yl)-4-methoxypyridine (0.60 g; 2.13 mmol), tert-butyl piperazine-1-carboxylate (0.44 g; 2.36 mmol), CPhos-3G-palladacycle methan sulfonate (0.17 g; 0.21 mmol) and cesium carbonate (2.10 g; 6.45 mmol) in 1,4-dioxane (15 mL) are stirred at 80° C. over night. The reaction mixture is purified by RP-HPLC (ACN/water+NH$_3$). The fractions containing tert-butyl 4-[6-(2,5-dimethyl-1H-pyrrol-1-yl)-4-methoxypyridin-3-yl]piperazine-1-carboxylate are collected and lyophilized.

ESI-MS: m/z=387 (M+H)$^+$ R$_t$(HPLC): 1.11 min (Method 7)

Step 2:

tert-Butyl 4-[6-(2,5-dimethyl-1H-pyrrol-1-yl)-4-methoxypyridin-3-yl]piperazine-1-carboxylate from the previous step is taken up in an appropriate amount of CH$_2$Cl$_2$ and TFA (1 mL) is added. After stirring over night at RT additional TFA (0.3 mL) is added and stirred for 3 hours at 40° C. The reaction mixture is concentrated under reduced pressure and used without further purification.

Yield: quantitative ESI-MS: m/z=287 (M+H)$^+$ R$_t$(HPLC): 0.67 min (Method 7)

4-Methoxy-5-(piperazin-1-yl)pyridin-2-amine

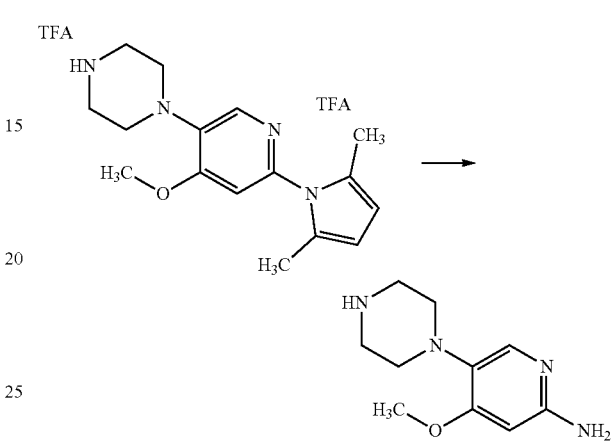

1-[6-(2,5-Dimethyl-1H-pyrrol-1-yl)-4-methoxypyridin-3-yl]piperazine bis-trifluoracetic acid (1.20 g; 2.33 mmol), hydroxylamine hydrochloride (0.70 g; 10.03 mmol) and triethylamine (1.00 mL; 7.11 mmol) in EtOH/water (1/1, 16 mL) are stirred overnight at 80° C. The organic solvent is removed under reduced pressure and the residue is purified by RP-HPLC (ACN/water+NH$_3$).

Yield: 0.29 g (60%) ESI-MS: m/z=209 (M+H)$^+$ R$_t$(HPLC): 0.35 min (Method 9)

4-Methoxy-5-[4-(4-methoxy-5-phenylpyridine-2-carbonyl)piperazin-1-yl]pyridin-2-amine

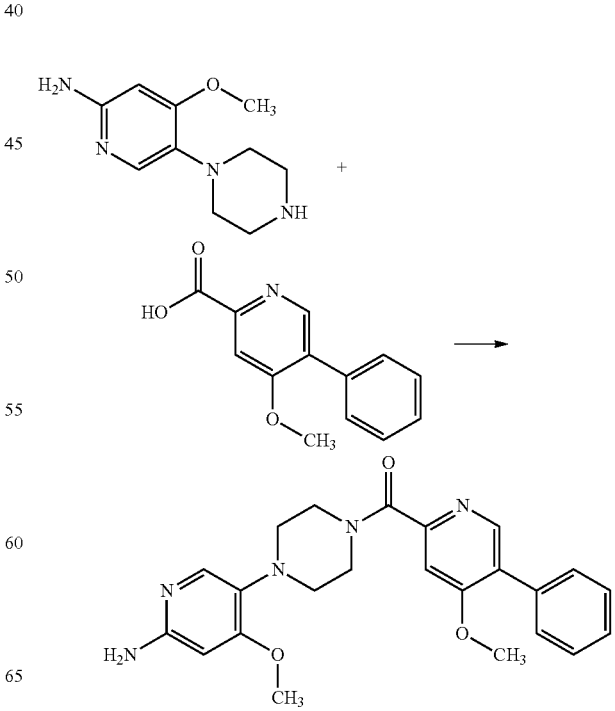

4-Methoxy-5-phenylpyridine-2-carboxylic acid (0.11 g; 0.46 mmol), HATU (0.18 g; 0.46 mmol) and DIPEA (200 µL; 1.16 mmol) in DMF (3 mL) are stirred at rt for 30 minutes. 4-Methoxy-5-(piperazin-1-yl)pyridin-2-amine (95.0 mg; 0.46 mmol) is added. After stirring overnight at rt the reaction mixture is purified by RP-HPLC (ACN/water+ NH₃).

Yield: 40 mg (21%) ESI-MS: m/z=420 (M+H)⁺
R_t(HPLC): 0.87 min (Method 9)

Alternative Preparation of Compound 27

6-(1-{4-Methoxy-5-[4-(trifluoromethyl)phenyl]pyridine-2-carbonyl}piperidin-4-yl)pyridazin-3-amine 4-Methoxy-5-[4-(trifluoromethyl)phenyl]pyridine-2-carboxylic acid

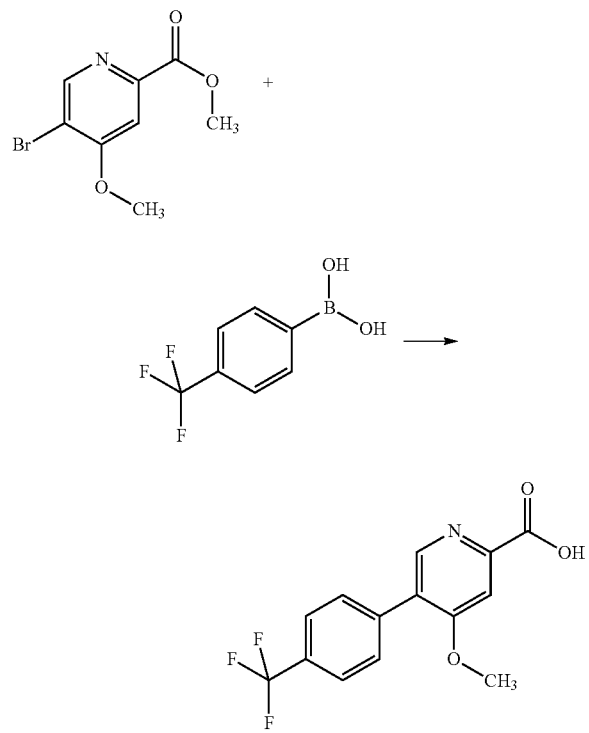

The reaction is performed under an argon atmosphere. Methyl 5-bromo-4-methoxypyridine-2-carboxylate (100.0 mg; 0.41 mmol), [4-(trifluoromethyl)phenyl]boronic acid (84.9 mg; 0.45 mmol), XPhos Pd G2 (9.6 mg; 0.01 mmol) and sodium carbonate (2 mol/L; aq. solution; 0.81 mL; 1.63 mmol) in 1,4-dioxane (20 mL) are stirred at 100° C. for 2 hours. The reaction mixture is purified by RP-HPLC (ACN/water+TFA).

Yield: 70 mg (58%) ESI-MS: m/z=298 (M+H)⁺
R_t(HPLC): 0.87 min (Method 7)

6-(Piperidin-4-yl)pyridazin-3-amine dihydrochloride

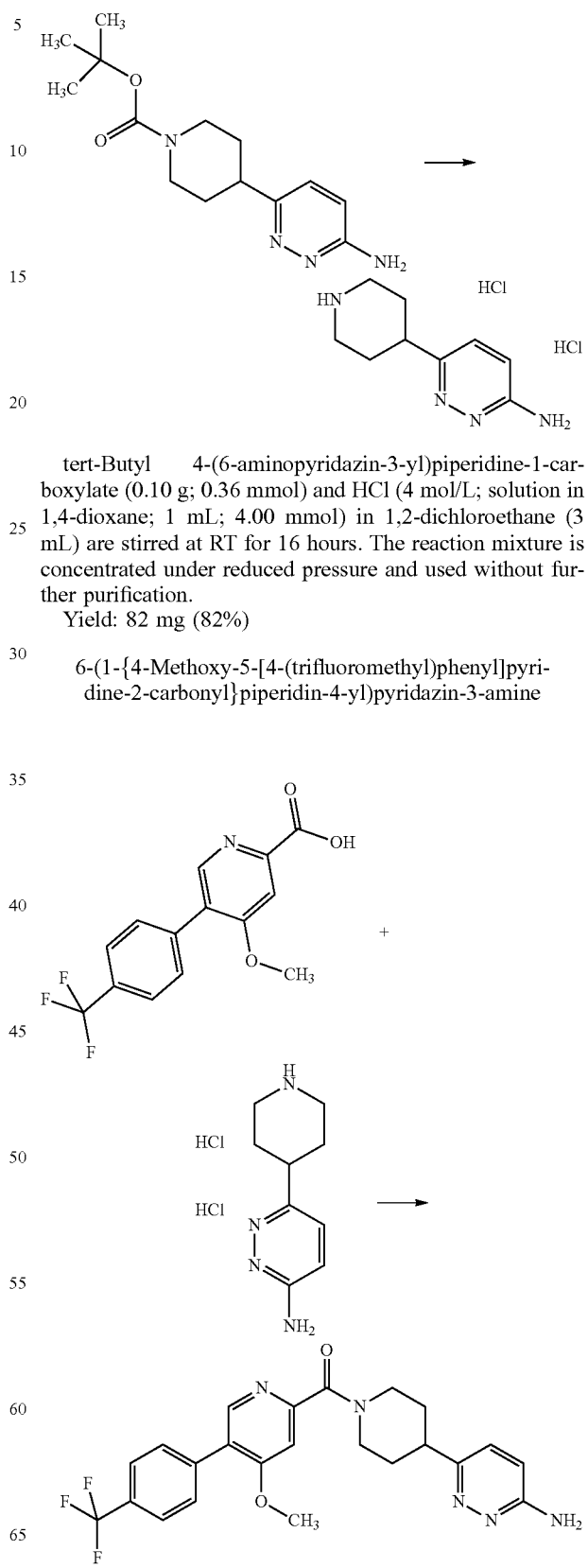

tert-Butyl 4-(6-aminopyridazin-3-yl)piperidine-1-carboxylate (0.10 g; 0.36 mmol) and HCl (4 mol/L; solution in 1,4-dioxane; 1 mL; 4.00 mmol) in 1,2-dichloroethane (3 mL) are stirred at RT for 16 hours. The reaction mixture is concentrated under reduced pressure and used without further purification.

Yield: 82 mg (82%)

6-(1-{4-Methoxy-5-[4-(trifluoromethyl)phenyl]pyridine-2-carbonyl}piperidin-4-yl)pyridazin-3-amine 4-Methoxy-5-[4-(trifluoromethyl)phenyl]pyridine-2-carboxylic acid (0.30 g; 1.01 mmol), 6-(piperidin-4-yl)pyridazin-3-amine dihydrochloride (0.22 g; 0.87 mmol), HATU (0.46 g; 1.21 mmol) and DIPEA (0.91 mL; 5.28 mmol) in DMA (5 mL) are stirred at rt for 2 hours. The reaction mixture is purified by RP-HPLC.

Yield: 0.10 g (22%) ESI-MS: m/z=458 (M+H)$^+$
R$_t$(HPLC): 0.60 min (Method 16)

Preparation of Compound 36

6-{1-[5-(4-Fluorophenyl)-4-methoxypyridine-2-carbonyl]piperidin-4-yl}pyridazin-3-amine 6-[1-(5-Bromo-4-methoxypyridine-2-carbonyl)piperidin-4-yl]pyridazin-3-amine

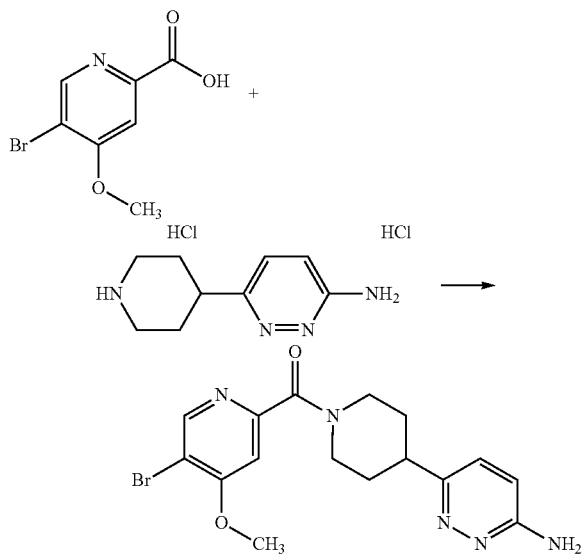

After stirring 5-bromo-4-methoxy-pyridine-2-carboxylic acid (0.18 g, 0.80 mmol), TBTU (0.26 g, 0.80 mmol) and DIPEA (0.55 mL, 3.19 mmol) in DMF (6 mL) for 5 minutes at RT 6-piperidin-4-yl-pyridazin-3-ylamine dihydrochloride (0.20 g, 0.80 mmol) is added. The reaction mixture is stirred for 2 h at 50° C. and afterwards overnight at rt. The reaction mixture is diluted with water and the resulting precipitate is filtered off to afford the title compound.

Yield: 0.15 g (49%) ESI-MS: m/z=392/394 (Br isotops) (M+H)$^+$
R$_t$(HPLC): 0.74 min (Method 7)

6-{1-[5-(4-Fluorophenyl)-4-methoxypyridine-2-carbonyl]piperidin-4-yl}pyridazin-3-amine*formic acid

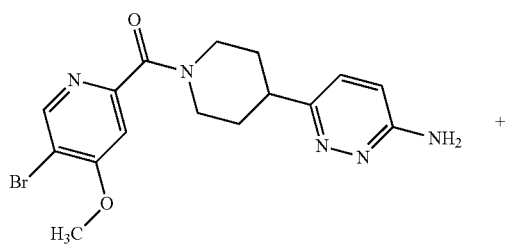

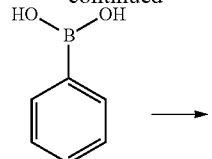

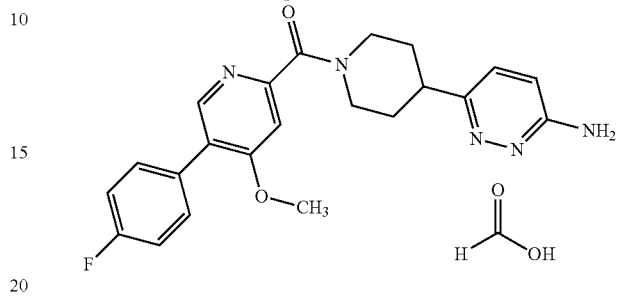

6-[1-(5-Bromo-4-methoxypyridine-2-carbonyl)piperidin-4-yl]pyridazin-3-amine (0.13 g; 0.32 mmol), (4-fluorophenyl)boronic acid (0.07 g; 0.48 mmol) and potassium phosphate (0.14 g; 0.64 mmol) in 1,4-dioxane/water (2 mL/0.25 mL) are purged with argon for 5 minutes. PdCl$_2$(dppf)*CH$_2$Cl$_2$ (0.05 g; 0.06 mmol) is added and again purged with argon for 5 minutes. The reaction mixture is stirred at 120° C. for 1 hour and afterwards the reaction mixture is purified by RP-HPLC (ACN/water/formic acid).

Yield: 40 mg (31%) ESI-MS: m/z=408 (M+H)$^+$
R$_t$(HPLC): 0.75 min (Method 7)

Alternative Synthesis for 5-(4-fluoro-phenyl)-4-methoxy-pyridine-2-carboxylic acid

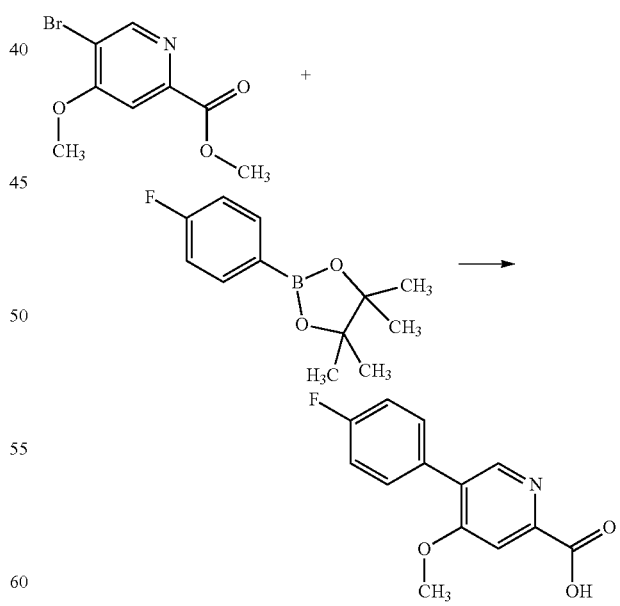

The reaction is performed under an argon atmosphere. Methyl 5-bromo-4-methoxypyridine-2-carboxylate (0.25 g; 1.00 mmol), 2-(4-fluorophenyl)-4,4,5,5-tetramethyl-1,3,2-dioxaborolane (0.22 g; 1.00 mmol) and sodium carbonate (2 mol/L; aq. solution; 2.00 mL; 4.00 mmol) in 1,4-dioxane (10 mL) are purged with argon for 5 minutes. XPhos Pd G2 (0.08 g; 0.10 mmol) as catalyst is added. After stirring at 80° C. over night the reaction mixture is diluted with water and washed with EtOAc twice. The aqueous layer is acidified to pH 5-6 using HCl (1 mol/L; aq. solution). The resulting precipitate is filtered, washed with water and dried.

Yield: 0.08 g (32%) ESI-MS: m/z=248 (M+H)+ R$_f$(HPLC): 0.60 min (Method 9)

Preparation of Compound 84

4-Methoxy-5-(1-{4-methoxy-5-[4-(trifluoromethyl)phenyl]pyridine-2-carbonyl}piperidin-4-yl)pyridin-2-amine tert-Butyl 6-amino-4-methoxy-1',2',3',6'-tetrahydro-[3,4'-bipyridine]-1'-carboxylate

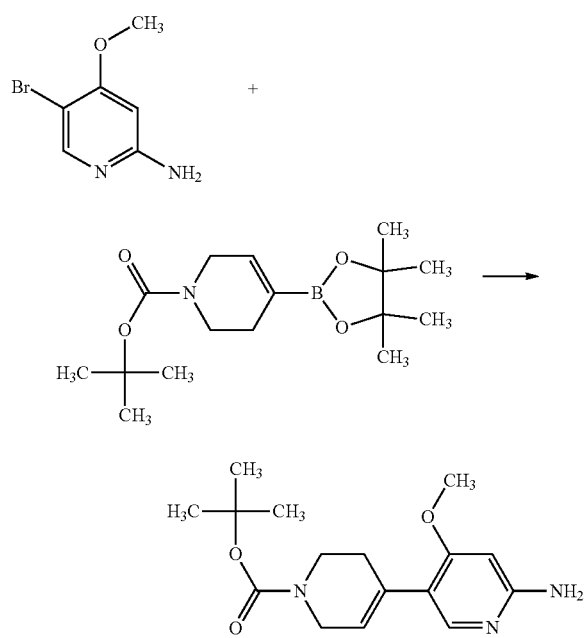

The reaction is performed under an argon atmosphere. 5-Bromo-4-methoxypyridin-2-amine (7.40 g; 32.80 mmol), tert-butyl 4-(4,4,5,5-tetramethyl-1,3,2-dioxaborolan-2-yl)-1,2,3,6-tetrahydropyridine-1-carboxylate (11.16 g; 36.08 mmol) and sodium carbonate (2 mol/L; aq. solution; 65.60 mL; 131.21 mmol) in 1,4-dioxane (300 mL) is purged with argon. After 5 minutes Xphos Pd 2$^{nd}$ Gen. (0.77 g; 0.98 mmol) is added and the reaction mixture is stirred over night in a sealed vial at 100° C. The reaction mixture is concentrated under reduced pressure. The residue is taken up in water and extracted several times with EtOAc. The combined organic layers are dried over Na$_2$SO$_4$, filtered and concentrated under reduced pressure. The residue is purified by silica gel chromatography (DCM/MeOH).

Yield: 9.69 g (97%) ESI-MS: m/z=306 [M+H]+ R$_f$(HPLC): 0.83 min (method 15)

tert.-Butyl 4-(6-amino-4-methoxypyridin-3-yl)-piperidine-1-carboxylate

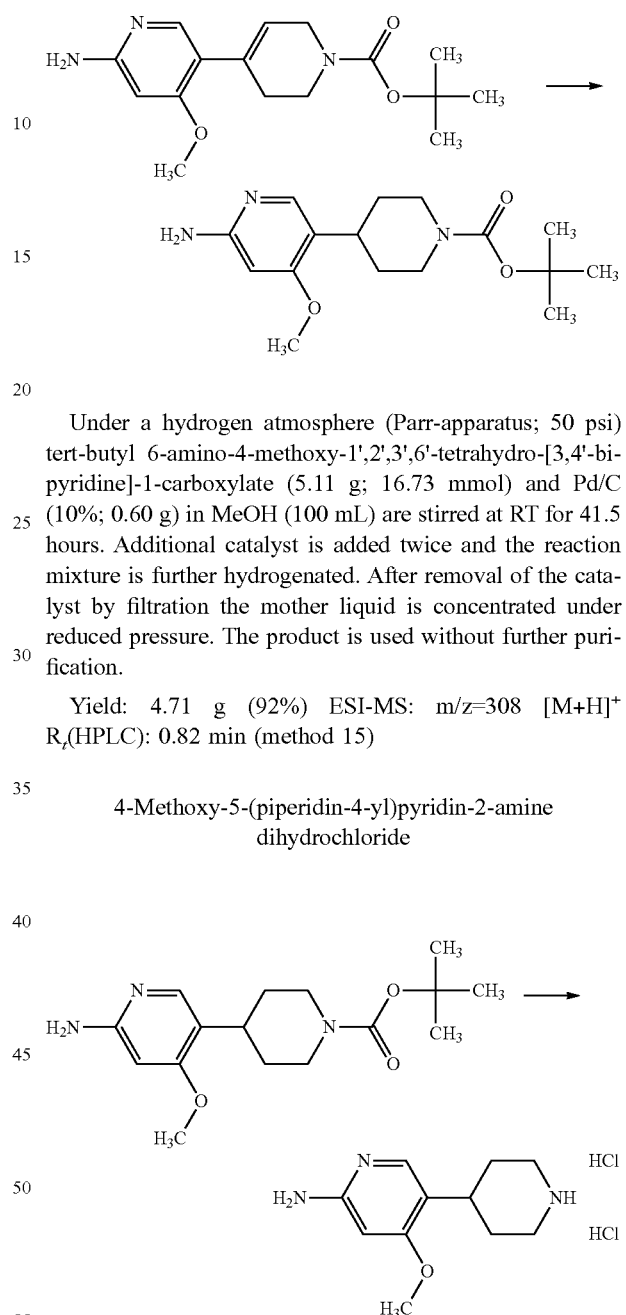

Under a hydrogen atmosphere (Parr-apparatus; 50 psi) tert-butyl 6-amino-4-methoxy-1',2',3',6'-tetrahydro-[3,4'-bipyridine]-1'-carboxylate (5.11 g; 16.73 mmol) and Pd/C (10%; 0.60 g) in MeOH (100 mL) are stirred at RT for 41.5 hours. Additional catalyst is added twice and the reaction mixture is further hydrogenated. After removal of the catalyst by filtration the mother liquid is concentrated under reduced pressure. The product is used without further purification.

Yield: 4.71 g (92%) ESI-MS: m/z=308 [M+H]+ R$_f$(HPLC): 0.82 min (method 15)

4-Methoxy-5-(piperidin-4-yl)pyridin-2-amine dihydrochloride

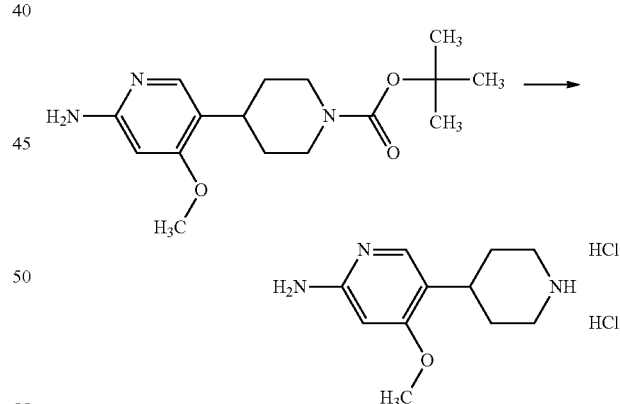

tert.-Butyl 4-(6-amino-4-methoxypyridin-3-yl)piperidine-1-carboxylate (6.90 g; 22.45 mmol) and HCl (4 mol/L; solution in 1,4-dioxane; 69.00 mL; 224.47 mmol) in DCM (89.70 mL) are stirred at RT over night. The reaction mixture is concentrated under reduced pressure. The residue is levigated in diethyl ether and filtered. The product is used without further purification.

Yield: 5.30 g (84%) ESI-MS: m/z=208 [M+H]+ R$_f$(HPLC): 0.66 min (method 9)

225

4-Methoxy-5-(1-{4-methoxy-5-[4-(trifluoromethyl)phenyl]pyridine-2-carbonyl}piperidin-4-yl)pyridin-2-amine*formic acid

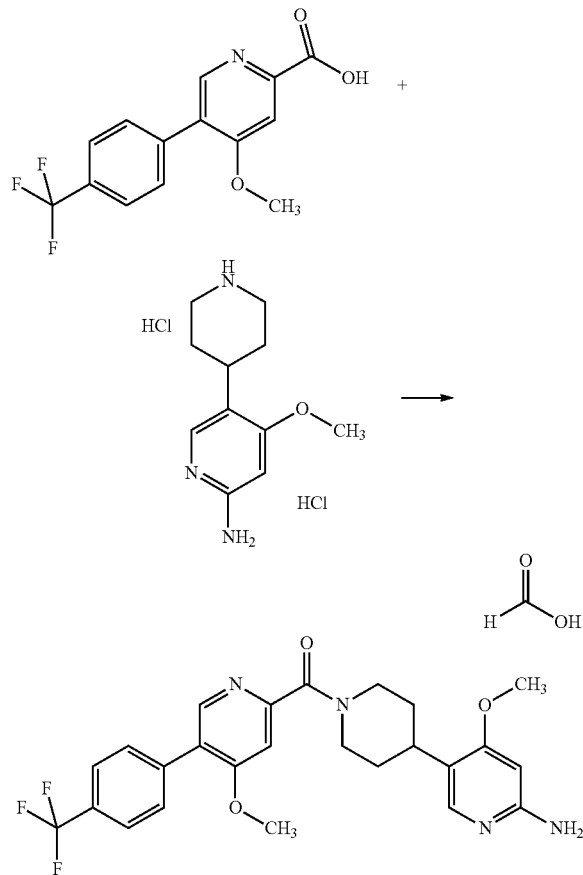

To 4-methoxy-5-[4-(trifluoromethyl)phenyl]pyridine-2-carboxylic acid (28.7 mg; 0.12 mmol) and HATU (53.7 mg; 0.12 mmol) in DMA (1.5 mL), 4-methoxy-5-(piperidin-4-yl)pyridin-2-amine dihydrochloride (35.0 mg; 0.12 mmol) and DIPEA (0.11 mL; 0.59 mmol) is added. After stirring over night at RT the reaction mixture is purified by RP-HPLC (ACN/water/formic acid).

Yield: 31 mg (53%) ESI-MS: m/z=487 (M+H)$^+$ R$_t$(HPLC): 1.13 min (method 5)

Preparation of Compound 68

5-[4-(4-Methoxy-5-phenylpyridine-2-carbonyl)piperazin-1-yl]pyridin-2-amine

5-[4-(5-Bromo-4-methoxypyridine-2-carbonyl)piperazin-1-yl]pyridin-2-amine

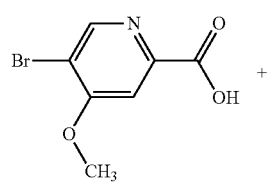

226

-continued

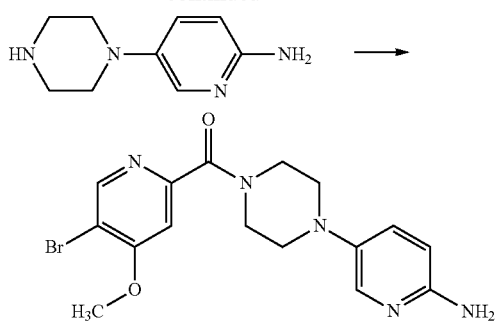

5-bromo-4-methoxy-pyridine-2-carboxylic acid (0.25 g, 1.08 mmol), 5-(piperazin-1-yl)pyridin-2-amine (0.19 g; 1.08 mmol), TBTU (0.52 g, 1.62 mmol) and DIPEA (0.39 mL, 2.26 mmol) in DMA (2.5 mL) are stirred for 2 hours. The resulting reaction mixture is purified by silica gel chromatography.

Yield: 42 mg (10%)

5-[4-(4-Methoxy-5-phenylpyridine-2-carbonyl)piperazin-1-yl]pyridin-2-amine

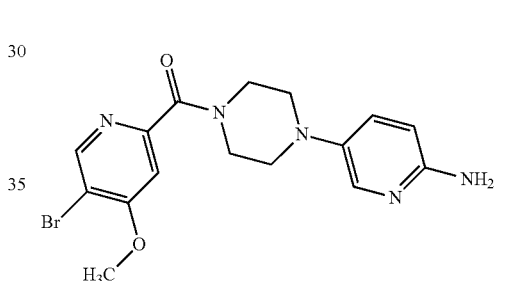

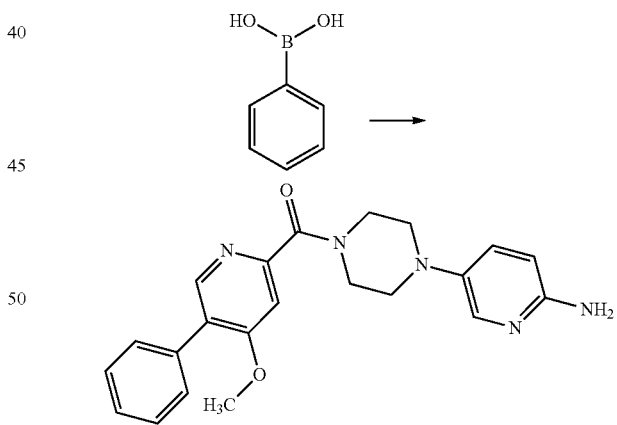

5-[4-(5-Bromo-4-methoxypyridine-2-carbonyl)piperazin-1-yl]pyridin-2-amine (50.0 mg; 0.13 mmol), phenylboronic acid (19.0 mg; 0.19 mmol) and potassium phosphate (25.0 mg; 0.25 mmol) in 1,4-dioxane/water (2 mL/0.25 mL) are purged with argon for 5 minutes. PdCl$_2$(dppf)*CH$_2$Cl$_2$ (21.0 mg; 0.03 mmol) is added and again purged with argon for 5 minutes. The reaction mixture is stirred at 120° C. for 1 hour. The reaction mixture is purified by RP-HPLC.

Yield: 5.2 mg (11%) ESI-MS: m/z=390 (M+H)$^+$ R$_t$(HPLC): 0.47 min (method 16)

Preparation of Compound 79

6-[1-(3-Methoxy-4-{6-[(1-methylcyclopropyl)methoxy]pyridin-3-yl}benzoyl)piperidin-4-yl]pyridazin-3-amine 5-Bromo-2-[(1-methylcyclopropyl)methoxy]pyridine

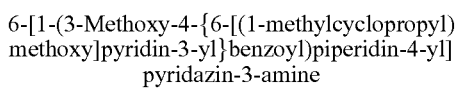

5-Bromo-2-fluoropyridine (0.25 g; 1.42 mmol), (1-methylcyclopropyl)methanol (0.18 g; 2.13 mmol) and potassium tert.-butoxide (0.29 g; 2.56 mmol) in THF (5 mL) are stirred at RT for 24 hours. The reaction mixture is diluted with EtOAc and water. The aqueous layer is extracted twice with EtOAc. The combined organic layers are washed with brine, separated, dried over $Na_2SO_4$, filtered and concentrated under reduced pressure. The residue is purified by silica gel chromatography (EtOAc/heptane).
Yield: 0.23 g (67%)

{4-[4-(6-Aminopyridazin-3-yl)piperidine-1-carbonyl]-2-methoxyphenyl}boronic acid

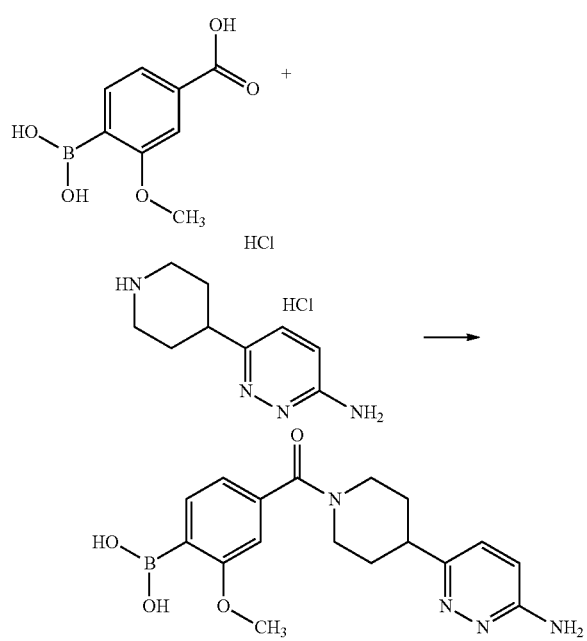

To 4-(dihydroxyboranyl)-3-methoxybenzoic acid (1.00 g; 5.10 mmol) and TBTU (4.92 g; 15.31 mmol) in N,N-dimethylacetamide (25 mL) are added 6-(piperidin-4-yl)pyridazin-3-amine dihydrochloride (1.64 g; 6.53 mmol) and DIPEA (6.22 mL; 35.72 mmol). After stirring over night at RT, the reaction mixture is concentrated under reduced pressure and purified by silica gel chromatography (DCM/MeOH/$NH_4OH$).

Yield: 1.40 g (77%)

6-[1-(3-Methoxy-4-{6-[(1-methylcyclopropyl)methoxy]pyridin-3-yl}benzoyl)piperidin-4-yl]pyridazin-3-amine*formic acid

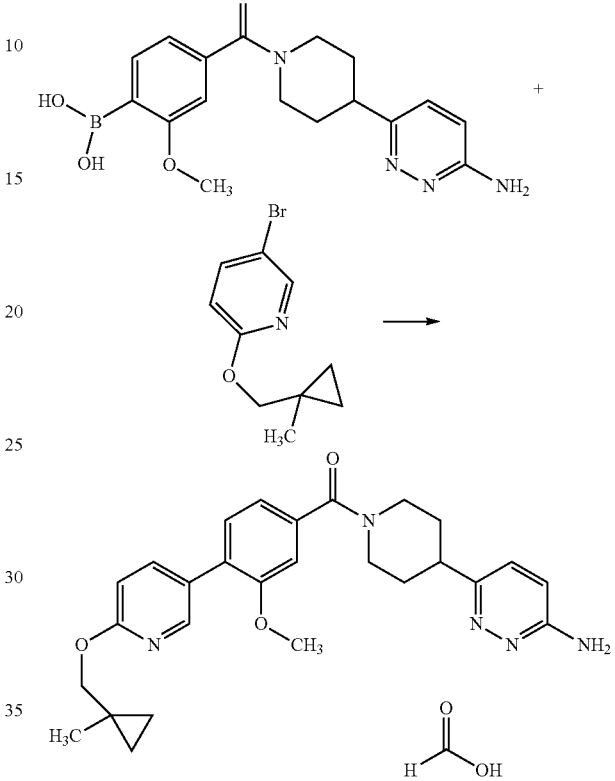

{4-[4-(6-Aminopyridazin-3-yl)piperidine-1-carbonyl]-2-methoxyphenyl}boronic acid (50.0 mg; 0.14 mmol), 5-bromo-2-[(1-methylcyclopropyl)methoxy]pyridine (34.0 mg; 0.14 mmol), potassium phosphate (59.6 mg; 0.28 mmol) and $PdCl_2(dppf)*CH_2Cl_2$ (22.9 mg; 0.03 mmol) are combined in degassed 1,4-dioxane/water (2 mL/0.25 mL) and purged with argon. The reaction mixture is stirred at 120° C. for 1 hour in a microwave. The reaction mixture is purified by RP-HPLC (ACN/water/formic acid).
Yield: 19.0 mg (29%) ESI-MS: m/z=475 (M+H)$^+$
$R_t$(HPLC): 0.66 min (method 16)

Preparation of Compound 35

6-{1-[5-(3-Fluorophenyl)-4-methoxypyridine-2-carbonyl]piperidin-4-yl}pyridazin-3-amine

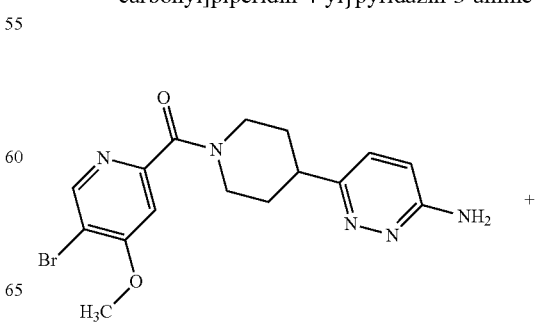

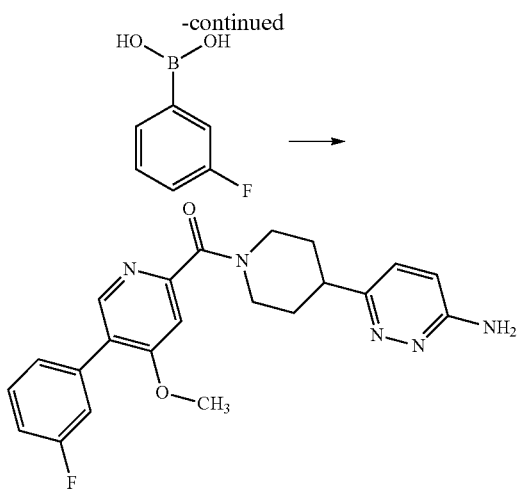

6-[1-(5-Bromo-4-methoxypyridine-2-carbonyl)piperidin-4-yl]pyridazin-3-amine (50.0 mg; 0.13 mmol), (3-fluorophenyl)boronic acid (21.4 mg; 0.15 mmol), potassium phosphate (54.1 mg; 0.26 mmol) and $PdCl_2(dppf)CH_2Cl_2$ (20.8 mg; 0.03 mmol) are combined in degassed 1,4-dioxane/water (2 mL/0.25 mL) and purged with argon. The reaction mixture is stirred at 120° C. for 1 hour in a microwave. The reaction mixture is purified by RP-HPLC.

Yield: 5 mg (10%) ESI-MS: m/z=408 $(M+H)^+$ $R_t$(HPLC): 0.50 min (method 16)

Assessment of Biological Activity

High Throughput Screening Assay

This screening assay measures human TRPC6 (transient receptor potential cation channel, subfamily C, member 6) ion channel activation via addition either of the commercially available DAG ligand analogue OAG (1-oleoyl-2-acetyl-sn-glycerol) or of the TRPC6 agonist 1-[1-(4,5,6,7,8-pentahydrocyclohepta[2,1-d]thiophen-2-ylcarbonyl)-4-piperidyl]-3-hydrobenzimidazol-2-one (GSK1702934A). The assay utilizes a fluorescent calcium sensor 4-(6-Acetoxymethoxy-2,7-difluoro-3-oxo-9-xanthenyl)-4'-methyl-2,2'-(ethylenedioxy)dianiline-N,N,N',N'-tetraacetic acid tetrakis (acetoxymethyl) ester (Fluo4/AM) dye from Molecular Devices. Changes (increases) in intracellular calcium concentration as measured by the fluorescent signal increase provide a measurement of channel activity.

The commercially available HEK293/TREx line (Invitrogen) was stably transfected with a human TRPC6 construct and screened by conventional calcium imaging to find clones with human TRPC6 expression following stimulation with 1 μg/ml tetracycline. These cells were maintained in the growth medium recommended by the manufacturer supplemented with 100 μg/ml hygromycin to promote retention of the human TRPC6 construct. After growing to near confluency, cells were plated at a density of ~35,000 cells/well in 384 well CellBind plates (Corning) in the presence of 1 μg/ml tetracycline, and allowed to grow for 20-30 hrs. A nearly confluent monolayer resulted. Growth media was removed from the wells and cells were then loaded with 25 mL Fluo4/AM diluted in Ringer's Solution (6.5 g NaCl, 0.42 g KCl, 0.25 g $CaCl_2$) and 0.2 g of sodium bicarbonate; pH 7.4) supplemented with 1% Pluronic F-127 to a final concentration of 0.5 μM and incubated for 60 min, at room temperature. Dye solution was then removed from the cells by inverting plates with a sharp flick, and replaced with 25 μl Ringer's. Following ~0.5 hour for recovery from loading, cells were assayed using the Hamamatsu FDSS 6000 system, which permitted illumination at 485 nm. Frames were acquired at a rate of 0.2 Hz. During the assay, the plates were continuously vortexed, with pipette mixing of wells following addition of each reagent. For the screening assay, 26 μl of a diluted compound stock (at 50 μM) was added to each well for 2 minutes following the collection of a short (4 frame) baseline. 13 μl of agonist solution consisting of 125 nM GSK1702934A diluted in high-Ca2+Ringer solution (containing 90 mM Ca2+) was then added to each well, achieving a final concentration of 20 mM Ca2+ and 10 μM test compound. Data was collected for ~3 minutes following addition of high Ca2+Ringer. The fluorescent intensity observed at a particular timepoint for each well was divided by the initial fluorescent intensity for that well and the overall response was determined by averaging the resulting fluorescent ratio of the last 4 frames acquired during the experiment excepting the final frame. Negative and Positive controls were included on each plate. Negative controls wells consisted of HEK293/TREx TRPC6 cells exposed to assay buffer and agonist solution, but no test compound. Positive control consisted of wells consisted of HEK293/TREx TRPC6 cells exposed to 25 μM 3-[(2-chlorophenoxy)methyl]phenyl piperidyl ketone (Chembridge) diluted in Ringer's solution and agonist solution. These controls defined zero percent and 100 percent block respectively, and intensity of each well was normalized to these values.

IC50s were determined using the above fluorescence method with the exception that instead of testing the compounds at 10 μM, compounds were tested at final concentrations of 20 μM, 6.667 μM, 2.222 μM, 0.741 μM, 0.247 μM, 0.082 μM, and 0.027 μM. Compounds were tested in triplicate at all concentrations. Standard software was used to fit IC50 curves.

TABLE 3

Antagonist effects of compounds of the invention against human TRPC6 ($IC_{50}$)

| Cpd | Fluorescence TRPC6 $IC_{50}$ (nM) |
| --- | --- |
| 1 | 3800 |
| 2 | 2000 |
| 3 | 1700 |
| 4 | 1900 |
| 5 | 2500 |
| 6 | 4400 |
| 7 | 3400 |
| 8 | 6700 |
| 9 | 5400 |
| 10 | 9200 |
| 11 | 2000 |
| 12 | 2400 |
| 13 | 88 |
| 14 | 3300 |
| 15 | 1700 |
| 16 | 390 |
| 17 | 75 |
| 18 | 2700 |
| 19 | 610 |
| 20 | 450 |
| 21 | 160 |
| 22 | 430 |
| 23 | 69 |
| 24 | 420 |
| 25 | 340 |
| 26 | 58 |
| 27 | 36 |
| 28 | 190 |
| 29 | 110 |
| 30 | 340 |

TABLE 3-continued

Antagonist effects of compounds of the invention against human TRPC6 (IC$_{50}$)

| Cpd | Fluorescence TRPC6 IC$_{50}$ (nM) |
|---|---|
| 31 | 94 |
| 32 | 110 |
| 33 | 62 |
| 34 | 100 |
| 35 | 220 |
| 36 | 27 |
| 37 | 320 |
| 38 | 180 |
| 39 | 320 |
| 40 | 73 |
| 41 | 130 |
| 42 | 700 |
| 43 | 390 |
| 44 | 1700 |
| 45 | 440 |
| 46 | 4000 |
| 47 | 200 |
| 48 | 130 |
| 49 | 140 |
| 50 | 190 |
| 51 | 900 |
| 52 | 240 |
| 53 | 3600 |
| 54 | 830 |
| 55 | 430 |
| 56 | 910 |
| 57 | 320 |
| 58 | 81 |
| 59 | 640 |
| 60 | 930 |
| 61 | 4100 |
| 62 | 1100 |
| 63 | 4700 |
| 64 | 1300 |
| 65 | 860 |
| 66 | 520 |
| 67 | 210 |
| 68 | 39 |
| 69 | 360 |
| 70 | 1400 |
| 71 | 27 |
| 72 | 27 |
| 73 | 510 |
| 74 | 140 |
| 75 | 91 |
| 76 | 380 |
| 77 | 160 |
| 78 | 460 |
| 79 | 120 |
| 80 | 130 |
| 81 | 220 |
| 82 | 340 |
| 83 | 8700 |
| 84 | 130 |
| 85 | 350 |
| 86 | 660 |
| 87 | 540 |
| 88 | 280 |
| 89 | 540 |
| 90 | 370 |
| 91 | 300 |
| 92 | 56 |
| 93 | 27 |
| 94 | 27 |
| 95 | 580 |
| 96 | 320 |
| 97 | 69 |
| 98 | 200 |
| 99 | 300 |
| 100 | 230 |
| 101 | 390 |
| 102 | 840 |
| 103 | 27 |
| 104 | 27 |
| 105 | 32 |
| 106 | 440 |
| 107 | 210 |
| 108 | 700 |
| 109 | 330 |
| 110 | 400 |
| 111 | 440 |
| 112 | 1400 |
| 113 | 2800 |
| 114 | 67 |
| 115 | 250 |
| 116 | 190 |

The biological activity of the claimed compounds can also be shown using a human TRPC6 patch clamp assay.

Methods of Therapeutic Use

The inhibition of TRPC6 is an attractive means for preventing and treating a variety of diseases or conditions that are exacerbated by TRPC6 activity. The compounds disclosed herein effectively inhibit TRPC6 activity. In particular, the compounds of the invention are selective ion channel inhibitors and have good metabolic stability in human microsomes. More particularly, the compounds of the invention have very good potency and selectivity on the TRPC6 channel as compared to other TRP channels including TRPC3, TRPC5 and TRPC7. Thus, the compounds of the invention are useful for the treatment of diseases and conditions as described in the Background and Detailed Description section, including the following conditions and diseases:

cardiac conditions (e.g., cardiac hypertrophy), hypertension (e.g., primary or secondary), pulmonary arterial hypertension (e.g., IPAH), a neurodegenerative disease or disorder (e.g., Alzheimer's disease (AD), Parkinson's disease, Huntington's disease, amyotrophic lateral sclerosis (ALS), and other brain disorders caused by trauma or other insults including aging), inflammatory diseases (e.g., asthma, emphysema, chronic obstructive pulmonary disease, rheumatoid arthritis, osteoarthritis, inflammatory bowel disease, multiple sclerosis, muscular dystrophy, Duchenne's muscular dystrophy, and disorders of the immune system), preeclampsia and pregnancy-induced hypertension, kidney diseases (focal segmental glomerulosclerosis, nephrotic syndrome, diabetic nephropathy or diabetic kidney disease, chronic kidney disease (CKD), renal insufficiency, end stage renal disease, nonalcoholic steatohepatitis (NASH), minimal change disease, ischemia or an ischemic reperfusion injury, cancer, metabolic disorders such as diabetes, idiopathic pulmonary fibrosis (IPF) and acute respiratory disease syndrome (ARDS). Methods for preventing or treating any of the foregoing or following diseases and conditions include treating any of the symptoms associated with these diseases or conditions. For example, methods for treating kidney disease contemplate treating symptoms including, but not limited to, secondary hypertension, proteinuria, lipiduria, hypercholesterolemia, hyperlipidemia, and coagulation abnormalities.

Because of the important role that calcium regulation plays in many cellular processes including cellular activation, cytoskeletal rearrangement, gene expression, cellular trafficking and apoptotic cell death, calcium dyshomeostasis is implicated in the many diseases and disorders. These diseases and disorders include neurological and neurodegenerative diseases and disorders; inflammatory diseases and disorders such as inflammatory bowel disease and Crohn's disease; kidney disease such as hypercalcemia, kidney stones, and polycystic kidney disease; metabolic diseases and disorders including obesity and diabetes; liver and kidney diseases and disorders; cardiovascular diseases and disorders including hypertension; respiratory diseases including COPD, IPAH, and asthma, and cancers, including cancers of the brain, breast, kidney, cervix, prostate, gastrointestinal tract, skin, and epithelia.

These disorders have been well characterized in man, but also exist with a similar etiology in other mammals, and can be treated by pharmaceutical compositions of the present invention.

Accordingly, a compound of the invention, as described herein, or a pharmaceutically acceptable salt thereof may be used for the preparation of a medicament for treating a disease or disorder mediated by TRPC6, including those mentioned above and in the Background and Detailed Description sections.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of the invention (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patients general health profile, the severity and course of the patients disorder or disposition thereto, and the judgment of the treating physician.

The compounds of the invention may be used alone or in combination of one or more additional therapeutic agents. Nonlimiting examples of additional therapeutic agents may include:

angiotensin II receptor antagonists (angiotensin receptor blockers (ARBs)) such as candesartan, eprosartan, candesartan, irbesartan, losartan, olmesartan, telmisartan, valsartan, azilsartan, and medoxomil;

angiotensin converting enzyme inhibitors (e.g., benazepril, captopril, enalapril, fosinopril, lisinopril, moexipril, and perindopril);

antidiabetics such as alpha-glucosidase inhibitors (e.g., miglitol and acarbose), amylin analogs (e.g., pramlintide), dipeptidyl peptidase 4 inhibitors (e.g., alogliptin, sitagliptin, saxagliptin, and linagliptin), incretin mimetics (e.g., liraglutide, exenatide, liraglutide, exenatide, dulaglutide, albiglutide, and lixisenatide), insulin, meglitinides (e.g., repaglinide and nateglinide), biguanides (e.g., metformin); SGLT-2 inhibitors (e.g., canagliflozin, empagliflozin, and dapagliflozin), sulfonylureas (e.g., chlorpropamide, glimepiride, glyburide, glipizide, glyburide, tolazamide, and tolbutamide), and thiazolidinediones (e.g., rosiglitazone and pioglitazone);

bronchodilators including short-acting and long-action beta agonists (e.g., albuterol, levalbuterol, salmeterol, formoterol, and arformoterol) and short- and long-acting anticholinergics (ipratropium, tiotropium, umeclidinium, glycopyrrolatei), and aclidinium).

steroids such as fluticasone and budesonide;

When used as combination treatment of a pharmaceutical combination, the compounds of the invention and the one or more additional agents can be administered in the same dosage form or different dosage forms. The compounds of the invention and the one or more additional agents can be administered simultaneously or separately, as part of a regimen.

What is claimed is:

1. A compound of formula (I)

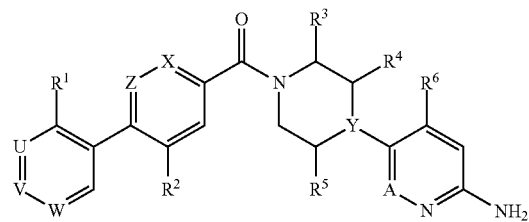

Wherein:

A is $CR^7$ or N;

U is CH or N;

V is $CR^8$ or N;

W is $CR^9$ or N;

X is CH, $CC_{1-6}$alkyl, $COC_{1-6}$alkyl, or N;

Y is CH or N;

Z is CH, COH, $COC_{1-6}$alkyl or N;

$R^1$ is selected from the group consisting of H and halogen;

$R^2$ is selected from the group consisting of H, $C_{1-6}$alkyl, —CN, —$CF_3$, —$OCF_3$, $C_{3-6}$cycloalkyl, $OC_{1-6}$alkyl, and $OC_{3-6}$cycloalkyl;

when Z is COH, $R^1$ may join with the hydroxyl group attached to the Z ring atom to form a central furanyl ring;

$R^3$ is selected from the group consisting of

H, $C_{1-6}$alkyl optionally substituted with one to three groups independently selected from the group consisting of halogen, hydroxy or methoxy, and $C_{3-6}$cycloalkyl;

$R^4$ is selected from the group consisting of H, $C_{1-6}$alkyl optionally substituted with hydroxyl, $C_{3-6}$cycloalkyl;

$R^5$ is H or $C_{1-6}$alkyl;

$R^3$ and $R^5$ can together form a bicyclic ring;

$R^6$ is selected from the group consisting of

H, $C_{1-6}$alkyl,

—CN,

—$CF_3$,

—$OCF_3$, $C_{3-6}$cycloalkyl, and $OC_{1-6}$alkyl optionally substituted one to three halogen;

$R^7$ is selected from the group consisting of H, $C_{1-6}$alkyl, and $OC_{1-6}$alkyl optionally substituted with one to three halogen;

$R^8$ is selected from the group consisting of

H, $C_{1-6}$alkyl optionally substituted with $C_{3-6}$cycloalkyl or one to three halogen, halogen,

—CN,

—$CF_3$,

—$NH_2$, phenyl, $C_{3-6}$cycloalkyl, $OC_{3-6}$cycloalkyl, $OC_{1-6}$alkyl optionally substituted with one to three halogen or $C_{3-6}$cycloalkyl optionally substituted with one to three halogen; and 1-fluoromethyl-cyclopropylmethoxy;

$R^9$ is selected from the group consisting of

H, $C_{1-6}$alkyl optionally substituted with one to three halogen, halogen,

—CN,

—$CF_3$,

OH, $C_{3-6}$cycloalkyl, $OC_{1-6}$alkyl optionally substituted with $C_{3-6}$cycloalkyl or one to three halogen, and $OC_{3-6}$cycloalkyl;

when V is $CR^8$ and W is $CR^9$, $R^8$ and $R^9$ can together form a 5- to 6-membered fused heterocyclic ring;

or a pharmaceutically acceptable salt thereof.

2. The compound according to claim 1, wherein $R^2$ is selected from the group consisting of H, $C_{1-6}$alkyl, and $OC_{1-6}$alkyl;

$R^3$ is selected from the group consisting of H and $C_{1-6}$alkyl optionally substituted with one to three groups independently selected from the group consisting of halogen and hydroxyl;

$R^4$ is selected from the group consisting of H and $C_{1-6}$alkyl optionally substituted with hydroxyl;

$R^5$ is H;

$R^6$ is selected from the group consisting of H, $C_{1-6}$alkyl, and $OC_{1-6}$alkyl optionally substituted with one to three halogen;

or a pharmaceutically acceptable salt thereof.

3. The compound according to claim 1, wherein Z is CH or a pharmaceutically acceptable salt thereof.

4. The compound according to claim 1 wherein:

U is N, V is $CR^8$, and W is $CR^9$,

X is CH or N, or a pharmaceutically acceptable salt thereof.

5. The compound according to claim 1, wherein:

A is N,

X is N,

Y is CH, or a pharmaceutically acceptable salt thereof.

6. The compound according to claim 1, wherein:

A is N,

X is CH,

Y is CH, or a pharmaceutically acceptable salt thereof.

7. The compound according to claim 1, wherein:

A is $CR^7$,

X is N,

Y is N, or a pharmaceutically acceptable salt thereof.

8. The compound according to claim 1, wherein

A is $CR^7$,

X is N,

Y is CH, or a pharmaceutically acceptable salt thereof.

9. The compound according to claim 1, wherein $R^8$ is selected from the group consisting H, F, $CF_3$, ethyl, methoxy, ethoxy, sec-butoxy, trifluoromethoxy, trifluoroethoxy, cyclopropyl, cyclopropylmethoxy, 1-cyclopropylethoxy, 1-methylcyclopropylmethoxy, 1-fluoromethylcyclopropylmethoxy, 2,2,2-trifluoroethoxy, 2,2,-dimethylcyclopropylmethoxy, 2,2,-diflurocyclopropylmethoxy, cyclopropoxy, and cyclobutoxy, or a pharmaceutically acceptable salt thereof.

10. The compound according to claim 1, wherein $R^2$ is H or OCH3, or a pharmaceutically acceptable salt thereof.

11. The compound according to claim 1, wherein $R^3$, $R^4$, $R^5$ and $R^6$ are each H, or a pharmaceutically acceptable salt thereof.

12. The compound according to claim 1, wherein $R^2$ is OCH3, or a pharmaceutically acceptable salt thereof.

13. The compound according to claim 1, wherein $R^8$ is selected from the group consisting of H, fluoro, chloro, $CF_3$, —CN, methyl, ethyl, isobutyl, tert-butyl, difluoromethyl, methoxy, difluoromethoxy, ethoxy, isopropoxy, trifluoromethoxy, 2,2,2-trifluoroethoxy, cyclopropylmethoxy, cyclopropoxy, and cyclopentoxy, or a pharmaceutically acceptable salt thereof.

14. The compound according to claim 1, wherein $R^2$ is H or $OCH_3$, or a pharmaceutically acceptable salt thereof.

15. The compound according to claim 1, wherein $R^2$ is $OCH_3$, or a pharmaceutically acceptable salt thereof.

16. The compound according to claim 1, wherein $R^2$ is H, or a pharmaceutically acceptable salt thereof.

17. The compound according to claim 1, selected from the group consisting of:

| Cpd No. | Structure | Structure Name |
|---|---|---|
| 1 | 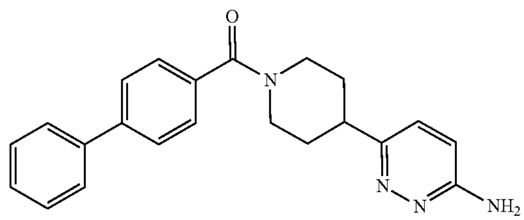 [SMILES: Nc1ccc(C2CCN(C(=O)c3ccc(-c4ccccc4)cc3)CC2)nn1] | [4-(6-Amino-pyridazin-3-yl)-piperidin-1-yl]-biphenyl-4-yl-methanone |
| 2 | 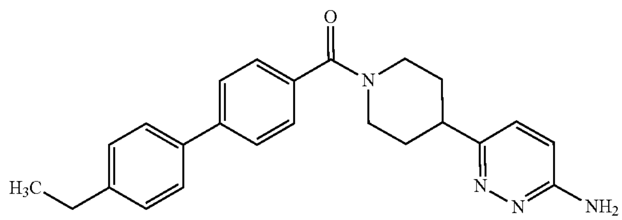 [SMILES: CCc1ccc(-c2ccc(C(=O)N3CCC(c4ccc(N)nn4)CC3)cc2)cc1] | [4-(6-Amino-pyridazin-3-yl)-piperidin-1-yl]-(4'-ethyl-biphenyl-4-yl)-methanone |
| 3 | 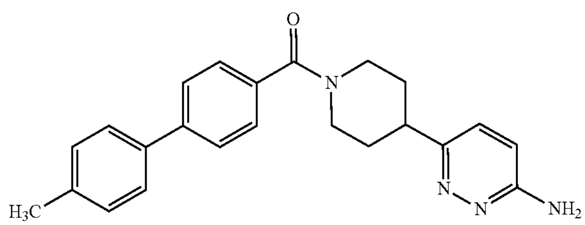 [SMILES: Cc1ccc(-c2ccc(C(=O)N3CCC(c4ccc(N)nn4)CC3)cc2)cc1] | [4-(6-Amino-pyridazin-3-yl)-piperidin-1-yl]-(4'-methyl-biphenyl-4-yl)-methanone |
| 4 | 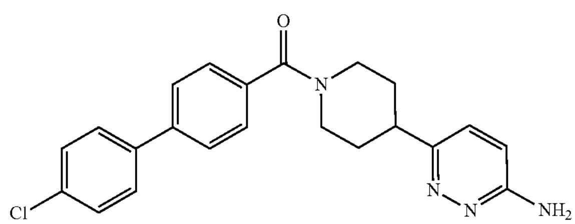 [SMILES: Nc1ccc(C2CCN(C(=O)c3ccc(-c4ccc(Cl)cc4)cc3)CC2)nn1] | [4-(6-Amino-pyridazin-3-yl)-piperidin-1-yl]-(4'-chloro-biphenyl-4-yl)-methanone |
| 5 | 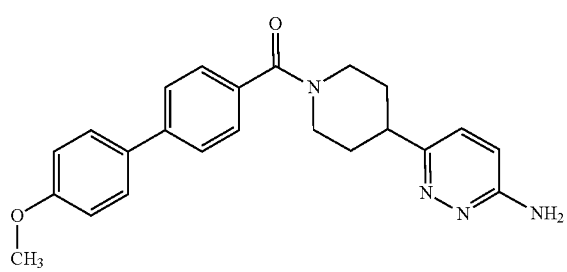 [SMILES: COc1ccc(-c2ccc(C(=O)N3CCC(c4ccc(N)nn4)CC3)cc2)cc1] | [4-(6-Amino-pyridazin-3-yl)-piperidin-1-yl]-(4'-methoxy-biphenyl-4-yl)-methanone |
| 6 | 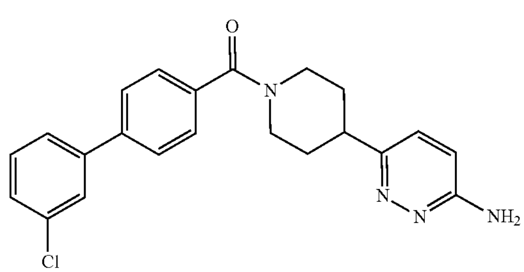 [SMILES: Nc1ccc(C2CCN(C(=O)c3ccc(-c4cccc(Cl)c4)cc3)CC2)nn1] | [4-(6-Amino-pyridazin-3-yl)-piperidin-1-yl]-(3'-chloro-biphenyl-4-yl)-methanone |

-continued

| Cpd No. | Structure | Structure Name |
|---|---|---|
| 7 | 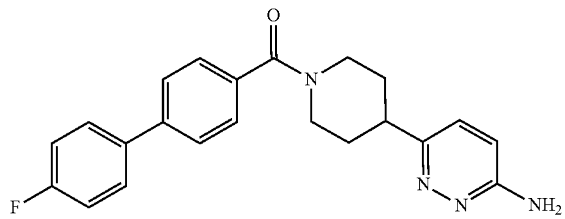 [SMILES: Nc1ccc(C2CCN(C(=O)c3ccc(-c4ccc(F)cc4)cc3)CC2)nn1] | [4-(6-Amino-pyridazin-3-yl)-piperidin-1-yl]-(4'-fluoro-biphenyl-4-yl)-methanone |
| 8 | 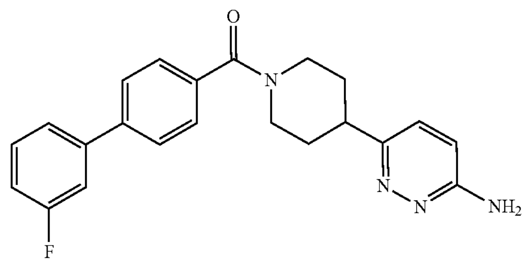 [SMILES: Nc1ccc(C2CCN(C(=O)c3ccc(-c4cccc(F)c4)cc3)CC2)nn1] | [4-(6-Amino-pyridazin-3-yl)-piperidin-1-yl]-(3'-fluoro-biphenyl-4-yl)-methanone |
| 9 | 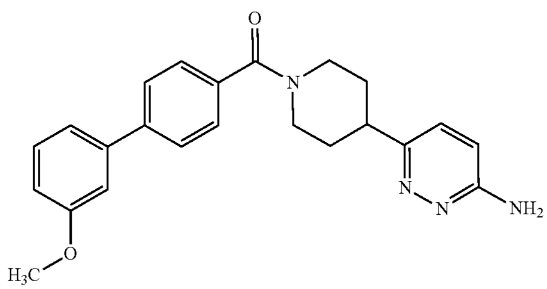 [SMILES: COc1cccc(-c2ccc(C(=O)N3CCC(c4ccc(N)nn4)CC3)cc2)c1] | [4-(6-Amino-pyridazin-3-yl)-piperidin-1-yl]-(3'-methoxy-biphenyl-4-yl)-methanone |
| 10 | 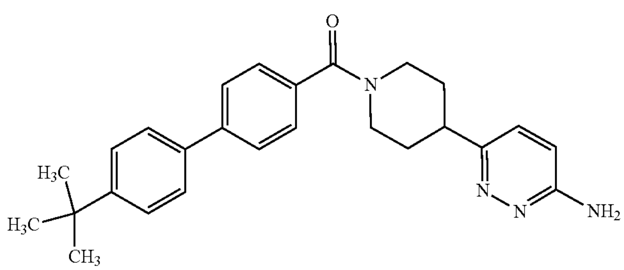 [SMILES: CC(C)(C)c1ccc(-c2ccc(C(=O)N3CCC(c4ccc(N)nn4)CC3)cc2)cc1] | [4-(6-Amino-pyridazin-3-yl)-piperidin-1-yl]-(4'-tert-butyl-biphenyl-4-yl)-methanone |
| 11 | 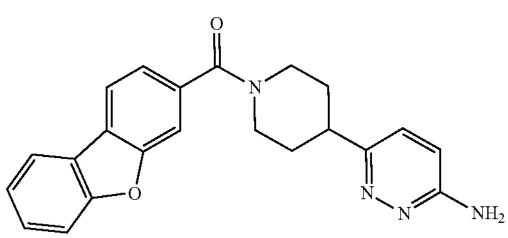 [SMILES: Nc1ccc(C2CCN(C(=O)c3ccc4c(c3)oc3ccccc34)CC2)nn1] | [4-(6-Amino-pyridazin-3-yl)-piperidin-1-yl]-dibenzofuran-3-yl-methanone |
| 12 | 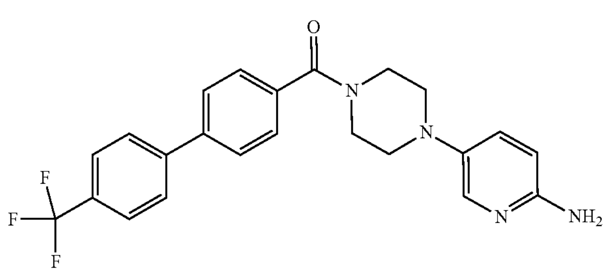 [SMILES: Nc1ccc(N2CCN(C(=O)c3ccc(-c4ccc(C(F)(F)F)cc4)cc3)CC2)cn1] | [4-(6-Amino-pyridin-3-yl)-piperazin-1-yl]-(4'-trifluoromethyl-biphenyl-4-yl)-methanone |

-continued

| Cpd No. | Structure | Structure Name |
|---|---|---|
| 13 | 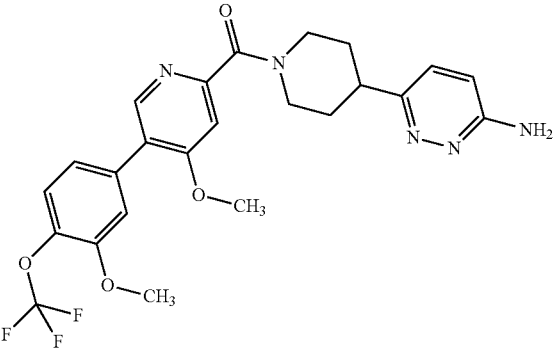 [SMILES: COc1cc(-c2cnc(C(=O)N3CCC(c4ccc(N)nn4)CC3)cc2OC)ccc1OC(F)(F)F] | [4-(6-Amino-pyridazin-3-yl)-piperidin-1-yl]-4-methoxy-5-(3-methoxy-4-trifluoromethoxy-phenyl)-pyridin-2-yl]-methanone |
| 14 | 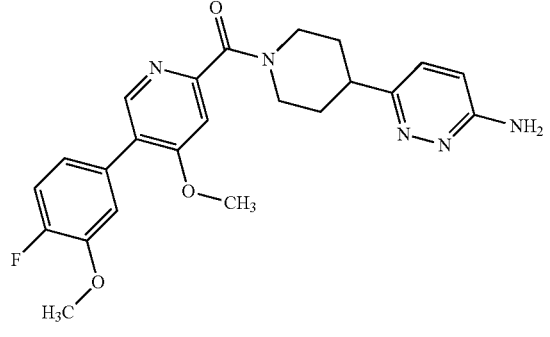 [SMILES: COc1cc(-c2cnc(C(=O)N3CCC(c4ccc(N)nn4)CC3)cc2OC)ccc1F] | [4-(6-Amino-pyridazin-3-yl)-piperidin-1-yl]-[5-(4-fluoro-3-methoxy-phenyl)-4-methoxy-pyridin-2-yl]-methanone |
| 15 | 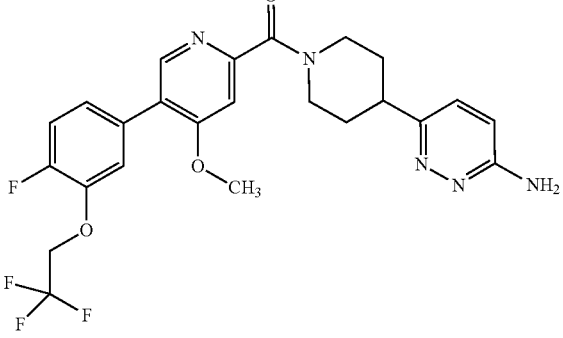 | [4-(6-Amino-pyridazin-3-yl)-piperidin-1-yl]-{5-[4-fluoro-3-(2,2,2-trifluoro-ethoxy)-phenyl]-4-methoxy-pyridin-2-yl}-methanone |
| 16 | 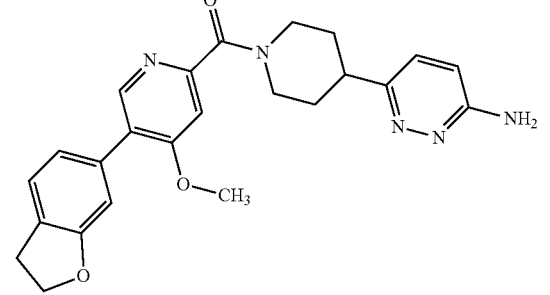 | [4-(6-Amino-pyridazin-3-yl)-piperidin-1-yl]-[5-(2,3-dihydro-benzofuran-6-yl)-4-methoxy-pyridin-2-yl]-methanone |

-continued

| Cpd No. | Structure | Structure Name |
|---|---|---|
| 17 | 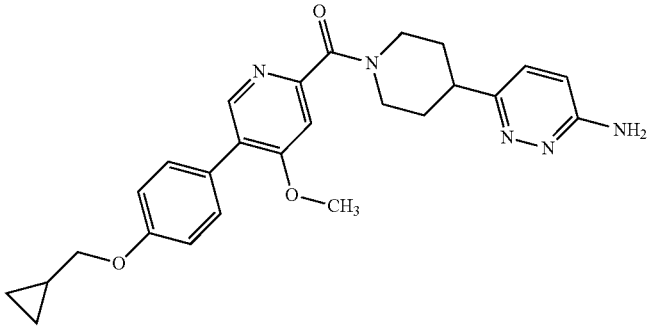 [SMILES: COc1cc(C(=O)N2CCC(c3ccc(N)nn3)CC2)ncc1-c1ccc(OCC2CC2)cc1] | [4-(6-Amino-pyridazin-3-yl)-piperidin-1-yl]-[5-(4-cyclopropylmethoxy-phenyl)-4-methoxy-pyridin-2-yl]-methanone |
| 18 | 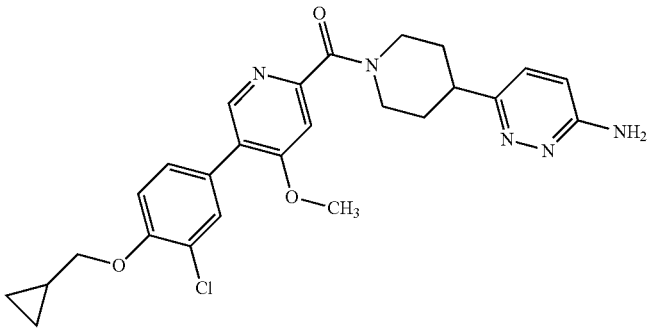 [SMILES: COc1cc(C(=O)N2CCC(c3ccc(N)nn3)CC2)ncc1-c1ccc(OCC2CC2)c(Cl)c1] | Amino-pyridazin-3-yl)-piperidin-1-yl]-[5-(3-chloro-4-cyclopropylmethoxy-phenyl)-4-methoxy-pyridin-2-yl]-methanone |
| 19 | 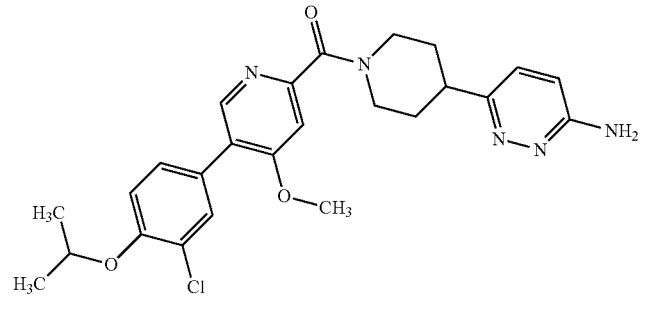 [SMILES: COc1cc(C(=O)N2CCC(c3ccc(N)nn3)CC2)ncc1-c1ccc(OC(C)C)c(F)c1] | [4-(6-Amino-pyridazin-3-yl)-piperidin-1-yl]-[5-(3-chloro-4-isopropoxy-phenyl)-4-methoxy-pyridin-2-yl]-methanone |
| 20 | 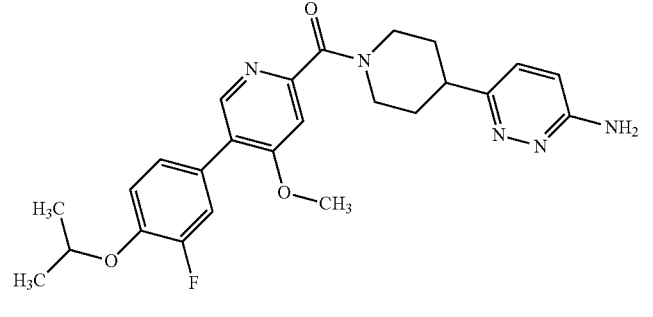 | [4-(6-Amino-pyridazin-3-yl)-piperidin-1-yl]-[5-(3-fluoro-4-isopropoxy-phenyl)-4-methoxy-pyridin-2-yl]-methanone |

| Cpd No. | Structure | Structure Name |
|---|---|---|
| 21 | 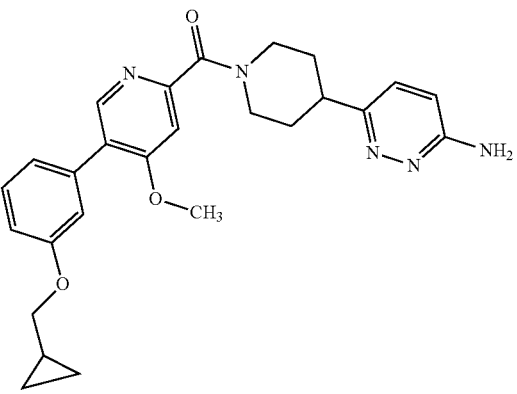 [SMILES: COc1cc(C(=O)N2CCC(c3ccc(N)nn3)CC2)ncc1-c1cccc(OCC2CC2)c1] | [4-(6-Amino-pyridazin-3-yl)-piperidin-1-yl]-[5-(3-cyclopropylmethoxy-phenyl)-4-methoxy-pyridin-2-yl]-methanone |
| 22 | 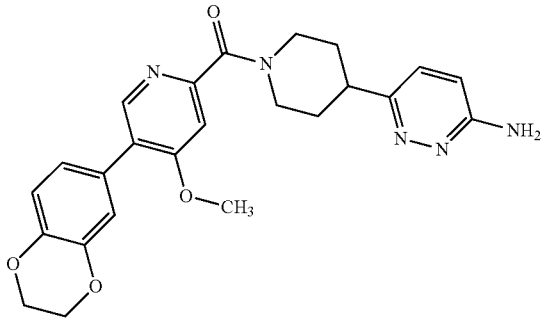 [SMILES: COc1cc(C(=O)N2CCC(c3ccc(N)nn3)CC2)ncc1-c1ccc2c(c1)OCCO2] | [4-(6-Amino-pyridazin-3-yl)-piperidin-1-yl]-[5-(2,3-dihydro-benzo[1,4]dioxin-6-yl)-4-methoxy-pyridin-2-yl]-methanone |
| 23 | 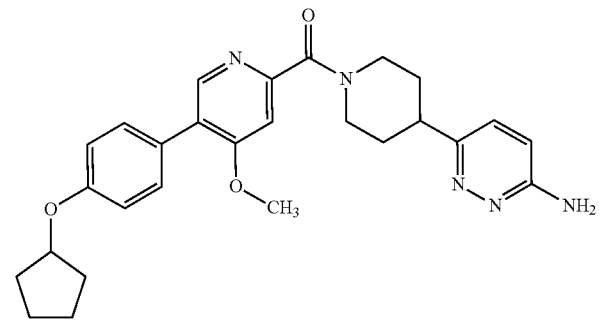 [SMILES: COc1cc(C(=O)N2CCC(c3ccc(N)nn3)CC2)ncc1-c1ccc(OC2CCCC2)cc1] | [4-(6-Amino-pyridazin-3-yl)-piperidin-1-yl]-[5-(4-cyclopentyloxy-phenyl)-4-methoxy-pyridin-2-yl]-methanone |
| 24 | 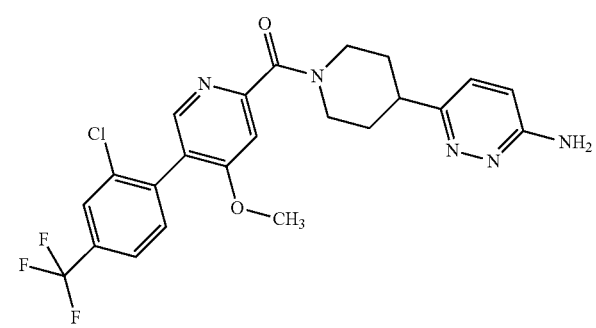 [SMILES: COc1cc(C(=O)N2CCC(c3ccc(N)nn3)CC2)ncc1-c1ccc(C(F)(F)F)cc1Cl] | [4-(6-Amino-pyridazin-3-yl)-piperidin-1-yl]-[5-(2-chloro-4-trifluoromethyl-phenyl)-4-methoxy-pyridin-2-yl]-methanone |

| Cpd No. | Structure | Structure Name |
|---|---|---|
| 25 | 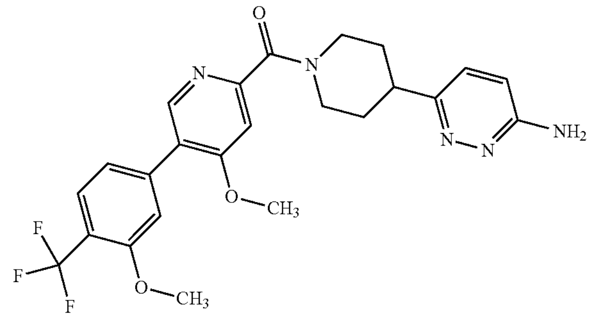 [SMILES: COc1cc(C(=O)N2CCC(c3ccc(N)nn3)CC2)ncc1-c1ccc(C(F)(F)F)c(OC)c1] | [4-(6-Amino-pyridazin-3-yl)-piperidin-1-yl]-[4-methoxy-5-(3-methoxy-4-trifluoromethyl-phenyl)-pyridin-2-yl]-methanone |
| 26 | 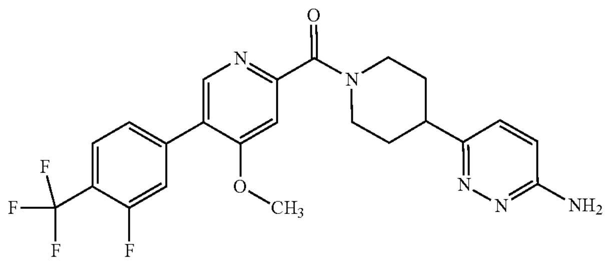 [SMILES: COc1cc(C(=O)N2CCC(c3ccc(N)nn3)CC2)ncc1-c1ccc(C(F)(F)F)c(F)c1] | [4-(6-Amino-pyridazin-3-yl)-piperidin-1-yl]-[5-(3-fluoro-4-trifluoromethyl-phenyl)-4-methoxy-pyridin-2-yl]-methanone |
| 27 | 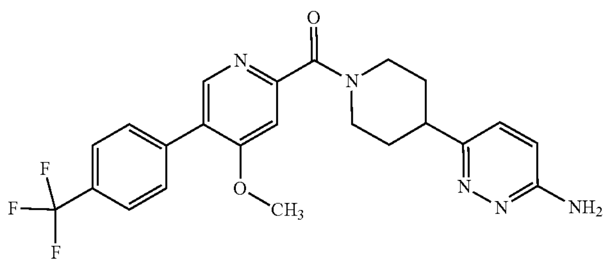 [SMILES: COc1cc(C(=O)N2CCC(c3ccc(N)nn3)CC2)ncc1-c1ccc(C(F)(F)F)cc1] | [4-(6-Amino-pyridazin-3-yl)-piperidin-1-yl]-[4-methoxy-5-(4-trifluoromethyl-phenyl)-pyridin-2-yl]-methanone |
| 28 | 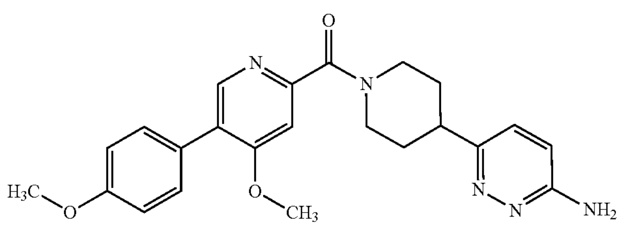 [SMILES: COc1ccc(-c2cnc(C(=O)N3CCC(c4ccc(N)nn4)CC3)cc2OC)cc1] | [4-(6-Amino-pyridazin-3-yl)-piperidin-1-yl]-[4-methoxy-5-(4-methoxy-phenyl)-pyridin-2-yl]-methanone |
| 29 | 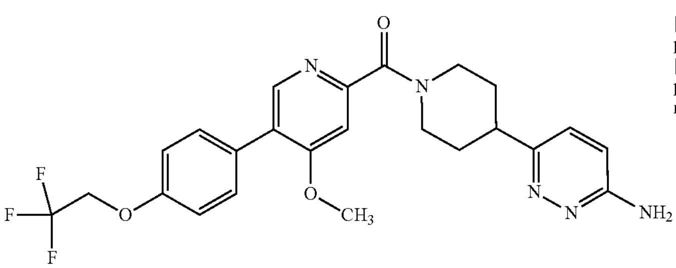 | [4-(6-Amino-pyridazin-3-yl)-piperidin-1-yl]-{4-methoxy-5-[4-(2,2,2-trifluoro-ethoxy)-phenyl]-pyridin-2-yl}-methanone |
| 30 | 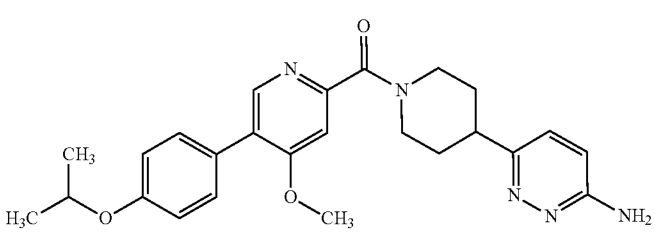 [SMILES: COc1cc(C(=O)N2CCC(c3ccc(N)nn3)CC2)ncc1-c1ccc(OC(C)C)cc1] | [4-(6-Amino-pyridazin-3-yl)-piperidin-1-yl]-[5-(4-isopropoxy-phenyl)-4-methoxy-pyridin-2-yl]-methanone |

| Cpd No. | Structure | Structure Name |
|---|---|---|
| 31 | 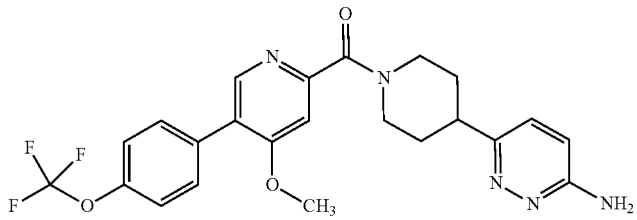 [SMILES: COc1cc(C(=O)N2CCC(c3ccc(N)nn3)CC2)ncc1-c1ccc(OC(F)(F)F)cc1] | [4-(6-Amino-pyridazin-3-yl)-piperidin-1-yl]-[4-methoxy-5-(4-trifluoromethoxy-phenyl)-pyridin-2-yl]-methanone |
| 32 | 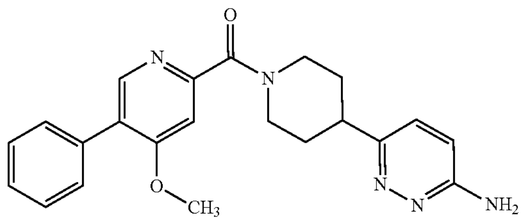 [SMILES: COc1cc(C(=O)N2CCC(c3ccc(N)nn3)CC2)ncc1-c1ccccc1] | [4-(6-Amino-pyridazin-3-yl)-piperidin-1-yl]-(4-methoxy-5-phenyl-pyridin-2-yl)-methanone |
| 33 | 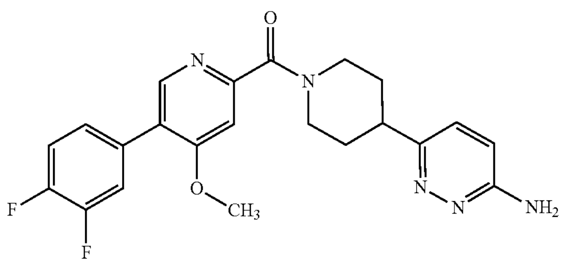 [SMILES: COc1cc(C(=O)N2CCC(c3ccc(N)nn3)CC2)ncc1-c1ccc(F)c(F)c1] | [4-(6-Amino-pyridazin-3-yl)-piperidin-1-yl]-[5-(3,4-difluoro-phenyl)-4-methoxy-pyridin-2-yl]-methanone |
| 34 | 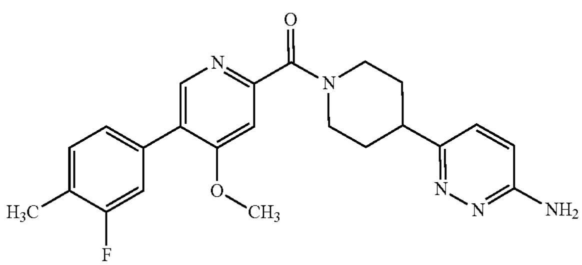 [SMILES: COc1cc(C(=O)N2CCC(c3ccc(N)nn3)CC2)ncc1-c1ccc(C)c(F)c1] | [4-(6-Amino-pyridazin-3-yl)-piperidin-1-yl]-[5-(3-fluoro-4-methyl-phenyl)-4-methoxy-pyridin-2-yl]-methanone |
| 35 | 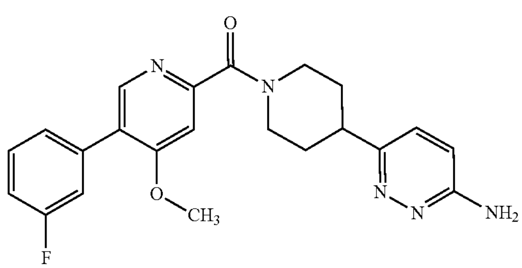 [SMILES: COc1cc(C(=O)N2CCC(c3ccc(N)nn3)CC2)ncc1-c1cccc(F)c1] | [4-(6-Amino-pyridazin-3-yl)-piperidin-1-yl]-[5-(3-fluoro-phenyl)-4-methoxy-pyridin-2-yl]-methanone |
| 36 | 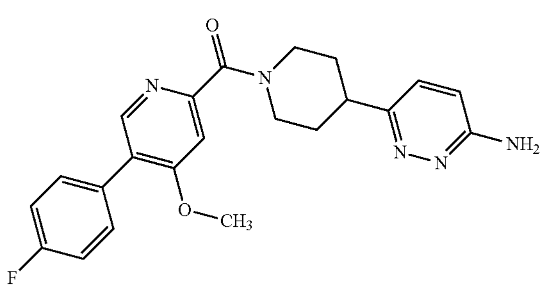 [SMILES: COc1cc(C(=O)N2CCC(c3ccc(N)nn3)CC2)ncc1-c1ccc(F)cc1] | [4-(6-Amino-pyridazin-3-yl)-piperidin-1-yl]-[5-(4-fluoro-phenyl)-4-methoxy-pyridin-2-yl]-methanone |

| Cpd No. | Structure | Structure Name |
|---|---|---|
| 37 | 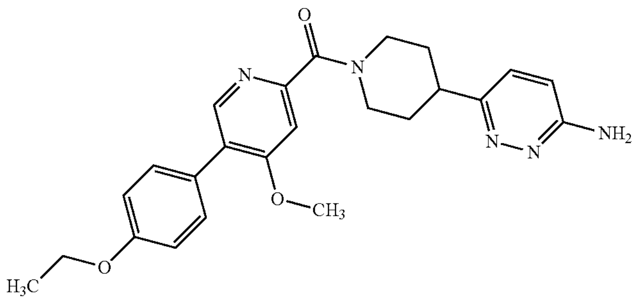 [SMILES: CCOc1ccc(-c2cnc(C(=O)N3CCC(c4ccc(N)nn4)CC3)cc2OC)cc1] | [4-(6-Amino-pyridazin-3-yl)-piperidin-1-yl]-[5-(4-ethoxy-phenyl)-4-methoxy-pyridin-2-yl]-methanone |
| 38 | 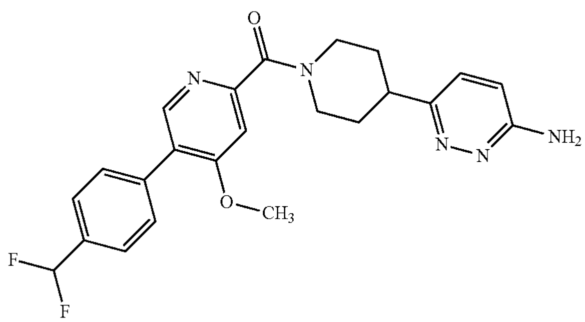 [SMILES: COc1cc(C(=O)N2CCC(c3ccc(N)nn3)CC2)ncc1-c1ccc(C(F)F)cc1] | [4-(6-Amino-pyridazin-3-yl)-piperidin-1-yl]-[5-(4-difluoromethyl-phenyl)-4-methoxy-pyridin-2-yl]-methanone |
| 39 | 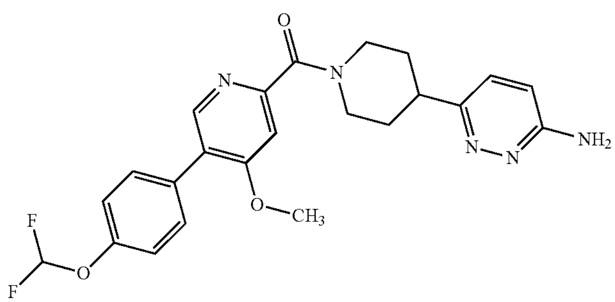 [SMILES: COc1cc(C(=O)N2CCC(c3ccc(N)nn3)CC2)ncc1-c1ccc(OC(F)F)cc1] | [4-(6-Amino-pyridazin-3-yl)-piperidin-1-yl]-[5-(4-difluoromethoxy-phenyl)-4-methoxy-pyridin-2-yl]-methanone |
| 40 | 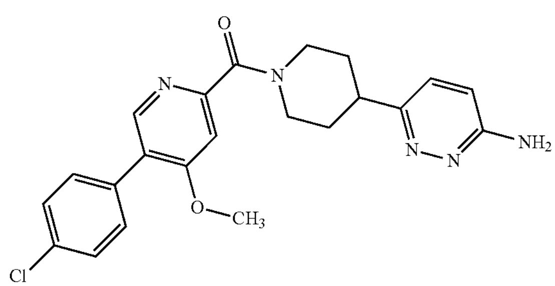 [SMILES: COc1cc(C(=O)N2CCC(c3ccc(N)nn3)CC2)ncc1-c1ccc(Cl)cc1] | [4-(6-Amino-pyridazin-3-yl)-piperidin-1-yl]-[5-(4-chloro-phenyl)-4-methoxy-pyridin-2-yl]-methanone |
| 41 | 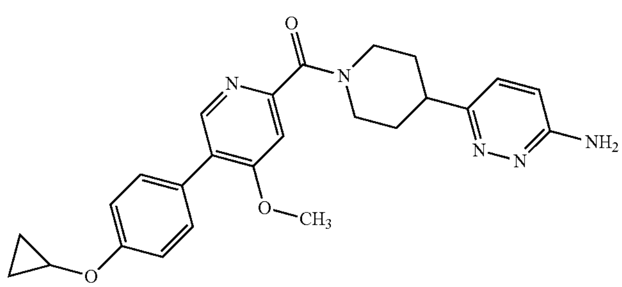 [SMILES: COc1cc(C(=O)N2CCC(c3ccc(N)nn3)CC2)ncc1-c1ccc(OC2CC2)cc1] | [4-(6-Amino-pyridazin-3-yl)-piperidin-1-yl]-[5-(4-cyclopropoxy-phenyl)-4-methoxy-pyridin-2-yl]-methanone |

-continued

| Cpd No. | Structure | Structure Name |
|---|---|---|
| 42 | 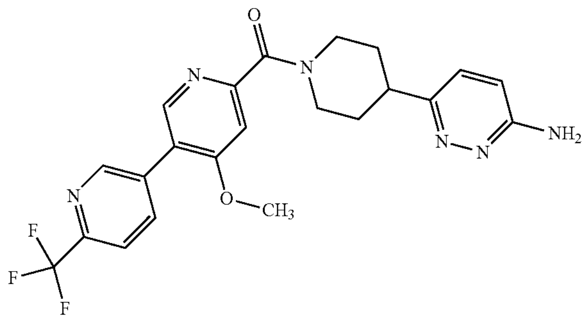 [SMILES: COc1cc(C(=O)N2CCC(c3ccc(N)nn3)CC2)ncc1-c1ccc(C(F)(F)F)nc1] | [4-(6-Amino-pyridazin-3-yl)-piperidin-1-yl]-(4-methoxy-6'-trifluoromethyl-[3,3']bipyridinyl-6-yl)-methanone |
| 43 | 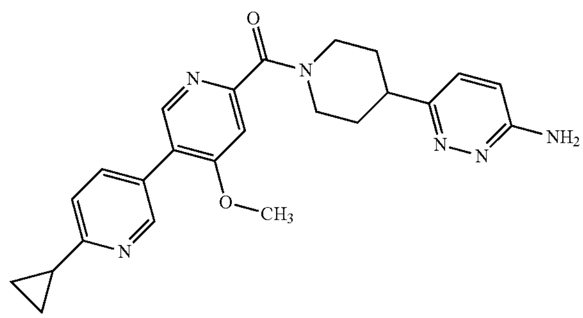 [SMILES: COc1cc(C(=O)N2CCC(c3ccc(N)nn3)CC2)ncc1-c1ccc(C2CC2)nc1] | [4-(6-Amino-pyridazin-3-yl)-piperidin-1-yl]-(6'-cyclopropyl-4-methoxy-[3,3']bipyridinyl-6-yl)-methanone |
| 44 | 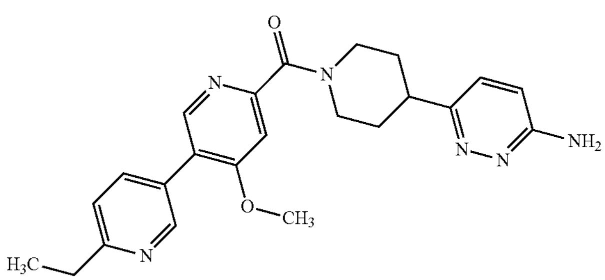 [SMILES: CCc1ccc(-c2cnc(C(=O)N3CCC(c4ccc(N)nn4)CC3)cc2OC)cn1] | [4-(6-Amino-pyridazin-3-yl)-piperidin-1-yl]-(6'-ethyl-4-methoxy-[3,3']bipyridinyl-6-yl)-methanone |
| 45 | 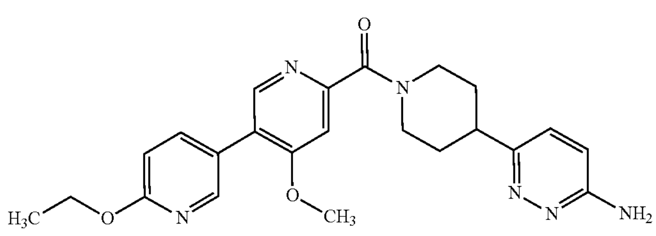 [SMILES: CCOc1ccc(-c2cnc(C(=O)N3CCC(c4ccc(N)nn4)CC3)cc2OC)cn1] | [4-(6-Amino-pyridazin-3-yl)-piperidin-1-yl]-(6'-ethoxy-4-methoxy-[3,3']bipyridinyl-6-yl)-methanone |
| 46 | 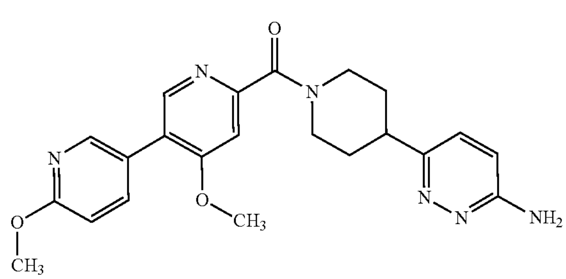 [SMILES: COc1ccc(-c2cnc(C(=O)N3CCC(c4ccc(N)nn4)CC3)cc2OC)cn1] | [4-(6-Amino-pyridazin-3-yl)-piperidin-1-yl]-(4,6'-dimethoxy-[3,3']bipyridinyl-6-yl)-methanone |

| Cpd No. | Structure | Structure Name |
|---------|-----------|----------------|
| 47 | 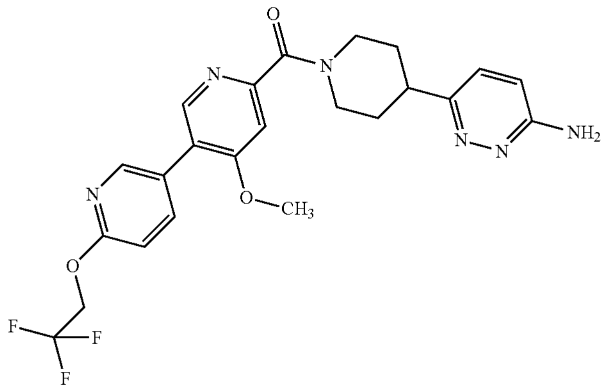 | [4-(6-Amino-pyridazin-3-yl)-piperidin-1-yl]-[4-methoxy-6'-(2,2,2-trifluoro-ethoxy)-[3,3']bipyridinyl-6-yl]-methanone |
| 48 | 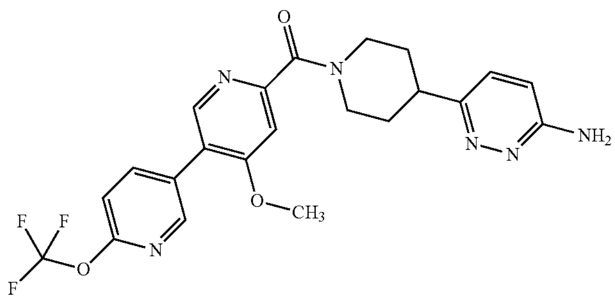 [SMILES: COc1cc(C(=O)N2CCC(c3ccc(N)nn3)CC2)ncc1-c1ccc(OC(F)(F)F)nc1] | [4-(6-Amino-pyridazin-3-yl)-piperidin-1-yl]-(4-methoxy-6'-trifluoromethoxy-[3,3']bipyridinyl-6-yl)-methanone |
| 49 | 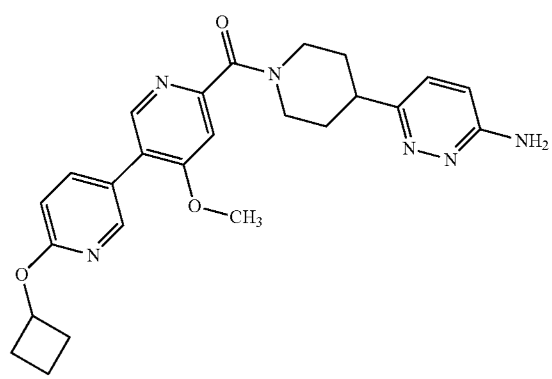 [SMILES: COc1cc(C(=O)N2CCC(c3ccc(N)nn3)CC2)ncc1-c1ccc(OC2CCC2)nc1] | [4-(6-Amino-pyridazin-3-yl)-piperidin-1-yl]-(6'-cyclobutoxy-4-methoxy-[3,3']bipyridinyl-6-yl)-methanone |
| 50 | 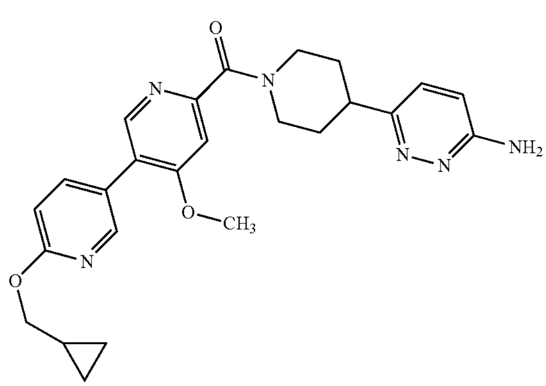 [SMILES: COc1cc(C(=O)N2CCC(c3ccc(N)nn3)CC2)ncc1-c1ccc(OCC2CC2)nc1] | [4-(6-Amino-pyridazin-3-yl)-piperidin-1-yl]-(6'-cyclopropylmethoxy-4-methoxy-[3,3']bipyridinyl-6-yl)-methanone |

-continued

| Cpd No. | Structure | Structure Name |
|---|---|---|
| 51 | 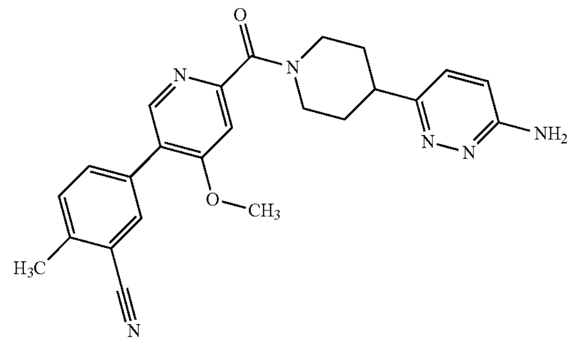 [SMILES: COc1cc(C(=O)N2CCC(c3ccc(N)nn3)CC2)ncc1-c1ccc(C)c(C#N)c1] | 5-{6-[4-(6-Amino-pyridazin-3-yl)-piperidine-1-carbonyl]-4-methoxy-pyridin-3-yl}-2-methyl-benzonitrile |
| 52 | 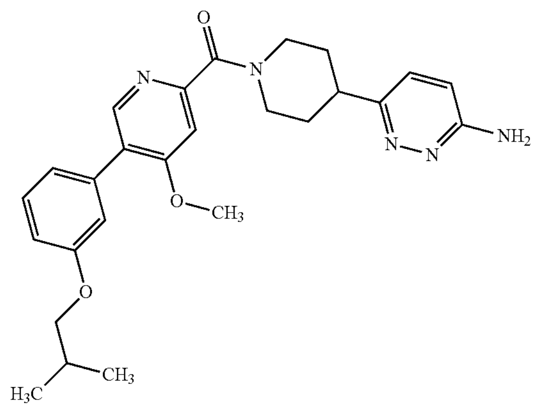 [SMILES: COc1cc(C(=O)N2CCC(c3ccc(N)nn3)CC2)ncc1-c1cccc(OCC(C)C)c1] | [4-(6-Amino-pyridazin-3-yl)-piperidin-1-yl]-[5-(3-isobutoxy-phenyl)-4-methoxy-pyridin-2-yl]-methanone |
| 53 | 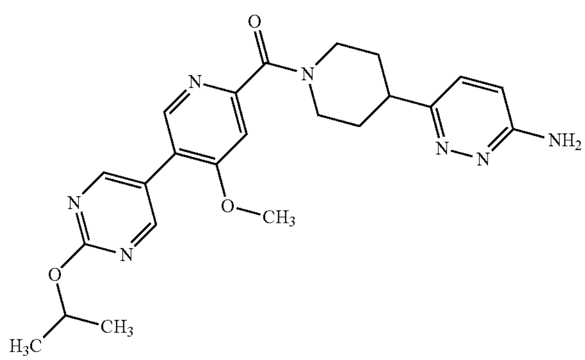 [SMILES: COc1cc(C(=O)N2CCC(c3ccc(N)nn3)CC2)ncc1-c1cnc(OC(C)C)nc1] | [4-(6-Amino-pyridazin-3-yl)-piperidin-1-yl]-[5-(2-isopropoxy-pyrimidin-5-yl)-4-methoxy-pyridin-2-yl]-methanone |
| 54 | 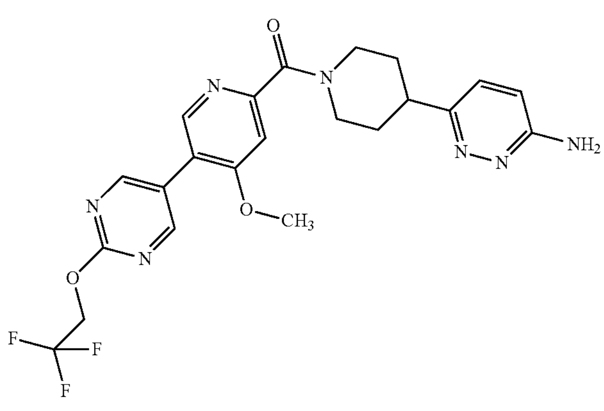 [SMILES: COc1cc(C(=O)N2CCC(c3ccc(N)nn3)CC2)ncc1-c1cnc(OCC(F)(F)F)nc1] | [4-(6-Amino-pyridazin-3-yl)-piperidin-1-yl]-{4-methoxy-5-[2-(2,2,2-trifluoro-ethoxy)-pyrimidin-5-yl]-pyridin-2-yl}-methanone |

| Cpd No. | Structure Name |
|---|---|
| 55 | [4-(6-Amino-pyridazin-3-yl)-piperidin-1-yl]-(2-methoxy-4'-trifluoromethyl-biphenyl-4-yl)-methanone |
| 56 | [4-(6-Amino-pyridazin-3-yl)-piperidin-1-yl]-(2-methoxy-4'-trifluoromethoxy-biphenyl-4-yl)-methanone |
| 57 | [4-(6-Amino-pyridazin-3-yl)-piperidin-1-yl]-(4'-isopropoxy-2-methoxy-biphenyl-4-yl)-methanone |
| 58 | [4-(6-Amino-pyridazin-3-yl)-piperidin-1-yl]-[2-methoxy-4'-(2,2,2-trifluoro-ethoxy)-biphenyl-4-yl]-methanone |
| 59 | [4-(6-Amino-pyridazin-3-yl)-piperidin-1-yl]-[3-methoxy-4-(6-trifluoromethyl-pyridin-3-yl)-phenyl]-methanone |
| 60 | [4-(6-Amino-pyridazin-3-yl)-piperidin-1-yl]-(2-methoxy-biphenyl-4-yl)-methanone |

| Cpd No. | Structure Name |
|---|---|
| 61 | [4-(6-Amino-pyridazin-3-yl)-piperidin-1-yl]-[3-methoxy-4-(2-trifluoromethyl-pyridin-4-yl)-phenyl]-methanone |
| 62 | [4-(6-Amino-pyridazin-3-yl)-piperidin-1-yl]-[4-(2-isopropoxy-pyrimidin-5-yl)-3-methoxy-phenyl]-methanone |
| 63 | [4-(6-Amino-pyridazin-3-yl)-piperidin-1-yl]-(2-methyl-4'-trifluoromethyl-biphenyl-4-yl)-methanone |
| 64 | [4-(6-Amino-pyridazin-3-yl)-piperidin-1-yl]-[6-methoxy-5-(4-trifluoromethyl-phenyl)-pyridin-2-yl]-methanone |
| 65 | [4-(6-Amino-pyridazin-3-yl)-piperidin-1-yl]-[5-methoxy-6-(4-trifluoromethyl-phenyl)-pyridin-3-yl]-methanone |
| 66 | [4-(6-Amino-pyridazin-3-yl)-piperidin-1-yl]-(3-methoxy-4'-trifluoromethyl-biphenyl-4-yl)-methanone |

-continued

| Cpd No. | Structure | Structure Name |
|---|---|---|
| 67 | 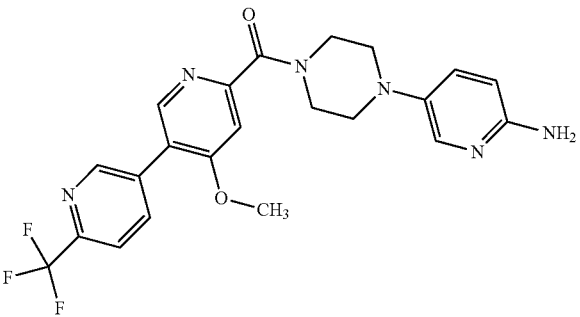 [SMILES: COc1cc(C(=O)N2CCN(c3ccc(N)nc3)CC2)ncc1-c1ccc(C(F)(F)F)nc1] | [4-(6-Amino-pyridin-3-yl)-piperazin-1-yl]-(4-methoxy-6'-trifluoromethyl-[3,3']bipyridinyl-6-yl)-methanone |
| 68 | 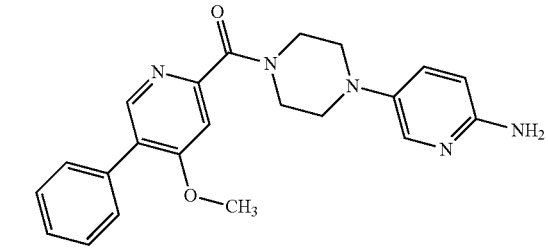 | [4-(6-Amino-pyridin-3-yl)-piperazin-1-yl]-(4-methoxy-5-phenyl-pyridin-2-yl)-methanone |
| 69 | 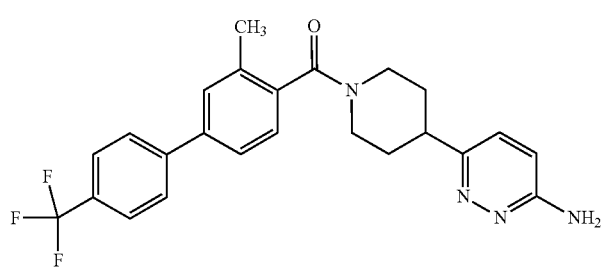 [SMILES: Cc1cc(-c2ccc(C(F)(F)F)cc2)ccc1C(=O)N1CCC(c2ccc(N)nn2)CC1] | [4-(6-Amino-pyridazin-3-yl)-piperidin-1-yl]-(3-methyl-4'-trifluoromethyl-biphenyl-4-yl)-methanone |
| 70 | 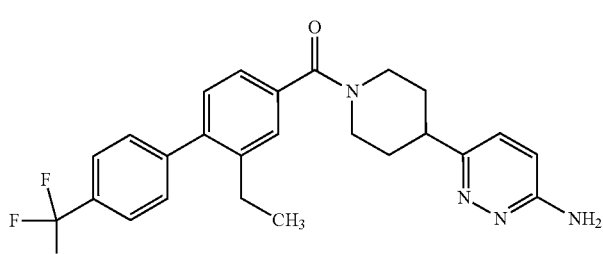 | [4-(6-Amino-pyridazin-3-yl)-piperidin-1-yl]-(2-ethyl-4'-trifluoromethyl-biphenyl-4-yl)-methanone |
| 71 | 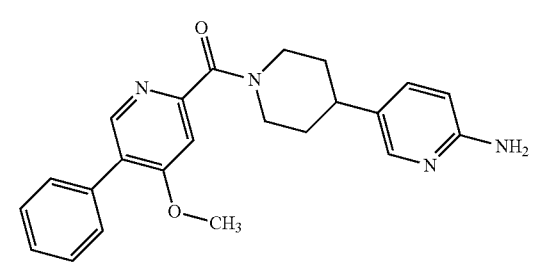 | (6-Amino-3',4',5',6'-tetrahydro-2'H-[3,4']bipyridinyl-1'-yl)-(4-methoxy-5-phenyl-pyridin-2-yl)-methanone |

-continued

| Cpd No. | Structure | Structure Name |
|---|---|---|
| 72 | 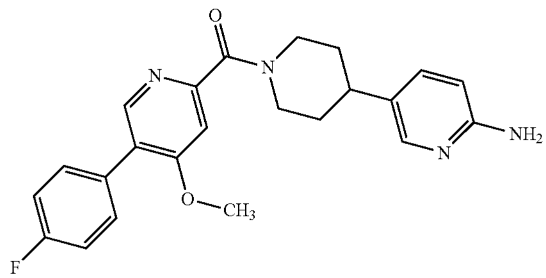 [SMILES: COc1cc(C(=O)N2CCC(c3ccc(N)nc3)CC2)ncc1-c1ccc(F)cc1] | (6-Amino-3',4',5',6'-tetrahydro-2'H-[3,4']bipyridinyl-1'-yl)-[5-(4-fluoro-phenyl)-4-methoxy-pyridin-2-yl]-methanone |
| 73 | 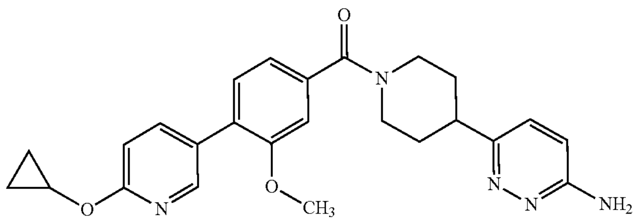 [SMILES: COc1cc(C(=O)N2CCC(c3ccc(N)nn3)CC2)ccc1-c1ccc(OC2CC2)nc1] | [4-(6-Amino-pyridazin-3-yl)-pipendin-1-yl]-[4-(6-cyclopropoxy-pyridin-3-yl)-3-methoxy-phenyl]-methanone |
| 74 | 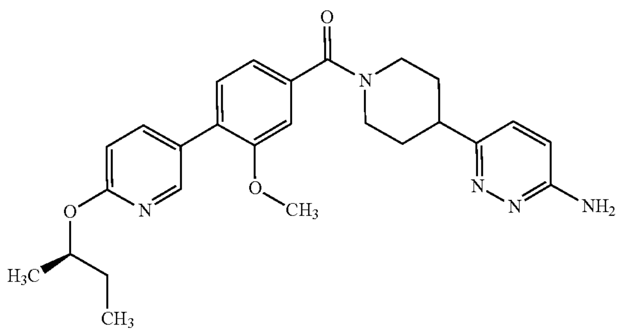 [SMILES: CC[C@@H](C)Oc1ccc(-c2ccc(C(=O)N3CCC(c4ccc(N)nn4)CC3)cc2OC)cn1] | [4-(6-Amino-pyridazin-3-yl)-piperidin-1-yl]-{4-[6-((R)-sec-butoxy)-pyridin-3-yl]-3-methoxy-phenyl}-methanone |
| 75 | 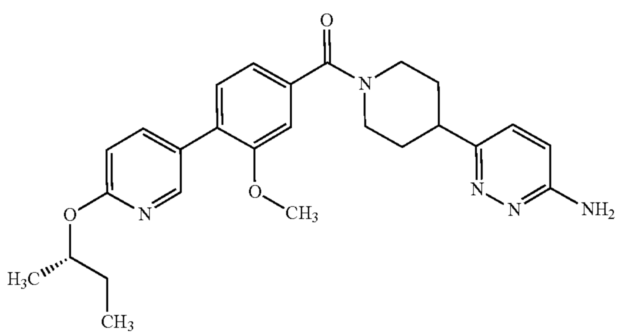 [SMILES: CC[C@H](C)Oc1ccc(-c2ccc(C(=O)N3CCC(c4ccc(N)nn4)CC3)cc2OC)cn1] | [4-(6-Amino-pyridazin-3-yl)-piperidin-1-yl]-{4-[6-((S)-sec-butoxy)-pyridin-3-yl]-3-methoxy-phenyl}-methanone |
| 76 | 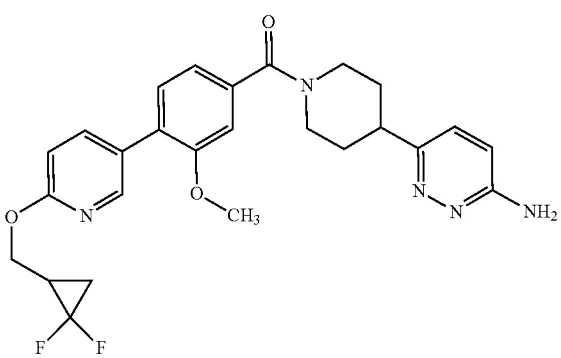 [SMILES: COc1cc(C(=O)N2CCC(c3ccc(N)nn3)CC2)ccc1-c1ccc(OCC2CC2(F)F)nc1] | [4-(6-Amino-pyridazin-3-yl)-piperidin-1-yl]-{4-[6-(2,2-difluoro-cyclopropylmethoxy)-pyridin-3-yl]-3-methoxy-phenyl}-methanone |

| Cpd No. | Structure | Structure Name |
|---|---|---|
| 77 | 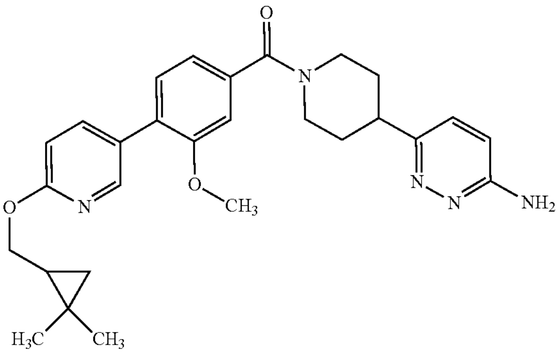 [SMILES: COc1cc(C(=O)N2CCC(c3ccc(N)nn3)CC2)ccc1-c1ccc(OCC2CC2(C)C)nc1] | [4-(6-Amino-pyridazin-3-yl)-piperidin-1-yl]-{4-[6-(2,2-dimethyl-cyclopropylmethoxy)-pyridin-3-yl]-3-methoxy-phenyl}-methanone |
| 78 | 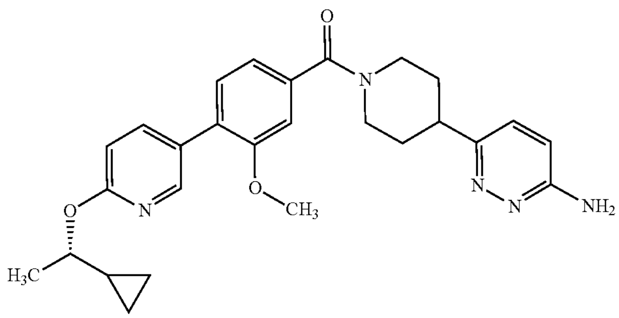 [SMILES: COc1cc(C(=O)N2CCC(c3ccc(N)nn3)CC2)ccc1-c1ccc(O[C@@H](C)C2CC2)nc1] | [4-(6-Amino-pyridazin-3-yl)-piperidin-1-yl]-{4-[6-((S)-1-cyclopropyl-ethoxy)-pyridin-3-yl]-3-methoxy-phenyl}-methanone |
| 79 | 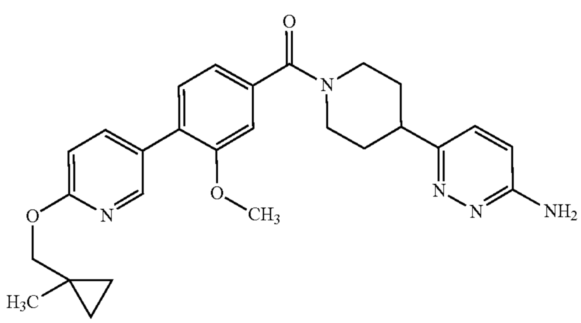 [SMILES: COc1cc(C(=O)N2CCC(c3ccc(N)nn3)CC2)ccc1-c1ccc(OCC2(C)CC2)nc1] | [4-(6-Amino-pyridazin-3-yl)-piperidin-1-yl]-{3-methoxy-4-[6-(1-methyl-cyclopropylmethoxy)-pyridin-3-yl]-phenyl}-methanone |
| 80 | 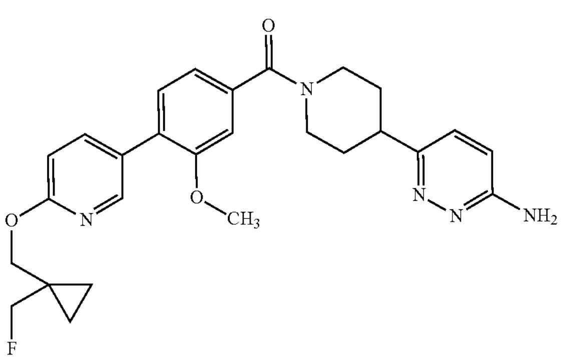 [SMILES: COc1cc(C(=O)N2CCC(c3ccc(N)nn3)CC2)ccc1-c1ccc(OCC2(CF)CC2)nc1] | [4-(6-Amino-pyridazin-3-yl)-piperidin-1-yl]-{4-[6-(1-fluoromethyl-cyclopropylmethoxy)-pyridin-3-yl]-3-methoxy-phenyl}-methanone |

| Cpd No. | Structure Name |
|---|---|
| 81 | [4-(6-Amino-pyridazin-3-yl)-piperidin-1-yl]-{4-[6-((R)-1-cyclopropyl-ethoxy)-pyridin-3-yl]-3-methoxy-phenyl}-methanone |
| 82 | [4-(6-Amino-pyridazin-3-yl)-piperidin-1-yl]-[4-(6-cyclopropylmethoxy-pyridin-3-yl)-3-methoxy-phenyl]-methanone |
| 83 | [4-(6-Amino-pyridazin-3-yl)-piperidin-1-yl]-(4'-isobutyl-biphenyl-4-yl)-methanone |
| 84 | (6-Amino-4-methoxy-3',4',5',6'-tetrahydro-2'H-[3,4]bipyridinyl-1'-yl)-[4-methoxy-5-(4-trifluoromethyl-phenyl)-pyridin-2-yl]-methanone |
| 85 | [4-(6-Amino-4-methoxy-pyridazin-3-yl)-piperidin-1-yl]-[4-methoxy-5-(4-trifluoromethyl-phenyl)-pyridin-2-yl]-methanone |

-continued

| Cpd No. | Structure | Structure Name |
|---|---|---|
| 86 | 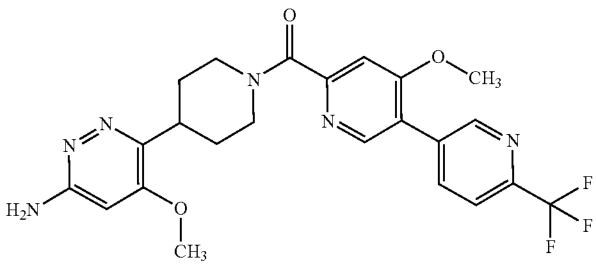 [SMILES: COc1cc(C(=O)N2CCC(c3nnc(N)cc3OC)CC2)ncc1-c1ccc(C(F)(F)F)cc1] | [4-(6-Amino-4-methoxy-pyridazin-3-yl)-piperidin-1-yl]-(4-methoxy-6'-trifluoromethyl-[3,3']bipyridinyl-6-yl)-methanone |
| 87 | 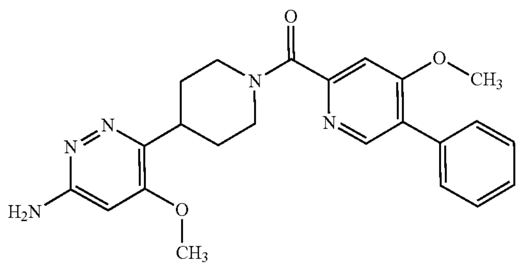 [SMILES: COc1cc(C(=O)N2CCC(c3nnc(N)cc3OC)CC2)ncc1-c1ccccc1] | [4-(6-Amino-4-methoxy-pyridazin-3-yl)-piperidin-1-yl]-(4-methoxy-5-phenyl-pyridin-2-yl)-methanone |
| 88 | 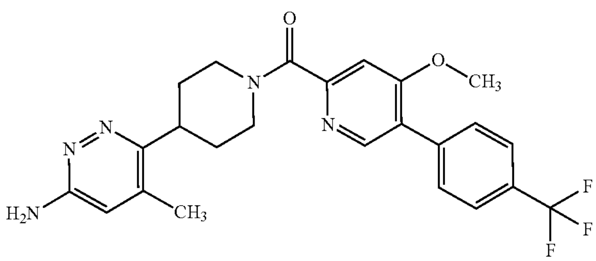 [SMILES: COc1cc(C(=O)N2CCC(c3nnc(N)cc3C)CC2)ncc1-c1ccc(C(F)(F)F)cc1] | [4-(6-Amino-4-methyl-pyridazin-3-yl)-piperidin-1-yl]-[4-methoxy-5-(4-trifluoromethyl-phenyl)-pyridin-2-yl]-methanone |
| 89 | 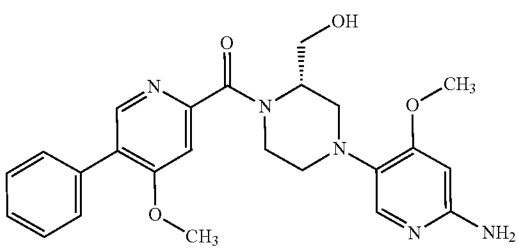 [SMILES: COc1cc(C(=O)N2CCN(c3cnc(N)cc3OC)C[C@H]2CO)ncc1-c1ccccc1] | [(S)-4-(6-Amino-4-methoxy-pyridin-3-yl)-2-hydroxymethyl-piperazin-1-yl]-(4-methoxy-5-phenyl-pyridin-2-yl)-methanone |
| 90 | 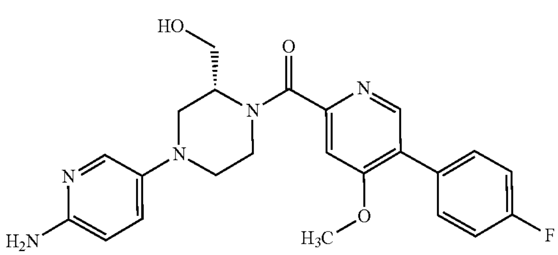 [SMILES: COc1cc(C(=O)N2CCN(c3ccc(N)nc3)C[C@@H]2CO)ncc1-c1ccc(F)cc1] | [(R)-4-(6-Amino-pyridin-3-yl)-2-hydroxymethyl-piperazin-1-yl]-[5-(4-fluoro-phenyl)-4-methoxy-pyridin-2-yl]-methanone |
| 91 | 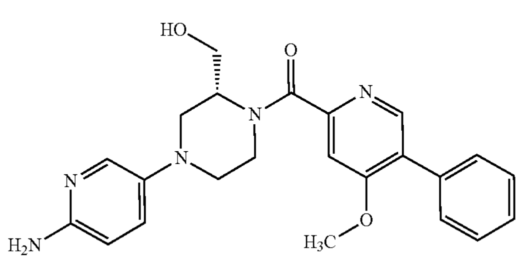 [SMILES: COc1cc(C(=O)N2CCN(c3ccc(N)nc3)C[C@@H]2CO)ncc1-c1ccccc1] | [(R)-4-(6-Amino-pyridin-3-yl)-2-hydroxymethyl-piperazin-1-yl]-(4-methoxy-5-phenyl-pyridin-2-yl)-methanone |

-continued

| Cpd No. | Structure | Structure Name |
|---|---|---|
| 92 | 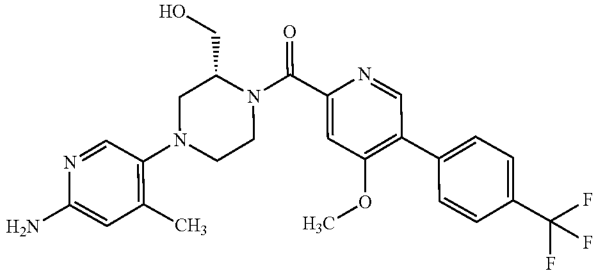 [SMILES: COc1cc(C(=O)N2CCN(c3cnc(N)cc3C)C[C@@H]2CO)ncc1-c1ccc(C(F)(F)F)cc1] | [(R)-4-(6-Amino-4-methyl-pyridin-3-yl)-2-hydroxymethyl-piperazin-1-yl]-[4-methoxy-5-(4-trifluoromethyl-phenyl)-pyridin-2-yl]-methanone |
| 93 | 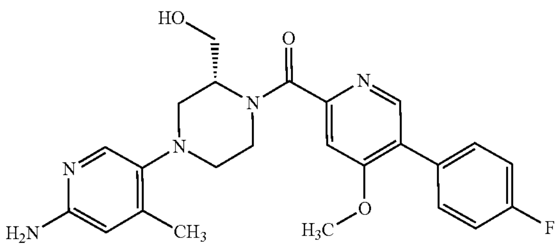 [SMILES: COc1cc(C(=O)N2CCN(c3cnc(N)cc3C)C[C@@H]2CO)ncc1-c1ccc(F)cc1] | [(R)-4-(6-Amino-4-methyl-pyridin-3-yl)-2-hydroxymethyl-piperazin-1-yl]-[5-(4-fluoro-phenyl)-4-methoxy-pyridin-2-yl]-methanone |
| 94 | 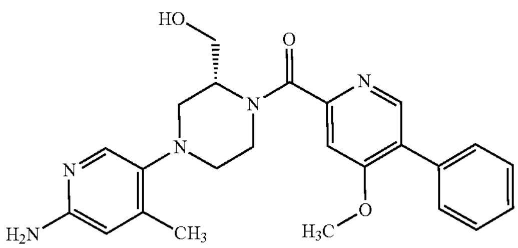 [SMILES: COc1cc(C(=O)N2CCN(c3cnc(N)cc3C)C[C@@H]2CO)ncc1-c1ccccc1] | [(R)-4-(6-Amino-4-methyl-pyridin-3-yl)-2-hydroxymethyl-piperazin-1-yl]-(4-methoxy-5-phenyl-pyridin-2-yl)-methanone |
| 95 | 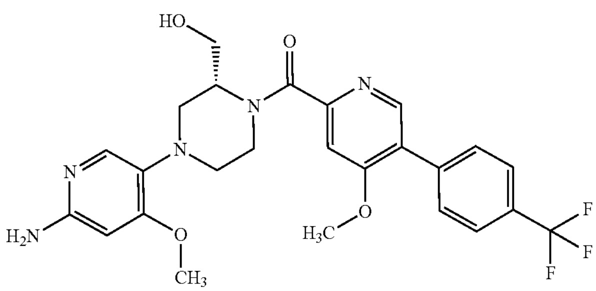 [SMILES: COc1cc(C(=O)N2CCN(c3cnc(N)cc3OC)C[C@@H]2CO)ncc1-c1ccc(C(F)(F)F)cc1] | [(R)-4-(6-Amino-4-methoxy-pyridin-3-yl)-2-hydroxymethyl-piperazin-1-yl]-[4-methoxy-5-(4-trifluoromethyl-phenyl)-pyridin-2-yl]-methanone |
| 96 | 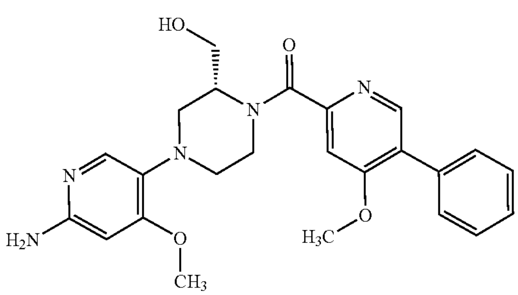 [SMILES: COc1cc(C(=O)N2CCN(c3cnc(N)cc3OC)C[C@@H]2CO)ncc1-c1ccccc1] | [(R)-4-(6-Amino-4-methoxy-pyridin-3-yl)-2-hydroxymethyl-piperazin-1-yl]-(4-methoxy-5-phenyl-pyridin-2-yl)-methanone |

| Cpd No. | Structure | Structure Name |
|---|---|---|
| 97 | 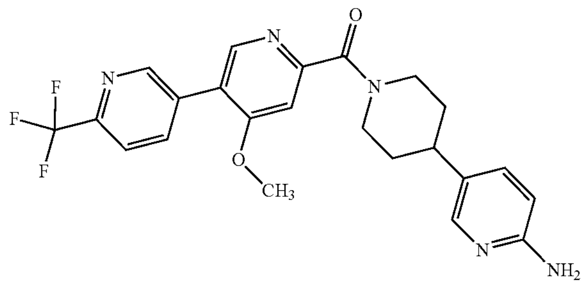 [SMILES: COc1cc(C(=O)N2CCC(c3ccc(N)nc3)CC2)ncc1-c1ccc(C(F)(F)F)nc1] | (6-Amino-3',4',5',6'-tetrahydro-2'H-[3,4']bipyridinyl-1'-yl)-(4-methoxy-6'-trifluoromethyl-[3,3']bipyridinyl-6-yl)-methanone |
| 98 | 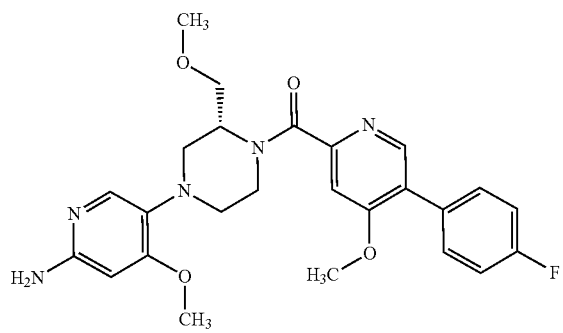 [SMILES: COC[C@H]1CN(c2cnc(N)cc2OC)CCN1C(=O)c1cc(OC)c(-c2ccc(F)cc2)cn1] | [(R)-4-(6-Amino-4-methoxy-pyridin-3-yl)-2-methoxymethyl-piperazin-1-yl]-[5-(4-fluoro-phenyl)-4-methoxy-pyridin-2-yl]-methanone |
| 99 | 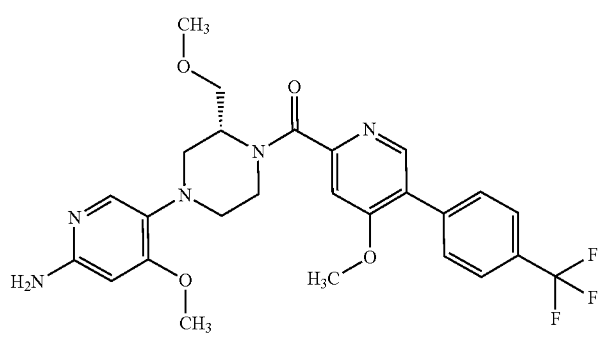 [SMILES: COC[C@H]1CN(c2cnc(N)cc2OC)CCN1C(=O)c1cc(OC)c(-c2ccc(C(F)(F)F)cc2)cn1] | [(R)-4-(6-Amino-4-methoxy-pyridin-3-yl)-2-methoxymethyl-piperazin-1-yl]-[4-methoxy-5-(4-trifluoromethyl-phenyl)-pyridin-2-yl]-methanone |
| 100 | 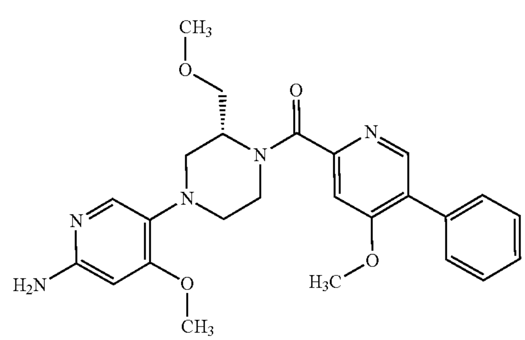 [SMILES: COC[C@H]1CN(c2cnc(N)cc2OC)CCN1C(=O)c1cc(OC)c(-c2ccccc2)cn1] | [(R)-4-(6-Amino-4-methoxy-pyridin-3-yl)-2-methoxymethyl-piperazin-1-yl]-(4-methoxy-5-phenyl-pyridin-2-yl)-methanone |
| 101 | 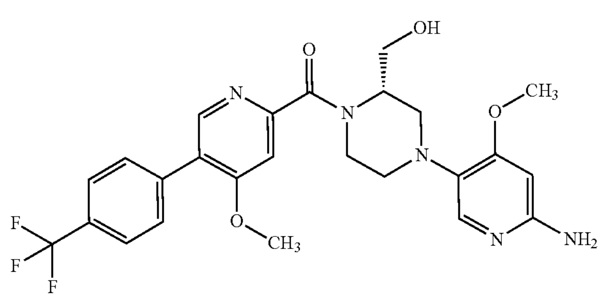 [SMILES: COc1cc(C(=O)N2CCN(c3cnc(N)cc3OC)C[C@H]2CO)ncc1-c1ccc(C(F)(F)F)cc1] | [(S)-4-(6-Amino-4-methoxy-pyridin-3-yl)-2-hydroxymethyl-piperazin-1-yl]-[4-methoxy-5-(4-trifluoromethyl-phenyl)-pyridin-2-yl]-methanone |

-continued

| Cpd No. | Structure | Structure Name |
|---|---|---|
| 102 | 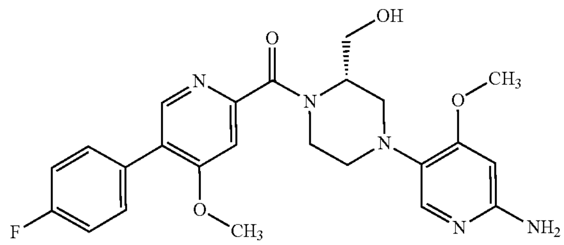 [SMILES: COc1cc(C(=O)N2CCN(c3cnc(N)cc3OC)C[C@H]2CO)ncc1-c1ccc(F)cc1] | [(S)-4-(6-Amino-4-methoxy-pyridin-3-yl)-2-hydroxymethyl-piperazin-1-yl]-[5-(4-fluoro-phenyl)-4-methoxy-pyridin-2-yl]-methanone |
| 103 | 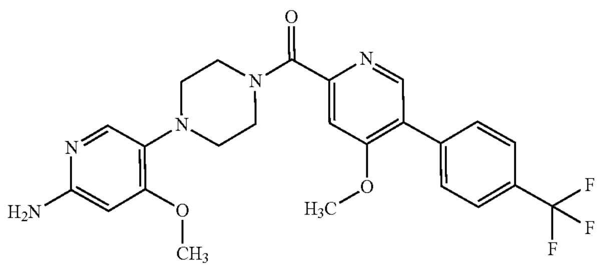 [SMILES: COc1cc(C(=O)N2CCN(c3cnc(N)cc3OC)CC2)ncc1-c1ccc(C(F)(F)F)cc1] | [4-(6-Amino-4-methoxy-pyridin-3-yl)-piperazin-1-yl]-[4-methoxy-5-(4-trifluoromethyl-phenyl)-pyridin-2-yl]-methanone |
| 104 | 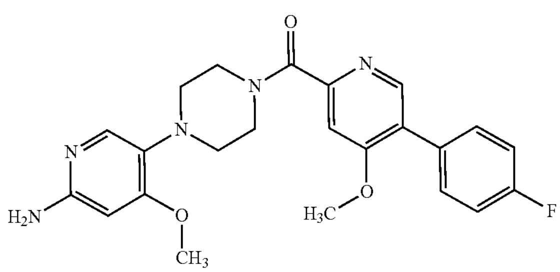 [SMILES: COc1cc(C(=O)N2CCN(c3cnc(N)cc3OC)CC2)ncc1-c1ccc(F)cc1] | [4-(6-Amino-4-methoxy-pyridin-3-yl)-piperazin-1-yl]-[5-(4-fluoro-phenyl)-4-methoxy-pyridin-2-yl]-methanone |
| 105 | 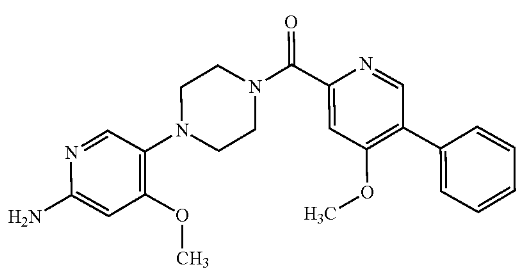 [SMILES: COc1cc(C(=O)N2CCN(c3cnc(N)cc3OC)CC2)ncc1-c1ccccc1] | [4-(6-Amino-4-methoxy-pyridin-3-yl)-piperazin-1-yl]-(4-methoxy-5-phenyl-pyridin-2-yl)-methanone |
| 106 | 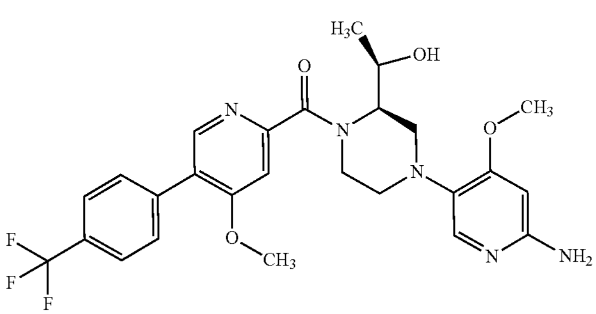 [SMILES: COc1cc(C(=O)N2CCN(c3cnc(N)cc3OC)C[C@@H]2[C@@H](C)O)ncc1-c1ccc(C(F)(F)F)cc1] | [(R)-4-(6-Amino-4-methoxy-pyridin-3-yl)-2-((R)-1-hydroxy-ethyl)-piperazin-1-yl]-[4-methoxy-5-(4-trifluoromethyl-phenyl)-pyridin-2-yl]-methanone |

-continued

| Cpd No. | Structure | Structure Name |
|---|---|---|
| 107 | 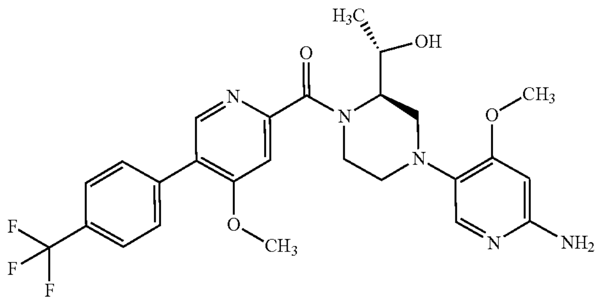 [SMILES: COc1cc(C(=O)N2CCN(c3cnc(N)cc3OC)C[C@@H]2[C@H](C)O)ncc1-c1ccc(C(F)(F)F)cc1] | [(R)-4-(6-Amino-4-methoxy-pyridin-3-yl)-2-((S)-1-hydroxy-ethyl)-piperazin-1-yl]-[4-methoxy-5-(4-trifluoromethyl-phenyl)-pyridin-2-yl]-methanone |
| 108 | 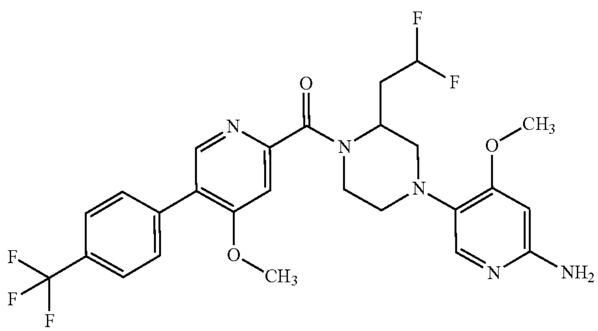 [SMILES: COc1cc(C(=O)N2CCN(c3cnc(N)cc3OC)CC2CC(F)F)ncc1-c1ccc(C(F)(F)F)cc1] | [4-(6-Amino-4-methoxy-pyridin-3-yl)-2-(2,2-difluoro-ethyl)-piperazin-1-yl]-[4-methoxy-5-(4-trifluoromethyl-phenyl)-pyridin-2-yl]-methanone |
| 109 | 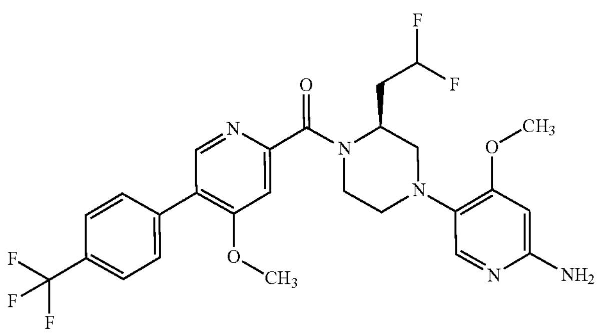 [SMILES: COc1cc(C(=O)N2CCN(c3cnc(N)cc3OC)C[C@@H]2CC(F)F)ncc1-c1ccc(C(F)(F)F)cc1] | [(S)-4-(6-Amino-4-methoxy-pyridin-3-yl)-2-(2,2-difluoro-ethyl)-piperazin-1-yl]-[4-methoxy-5-(4-trifluoromethyl-phenyl)-pyridin-2-yl]-methanone |
| 110 | 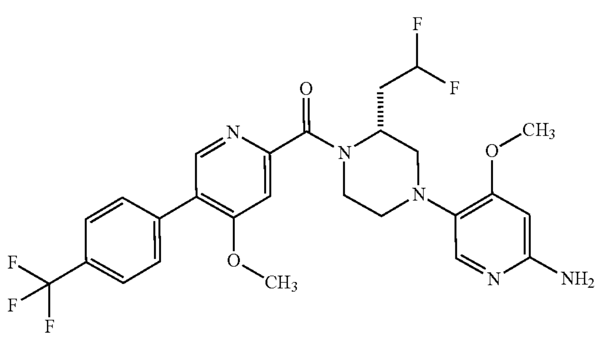 [SMILES: COc1cc(C(=O)N2CCN(c3cnc(N)cc3OC)C[C@H]2CC(F)F)ncc1-c1ccc(C(F)(F)F)cc1] | [(R)-4-(6-Amino-4-methoxy-pyridin-3-yl)-2-(2,2-difluoro-ethyl)-piperazin-1-yl]-[4-methoxy-5-(4-trifluoromethyl-phenyl)-pyridin-2-yl]-methanone |
| 111 | 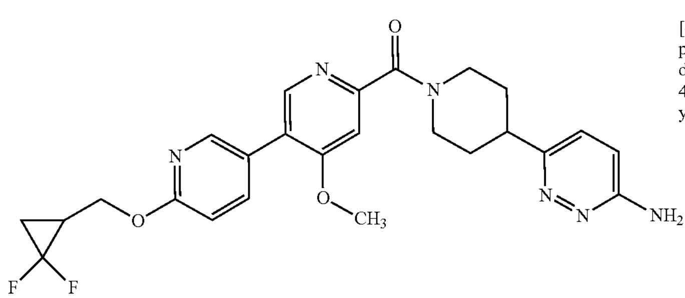 [SMILES: COc1cc(C(=O)N2CCC(c3ccc(N)nn3)CC2)ncc1-c1ccc(OCC2CC2(F)F)nc1] | [4-(6-Amino-pyridazin-3-yl)-piperidin-1-yl]-[6'-(2,2-difluoro-cyclopropylmethoxy)-4-methoxy-[3,3']bipyridinyl-6-yl]-methanone |

| Cpd No. | Structure | Structure Name |
|---|---|---|
| 112 | 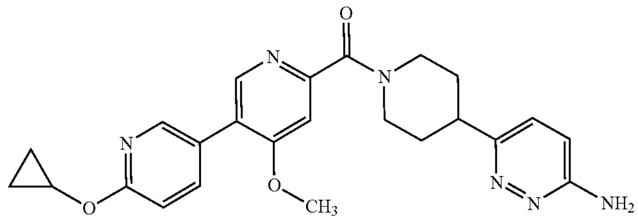 [SMILES: COc1cc(C(=O)N2CCC(c3ccc(N)nn3)CC2)ncc1-c1ccc(OC2CC2)nc1] | [4-(6-Amino-pyridazin-3-yl)-piperidin-1-yl]-(6'-cyclopropoxy-4-methoxy-[3,3']bipyridinyl-6-yl)-methanone |
| 113 | 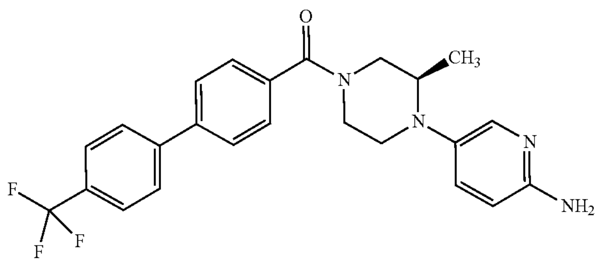 [SMILES: C[C@@H]1CN(C(=O)c2ccc(-c3ccc(C(F)(F)F)cc3)cc2)CCN1c1ccc(N)nc1] | [(R)-4-(6-Amino-pyridin-3-yl)-3-methyl-piperazin-1-yl]-(4'-trifluoromethyl-biphenyl-4-yl)-methanone |
| 114 | 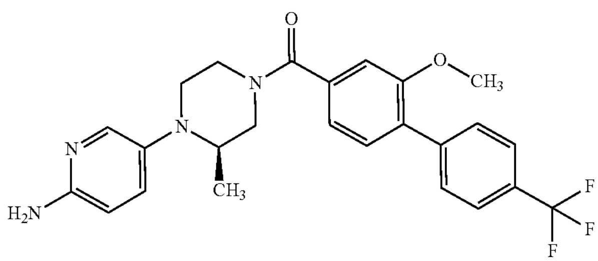 [SMILES: COc1cc(C(=O)N2CCN(c3ccc(N)nc3)[C@H](C)C2)ccc1-c1ccc(C(F)(F)F)cc1] | [(R)-4-(6-Amino-pyridin-3-yl)-3-methyl-piperazin-1-yl]-(2-methoxy-4'-trifluoromethyl-biphenyl-4-yl)-methanone |
| 115 | 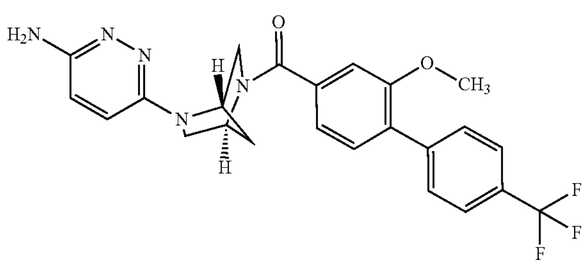 [SMILES: COc1cc(C(=O)N2C[C@@H]3C[C@H]2CN3c2ccc(N)nn2)ccc1-c1ccc(C(F)(F)F)cc1] | [(1S,4S)-5-(6-Amino-pyridazin-3-yl)-2,5-diaza-bicyclo[2.2.1]hept-2-yl]-(2-methoxy-4'-trifluoromethyl-biphenyl-4-yl)-methanone |
| 116 | | [(1S,4S)-5-(6-Amino-pyridazin-3-yl)-2,5-diaza-bicyclo[2.2.1]hept-2-yl]-[4-methoxy-5-(4-trifluoromethyl-phenyl)-pyridin-2-yl]-methanone, | or a pharmaceutically acceptable salt thereof.

18. A pharmaceutical composition comprising a compound according to claim 1, or a pharmaceutically acceptable salt thereof, and a pharmaceutically acceptable excipient or carrier.

19. A method of treating a disease or disorder that can be alleviated by TRPC6 inhibition comprising administering a therapeutically effective amount of a compound according to claim 1, or a pharmaceutically acceptable salt thereof, to a patient in need thereof.

20. The method according to claim 19, wherein the disease or disorder is selected from sepsis, severe sepsis, septic shock, cardiac hypertrophy, ischemia, ischemic reperfusion injury, hypertension, pulmonary arterial hypertension, idiopathic pulmonary arterial hypertension, restenosis, chronic obstructive pulmonary disease, cystic fibrosis, Alzheimer's disease, Parkinson's disease, Huntington's disease, amyotrophic lateral sclerosis (ALS), trauma induced brain disorders, asthma, chronic obstructive pulmonary disease, rheumatoid arthritis, osteoarthritis, inflammatory bowel disease, multiple sclerosis, muscular dystrophy, Duchenne's muscular dystrophy, preeclampsia and pregnancy-induced hypertension, non-alcoholic steatohepatitis (NASH), minimal change disease, focal segmental glomerulosclerosis (FSGS), nephrotic syndrome, diabetic nephropathy or diabetic kidney disease (DKD), chronic kidney disease (CKD), renal insufficiency, end stage renal disease, ischemia or an ischemic reperfusion injury, cancer, diabetes, lung fibrosis, idiopathic pulmonary fibrosis (IPF), emphysema and acute respiratory disease syndrome (ARDS).

* * * * *